US008841109B2

(12) United States Patent
Holyoak et al.

(10) Patent No.: US 8,841,109 B2
(45) Date of Patent: Sep. 23, 2014

(54) IGA1 PROTEASE POLYPEPTIDE AGENTS AND USES THEREOF

(75) Inventors: Todd Holyoak, Lenexa, KS (US); Jiazhou Qiu, Westborough, MA (US); Andrew G. Plaut, Lexington, MA (US)

(73) Assignees: The University of Kansas, Kansas City, KS (US); Tufts Medical Center, Inc., Boston, MA (US)

( * ) Notice: Subject to any disclaimer, the term of this patent is extended or adjusted under 35 U.S.C. 154(b) by 135 days.

(21) Appl. No.: 13/265,479

(22) PCT Filed: Apr. 20, 2010

(86) PCT No.: PCT/US2010/031733
§ 371 (c)(1),
(2), (4) Date: Jan. 23, 2012

(87) PCT Pub. No.: WO2010/123885
PCT Pub. Date: Oct. 28, 2010

(65) Prior Publication Data
US 2012/0114629 A1    May 10, 2012

Related U.S. Application Data

(60) Provisional application No. 61/170,935, filed on Apr. 20, 2009.

(51) Int. Cl.
*C12N 9/50* (2006.01)
*A61K 38/16* (2006.01)
*A61K 38/00* (2006.01)

(52) U.S. Cl.
CPC .............. *C21N 9/52* (2013.01); *C07K 2299/00* (2013.01); *A61K 38/00* (2013.01)
USPC .......................................... 435/219; 514/21.2

(58) Field of Classification Search
None
See application file for complete search history.

(56) References Cited

U.S. PATENT DOCUMENTS

| 5,079,344 A | 1/1992 | Chang et al. |
| 5,413,918 A | 5/1995 | Faulmann |
| 7,407,653 B2 | 8/2008 | Plaut et al. |
| 2003/0035800 A1 | 2/2003 | Leung et al. |
| 2003/0073166 A1* | 4/2003 | Geme, III .................... 435/69.1 |

FOREIGN PATENT DOCUMENTS

| EP | 2 042 513 A1 | 4/2009 |
| WO | 90/11367 A1 | 10/1990 |
| WO | 00/63383 A1 | 10/2000 |
| WO | WO 2004/078949 | * 9/2004 |
| WO | 2004/096157 A2 | 11/2004 |

OTHER PUBLICATIONS

Poulson et al., "A Comparative Genetic Study of Serologically Distinct *Haemophilus influenzae* Type 1 Immunoglobulin A1 Proteases", Journal of Bacteriology, May 1992, p. 2913-2921.*
Roberts et al. "Chemistry for peptide and protein PEGylation", Advanced Drug Delivery Reviews, 2002, vol. 54, pp. 459-476.*
Molineaux, G., "Pegylation: engineering improved pharmaceuticals for enhanced therapy", Cancer Treatment Reviews, 2002, vol. 28, Supplement A, pp. 13-16.*
Soares et al., "Effects of polyethylene glycol attachment on physicochemical and biological stability of *E. coli* L-asparaginase", International Journal of Pharmaceutics 237 (2002) 163-170.*
Allen et al., "Galactosylation of N- and O-linked carbohydrate moieties of IgA1 and IgG in IgA nephropathy", Clin. Exp. Immunol., 100:470-474 (1995).
Appel et al., "The IgA nephropathy treatment dilemma", Kidney Int., 69(11):1939-1944 (2006).
Ballardie, "IgA nephropathy treatment 25 years on: can we halt progression? The evidence base", Nephrol. Dial. Transplant., 19(5):1041-1046 (2004).
Barratt et al., "IgA Nephropathy", J. Am. Soc. Nephrol., 16:2088-2097 (2005).
Barratt et al., "Immunopathogenesis of IgAN", Semin. Immunopathol., 29:427-443 (2007).
Coppo et al., "Aberrant glycosylation in IgA nephropathy (IgAN)", Kidney Int., 65(5):1544-1547 (2004).
Database Uniprot (online) Sep. 5, 2006 XP002595606, Database accession No. QOPVD5, abstract.
Definition: "focal glomerulonephritis" in: Stedman's medical dictionary Ed 26 1995 pp. 727.
Galye et al., "Identification of regions in interleukin-1 alpha important for activity", J. Biol. Chem., 268(29):22105-22111 (1993).
Gesualdo et al., "Enzymolysis of Glomerular Immune Deposits in Vivo with Dextranase/Protease Ameliorates Proteinuria, Hematuria, and Mesangial Proliferation in Murine Experimental IgA Nephropathy", J. Clin. Invest., 86:715-722 (1990).
Govindan et al., "Use of Galactosylated-Streptavidin as a Clearing Agent with 111In-Labeled, Biotinylated Antibodies to Enhance Tumor/Non-Tumor Localization Ratios", Cancer Biotherapy & Radiopharmaceuticals, 17(3):307-316 (2002).
Grundy et al., "Localization of the cleavage site specificity determinant of *Haemophilus influenza* immunoglobulin A1 protease genes", Infect. Immun., 58(2):320-331 (1990).
Halter et al., "IgA protease of *Neisseria gonorrhoeae*: isolation and characterization of the gene and its extracellular product", EMBO J., 3(7):1595-1601 (1984).
Hsu et al., "The molecular pathogenesis and experimental therapy of IgA nephropathy: recent advances and future directions", Curr. Mol. Med., 1(2):183-196 (2001).
Julian et al., "IgA nephropathy: an update", Curr. Opin. Nephrol. Hypertens., 13:171-179 (2004).

(Continued)

*Primary Examiner* — Suzanne M Noakes
(74) *Attorney, Agent, or Firm* — Choate Hall & Stewart LLP; Brenda Herschbach Jarrell

(57) ABSTRACT

Polypeptide agents useful in the treatment of IgA1 deposition diseases and methods of using such polypeptide agents. Methods of screening for inhibitors of IgA1 proteases and agents that inhibit IgA1 proteases are also disclosed.

19 Claims, 24 Drawing Sheets
(12 of 24 Drawing Sheet(s) Filed in Color)

(56) References Cited

OTHER PUBLICATIONS

Kilian et al., "Pathogenic species of the genus *Haemophilus* and *Streptococcus pneumoniae* produce immunoglobulin A1 protease", Infect. Immun., 26(1):143-149 (1979).

Kilian et al., "IgA1 proteases from *Haemophilus influenza, Streptococcus pneumoniae, Neisseria meningitis*, and *Streptococcus sanguis*: comparative immunochemical studies" J. Immunol. 124(6):2596-2600 (1980).

Kobayashi et al., " IgA protease from *Clostridium ramosum* that cleaves IgA1 and IgA2, A2m(1): the site of cleavage and digestion of secretory IgA", Adv. Exp. Med. Biol., 216B:1289-1296 (1987).

Kojima et al., "Enhancement of clearance of plant lectins as radiopharmaceuticals by chemically glycosylated antilectin antibody", Eur. J. Nucl. Med., 15:373-375 (1989).

Kokubo et al., "Humoral immunity against the proline-rich peptide epitope of the IgA1 hinge region in IgA nephropathy", Nephrol. Dial. Transplant, 15:28-33 (2000).

Koshland et al., "Selective proteolysis of the J chain component in human polymeric immunoglobin", J. Immunol., 118 (3):775-781 (1977).

Lamm et al., "Microbial IgA Protease Removes IgA Immune Complexes from Mouse Glomeruli in Vivo: Potential Therapy for IgA Nephropathy", Am. J. Pathol., 172(1):31-36 (2008).

Launay et al., "Fcalpha receptor (CD89) mediates the development of immunoglobulin a (IgA) nephropathy (Berger's disease). Evidence for pathogenic soluble receptor-Iga complexes in patients and CD89 transgenic mice", J. Exp. Med., 191(11):1999-2009 (2000).

Medzihradszky et al., "Glycoforms obtained by expression in *Pichia pastoris* improve cancer targeting potential of a recombinant antibody-enzyme fusion protein", Glycobiology, 14(1):27-37 (2004).

Mestecky et al., "Defective Galactosylation and Clearance of IgA1 Molecules as a Possible Etiopathogenic Factor in IgA Nephropathy", Contributions of Nephrology, 104:172-182 (1993).

Michael et al., "Recurrent haematuria: role of renal biopsy and investigative morbidity", Br. Med. J., 1:686-688 (1976).

Moura et al., "Glycosylation and Size of IgA1 are Essential for Interaction with Mesangial Transferrin Receptor in IgA Nephropathy", J. Am. Nephrol., 15:622-634 (2004).

Nakazawa et al., "Proteolytic enzyme treatment reduces glomerular immune deposits and proteinuria in passive Heymann nephritis", J. Exp. Med., 164:1973-1987 (1986).

Nikolova et al., "The role of the carbohydrate chains in complement (C3) fixation by solid-phase-bound human IgA", Immunology, 82:321-327 (1994).

Piesecki et al., "Immobilization of beta-galactosidase for application in organic chemistry using a chelating peptide", Biotech. & Bioeng., 42(2):178-184 (1993).

Plaut et al., "Human lactoferrin proteolytic activity: analysis of the cleaved region in the IgA protease of *Haemophilus influenzae*", Vaccine, 19:S148-S152 (2001).

Rostoker et al. "High-dose immunoglobulin therapy for severe IgA nephropathy and Henoch-Schönlein purpura", Ann. Intern. Med., 120(6):476-484 (1994).

Smith et al., "New insights into the pathogenesis of IgA nephropathy", Springer Semin. Immunopathol., 24:477-493 (2003).

Strauss et al., "C-terminal glycine-histidine tagging of the outer membrane protein Iga beta of *Neisseria gonorrhoeae*", FEMS Microbiol. Lett., 127(3):249-254 (1995).

Whisstock et al., "Prediction of protein function from protein sequence and structure", Q. Rev. Biophys., 36 (3):307-340 (2003).

International Search Report for PCT/US04/06615, dated Aug. 16, 2005.

International Search Report for PCT/US2010/031733, mailed Nov. 17, 2010.

International Preliminary Report on Patentability for PCT/US2010/031733, mailed Nov. 3, 2011.

Turkova, "Oriented immobilization of biologically active proteins as a tool for revealing protein interactions and functions", J. Chromatography B, 722:11-31 (1999).

\* cited by examiner

CLUSTAL 2.0.10 multiple sequence alignment

```
Seq ID NO:14 Rd          MLNKKFKLNFIALTVAYALTPYTEAALVRDDVDYQIFRDFAENKGRFSVGATNVEVRDKN    60
Seq ID NO:12 M87489      MLNKKFKLNFIALTVAYALTPYTEAALVRDDVDYQIFRDFAENKGRFSVGATNVEVRDKN    60
Seq ID NO:2  X59800      MLNKKFKLNFIALTVAYALTPYTEAALVRDDVDYQIFRDFAENKGRFSVGATNVEVRDKN    60
Seq ID NO:4  X64357      MLNKKFKLNFIALTVAYALTPYTEAALVRDDVDYQIFRDFAENKGKFSVGATNVLVKDKN    60
Seq ID NO:6  M87492      MLNKKFKLNFIALTVAYALTPYTEAALVRDDVDYQIFRDFAENKGKFSVGATNVLVKDKN    60
Seq ID NO:10 M87490      MLNKKFKLNFIALTVAYALTPYTEAALVRDDVDYQIFRDFAENKGKFSVGATNVEVRDKN    60
Seq ID NO:8  M87491      MLNKKFKLNFIALTVAYALTPYTEAALVRDDVDYQIFRDFAENKGKFSVGATNVEVRDKK    60
Seq ID NO:19 aegyptius   MLNKKFKLNFIALTVAYALTPYTEAALVRDDVDYQIFRDFAENKGRFSVGATNVEVRDKN    60
                         ********************************************:*******  *:**:

Seq ID NO:23 Consensus   MLNKKFKLNFIALTVAYALTPYTEAALVRDDVDYQIFRDFAENKGKFSVGATNVEVRDKN Seq ID NO:14 Rd          NHSLGNVLPNGIPMIDFSVVDVDKRIATLINPQYVVGVKHVSNGVSELHFGNLNGNMNNG   120
Seq ID NO:12 M87489      NHSLGNVLPNGIPMIDFSVVDVDKRIATLINPQYVVGVKHVSNGVSELHFGNLNGNMNNG   120
Seq ID NO:2  X59800      NHSLGNVLPNGIPMIDFSVVDVDKRIATLINPQYVVGVKHVSNGVSELHFGNLNGNMNNG   120
Seq ID NO:4  X64357      NKDLGTALPNGIPMIDFSVVDVDKRIATLINPQYVVGVKHVSNGVSELHFGNLNGNMNNG   120
Seq ID NO:6  M87492      NKDLGTALPNGIPMIDFSVVDVDKRIATLINPQYVVGVKHVSNGVSELHFGNLNGNMNNG   120
Seq ID NO:10 M87490      NRPLGNVLPNGIPMIDFSVVDVDKRIATLVNPQYVVGVKHVSNGVSELHFGNLNGNMNNG   120
Seq ID NO:8  M87491      NQSLGSALPNGIPMIDFSVVDVDKRIATLVNPQYVVGVKHVSNGVSELHFGNLNGNMNNG   120
Seq ID NO:19 aegyptius   NHSLGNALPNGIPMIDFSVVDVNKRIGTLVDPQYIVSVKHAHQYMNDFYFGHYNG-----   115
                         *: **..**************:***:.**.:***:*.***. : :.:::**:**

Seq ID NO:23 Consensus   NHSLGNALPNGIPMIDFSVVDVDKRIATLINPQYVVGVKHVSNGVSELHFGNLNGNMNNG Seq ID NO:14 Rd          NAKSHRDVSSEENRYFSVEKNEYPTKLNGKAVTTEDQ-TQKRREDYYMPRLDKFVTEVAP   179
Seq ID NO:12 M87489      NDKSHRDVSSEENRYFSVEKNEYPTKLNGKAVTTEDQ-TQKRREDYYMPRLDKFVTEVAP   179
Seq ID NO:2  X59800      NAKSHRDVSSEENRYFSVEKNEYPTKLNGKAVTTEDQ-TQKRREDYYMPRLDKFVTEVAP   179
Seq ID NO:4  X64357      NAKAHRDVSSEENRYFSVEKNEYPTKLNGKTVTTEDQ-TQKRREDYYMPRLDKFVTEVAP   179
Seq ID NO:6  M87492      NAKAHRDVSSEENRYFSVEKNEYPTKLNGKTVTTEDQ-TQKRREDYYMPRLDKFVTEVAP   179
Seq ID NO:10 M87490      NAKAHRDVSSEENRYYTVEKNEYPTKLNGKAVTTEDQ-AQKRREDYYMPRLDKFVTEVAP   179
Seq ID NO:8  M87491      NAKSHRDVSSEENRYYTVEKNNFPTENVTSFTTKEEQDAQKRREDYYMPRLDKFVTEVAP   180
Seq ID NO:19 aegyptius   ----HRDVSVTQN--------NVNSSEKWDVNKRLDDYNMPRLNKFVTEVAP   180
                         *****.:**:*    * :*      . :.*. .:** :** ****:********

Seq ID NO:23 Consensus   NAKSHRDVSSEENRYFSVEKNEYPTKLNGKAVTTEDQDTQKRREDYYMPRLDKFVTEVAP Seq ID NO:14 Rd          IEASTASSDAGTYNDQNKYPAFVRLGSGSQFIYKKGDNYSLILNN---------HEVGG   229
Seq ID NO:12 M87489      IEASTASSDAGTYNDQNKYPAFVRLGSGSQFIYKKGDNYSLILNN---------HEVGG   229
Seq ID NO:2  X59800      IEASTASSDAGTYNDQNKYPAFVRLGSGSQFIYKKGDNYSLILNN---------HEVGG   229
Seq ID NO:4  X64357      IEASTASSDAGTYNDQNKYPAFVRLGSGSQFIYKKGDNYSLILNN---------HEVGG   229
Seq ID NO:6  M87492      IEASTASSDAGTYNDQNKYPAFVRLGSGSQFIYKKGDNYSLILNN---------HEVGG   229
Seq ID NO:10 M87490      IEASTDSSTAGTYNNKDYPYFVRLGSGTQFIYENGTRYELWLGKEGQK------SDAGG   233
Seq ID NO:8  M87491      IEASTANNNKGEYNNSDKYPAFVRLGSGSQFIYKKGSRYQLILTEKDKQGNLLRNWDVGG   240
Seq ID NO:19 aegyptius   TTPTLAGDDLETYKDKEKYPSFVRVGAGRQLVYEKGSRHVEGNEH--------------G   209
                         .:  ..   *::.:*** ***:*:* *::*::*.             *

Seq ID NO:23 Consensus   IEASTASSDAGTYNDQNKYPAFVRLGSGSQFIYKKGDNYSLILNN---------HEVGG
```

Figure 3A

```
Seq ID NO:14  Rd          NNLKLVGDAYTYGIAGTPYK-----VNHENNGLIGFGNSKEEHS-DPKGILSQDPLTNYA    283
Seq ID NO:12  M87489      NNLKLVGDAYTYGIAGTPYK-----VNHENNGLIGFGNSKEEHS-DPKGILSQDPLTNYA    283
Seq ID NO:2   X59800      NNLKLVGDAYTYGIAGTPYK-----VNHGVNGLIGFGNSKEEHS-DPKAILSQDPLTNYA    283
Seq ID NO:4   X64357      NNLKLVGDAYTYGIAGTPYK-----VNHENNGLIGFGNSKEEHS-DPKGILSQDPLTNYA    283
Seq ID NO:6   M87492      NNLKLVGDAYTYGIAGTPYK-----VNHENNGLIGFGNSKEEHS-DPKGILSQDPLTNYA    283
Seq ID NO:10  M87490      YNLKLVGNAYTYGIAGTPYE-----VNHENDGLIGFGNSNNEYI-NPKEILSKKPLTNYA    287
Seq ID NO:8   M87491      DNLELVGNAYTYGIAGTPYK-----VNHENNGLIGFGNSKEEHS-DPKGILSQDPLTNYA    294
Seq ID NO:19  aegyptius   EDLKQLSVAYNYAISGTPYEGINIDPSQSKKGLIGFGDSRKDHVIDTKILLSQAPLTNYG    269
                          :*: :.  **.*,*.****:          .: .*******:*.:::   :.* :**: *****.
Seq ID NO:23  Consensus   NNLKLVGDAYTYGIAGTPYKVNHENNGLIGFGNSKEEHS-DPKGILSQDPLTNYA Seq ID NO:14  Rd          VLGDSGSPLFVYDREKGKWLFLGSYDFWAGYNKKSWQEWNIYKPEFAKTVLDKDTAGSLT    343
Seq ID NO:12  M87489      VLGDSGSPLFVYDREKGKWLFLGSYDFWAGYNKKSWQEWNIYKPEFAKTVLDKDTAGSLT    343
Seq ID NO:2   X59800      VLGDSGSPLFVYDREKGKWLFLGSYDFWAGYNKKSWQEWNIYKPEFAKTVLDKDTAGSLT    343
Seq ID NO:4   X64357      VLGDSGSPLFVYDREKGKWLFLGSYDFWAGYNKKSWQEWNIYKSQFTKDVLNKDSAGSLI    343
Seq ID NO:6   M87492      VLGDSGSPLFVYDREKGKWLFLGSYDFWAGYNKKSWQEWNIYKSQFTKDVLNKDSAGSLI    343
Seq ID NO:10  M87490      VLGDSGSPLFVYDREKGKWLFLGSYDYWAGYNKKSWQEWNIYKPEFAEKIYEQYSAGSLI    347
Seq ID NO:8   M87491      VLGDSGSPLFVYDREKGKWLFLGSYDFWAGYNKKSWQEWNIYKHEFAEKIYQQYSAGSLT    354
Seq ID NO:19  aegyptius   VLGDSGSPLFAFDKQQNKWIFIGPYTYWAGYEKKSWQEWNIYKTTFADGIKNRDNAKPVP    329
                          **********.:*::.***:*:*.* :*****:************  *:.  :  :: .* .:
Seq ID NO:23  Consensus   VLGDSGSPLFVYDREKGKWLFLGSYDFWAGYNKKSWQEWNIYKPEFAKTVLDKDSAGSLT Seq ID NO:14  Rd          GSNTQYNWN-PTGKTSVISNGSESLNVDLFDSSQDTD-----SKKNNHGKSVTLRGSG---    395
Seq ID NO:12  M87489      GSNTQYNWN-PTGKTSVISNGSESLNVDLFDSSQDTD-----SKKNNHGKSVTLRGSG---    395
Seq ID NO:2   X59800      GSNTQYNWN-PTGKTSVISNGSESLNVDLFDSSQDTD-----SKKNNHGKSVTLRGSG---    395
Seq ID NO:4   X64357      GSKTDYSWS-SNGKTSTITGGEKSLNVDLADGKD---------KPNHGKSVTFEGSG---    390
Seq ID NO:6   M87492      GSKTDYSWS-SNGKTSTITGGEKSLNVDLADGKD---------KPNHGKSVTFEGSG---    390
Seq ID NO:10  M87490      GSKTDYSWS-SNGKTSTITGGEKSLNVDLADGKD---------KPNHGKSVTFEGSG---    394
Seq ID NO:8   M87491      GSNTQYTWQ-ATGSTSTITGGGEPLSVDLTDGKD---------KPNHGKSITLKGSG---    401
Seq ID NO:19  aegyptius   FSNKEYRWTNTTTNHQSEIKNTDHTITVTLFSDPDRLVNYQKEENKNTGQNVIFEGNGNSK    389
                          *:..:* *   ...  * *..  ...:.* *  ..:         : * *::: :..*.*
Seq ID NO:23  Consensus   GSNTQYNWN-PTGKTSTITGGEESLNVDLADGKDDTD----SKKPNHGKSVTFEGSG---

Seq ID NO:14  Rd          -TLTLNNNIDQGAGGLFFEGDYEVKGTSDSTTWKGAGVSVADGKTVTWKVHNPKSDRLAK    454
Seq ID NO:12  M87489      -TLTLNNNIDQGAGGLFFEGDYEVKGTSDSTTWKGAGVSVADGKTVTWKVHNPKSDRLAK    454
Seq ID NO:2   X59800      -TLTLNNNIDQGAGGLFFEGDYEVKGTSDSTTWKGAGVSVADGKTVTWKVHNPKSDRLAK    454
Seq ID NO:4   X64357      -TLTLNNNIDQGAGGLFFEGDYEVKGTSDNTTWKGAGVSVAEGKTVTWKVHNPQYDRLAK    449
Seq ID NO:6   M87492      -TLTLNNNIDQGAGGLFFEGDYEVKGTSDNTTWKGAGVSVAEGKTVTWKVHNPQYDRLAK    449
Seq ID NO:10  M87490      -TLTLNNNIDQGAGGLFFEGDYEVKGTSDNTTWKGAGVSVAEGKTVTWKVHNPQYDRLAK    453
Seq ID NO:8   M87491      -TLTLNNHIDQGAGGLFFEGDYEVKGTSDSTTWKGAGVSVADGKTVTWKVHNPKYDRLAK    460
Seq ID NO:19  aegyptius   NTLVLENNINQGAGGLFFKGNYEVKGTTDNITWVGGGIDVAEGKTVTWKVHNPEKDHLAK    449
                          **.*:*:*:*******:*:*****:*.  **  *.*:;************: *;***
Seq ID NO:23  Consensus   -TLTLNNNIDQGAGGLFFEGDYEVKGTSDNTTWKGAGVSVADGKTVTWKVHNPKYDRLAK
```

Figure 3B

```
Seq ID NO:14  Rd         IGKGTLIVEGKGENKGSLKVGDGTVILKQQADANNKVKAFSQVGIVSGRSTVVLNDDKQV  514
Seq ID NO:12  M87489     IGKGTLIVEGKGENKGSLKVGDGTVILKQQADANNKVKAFSQVGIVSGRSTVVLNDDKQV  514
Seq ID NO:2   X59800     IGKGTLIVEEKGENKGSLKVGDGTVILKQQADANNKVKAFSQVGIVSGRSTVVLNDDKQV  514
Seq ID NO:4   X64357     IGKGTLIVEGTGDNKGSLKVGDGTVILKQQTNGS-GQHAFASVGIVSGRSTLVLNDDKQV  508
Seq ID NO:6   M87492     IGKGTLIVEGTGDNKGSLKVGDGTVILKQQTNGS--GQHAFASVGIVSGRSTLVLNDDKQV 508
Seq ID NO:10  M87490     IGKGTLIVEGTGDNKGSLKVGDGTVILKQQTNGS--GQHAFASVGIVSGRSTLVLNDDKQV 512
Seq ID NO:8   M87491     IGKGTLVVEGKGKNEGLLKVGDGTVILKQRADANNKVQAFSQVGIVSGRSTLVLNDDKQV  520
Seq ID NO:19  aegyptius  IGKGKLIVEGKGDNKGSLKVGDGTVVLKQQTTTG--QHAFASVGIVSGRSTVVLNDDKQV  507
                         ****.:***.**.:*:*.*********:***::.    :**:*********:*******
Seq ID NO:23  Consensus  IGKGTLIVEGKGDNKGSLKVGDGTVILKQQADANNKQHAFAQVGIVSGRSTLVLNDDKQV Seq ID NO:14  Rd         DPNSIYFGFRGGRLDANGNNLTFEHIRNIDDGARLVNHNTSKTSTVTITGESLITDPNTI  574
Seq ID NO:12  M87489     DPNSIYFGFRGGRLDANGNNLTFEHIRNIDDGARLVNHNTSKTSTVTITGESLITDPNTI  574
Seq ID NO:2   X59800     DPNSIYFGFRGGRLDANGNNLTFEHIRNIDDGARLVNHNTSKTSTVTITGESLITDPNTI  574
Seq ID NO:4   X64357     DPNSIYFGFRGGRLDLNGNSLTFDHIRNIDDGARLVNHNMTNASNITITGESLITDPNTI  568
Seq ID NO:6   M87492     DPNSIYFGFRGGRLDLNGNSLTFDHIRNIDDGARLVNHNMTNASNITITGESLITDPNTI  568
Seq ID NO:10  M87490     DPNSIYFGFRGGRLDLNGNSLTFDHIRNIDEGARLVNHSTSKHSTVTITGDNLITDPNNV  572
Seq ID NO:8   M87491     DPNSIYFGFRGGRLDLNGNSLTFDHIRNIDDGARVVNHNMTNTSNITITGESLITNPNTI  580
Seq ID NO:19  aegyptius  DPNSIYFGFRGGRLDLNGNSLTFDHIRNIDDGARLVNHNMTNASNITITGESLITDPKKI  567
                         ***************  ***.***:******:***.**. :: *,:****:.****:..:
Seq ID NO:23  Consensus  DPNSIYFGFRGGRLDLNGNSLTFDHIRNIDDGARLVNHNMSKTSNITITGESLITDPNTI Seq ID NO:14  Rd         TPYNIDAPDEDNPYAFRRIKDGGQLYLNLENYTYYALRKGASTRSELPKNSGESNENWLY  634
Seq ID NO:12  M87489     TPYNIDAPDEDNPYAFRRIKDGGQLYLNLENYTYYALRKGASTRSELPKNSGESNENWLY  634
Seq ID NO:2   X59800     TPYNIDAPDEDNPYAFRRIKDGGQLYLNLENYTYYALRKGASTRSELPKNSGESNENWLY  634
Seq ID NO:4   X64357     TPYNIDAPDEDNPYAFRRIKDGGQLYLNLENYTYYALRKGASTRSELPKNSGESNENWLY  628
Seq ID NO:6   M87492     TPYNIDAPDEDNPYAFRRIKDGGQLYLNLENYTYYALRKGASTRSELPKNSGESNENWLY  628
Seq ID NO:10  M87490     SIYYVKPLEDDNPYAIRQIKYGYQLYFNEENRTYYALKKDASIRSEFPQNRGESNNSWLY  632
Seq ID NO:8   M87491     TSYNIBAQDDDHPLRIRSIPYR-QLYFNQDNRSYYTLKKGASTRSELPQNSGESNENWLY  639
Seq ID NO:19  aegyptius  NPYYIKAREEDNPYAPRWIKDGEQLYFNLENYTYYALKKGASTRSELPYNDKESNENWLY  627
                         . * :.. ::*:*  :* *   ***:* :*  :**;*:*,,, .*::* *  ***:.***
Seq ID NO:23  Consensus  TPYNIDAPDEDNPYAFRRIKDGGQLYLNLENYTYYALRKGASTRSELPKNSGESNENWLY Seq ID NO:14  Rd         MGKTSDEAKRNVMNHINNERMNGFNGYFGEEEGKN--NGNLNVTFKGKSEQNRFLLTGGT  692
Seq ID NO:12  M87489     MGKTSDEAKRNVMNHINNERMNGFNGYFGEEEGKN--NGNLNVTFKGKSEQNRFLLTGGT  692
Seq ID NO:2   X59800     MGKTSDEAKRNVMNHINNERMNGFNGYFGEEEGKN--NGNLNVTFKGKSEQNRFLLTGGT  692
Seq ID NO:4   X64357     MGKTSDEAKRNVMNHINNERMNGFNGYFGEEEGKN--NGNLNVTFKGKSEQNRFLLTGGT  686
Seq ID NO:6   M87492     MGKTSDEAKRNVMNHINNERMNGFNGYFGEEEGKN--NGNLNVTFKGKSEQNRFLLTGGT  686
Seq ID NO:10  M87490     MGTEKADAQKNAMNHINNERMNGFNGYFGEEEGKN--NGNLNVTFKGKSEQNRFLLTGGT  690
Seq ID NO:8   M87491     MGRTSDEAKRNVMNHINNERMNGFNGYFGEEETKATQNGKLNVTFNGKSDQNRFLLTGGT  699
Seq ID NO:19  aegyptius  MGKNADEAKRNVMKHINNERMNGFNGYFGEEEGKD--NGNLNVTFKGKTEQNRFLLTGGT  685
                         **    :*:.*.*:*******   *  ******** *  **:*****:**:********
Seq ID NO:23  Consensus  MGKTSDEAKRNVMNHINNERMNGFNGYFGEEEGKN--NGNLNVTFKGKSEQNRFLLTGGT
```

Figure 3C

```
Seq ID NO:14  Rd        NLNGDLKVEKGTLFLSGRPTPHARDIAGISSTKKDQHFAENNEVVVEDDWINRNFKATNI   752
Seq ID NO:12  M87489    NLNGDLKVEKGTLFLSGRPTPHARDIAGISSTKKDQHFAENNEVVVEDDWINRNFKATNI   752
Seq ID NO:2   X59800    NLNGDLKVEKGTLFLSGRPTPHARDIAGISSTKKDQHFAENNEVVVEDDWINRNFKATNI   752
Seq ID NO:4   X64357    NLNGDLTVEKGTLFLSGRPTPHARDIAGISSTKKDPHFAENNEVVVEDDWINRNFKATTM   746
Seq ID NO:6   M87492    NLNGDLTVEKGTLFLSGRPTPHARDIAGISSTKKDPHFAENNEVVVEDDWINRNFKATTM   746
Seq ID NO:10  M87490    NLNGDLNVQQGTLFLSGRPTPHARDIAGISSTKKDSHFTENNEVVVEDDWINRNFKATNI   750
Seq ID NO:8   M87491    NLNGDLNVEKGTLFLSGRPTPHARDIAGISSTKKDPHFTENNEVVVEDDWINRNFKATTM   759
Seq ID NO:19  aegyptius NLNGNLKVEQGTLFLSGRPTPHARDIAGISSTKKDSBFAENNEVVVEDDWINRNFKATTM   745
                        ****;*.*;;***************** **;******************;:

Seq ID NO:23  Consensus NLNGDLKVEKGTLFLSGRPTPHARDIAGISSTKKDPHFAENNEVVVEDDWINRNFKATNI Seq ID NO:14  Rd        NVTNNATLYSGRNVANITSNITASDNAKVHIGYKAGDTVCVRSDYTGYVTCTTDKLSDKA   812
Seq ID NO:12  M87489    NVTNNATLYSGRNVANITSNITASDNAKVHIGYKAGDTVCVRSDYTGYVTCTTDKLSDKA   812
Seq ID NO:2   X59800    NVTNNATLYSGRNVANITSNITASDNAKVHIGYKAGDTVCVRSDYTGYVTCTTDKLSDKA   812
Seq ID NO:4   X64357    NVTGNASLYSGRNVANITSNITASNKAQVHIGYKTGDTVCVRSDYTGYVTCTTDKLSDKA   806
Seq ID NO:6   M87492    NVTGNASLYSGRNVANITSNITASNKAQVHIGYKTGDTVCVRSDYTGYVTCTTDKLSDKA   806
Seq ID NO:10  M87490    NVTNNATLYSGRNVESITSNITASNNAKVHIGYKAGDTVCVRSDYTGYVTCTTDKLSDKA   810
Seq ID NO:8   M87491    NVTGNASLYSGRNVANITSNITASNNAQVHIGYKTGDTVCVRSDYTGYVTCHNSNLSEKA   819
Seq ID NO:19  aegyptius NVTGNASLYSGRNVESITSNITASSKAQVHIGYKKGDTVCVRSDYTGYVTCHNGDLSEKA   805
                        ***.**;******* ,********.;*.;****** ***************...**;**

Seq ID NO:23  Consensus NVTGNASLYSGRNVANITSNITASNNAKVHIGYKAGDTVCVRSDYTGYVTCTTDKLSDKA Seq ID NO:14  Rd        LNSFNATNVSGNVNLSGNANFVLGKANLFGTISGTGNSQVRLTENSHWHLTGDSNVNQLN   872
Seq ID NO:12  M87489    LNSFNATNVSGNVNLSGNANFVLGKANLFGTISGTGNSQVRLTENSHWHLTGDSNVNQLN   872
Seq ID NO:2   X59800    LNSFNATNVSGNVNLSGNANFVLGKANLFGTISGTGNSQVRLTENSHWHLTGDTNVNQLN   872
Seq ID NO:4   X64357    LNSFNPTNLRGNVNLTESANFVLGKANLFGTIQSRGNSQVRLTENSHWHLTGNSDVHQLD   866
Seq ID NO:6   M87492    LNSFNPTNLRGNVNLTESANFVLGKANLFGTIQSRGNSQVRLTENSHWHLTGNSDVHQLD   866
Seq ID NO:10  M87490    LNSFNPTNLRGNVNLTESANFVLGKANLFGTIQSRGNSQVRLTENSHWHLTGNSDVHQLD   870
Seq ID NO:8   M87491    LNSFNPTNLRGNVNLTENASFTLGKANLFGTIQSIGTSGVNLKENSHWHLTGNSNVNQLN   879
Seq ID NO:19  aegyptius LNSFNATNVFGNVNLSGNANFTLGKANLHGSIQAGGNSQVHLTENSHWYLTGDSNVHQLD   865
                        *****,**; *****; .*.*,******.*;;(.,  *.***.* ;***;*** ;;;*;**;

Seq ID NO:23  Consensus LNSFNATNLRGNVNLSENANFVLGKANLFGTIQSRGNSQVRLTENSHWHLTGDSNVHQLD Seq ID NO:14  Rd        LDKGHIHLNAQNDANKVTTYNTLTVNSLSGNGSFYYLTDLSNKQGDKVVVTKSATGNFTL   932
Seq ID NO:12  M87489    LDKGHIHLNAQNDANKVTTYNTLTVNSLSGNGSFYYLTDLSNKQGDKVVVTKSATGNFTL   932
Seq ID NO:2   X59800    LDKGHIHLNAQNDANKVTTYNTLTVNSLSGNGSFYYLTDLSNKQGDKVVVTKSATGNFTL   932
Seq ID NO:4   X64357    LANGHIHLNSADNSNNVTKYNTLTVNSLSGNGSFYYLTDLSNKQGDKVVVTKSATGNFTL   926
Seq ID NO:6   M87492    LANGHIHLNSADNSNNVTKYNTLTVNSLSGNGSFYYLTDLSNKQGDKVVVTKSATGNFTL   926
Seq ID NO:10  M87490    LANGHIHLNSADNSNNVTKYNTLTVNSLSGNGSFYYLTDLSNKQGDKVVVTKSATGNFTL   930
Seq ID NO:8   M87491    LTNGHIHLNAQNDANKVTTYNTLTVNSLSGNGSFYYVDFTNNKSNKVVVNKSATGNFTL   939
Seq ID NO:19  aegyptius LKNGHIHLNSADNKNNVTKYNTLNISNLSGNGSFYYLTDLSNKQGDKVVVTKSAKGNFTL   925
                        *  ;*******  ;;;  *;**.****.;;.*********  .*;;;;;;.;****.***.*****

Seq ID NO:23  Consensus LANGHIHLNAADDANKVTKYNTLTVNSLSGNGSFYYLTDLSNKQGDKVVVTKSATGNFTL
```

Figure 3D

```
Seq ID NO:14  Rd         QVADKTGEPTKNELTLFDASNATRNNLNVSLVGNTVDLGAWKYKLRNVNGRYDLYNPEVE   992
Seq ID NO:12  M87489     QVADKTGEPTKNELTLFDASNATRNNLNVSLVGNTVDLGAWKYKLRNVNGRYDLYNPEVE   992
Seq ID NO:2   X59800     QVADKTGEPTKNELTLFDASNATRNNLNVSLVGNTVDLGAWKYKLRNVNGRYDLYNPEVE   992
Seq ID NO:4   X64357     QVADKTGEPNHNELTLFDASKAQRDHLNVSLVGNTVDLGAWKYKLRNVNGRYDLYNPEVE   986
Seq ID NO:6   M87492     QVADRTGEPNHNELTLFDASKAQRDHLNVSLVGNTVDLGAWKYKLRNVNGRYDLYNPEVE   986
Seq ID NO:10  M87490     QVADKTGEPNHNELTLFDASKAQRDHLNVSLVGNTVDLGAWKYKLRNVNGRYDLYNPEVE   990
Seq ID NO:8   M87491     QVADKTGEPTKNELTLFDASNATRNNLEVTLANGSVDRGAWKYKLRNVNGRYDLYNPEVE   999
Seq ID NO:19  aegyptius  QVADRTGEPTKNELTLFDASNATRSNLVVTLANGSVDRGAWKYKLRENNGRYDLYNPEVE   985
                         ********.:***********:* *.:* *:*...:** *******: ***********
Seq ID NO:23  Consensus  QVADKTGEPNHNELTLFDASNATRNNLNVSLVGNTVDLGAWKYKLRNVNGRYDLYNPEVE Seq ID NO:14  Rd         KRNQTVDTTNITTPNNIQADVPSVPSNNEEIARV-ETPVPP---PAPAT-----------  1037
Seq ID NO:12  M87489     KRNQTVDTTNITTPNNIQADVPSVPSNNEEIARV-ETPVPP---PAPAT-----------  1037
Seq ID NO:2   X59800     KRNQTVDTTNITTPNNIQADVPSVPSNNEEIARV-ETPVPP---PAPDT-----------  1037
Seq ID NO:4   X64357     KRNQTVDTTNITTPNNIQADVPSVPSNNEEIARVDEAPVPP---PAPAT-----------  1032
Seq ID NO:6   M87492     KRNQTVDTTNITTPNNIQADVPSVPSNNEEIARVDEAPVPP---PAPAT-----------  1032
Seq ID NO:10  M87490     KRNQTVDTTNITTPNNIQADVPSVPSNNEEIARVDEAPVPP---PAPAT-----------  1036
Seq ID NO:8   M87491     KRNQTVDTTNITTPNDIQADAPSAQSNNEEIARV-ETPVPP---PAPATESAIASEQPET  1055
Seq ID NO:19  aegyptius  RPHQTVDTPSVEMPNDMQADAPSAPSNNEEIARV-DAPVPPPAPPAPATGSAMAKEQPKT  1044
                         ;*:******..:: **:***.**.**********  :****   *** *
Seq ID NO:23  Consensus  KRNQTVDTTNITTPNNIQADVPSVPSNNEEIARVDEAPVPP---PAPAT-SA-A-EQP-T Seq ID NO:14  Rd         -------------------------------------------PSETTETVAENSKQESKTVEK  1058
Seq ID NO:12  M87489     -------------------------------------------PSETTETVAENSKQESKTVEK  1058
Seq ID NO:2   X59800     -------------------------------------------PSETTETVAENSKQESKTVEK  1058
Seq ID NO:4   X64357     -------------------------------------------PSETTETVAENSKQESKTVEK  1053
Seq ID NO:6   M87492     -------------------------------------------PSETTETVAENSKQESKTVEK  1053
Seq ID NO:10  M87490     -------------------------------------------PSETTETVAENSKQESKTVEK  1057
Seq ID NO:8   M87491     RPAETAQPAMEETNTANSTETAPKSDTATQTENPNSESVPSETTERVAENPPQENETVAK  1115
Seq ID NO:19  aegyptius  RPAETAQPTMEETKAANSTETAPKSDTTTQADTSNSESVPSETTETVAENSPQESASVEK  1104
                                                                    ******.***. **. :* *
Seq ID NO:23  Consensus  RPAETAQP-MEET--ANSTETAPKSDT-TQ----NSESVPSETTETVAENSKQESKTVEK Seq ID NO:14  Rd         NEQDATETTAQNGEVABEEAKPSVKANTQTNEVAQSGSETEETQTTEIK-----------  1106
Seq ID NO:12  M87489     NEQDATETTAQNGEVAEEAKPSVKANTQTNEVAQSGSETEETQTTEIK-----------  1106
Seq ID NO:2   X59800     NEQDATETTAQNGEVGEEAKPSVKANTQTNEVAQSGSETEETQTTEIK-----------  1106
Seq ID NO:4   X64357     NEQDATETTAQNREVAKEAKSNVKANTQTNEVAQSGSETKETQTTETK-----------  1101
Seq ID NO:6   M87492     NEQDATETTAQNREVAKEAKSNVKANTQTNEVAQSGSETKETQTTETK-----------  1101
Seq ID NO:10  M87490     NEQDATETTAQNREVAKEAKSNVKANTQTNEVAQSGSETKETQTTETK-----------  1105
Seq ID NO:8   M87491     NEQEATEPTPQNGEVAKEDQPTVEANTQTNEATQSEGKTEETQTAETKSEPTESVTVSEN  1175
Seq ID NO:19  aegyptius  NAEEATETTPQNDEVAKEAKPTVETKDQTNEMQSGSENTTETQAENKVSQP--------  1156
                         * ::***.*.** **.:*  ..*::: **** :** .:.      :* *
Seq ID NO:23  Consensus  NEQDATETTAQNGEVAKEAKPNVKANTQTNEVAQSGSETEETQTTETK-----------
```

Figure 3E

```
Seq ID NO:14  Rd         ----------ETAKVEKEEKAKVEK--------DEIQEAPQMASETSPKQAKPAPKEVS    1147
Seq ID NO:12  M87489     ----------ETAKVEKEEKAKVEKEEKAKVEKDEIQEAPQMASETSPKQAKPAPKEVS    1155
Seq ID NO:2   X59800     ----------ETAKVEKEEKAKVEK--------DEIQEAPQMASETSPKQAKPAPKEVS    1147
Seq ID NO:4   X64357     ----------ETATVEKEEK---------------------------------------    1111
Seq ID NO:6   M87492     ----------ETATVEKEEK---------------------------------------    1111
Seq ID NO:10  M87490     ----------ETATVEKEEK---------------------------------------    1115
Seq ID NO:8   M87491     QPEKTVSQSTEDKVVVEKEEKAKVET---------EETQKAPQVTSKEPPKQAEPAPEEVP    1227
Seq ID NO:19  aegyptius  -------TETDKIATVETEETARVEKE--------ETQVASQTFPKQEEPEMTKQQAEPET    1202
                                . . **.**.
Seq ID NO:23  Consensus  ----------T-ETATVEKEEKAKVEKE--------DEIQEAPQMASETSPKQAKPAPKEVS Seq ID NO:14  Rd         TDTKVEETQVQAQPQTQSTTVAAAEATSPNSKPAEETQ-PSEKTNAEPVTPVVSKNQTEN    1206
Seq ID NO:12  M87489     TDTKVEETQVQAQPQTQSTTVAAAEATSPNSKPAEETQ-PSEKTNAEPVTPVVSKNQTEN    1214
Seq ID NO:2   X59800     TDTKVEETQVQAQPQTQSTTVAAAEATSPNSKPAEETQ-PSEKTNAEPVTPVVSKNQTEN    1206
Seq ID NO:4   X64357     -----------------------------------------------------------
Seq ID NO:6   M87492     -----------------------------------------------------------
Seq ID NO:10  M87490     -----------------------------------------------------------
Seq ID NO:8   M87491     TDTN--AEEAQALQQTQPTTVAAAETTSPNSKPAEETQQPSEKTNAEPVTPVVSEN----    1281
Seq ID NO:19  aegyptius  RNVPIVNNLEEAQPQTKPITVATAETPTSNSKSAEKTQ-PSGETNAEPVTPVVSENQPE    1261
Seq ID NO:23  Consensus  TDTKVEETQVQAQPQTQSTTVAAAEATSPNSKPAEETQ-PSEKTNAEPVTPVVSKNQTEN Seq ID NO:14  Rd         TTDQPTEREKTAKVETEK--------TQEPPQVASQASPKQEQ-----------------    1241
Seq ID NO:12  M87489     TTDQPTEREKTAKVETEK--------TQEPPQVASQASPKQEQ-----------------    1249
Seq ID NO:2   X59800     TTDQPTEREKTAKVETEK--------TQEPPQVASQASPKQEQ-----------------    1241
Seq ID NO:4   X64357     -----------AKVETEK--------TQEVPKVTSQVSPKQEQ-----------------    1135
Seq ID NO:6   M87492     -----------AKVETEK--------TQEVPKVTSQVSPKQEQ-----------------    1135
Seq ID NO:10  M87490     -----------AKVETEK--------TQEVPKVTSQVSPKQEQ-----------------    1139
Seq ID NO:8   M87491     TATQPTETEETAKVEKEK--------TQEVPQVASQESPKQEQPAAKPQAQTKPQAEPAR    1333
Seq ID NO:19  aegyptius  NTISQPTEDTVVKVETEETPKVETGGTKEAPQVASQTSPKEE------------------    1304
                                .***.*;          *;* *;*;*;** *****;:
Seq ID NO:23  Consensus  TTDQPTEREKTAKVETEK--------TQEVPQVASQASPKQEQ-----------------

Seq ID NO:14  Rd         --------------------------------------SETVQPQAVLESENVPTVN    1260
Seq ID NO:12  M87489     --------------------------------------SETVQPQAVLESENVPTVN    1268
Seq ID NO:2   X59800     --------------------------------------SETVQPQAVLESENVPTVN    1260
Seq ID NO:4   X64357     --------------------------------------SETVQPQAEPARENDPTVN    1154
Seq ID NO:6   M87492     --------------------------------------SETVQPQAEPARENDPTVN    1154
Seq ID NO:10  M87490     --------------------------------------SETVQPQAEPARENDPTVN    1158
Seq ID NO:8   M87491     ENVLTTKNVGEPQPQAQPQTQSTAVPTTGETAANSKPAAKPQAQAKPQTEPARENVSTVN    1393
Seq ID NO:19  aegyptius  ---------------------------------------PETVQPQAEFAQENSPTVN    1323
                                                                  .:**;   ** .***
Seq ID NO:23  Consensus  --------------------------------------SETVQPQAEPARENVPTVN
```

Figure 3F

```
Seq ID NO:14  Rd        NAEEVQAQLQTQTSATVSTKQPAPEN-----------SINTGSATAITETAEKSDKPQTE    1309
Seq ID NO:12  M87489    NAEEVQAQLQTQTSATVSTKQPAPEN-----------SINTGSATAITETAEKSDKPQTE    1317
Seq ID NO:2   X59800    NAEEVQAQLQTQTSATVSTKQPAPEN-----------SINTGSATAITETAEKSDKPQTE    1309
Seq ID NO:4   X64357    -----IKEPQSQTNTTADTEQPAKET-----------SSN--------------VEQP---   1182
Seq ID NO:6   M87492    -----IKEPQSQTNTTADTEQPAKET-----------SSN--------------VEQP---   1182
Seq ID NO:10  M87490    -----IKEPQSQTNTTADTEQPAKET-----------SSN--------------VEQP---   1186
Seq ID NO:8   M87491    ------TKEPQSTSATVSTEQPAKETSSNVEQPAPENSINTGSATTMTETAEKSDKPQME    1448
Seq ID NO:19  aegyptius N-VEEAQPQTQPTIVAAKEITAPNS-----------AQKETAQSVANPKTAEQPVTVSTE    1371
                        : *:*.. .. .: .* :.                  . :
Seq ID NO:23  Consensus NAEEVIAEPQSQTSATASTEQPAKET-----------SINTGSATAITETAEKSDKPQTE Seq ID NO:14  Rd        TAASTEDASQHKANTVADNSVANNSESSDPKSRRRRSISQPQETSAEETTAASTDETTIA    1369
Seq ID NO:12  M87489    TAASTEDASQHKANTVADNSVANNSESSDPKSRRRRSISQPQETSAEETTAASTDETTIA    1377
Seq ID NO:2   X59800    TAASTEDASQHKANTVADNSVANNSESSDPKSRRRRSISQPQETSAEETTAASTDETTIA    1369
Seq ID NO:4   X64357    ---VTESTTVNTGNSVVEN--------------------------PENTTPATTQPTVNS    1213
Seq ID NO:6   M87492    ---VTESTTVNTGNSVVEN--------------------------PENTTPATTQPTVNS    1213
Seq ID NO:10  M87490    ---VTESTTVNTGNSVVEN--------------------------PENTTPATTQPTVNS    1217
Seq ID NO:8   M87491    T---VTENDRQPEANTVADNSVANNSESSESKSRRRRSVSQPKETSAEETTVASTQETTVD    1506
Seq ID NO:19  aegyptius NPVVENPENTTQPAVNSEAVQPETATTGTVSQPKEASTDETTVASTDETTGTSAEETTVA    1431
                           :         :            .::** :::: *.
Seq ID NO:23  Consensus TAAVTEDASQHKANTVADNSVANNSESSDPKSRRRRSISQPQETSAEETTAASTQETTIA Seq ID NO:14  Rd        DNS--KPSK-PNRRSRRSVPS------EPTVTNGS-----------DRSTVALRDLTSTN    1409
Seq ID NO:12  M87489    DNS--KRSK-PNRRSRRSVRS------EPTVTNGS-----------DRSTVALRDLTSTN    1417
Seq ID NO:2   X59800    DNS--KRSK-PNRRSPRSVRS------EPTVTNGS-----------DRSTVALRDLTSTN    1409
Seq ID NO:4   X64357    ESS--NKPKNRHRRSVRSVPHN----VEPATTSSN-----------DRSTVALCDLTSTN    1256
Seq ID NO:6   M87492    ESS--NKPKNRHRRSVRSVPHN----VEPATTSSN-----------DRSTVALCDLTSTN    1256
Seq ID NO:10  M87490    ESS--NKPKNRHRRSVRSVPHN----VEPATTSSN-----------DRSTVALCDLTSTN    1260
Seq ID NO:8   M87491    NSV--STPKPRSRRTRRSVQTNSYEPVELPTENAENAENVQSGNNVANSQPALRNLTSKN    1564
Seq ID NO:19  aegyptius DNSEASKPKRRSRRDVSSTPHN----VEPAVTGGGR---------DRSAVVPLRDLTSTN    1479
                        :.  . .* ** **  *.        * ... ..           .* ;***.*
Seq ID NO:23  Consensus DNS-KKPK-NRHRRSRRSVPHN----VEPATTNGN-----------DRSTVALRDLTSTN Seq ID NO:14  Rd        TNAVISDAMAKAQFVALNVGKAVSQHISQLEMNNEGQYNVWVSNTSMNENYSSSQYRRFS    1469
Seq ID NO:12  M87489    TNAVISDAMAKAQFVALNVGKAVSQHISQLEMNNEGQYNVWVSNTSMNENYSSSQYRRFS    1477
Seq ID NO:2   X59800    TNAVISDAMAKGQFVALNVGKAVSQHISQLEMNNEGQYNVWVSNTSMNENYSSSQYRRFS    1469
Seq ID NO:4   X64357    TNAVLSDARAKAQFVALNVGKAVSQHISQLEMNNEGQYNVWVSNTSMNKNYSSSQYRRFS    1316
Seq ID NO:6   M87492    TNAVLSDARAKAQFVALNVGKAVSQHISQLEMNNEGQYNVWVSNTSMNKNYSSSQYRRFS    1316
Seq ID NO:10  M87490    TNAVLSDARAKAQFVALNVGKAVSQHISQLEMNNEGQYNVWVSNTSMNKNYSSSQYRRFS    1320
Seq ID NO:8   M87491    TNAVLSNAMAKAQFVALNVGKAVSQHISQLEMNNEGQYNVWISNTSMNKNYSSEQYRRFS    1624
Seq ID NO:19  aegyptius TNAVLSDAMAKAQFVALNVGKAVSQHISQLEMNNEGQYNVWVSNTSMNENYSSDQYRRFS    1539
                        ****:*;.* **.*******************.*******;*****;****.******
Seq ID NO:23  Consensus TNAVLSDAMAKAQFVALNVGKAVSQHISQLEMNNEGQYNVWVSNTSMNENYSSSQYRRFS
```

Figure 3G

```
Seq ID NO:14  Rd         SKSTQTQLGWDQTISNNVQLGGVFTYVRNSNNFDKASSKNTLAQVNFYSKYYADNHWYLG   1529
Seq ID NO:12  M87489     SKSTQTQLGWDQTISNNVQLGGVFTYVRNSNNFDKASSKNTLAQVNFYSKYYADNHWYLG   1537
Seq ID NO:2   X59800     SKSTQTQLGWDQTISNNVQLGGVFTYVRNSNNFDKASSKNTLAQVNFYSKYYADNHWYLG   1529
Seq ID NO:4   X64357     SKSTQTQLGWDQTISNNVQLGGVFTYVRNSNNFDKATSKNTLAQVNFYSKYYADNHWYLG   1376
Seq ID NO:6   M87492     SKSTQTQLGWDQTISNNVQLGGVFTYVRNSNNFDKATSKNTLAQVNFYSKYYADNHWYLG   1376
Seq ID NO:10  M87490     SKSTQTQLGWDQTISNNVQLGGVFTYVRNSNNFDKATSKNTLAQVNFYSKYYADNHWYLG   1380
Seq ID NO:8   M87491     SKSTQTQLGWDQTISNNVQLGGVFTYVRNSNNFDKASSKNTLAQVNFYSKYYADNHWYLG   1684
Seq ID NO:19  aegyptius  SKSAQTQLGWDQTISNNVQLGGILTYVRNSNSPDKASSKNTLAQANFYSKYYADNHWYLA   1599
                         ***:************************ **** *****:********.*********:
Seq ID NO:23  Consensus  SKSTQTQLGWDQTISNNVQLGGVFTYVRNSNNFDKASSKNTLAQVNFYSKYYADNHWYLG Seq ID NO:14  Rd         IDLGYGKFQSNLKTNHNAKFARHTAQFGLTAGKAFNLGNFGITPIVGVRYSLSNANFAL   1589
Seq ID NO:12  M87489     IDLGYGKFQSNLKTNHNAKFARHTAQFGLTAGKAFNLGNFGITPIVGVRYSLSNANFAL   1597
Seq ID NO:2   X59800     IDLGYGKFQSNLKTNTNAKFARHTAQFGLTAGKAFNLGNFGITPIVGVRYSLSNANFAL   1589
Seq ID NO:4   X64357     IDLGYGKFQSNLQTNHNAKFARHTAQFGLTAGKAFNLGNFGITPIVGVRYSLSNADFAL   1436
Seq ID NO:6   M87492     IDLGYGKFQSNLQTNHNAKFARHTAQFGLTAGKAFNLGNFGITPIVGVRYSLSNADFAL   1436
Seq ID NO:10  M87490     IDLGYGKFQSKLQTNHNAKFARHTAQFGLTAGKAFNLGNFGITPIVGVRYSLSNADFAL   1440
Seq ID NO:8   M87491     IDLGYGKFQSNLTNNAKFARHTAQIGLTAGKAFNLGNFAVKPTVGVRYSLSNADFAL   1744
Seq ID NO:19  aegyptius  VDLGYGNFQSNLQTNHNAKFDRHTAQIGLTAGKAFNLGNVAVKPTVGVRYSLSNADFAL   1659
                         :****:****::** ****:*****:**********:.:.:.******:***
Seq ID NO:23  Consensus  IDLGYGKFQSNLQTNHNAKFARHTAQFGLTAGKAFNLGNFGITPIVGVRYSLSNADFAL Seq ID NO:14  Rd         AKDRIKVNPISVKTAFAQVDLSYTYHLGEFSVTPILSARYDTNQGSGKINVNQYDFAYNV   1649
Seq ID NO:12  M87489     AKDRIKVNPISVKTAFAQVDLSYTYHLGEFSVTPILSARYDTNQGSGKINVNQYDFAYNV   1657
Seq ID NO:2   X59800     AKDRIKVNPISVKTAFAQVDLSYTYHLGEFSVTPILSARYDTNQGSGKINVNQYDFAYNV   1649
Seq ID NO:4   X64357     DQARIKVNPISVKTAFAQVDLSYTYHLGEFSVTPILSARYDANQGSGKINVNGYDFAYNV   1496
Seq ID NO:6   M87492     DQARIKVNPISVKTAFAQVDLSYTYHLGEFSVTPILSARYDANQGSGKINVNGYDFAYNV   1496
Seq ID NO:10  M87490     DQARIKVNPISVKTAFAQVDLSYTYHLGEFSVTPILSARYDANQGSGKINVNGYDFAYNV   1500
Seq ID NO:8   M87491     AQDRIKVNPISVKTAFAQVDLSYTYHLGEFSITPILSARYDANQGNGKINVSVYDFAYNV   1804
Seq ID NO:19  aegyptius  DQDRIKVNPISVKTAFAQVDLSYTYNLGEFAITPILSARYDANQGNGKINVSGYAFAYNV   1719
                         : **********************:****::*********:****.****. * ****
Seq ID NO:23  Consensus  AQDRIKVNPISVKTAFAQVDLSYTYHLGEFSVTPILSARYDANQGSGKINVNGYDFAYNV Seq ID NO:14  Rd         ENQQQYNAGLKLKYHNVKLSLIGGLTKAKQAEKQKTAELKLSFSF   1694
Seq ID NO:12  M87489     ENQQQYNAGLKLKYHNVKLSLIGGLTKAKQAEKQKTAELKLSFSF   1702
Seq ID NO:2   X59800     ENQQQYNAGLKLKYHNVKLSLIGGLTKAKQAEKQKTAELKLSFSF   1694
Seq ID NO:4   X64357     ENQQQYNAGLKLKYHNVKLSLIGGLTKAKQAEKQKTAELKLSFSF   1541
Seq ID NO:6   M87492     ENQQQYNAGLKLKYHNVKLSLIGGLTKAKQAEKQKTAELKLSFSF   1541
Seq ID NO:10  M87490     ENQQQYNAGLKLKYHNVKLSLIGGLTKAKQAEKQKTAELKLSFSF   1545
Seq ID NO:8   M87491     ENQQQYNAGLKLKYHNVKLSLIGGLTKAKQAEKQKTAEVKLSFSF   1849
Seq ID NO:19  aegyptius  ENQQQYNAGLKLKYHNVKLSMGGLTKAKQAEKQKTAEVKLSFSF   1764
                         ********************::*******************:*****
Seq ID NO:23  Consensus  ENQQQYNAGLKLKYHNVKLSLIGGLTKAKQAEKQKTAELKLSFSF
```

Figure 3H

SEQUENCE LISTING

```
<160> NUMBER OF SEQ ID NOS: 49

<210> SEQ ID NO 1
<211> LENGTH: 5657
<212> TYPE: DNA
<213> ORGANISM: Haemophilus influenzae
<220> FEATURE:
<221> NAME/KEY: misc_feature
<222> LOCATION: (1)..(5657)
<223> OTHER INFORMATION: Encodes IgA1 protease

<400> SEQUENCE: 1
tttttaaaaa ttattatcat tacctcataa atgtaattca agttttgagc gatttatgct      60
ataaagctcg ctcattataa agatgaagac aacttgcaaa ttatcaacgc aacacagcca     120
aaatttgaat caacttgtaa ccgtatatca aattgtgtcc tatcaaatct acttttaaa     180 cttaattaat aaggacagct tctatgctaa ataaaaaatt caaactcaat tttattgcgc     240
ttactgtcgc ctacgcatta accccttata cagaagctgc gttagtgaga gacgatgtgg     300
attatcaaat atttcgtgat tttgcagaaa ataaagggag attttctgtt ggtgcaacaa     360
atgtggaagt gagagataaa aataaccact ctttaggcaa tgttttacct aatggcattc     420
cgatgattga tttagtgtt gtggatgtag ataaacgcat cgccacattg ataaatccac     480
aatatgtagt aggtgtaaaa cacgttagta acggcgtgag tgaactacac tttgggaact     540
```

```
taaatggcaa tatgaataat ggcaatgcta atcgcaccg agatgtatct tcagaagaaa      600
atagatattt ttccgttgag aaaaatgagt atccaactaa attgaatgga aaagcagtaa      660
ctactgaaga tcaaactcaa aaacgccgtg aagactacta tatgccacgt cttgataaat      720
ttgttaccga agttgcacca atagaggctt caactgcaag tagtgatgct ggcacatata      780
atgatcagaa taaatatcct gcttttgtaa gactaggaag tggtagtcaa tttatttata      840
aaaaaggaga taattacagc ttaattttaa ataatcatga ggttggaggc aataatctta      900
aattggtggg cgatgcctat acctatggta ttgcaggcac accttataaa gtaaaccacg      960
gggttaatgg actaattggt tttggcaatt caaaagagga acacagcgat ccaaaagcca     1020
tattatctca agatccgctt accaattatg ctgttttagg cgacagtggc tccccattat     1080
ttgtatatga tagagaaaaa ggaaaatggc ttttcttgg gtcttatgat ttttgggcag      1140
gttataacaa aaaatcttgg caagaatgga atatttataa acctgaattt gcaaaaactg     1200
ttctagataa agatactgca ggttctttaa ctggttctaa cacccaatac aattggaatc     1260
ctactggcaa acaagcgtt atttctaatg gttctgaatc tctaaatgtt gatttattcg      1320
atagtagtca ggatacggac tctaagaaga acaatcacgg aaaaagtgtg actcttagag     1380
gaagtggaac gcttacctta aataataata tcgatcaagg cgcaggcggc ttgttctttg     1440
aaggagatta tgaagttaaa ggcacttctg atagtaccac ttggaaagga gctggcgttt     1500
ctgttgctga tggaaaaaca gtaacgtgga aagtacataa cccgaaatct gatcgtttag     1560
ctaaaatcgg caaaggaaca ttaattgtag aagaaaaggg agaaaataaa ggttcgctaa     1620
aagtgggcga tggtactgtt atcttaaaac aacaagctga tgccaataat aaagttaaag     1680
ccttttcaca agtaggtata gtaagtggtc gctcaactgt tgtacttaat gatgataagc     1740
aagtagatcc aaattccatt tactttggct ttagaggtgg tcgattagat gccaatggca     1800
ataatctcac ttttgaacat atccgtaata ttgatgatgg cgcaagacta gtaaatcaca     1860
ataccagcaa aacctctact gtaacaatta ctggggaaag tctaattaca gatccaaata     1920
caattactcc atataatata acgcaccag atgaagataa tccttatgcc tttcgacgga     1980
ttaaagatgg aggacagctc tatttaaatt tggaaaatta cacttattat gcgttaagaa     2040
aaggtgcgag cactcgttca gaattaccta aaaatagtgg cgaaagcaat gaaaattggc     2100
tatatatggg taaaacttcc gatgaagcca aagaaatgt aatgaaccat atcaacaacg     2160
agcgtatgaa tggctttaac ggttattttg gcgaggaaga gggtaaaaat aacggtaatc     2220
taaatgtgac ttttaaaggc aaaagtgagc aaaatcgctt tttattaaca ggcggaacaa     2280
accttaatgg cgatttaaag gttgaaaaag gcacattatt cctttctggc agaccaacac     2340
cgcacgcaag agatattgca ggtatttctt cgacaaaaaa agatcaacac tttgctgaaa     2400
ataatgaagt ggtagtagaa gatgactgga ttaaccgcaa ttttaaagca acaaatatta     2460
atgtaaccaa taacgcaacc ctttattcag gtcgcaatgt tgcaaacatt acttcaaata     2520
tcacagcttc tgataatgca aaagtacata ttggctataa agcaggcgat accgtttgtg     2580
tacgttctga ctatacgggc tatgtgactt gcactactga caagttatcc gataaagccc     2640
ttaatagctt taacgccacc aatgtatctg gcaatgtaaa tttatcaggt aatgcaaact     2700
ttgtcttagg caaagctaac ttattcggca caattagcgg cacgggaaat agccaagtac     2760
gtttaaccga aaatagccat tggcatttaa caggcgatac gaatgttaat cagttaaatt     2820
tagacaaggg gcatattcat ttaaatgcac aaaacgatgc aaataaagta actacatata     2880
```

```
acacgctgac tgtgaatagc ttatcaggta acggttcttt ctattattta actgatcttt    2940
ccaataaaca aggcgacaaa gttgttgtaa ctaaatccgc cacaggtaac tttacattac    3000
aagtggcaga taaaacaggc gagcctacaa aaatgaact cacgcttttt gatgcgtcaa     3060
atgctacaag aaataatttg aatgtgtcat tagttgggaa taccgttgat ttaggtgctt    3120
ggaaatataa attacgtaat gttaatggac gttacgattt gtataaccca gaggtggaaa    3180
aaagaaatca aactgtcgat acgacaaata tcaacaacc taataatatt caagctgatg     3240
tgcctagcgt accaagtaac aatgaagaaa tagcccgtgt tgaaacacca gttccaccac    3300
ctgcgcctga tacaccatca gagacaactg aaacagtggc tgaaaatagt aagcaagaaa    3360
gtaaaacagt agagaaaaac gagcaagacg caaccgagac aacagctcaa aatggagaag    3420
ttggagaaga agctaaacca agtgtaaaag ctaatactca aacaaatgaa gtggctcaaa    3480
gtggaagtga accgaggaa actcaaacga ctgaaataaa agaaacagct aaagtagaaa     3540
aagaggaaaa ggctaaagta gaaaagatg aaattcaaga agcacctcaa atggcttctg     3600
aaacgtctcc gaaacaagca aagcctgctc ctaaagaagt ttcaactgat acgaaagtag    3660
aagaaactca agttcaagct caaccgcaaa cacaatcgac aactgttgct gcggcagagg    3720
caacttcgcc aaacagtaaa ccagcggaag aaactcaacc aagtgaaaaa actaacgctg    3780
aacctgtaac gcctgtagta tcaaaaaatc aaacagaaaa tacgaccgac caaccaacag    3840
aaagagagaa aacggctaaa gtagaaacag agaaaactca agaaccccct caagtggctt    3900
ctcaagcgtc tccgaaacag gaacagtctg aaactgttca accgcaagca gtgcttgaaa    3960
gtgaaaatgt tccgactgtt aataatgcag aagaagttca agctcaactg caaacacaaa    4020
caagtgcaac agtaagcact aaacaacctg caccagagaa ttcaataaat actggatctg    4080
caaccgcaat aacagaaact gctgaaaaat ccgataaacc acaaacggaa actgcggctt    4140
cgactgaaga tgctagtcag cataaagcga atactgttgc ggataattct gtagcaaata    4200
attcagaaag cagtgatcca aagagtagac gtagaagaag tattagccag ccgcaagaga    4260
cttctgctga agaaacaaca gcagcttcta ctgacgaaac aacaatagct gataattcaa    4320
aacgcagtaa gccaaatcgt agaagtagaa gaagtgttcg ctcggaacca actgttacaa    4380
atggcagcga tcgttctaca gtagcattgc gcgatctcac aagtacaaac acaaatgcgg    4440
taatttctga tgcaatggca aaaggacaat ttgttgcatt aaatgtgggg aaagcagttt    4500
ctcaacatat tagccagtta gaaatgaata acgaggggca atataacgtt tgggtatcta    4560
atacttcaat gaacgaaaat tattcctcaa gtcaatatcg tcgttttagt tctaaaagta    4620
cgcaaactca acttggttgg gatcaaacaa tctcaaacaa tgttcagtta ggtggcgtgt    4680
ttacttatgt tcgcaatagt aacaactttg ataaggcaag cagtaaaaat actctagcac    4740
aagttaattt ctattctaaa tattatgcgg ataatcattg gtatttgggc attgatttag    4800
gctacggcaa gttccaaagc aacctaaaaa ccaatactaa tgcgaaattt gctcgccata    4860
ctgcacaatt tggtttaacc gcaggcaaag catttaatct tggcaatttt ggtattacgc    4920
caatagtagg cgtgcgttat agctatttat caaacgctaa ttttgcatta gctaaagatc    4980
gcattaaagt aaatccaata tctgtcaaaa cagcctttgc tcaagttgat ttaagttata    5040
cttatcactt aggcgagttt tccgttacgc caattttgtc tgctcgatat gatacaaatc    5100
aaggcagcgg aaaaattaat gtaaatcaat atgattttgc ttacaacgtg gaaaaccaac    5160
agcaatataa cgcagggctt aaattgaaat atcataatgt gaaattaagt ctaataggcg    5220
gattaacaaa agcgaaacaa gcggaaaaac aaaaaactgc agaattaaaa ctaagttta    5280
```

```
gtttttaata agcctgtttg aattaacgtt ataaacaaca aagccctgtg tcttacaggg    5340
ctttattttt gaatgaaatt cagtgattaa gtgcggtgaa aaatcagcgc attttttatt    5400
tttaacgtaa aaacgctgga atattttttct cgtatgctga gattttgtct tcgtgctgaa    5460
gagttaagcc gatattatct aaaccgttta gcaaacaatg gcggcggaat tcatcaagct    5520
caaaagtata aactttatcc cctacagtga ccgagatcgc ttctaaatct acgtggattt    5580
gtttgccttc atttgcccat acccattgga agatttcttc tacttcttct tcgcttaaac    5640
gaatcggtaa catatgc                                                   5657
```

<210> SEQ ID NO 2
<211> LENGTH: 1694
<212> TYPE: PRT
<213> ORGANISM: Haemophilus influenzae
<220> FEATURE:
<221> NAME/KEY: misc_feature
<222> LOCATION: (1)..(1694)
<223> OTHER INFORMATION: Full-length precursor IgA1 protease

<400> SEQUENCE: 2

```
Met Leu Asn Lys Lys Phe Lys Leu Asn Phe Ile Ala Leu Thr Val Ala
1               5                   10                  15

Tyr Ala Leu Thr Pro Tyr Thr Glu Ala Ala Leu Val Arg Asp Asp Val
            20                  25                  30

Asp Tyr Gln Ile Phe Arg Asp Phe Ala Glu Asn Lys Gly Arg Phe Ser
        35                  40                  45

Val Gly Ala Thr Asn Val Glu Val Arg Asp Lys Asn Asn His Ser Leu
    50                  55                  60

Gly Asn Val Leu Pro Asn Gly Ile Pro Met Ile Asp Phe Ser Val Val
65                  70                  75                  80

Asp Val Asp Lys Arg Ile Ala Thr Leu Ile Asn Pro Gln Tyr Val Val
                85                  90                  95

Gly Val Lys His Val Ser Asn Gly Val Ser Glu Leu His Phe Gly Asn
            100                 105                 110

Leu Asn Gly Asn Met Asn Asn Gly Asn Ala Lys Ser His Arg Asp Val
        115                 120                 125

Ser Ser Glu Glu Asn Arg Tyr Phe Ser Val Lys Asn Glu Tyr Pro
    130                 135                 140

Thr Lys Leu Asn Gly Lys Ala Val Thr Thr Glu Asp Gln Thr Gln Lys
145                 150                 155                 160

Arg Arg Glu Asp Tyr Tyr Met Pro Arg Leu Asp Lys Phe Val Thr Glu
                165                 170                 175

Val Ala Pro Ile Glu Ala Ser Thr Ala Ser Ser Asp Ala Gly Thr Tyr
            180                 185                 190

Asn Asp Gln Asn Lys Tyr Pro Ala Phe Val Arg Leu Gly Ser Gly Ser
        195                 200                 205

Gln Phe Ile Tyr Lys Lys Gly Asp Asn Tyr Ser Leu Ile Leu Asn Asn
    210                 215                 220

His Glu Val Gly Gly Asn Asn Leu Lys Leu Val Gly Asp Ala Tyr Thr
225                 230                 235                 240

Tyr Gly Ile Ala Gly Thr Pro Tyr Lys Val Asn His Gly Val Asn Gly
                245                 250                 255

Leu Ile Gly Phe Gly Asn Ser Lys Glu Glu His Ser Asp Pro Lys Ala
            260                 265                 270

Ile Leu Ser Gln Asp Pro Leu Thr Asn Tyr Ala Val Leu Gly Asp Ser
```

-continued

```
            275                 280                 285
Gly Ser Pro Leu Phe Val Tyr Asp Arg Glu Lys Gly Lys Trp Leu Phe
    290                 295                 300
Leu Gly Ser Tyr Asp Phe Trp Ala Gly Tyr Asn Lys Lys Ser Trp Gln
305                 310                 315                 320
Glu Trp Asn Ile Tyr Lys Pro Glu Phe Ala Lys Thr Val Leu Asp Lys
                    325                 330                 335
Asp Thr Ala Gly Ser Leu Thr Gly Ser Asn Thr Gln Tyr Asn Trp Asn
                340                 345                 350
Pro Thr Gly Lys Thr Ser Val Ile Ser Asn Gly Ser Glu Ser Leu Asn
            355                 360                 365
Val Asp Leu Phe Asp Ser Ser Gln Asp Thr Asp Ser Lys Lys Asn Asn
        370                 375                 380
His Gly Lys Ser Val Thr Leu Arg Gly Ser Gly Thr Leu Thr Leu Asn
385                 390                 395                 400
Asn Asn Ile Asp Gln Gly Ala Gly Gly Leu Phe Phe Glu Gly Asp Tyr
                    405                 410                 415
Glu Val Lys Gly Thr Ser Asp Ser Thr Thr Trp Lys Gly Ala Gly Val
                420                 425                 430
Ser Val Ala Asp Gly Lys Thr Val Thr Trp Lys Val His Asn Pro Lys
            435                 440                 445
Ser Asp Arg Leu Ala Lys Ile Gly Lys Gly Thr Leu Ile Val Glu Glu
        450                 455                 460
Lys Gly Glu Asn Lys Gly Ser Leu Lys Val Gly Asp Gly Thr Val Ile
465                 470                 475                 480
Leu Lys Gln Gln Ala Asp Ala Asn Asn Lys Val Lys Ala Phe Ser Gln
                    485                 490                 495
Val Gly Ile Val Ser Gly Arg Ser Thr Val Val Leu Asn Asp Asp Lys
                500                 505                 510
Gln Val Asp Pro Asn Ser Ile Tyr Phe Gly Phe Arg Gly Gly Arg Leu
            515                 520                 525
Asp Ala Asn Gly Asn Asn Leu Thr Phe Glu His Ile Arg Asn Ile Asp
        530                 535                 540
Asp Gly Ala Arg Leu Val Asn His Asn Thr Ser Lys Thr Ser Thr Val
545                 550                 555                 560
Thr Ile Thr Gly Glu Ser Leu Ile Thr Asp Pro Asn Thr Ile Thr Pro
                    565                 570                 575
Tyr Asn Ile Asp Ala Pro Asp Glu Asp Asn Pro Tyr Ala Phe Arg Arg
                580                 585                 590
Ile Lys Asp Gly Gly Gln Leu Tyr Leu Asn Leu Glu Asn Tyr Thr Tyr
            595                 600                 605
Tyr Ala Leu Arg Lys Gly Ala Ser Thr Arg Ser Glu Leu Pro Lys Asn
        610                 615                 620
Ser Gly Glu Ser Asn Glu Asn Trp Leu Tyr Met Gly Lys Thr Ser Asp
625                 630                 635                 640
Glu Ala Lys Arg Asn Val Met Asn His Ile Asn Asn Glu Arg Met Asn
                    645                 650                 655
Gly Phe Asn Gly Tyr Phe Gly Glu Glu Glu Lys Asn Asn Gly Asn
                660                 665                 670
Leu Asn Val Thr Phe Lys Gly Lys Ser Glu Gln Asn Arg Phe Leu Leu
            675                 680                 685
Thr Gly Gly Thr Asn Leu Asn Gly Asp Leu Lys Val Glu Lys Gly Thr
        690                 695                 700
```

```
Leu Phe Leu Ser Gly Arg Pro Thr Pro His Ala Arg Asp Ile Ala Gly
705                 710                 715                 720

Ile Ser Ser Thr Lys Asp Gln His Phe Ala Glu Asn Asn Glu Val
            725                 730                 735

Val Val Glu Asp Asp Trp Ile Asn Arg Asn Phe Lys Ala Thr Asn Ile
            740                 745                 750

Asn Val Thr Asn Asn Ala Thr Leu Tyr Ser Gly Arg Asn Val Ala Asn
            755                 760                 765

Ile Thr Ser Asn Ile Thr Ala Ser Asp Asn Ala Lys Val His Ile Gly
            770                 775                 780

Tyr Lys Ala Gly Asp Thr Val Cys Val Arg Ser Asp Tyr Thr Gly Tyr
785                 790                 795                 800

Val Thr Cys Thr Thr Asp Lys Leu Ser Asp Lys Ala Leu Asn Ser Phe
                805                 810                 815

Asn Ala Thr Asn Val Ser Gly Asn Val Asn Leu Ser Gly Asn Ala Asn
                820                 825                 830

Phe Val Leu Gly Lys Ala Asn Leu Phe Gly Thr Ile Ser Gly Thr Gly
                835                 840                 845

Asn Ser Gln Val Arg Leu Thr Glu Asn Ser His Trp His Leu Thr Gly
850                 855                 860

Asp Thr Asn Val Asn Gln Leu Asn Leu Asp Lys Gly His Ile His Leu
865                 870                 875                 880

Asn Ala Gln Asn Asp Ala Asn Lys Val Thr Thr Tyr Asn Thr Leu Thr
                885                 890                 895

Val Asn Ser Leu Ser Gly Asn Gly Ser Phe Tyr Tyr Leu Thr Asp Leu
                900                 905                 910

Ser Asn Lys Gln Gly Asp Lys Val Val Thr Lys Ser Ala Thr Gly
                915                 920                 925

Asn Phe Thr Leu Gln Val Ala Asp Lys Thr Gly Glu Pro Thr Lys Asn
930                 935                 940

Glu Leu Thr Leu Phe Asp Ala Ser Asn Ala Thr Arg Asn Asn Leu Asn
945                 950                 955                 960

Val Ser Leu Val Gly Asn Thr Val Asp Leu Gly Ala Trp Lys Tyr Lys
                965                 970                 975

Leu Arg Asn Val Asn Gly Arg Tyr Asp Leu Tyr Asn Pro Glu Val Glu
                980                 985                 990

Lys Arg Asn Gln Thr Val Asp Thr Thr Asn Ile Thr Thr Pro Asn Asn
                995                 1000                1005

Ile Gln Ala Asp Val Pro Ser Val Pro Ser Asn Asn Glu Glu Ile
    1010                1015                1020

Ala Arg Val Glu Thr Pro Val Pro Pro Ala Pro Asp Thr Pro
    1025                1030                1035

Ser Glu Thr Thr Glu Thr Val Ala Glu Asn Ser Lys Gln Glu Ser
    1040                1045                1050

Lys Thr Val Glu Lys Asn Glu Gln Asp Ala Thr Glu Thr Thr Ala
    1055                1060                1065

Gln Asn Gly Glu Val Gly Glu Ala Lys Pro Ser Val Lys Ala
    1070                1075                1080

Asn Thr Gln Thr Asn Glu Val Ala Gln Ser Gly Ser Glu Thr Glu
    1085                1090                1095

Glu Thr Gln Thr Thr Glu Ile Lys Glu Thr Ala Lys Val Glu Lys
    1100                1105                1110
```

```
Glu Glu Lys Ala Lys Val Glu Lys Asp Glu Ile Gln Glu Ala Pro
    1115                1120                1125

Gln Met Ala Ser Glu Thr Ser Pro Lys Gln Ala Lys Pro Ala Pro
    1130                1135                1140

Lys Glu Val Ser Thr Asp Thr Lys Val Glu Glu Thr Gln Val Gln
    1145                1150                1155

Ala Gln Pro Gln Thr Gln Ser Thr Thr Val Ala Ala Ala Glu Ala
    1160                1165                1170

Thr Ser Pro Asn Ser Lys Pro Ala Glu Glu Thr Gln Pro Ser Glu
    1175                1180                1185

Lys Thr Asn Ala Glu Pro Val Thr Pro Val Val Ser Lys Asn Gln
    1190                1195                1200

Thr Glu Asn Thr Thr Asp Gln Pro Thr Glu Arg Glu Lys Thr Ala
    1205                1210                1215

Lys Val Glu Thr Glu Lys Thr Gln Glu Pro Pro Gln Val Ala Ser
    1220                1225                1230

Gln Ala Ser Pro Lys Gln Glu Gln Ser Glu Thr Val Gln Pro Gln
    1235                1240                1245

Ala Val Leu Glu Ser Glu Asn Val Pro Thr Val Asn Asn Ala Glu
    1250                1255                1260

Glu Val Gln Ala Gln Leu Gln Thr Gln Thr Ser Ala Thr Val Ser
    1265                1270                1275

Thr Lys Gln Pro Ala Pro Glu Asn Ser Ile Asn Thr Gly Ser Ala
    1280                1285                1290

Thr Ala Ile Thr Glu Thr Ala Glu Lys Ser Asp Lys Pro Gln Thr
    1295                1300                1305

Glu Thr Ala Ala Ser Thr Glu Asp Ala Ser Gln His Lys Ala Asn
    1310                1315                1320

Thr Val Ala Asp Asn Ser Val Ala Asn Asn Ser Glu Ser Ser Asp
    1325                1330                1335

Pro Lys Ser Arg Arg Arg Ser Ile Ser Gln Pro Gln Glu Thr
    1340                1345                1350

Ser Ala Glu Glu Thr Thr Ala Ala Ser Thr Asp Glu Thr Thr Ile
    1355                1360                1365

Ala Asp Asn Ser Lys Arg Ser Lys Pro Asn Arg Arg Ser Arg Arg
    1370                1375                1380

Ser Val Arg Ser Glu Pro Thr Val Thr Asn Gly Ser Asp Arg Ser
    1385                1390                1395

Thr Val Ala Leu Arg Asp Leu Thr Ser Thr Asn Thr Asn Ala Val
    1400                1405                1410

Ile Ser Asp Ala Met Ala Lys Gly Gln Phe Val Ala Leu Asn Val
    1415                1420                1425

Gly Lys Ala Val Ser Gln His Ile Ser Gln Leu Glu Met Asn Asn
    1430                1435                1440

Glu Gly Gln Tyr Asn Val Trp Val Ser Asn Thr Ser Met Asn Glu
    1445                1450                1455

Asn Tyr Ser Ser Ser Gln Tyr Arg Arg Phe Ser Ser Lys Ser Thr
    1460                1465                1470

Gln Thr Gln Leu Gly Trp Asp Gln Thr Ile Ser Asn Asn Val Gln
    1475                1480                1485

Leu Gly Gly Val Phe Thr Tyr Val Arg Asn Ser Asn Asn Phe Asp
    1490                1495                1500

Lys Ala Ser Ser Lys Asn Thr Leu Ala Gln Val Asn Phe Tyr Ser
```

| | | | | | | | | | |
|---|---|---|---|---|---|---|---|---|---|
| | | 1505 | | | 1510 | | | 1515 | |
| Lys | Tyr | Tyr | Ala | Asp | Asn | His | Trp | Tyr | Leu | Gly | Ile | Asp | Leu | Gly |
| 1520 | | | | | 1525 | | | | | 1530 |

Lys Tyr Tyr Ala Asp Asn His Trp Tyr Leu Gly Ile Asp Leu Gly
   1520                1525                    1530

Tyr Gly Lys Phe Gln Ser Asn Leu Lys Thr Asn Thr Asn Ala Lys
   1535                1540                    1545

Phe Ala Arg His Thr Ala Gln Phe Gly Leu Thr Ala Gly Lys Ala
   1550                1555                    1560

Phe Asn Leu Gly Asn Phe Gly Ile Thr Pro Ile Val Gly Val Arg
   1565                1570                    1575

Tyr Ser Tyr Leu Ser Asn Ala Asn Phe Ala Leu Ala Lys Asp Arg
   1580                1585                    1590

Ile Lys Val Asn Pro Ile Ser Val Lys Thr Ala Phe Ala Gln Val
   1595                1600                    1605

Asp Leu Ser Tyr Thr Tyr His Leu Gly Glu Phe Ser Val Thr Pro
   1610                1615                    1620

Ile Leu Ser Ala Arg Tyr Asp Thr Asn Gln Gly Ser Gly Lys Ile
   1625                1630                    1635

Asn Val Asn Gln Tyr Asp Phe Ala Tyr Asn Val Glu Asn Gln Gln
   1640                1645                    1650

Gln Tyr Asn Ala Gly Leu Lys Leu Lys Tyr His Asn Val Lys Leu
   1655                1660                    1665

Ser Leu Ile Gly Gly Leu Thr Lys Ala Lys Gln Ala Glu Lys Gln
   1670                1675                    1680

Lys Thr Ala Glu Leu Lys Leu Ser Phe Ser Phe
   1685                1690

<210> SEQ ID NO 3
<211> LENGTH: 5096
<212> TYPE: DNA
<213> ORGANISM: Haemophilus influenzae
<220> FEATURE:
<221> NAME/KEY: misc_feature
<222> LOCATION: (1)..(5096)
<223> OTHER INFORMATION: Encodes IgA1 protease

<400> SEQUENCE: 3

| | |
|---|---|
| catcattacg ccttaaatta accaaaagtg cggtaaaaaa tagccaattt tttaaaaaat | 60 |
| atcaaaaatc attatcatta cctcgtaaat gtaattcaag ttttgagcga tttatgctat | 120 |
| aaaacccact cattataaaa atgaagacaa cttgcaaact atcaatgcaa cacagccaag | 180 |
| atttgaatca acttgtagcc gtatatcaaa ttgtgtccta tcaaatctac tttttaaact | 240 |
| taattaataa agacagcttc tatgctaaat aaaaaattca aactcaattt tattgcactt | 300 |
| actgtcgcct acgcattaac cccttataca gaagccgcgt tagtgagaga cgatgtggat | 360 |
| tatcaaatat tccgtgattt tgcagagaat aaagggaagt tttctgttgg tgcaacaaat | 420 |
| gtgctggtaa aggataaaaa taataaagat ttgggcactg ccttacctaa cggtattccg | 480 |
| atgattgatt ttagcgtggt agatgtagat aaacgcattg ccacattgat aaatccacaa | 540 |
| tatgtagtag gtgtaaaaca cgttagtaac ggcgtgagtg aactacattt tggtaactta | 600 |
| aacggcaata tgaataatgg caatgccaag gcacaccgag atgtatcttc agaagaaaat | 660 |
| agatattttt ccgttgagaa aaatgagtat ccaactaaat tgaatggaaa aacagtaact | 720 |
| acggaagatc aaactcaaaa acgccgtgaa gactactata tgccacgtct tgataaattt | 780 |
| gttacgaaag ttgcaccaat agaggcttca accgcaagta gtgatgctgg cacatataat | 840 |
| gatcagaata aatatcctgc ttttgtaaga ctaggaagtg gtagtcaatt tatttataaa | 900 |

```
aaaggagata attacagctt aattttaaat aatcatgagg ttggaggcaa taatcttaaa      960
ttggtgggcg atgcctatac ctatggtatt gcaggtacac cttataaagt aaaccacgag     1020
aataatggac taattggttt tggcaattca aaagaggaac acagcgatcc aaaaggaata     1080
ttatctcaag atcctcttac caattatgct gttttaggcg acagtggctc cccattattt     1140
gtatatgata gagaaaaagg aaaatggctt tttcttgggt cttatgattt ttgggcgggt     1200
tataacaaaa aatcttggca agaatggaat atttataaat ctcaatttac taaagatgtt     1260
ctcaataaag atagtgcagg ttctttaatt ggttccaaga cagattatag ttggtcttct     1320
aatggcaaga caagtacgat tacgggaggg gagaaatctt taaatgttga tttagctgac     1380
ggaaaagata aacctaatca cgggaaaagt gttacatttg aagggagtgg aacgcttacc     1440
ttaaataata atatcgatca aggtgcaggc ggattattct ttgaaggcga ttatgaagtt     1500
aaaggtactt ctgataatac tacttggaaa ggagcaggtg tctctgttgc cgaaggaaaa     1560
actgtaacgt ggaaagtgca taatcctcaa tatgatcgtt tagcaaaaat tggcaaaggg     1620
acattaattg ttgaaggaac aggagataat aaaggttcgc taaaagtggg cgatggcacc     1680
gttattttaa aacaacaaac aaatggttcg ggacaacacg cttttgcttc tgtagggatt     1740
gtaagtggtc gctcaactct tgtgcttaat gatgataaac aagtagatcc aaattcaatt     1800
tactttggct ttagaggcgg tcgattagac ttaaacggta attcactaac ctttgatcac     1860
atcagaaata ttgatgatgg tgcaagacta gttaatcata atatgactaa tgcctcaaat     1920
ataacgatta ctgggaaaag tctaattaca gatccaaata caattactcc atataatata     1980
gacgcaccag atgaagataa tccttatgcc tttcgacgga ttaaagatgg aggacagctc     2040
tatttaaatt tggaaaatta cacttattat gcgttaagaa aaggtgcgag cactcgttca     2100
gaattaccta aaaatagtgg cgaaagcaat gaaaattggc tatatatggg taaaacttcc     2160
gatgaagcca aaagaaatgt aatgaaccat atcaacaacg agcgtatgaa tggctttaat     2220
ggttattttg gcgaggaaga gggtaaaaat aacggtaatc taaatgtgac tttttaaaggc     2280
aaaagtgagc aaaatcgctt tttattaaca ggcggtacaa accttaatgg cgatttaacg     2340
gttgaaaaag gcaccttatt cctttcaggc agaccaacac cgcacgcaag agatattgca     2400
ggtatttctt cgacaaaaaa agatcctcac tttgctgaaa ataatgaagt ggtagtagaa     2460
gatgactgga ttaaccgcaa ttttaaagca accacaatga acgtgactgg caatgcctca     2520
ctttattcag gtcgcaatgt tgcaaacatt acgtcaaata tcacagcttc taataaagca     2580
caagttcata tcggctataa acaggcgat accgtttgtg tacgttctga ctatacgggc     2640
tatgtgactt gtactactga caagttatcc gataaagccc ttaatagctt taatccaacc     2700
aatctacgcg gcaatgtaaa tttaaccgaa agtgcaaact ttgtcttagg caaagccaac     2760
ttattcggca caattcaaag cagaggaaat agccaagtac gtttaaccga aaatagccat     2820
tggcattttaa caggaaatag tgatgttcat caattagatc tagcaaatgg gcatattcat     2880
ttaaattcag cagacaattc aaacaatgtg acaaaatata cacgctgac tgtgaatagc     2940
ttatcaggta acggttcttt ctattattta actgatcttt ccaataaaca aggcgacaaa     3000
gttgttgtaa ctaaatccgc cacaggtaac tttacattac aagtggcaga taaaacaggc     3060
gagccaaatc ataatgaact cacactttt gatgcttcaa aagctcaaag agatcatttg     3120
aatgtgtcat tagttgggaa taccgttgat ttaggtgctt ggaaatataa attacgtaat     3180
gttaatggac gttacgattt gtataaccca gaggtggaaa aaagaaatca aactgtcgat     3240
```

```
acgacaaata tcacaacacc taataatatt caagctgatg tgcctagcgt accaagtaac   3300
aatgaagaaa tagcccgtgt tgatgaagca ccagttccac cacctgcgcc tgctacacca   3360
tcagagacaa ctgaaacagt ggctgaaaat agtaagcaag aaagtaaaac agtagagaaa   3420
aacgagcaag acgcaaccga dacaacagct caaaatagag aagttgcaaa agaagctaaa   3480
tcaaatgtaa aagctaatac tcaaacaaat gaagtagctc aaagtggaag tgaaaccaag   3540
gaaactcaaa cgactgaaac aaaagaaaca gctacggtag aaaagaaga aaaggctaaa   3600 gtagaaacag agaaaactca agaagtccct aaagtgactt ctcaagtgtc tccgaaacag   3660
gaacagtctg aaactgttca accgcaagca gagcctgctc gtgaaaatga tccgactgtt   3720
aatataaaag agcctcaatc tcaaacaaat acaacagcag acactgaaca acctgcgaaa   3780
gagactagct caaatgttga acaaccagtg acagaaagca caacagtaaa cactggaaac   3840
tctgtagtgg aaaatccaga gaatacaaca cctgctacaa ctcaacctac ggttaattca   3900
gaaagcagta ataagccaaa gaatagacat agaagaagtg ttcgctcagt tccgcataat   3960
gttgaaccag ctacaacaag tagcaacgat cgttctacag tagcattgtg cgatctcaca   4020
agtacaaaca caaatgcggt actttctgat gcaagggcaa aagcacaatt tgttgcatta   4080
aatgtgggga aagcagtttc tcaacatatt agccagttag aaatgaataa cgaggggcaa   4140
tataacgttt gggtatctaa tacttcaatg aacaaaaatt attcctcaag tcaatatcgt   4200
cgttttagtt ctaaaagtac gcaaactcaa ctgggttggg atcaaacaat ctcaaacaat   4260
gttcagttag gtggcgtgtt tacttatgtt cgcaatagta acaactttga taaggcaaca   4320
agtaaaaata ctctagcaca agttaatttc tattctaaat attatgcgga taatcattgg   4380
tatttgggca ttgatttagg ctacggcaag ttccaaagca aattacaaac taatcataat   4440
gcgaaatttg ctcgccatac tgcacaattt ggtttaaccg caggcaaagc atttaatctt   4500
ggcaattttg gtattacgcc aatagtaggc gtgcgttata gctatttatc aaacgctgat   4560
tttgcattag atcaagctcg cattaaagta aatccaatat ctgtcaaaac agcctttgct   4620
caagttgatt taagttatac ttatcactta ggcgagtttt ccgttacgcc aattttgtct   4680
gctcgatatg atgcaaacca aggcagcgga aaaattaatg taaatggata tgattttgct   4740
tacaacgtgg aaaaccaaca gcaatataac gcagggctta aattgaaata tcataatgtg   4800
aaattaagtc taataggcgg attaacaaaa gcgaaacaag cggaaaaaca aaaaactgca   4860
gaattaaaac taagttttag ttttttaataa gcctgtttga attaacgtta taaacaacaa   4920
agccctgtgt attacagggc tttattttttg aatgaaattc agtgattaag tgcggtgaaa   4980
aatcagcgca tttttattt ttaacgtaaa aacgctggaa tattttctc atatgctgag   5040 attttgtctt cgtgctgaag ggttaaaccg atattatcta aaccgtttag caaaca      5096
```

<210> SEQ ID NO 4
<211> LENGTH: 1541
<212> TYPE: PRT
<213> ORGANISM: Haemophilus influenzae
<220> FEATURE:
<221> NAME/KEY: misc_feature
<222> LOCATION: (1)..(1541)
<223> OTHER INFORMATION: Full-length precursor IgA1 protease

<400> SEQUENCE: 4

Met Leu Asn Lys Lys Phe Lys Leu Asn Phe Ile Ala Leu Thr Val Ala
1               5                   10                  15

Tyr Ala Leu Thr Pro Tyr Thr Glu Ala Ala Leu Val Arg Asp Asp Val
            20                  25                  30

-continued

Asp Tyr Gln Ile Phe Arg Asp Phe Ala Glu Asn Lys Gly Lys Phe Ser
         35                  40                  45

Val Gly Ala Thr Asn Val Leu Val Lys Asp Lys Asn Asn Lys Asp Leu
 50                  55                  60

Gly Thr Ala Leu Pro Asn Gly Ile Pro Met Ile Asp Phe Ser Val Val
 65                  70                  75                  80

Asp Val Asp Lys Arg Ile Ala Thr Leu Ile Asn Pro Gln Tyr Val Val
             85                  90                  95

Gly Val Lys His Val Ser Asn Gly Val Ser Glu Leu His Phe Gly Asn
                100                 105                 110

Leu Asn Gly Asn Met Asn Asn Gly Asn Ala Lys Ala His Arg Asp Val
            115                 120                 125

Ser Ser Glu Glu Asn Arg Tyr Phe Ser Val Glu Lys Asn Glu Tyr Pro
130                 135                 140

Thr Lys Leu Asn Gly Lys Thr Val Thr Thr Glu Asp Gln Thr Gln Lys
145                 150                 155                 160

Arg Arg Glu Asp Tyr Tyr Met Pro Arg Leu Asp Lys Phe Val Thr Glu
                165                 170                 175

Val Ala Pro Ile Glu Ala Ser Thr Ala Ser Ser Asp Ala Gly Thr Tyr
            180                 185                 190

Asn Asp Gln Asn Lys Tyr Pro Ala Phe Val Arg Leu Gly Ser Gly Ser
            195                 200                 205

Gln Phe Ile Tyr Lys Lys Gly Asp Asn Tyr Ser Leu Ile Leu Asn Asn
210                 215                 220

His Glu Val Gly Gly Asn Leu Lys Leu Val Gly Asp Ala Tyr Thr
225                 230                 235                 240

Tyr Gly Ile Ala Gly Thr Pro Tyr Lys Val Asn His Glu Asn Asn Gly
                245                 250                 255

Leu Ile Gly Phe Gly Asn Ser Lys Glu Glu His Ser Asp Pro Lys Gly
            260                 265                 270

Ile Leu Ser Gln Asp Pro Leu Thr Asn Tyr Ala Val Leu Gly Asp Ser
        275                 280                 285

Gly Ser Pro Leu Phe Val Tyr Asp Arg Glu Lys Gly Lys Trp Leu Phe
290                 295                 300

Leu Gly Ser Tyr Asp Phe Trp Ala Gly Tyr Asn Lys Lys Ser Trp Gln
305                 310                 315                 320

Glu Trp Asn Ile Tyr Lys Ser Gln Phe Thr Lys Asp Val Leu Asn Lys
                325                 330                 335

Asp Ser Ala Gly Ser Leu Ile Gly Ser Lys Thr Asp Tyr Ser Trp Ser
            340                 345                 350

Ser Asn Gly Lys Thr Ser Thr Ile Thr Gly Gly Glu Lys Ser Leu Asn
            355                 360                 365

Val Asp Leu Ala Asp Gly Lys Asp Lys Pro Asn His Gly Lys Ser Val
370                 375                 380

Thr Phe Glu Gly Ser Gly Thr Leu Thr Leu Asn Asn Asn Ile Asp Gln
385                 390                 395                 400

Gly Ala Gly Gly Leu Phe Phe Glu Gly Asp Tyr Glu Val Lys Gly Thr
                405                 410                 415

Ser Asp Asn Thr Thr Trp Lys Gly Ala Gly Val Ser Val Ala Glu Gly
            420                 425                 430

Lys Thr Val Thr Trp Lys Val His Asn Pro Gln Tyr Asp Arg Leu Ala
            435                 440                 445

```
Lys Ile Gly Lys Gly Thr Leu Ile Val Glu Gly Thr Gly Asp Asn Lys
    450                 455                 460
Gly Ser Leu Lys Val Gly Asp Gly Thr Val Ile Leu Lys Gln Gln Thr
465                 470                 475                 480
Asn Gly Ser Gly Gln His Ala Phe Ala Ser Val Gly Ile Val Ser Gly
                485                 490                 495
Arg Ser Thr Leu Val Leu Asn Asp Asp Lys Gln Val Asp Pro Asn Ser
                500                 505                 510
Ile Tyr Phe Gly Phe Arg Gly Gly Arg Leu Asp Leu Asn Gly Asn Ser
            515                 520                 525
Leu Thr Phe Asp His Ile Arg Asn Ile Asp Asp Gly Ala Arg Leu Val
        530                 535                 540
Asn His Asn Met Thr Asn Ala Ser Asn Ile Thr Ile Thr Gly Glu Ser
545                 550                 555                 560
Leu Ile Thr Asp Pro Asn Thr Ile Thr Pro Tyr Asn Ile Asp Ala Pro
                565                 570                 575
Asp Glu Asp Asn Pro Tyr Ala Phe Arg Arg Ile Lys Asp Gly Gly Gln
                580                 585                 590
Leu Tyr Leu Asn Leu Glu Asn Tyr Thr Tyr Tyr Ala Leu Arg Lys Gly
            595                 600                 605
Ala Ser Thr Arg Ser Glu Leu Pro Lys Asn Ser Gly Glu Ser Asn Glu
        610                 615                 620
Asn Trp Leu Tyr Met Gly Lys Thr Ser Asp Glu Ala Lys Arg Asn Val
625                 630                 635                 640
Met Asn His Ile Asn Asn Glu Arg Met Asn Gly Phe Asn Gly Tyr Phe
                645                 650                 655
Gly Glu Glu Glu Gly Lys Asn Asn Gly Asn Leu Asn Val Thr Phe Lys
                660                 665                 670
Gly Lys Ser Glu Gln Asn Arg Phe Leu Leu Thr Gly Gly Thr Asn Leu
            675                 680                 685
Asn Gly Asp Leu Thr Val Glu Lys Gly Thr Leu Phe Leu Ser Gly Arg
        690                 695                 700
Pro Thr Pro His Ala Arg Asp Ile Ala Gly Ile Ser Ser Thr Lys Lys
705                 710                 715                 720
Asp Pro His Phe Ala Glu Asn Asn Glu Val Val Val Glu Asp Asp Trp
                725                 730                 735
Ile Asn Arg Asn Phe Lys Ala Thr Thr Met Asn Val Thr Gly Asn Ala
                740                 745                 750
Ser Leu Tyr Ser Gly Arg Asn Val Ala Asn Ile Thr Ser Asn Ile Thr
            755                 760                 765
Ala Ser Asn Lys Ala Gln Val His Ile Gly Tyr Lys Thr Gly Asp Thr
        770                 775                 780
Val Cys Val Arg Ser Asp Tyr Thr Gly Tyr Val Thr Cys Thr Thr Asp
785                 790                 795                 800
Lys Leu Ser Asp Lys Ala Leu Asn Ser Phe Asn Pro Thr Asn Leu Arg
                805                 810                 815
Gly Asn Val Asn Leu Thr Glu Ser Ala Asn Phe Val Leu Gly Lys Ala
                820                 825                 830
Asn Leu Phe Gly Thr Ile Gln Ser Arg Gly Asn Ser Gln Val Arg Leu
            835                 840                 845
Thr Glu Asn Ser His Trp His Leu Thr Gly Asn Ser Asp Val His Gln
        850                 855                 860
Leu Asp Leu Ala Asn Gly His Ile His Leu Asn Ser Ala Asp Asn Ser
```

```
                865                 870                 875                 880
        Asn Asn Val Thr Lys Tyr Asn Thr Leu Thr Val Asn Ser Leu Ser Gly
                        885                 890                 895
        Asn Gly Ser Phe Tyr Tyr Leu Thr Asp Leu Ser Asn Lys Gln Gly Asp
                        900                 905                 910
        Lys Val Val Thr Lys Ser Ala Thr Gly Asn Phe Thr Leu Gln Val
                    915                 920                 925
        Ala Asp Lys Thr Gly Glu Pro Asn His Asn Glu Leu Thr Leu Phe Asp
        930                 935                 940
        Ala Ser Lys Ala Gln Arg Asp His Leu Asn Val Ser Leu Val Gly Asn
        945                 950                 955                 960
        Thr Val Asp Leu Gly Ala Trp Lys Tyr Lys Leu Arg Asn Val Asn Gly
                    965                 970                 975
        Arg Tyr Asp Leu Tyr Asn Pro Glu Val Glu Lys Arg Asn Gln Thr Val
                        980                 985                 990
        Asp Thr Thr Asn Ile Thr Thr Pro  Asn Asn Ile Gln Ala  Asp Val Pro
                    995                 1000                1005
        Ser Val  Pro Ser Asn Asn Glu  Glu Ile Ala Arg Val  Asp Glu Ala
             1010                1015                1020
        Pro Val  Pro Pro Ala Pro  Ala Thr Pro Ser Glu  Thr Thr Glu
             1025                1030                1035
        Thr Val  Ala Glu Asn Ser Lys  Gln Glu Ser Lys Thr  Val Glu Lys
             1040                1045                 1050
        Asn Glu  Gln Asp Ala Thr Glu  Thr Thr Ala Gln Asn  Arg Glu Val
             1055                1060                 1065
        Ala Lys  Glu Ala Lys Ser Asn  Val Lys Ala Asn Thr  Gln Thr Asn
             1070                1075                 1080
        Glu Val  Ala Gln Ser Gly Ser  Glu Thr Lys Glu Thr  Gln Thr Thr
             1085                1090                 1095
        Glu Thr  Lys Glu Thr Ala Thr  Val Glu Lys Glu Glu  Lys Ala Lys
             1100                1105                 1110
        Val Glu  Thr Glu Lys Thr Gln  Glu Val Pro Lys Val  Thr Ser Gln
             1115                1120                 1125
        Val Ser  Pro Lys Gln Glu Gln  Ser Glu Thr Val Gln  Pro Gln Ala
             1130                1135                 1140
        Glu Pro  Ala Arg Glu Asn Asp  Pro Thr Val Asn Ile  Lys Glu Pro
             1145                1150                 1155
        Gln Ser  Gln Thr Asn Thr Thr  Ala Asp Thr Glu Gln  Pro Ala Lys
             1160                1165                 1170
        Glu Thr  Ser Ser Asn Val Glu  Gln Pro Val Thr Glu  Ser Thr Thr
             1175                1180                 1185
        Val Asn  Thr Gly Asn Ser Val  Val Glu Asn Pro Glu  Asn Thr Thr
             1190                1195                 1200
        Pro Ala  Thr Thr Gln Pro Thr  Val Asn Ser Glu Ser  Ser Asn Lys
             1205                1210                 1215
        Pro Lys  Asn Arg His Arg Arg  Ser Val Arg Ser Val  Pro His Asn
             1220                1225                 1230
        Val Glu  Pro Ala Thr Thr Ser  Ser Asn Asp Arg Ser  Thr Val Ala
             1235                1240                 1245
        Leu Cys  Asp Leu Thr Ser Thr  Asn Thr Asn Ala Val  Leu Ser Asp
             1250                1255                 1260
        Ala Arg  Ala Lys Ala Gln Phe  Val Ala Leu Asn Val  Gly Lys Ala
             1265                1270                 1275
```

```
Val Ser Gln His Ile Ser Gln Leu Glu Met Asn Asn Glu Gly Gln
    1280            1285                1290

Tyr Asn Val Trp Val Ser Asn Thr Ser Met Asn Lys Asn Tyr Ser
    1295            1300                1305

Ser Ser Gln Tyr Arg Arg Phe Ser Ser Lys Ser Thr Gln Thr Gln
    1310            1315                1320

Leu Gly Trp Asp Gln Thr Ile Ser Asn Asn Val Gln Leu Gly Gly
    1325            1330                1335

Val Phe Thr Tyr Val Arg Asn Ser Asn Asn Phe Asp Lys Ala Thr
    1340            1345                1350

Ser Lys Asn Thr Leu Ala Gln Val Asn Phe Tyr Ser Lys Tyr Tyr
    1355            1360                1365

Ala Asp Asn His Trp Tyr Leu Gly Ile Asp Leu Gly Tyr Gly Lys
    1370            1375                1380

Phe Gln Ser Lys Leu Gln Thr Asn His Asn Ala Lys Phe Ala Arg
    1385            1390                1395

His Thr Ala Gln Phe Gly Leu Thr Ala Gly Lys Ala Phe Asn Leu
    1400            1405                1410

Gly Asn Phe Gly Ile Thr Pro Ile Val Gly Val Arg Tyr Ser Tyr
    1415            1420                1425

Leu Ser Asn Ala Asp Phe Ala Leu Asp Gln Ala Arg Ile Lys Val
    1430            1435                1440

Asn Pro Ile Ser Val Lys Thr Ala Phe Ala Gln Val Asp Leu Ser
    1445            1450                1455

Tyr Thr Tyr His Leu Gly Glu Phe Ser Val Thr Pro Ile Leu Ser
    1460            1465                1470

Ala Arg Tyr Asp Ala Asn Gln Gly Ser Gly Lys Ile Asn Val Asn
    1475            1480                1485

Gly Tyr Asp Phe Ala Tyr Asn Val Glu Asn Gln Gln Tyr Asn
    1490            1495                1500

Ala Gly Leu Lys Leu Lys Tyr His Asn Val Lys Leu Ser Leu Ile
    1505            1510                1515

Gly Gly Leu Thr Lys Ala Lys Gln Ala Glu Lys Gln Lys Thr Ala
    1520            1525                1530

Glu Leu Lys Leu Ser Phe Ser Phe
    1535            1540

<210> SEQ ID NO 5
<211> LENGTH: 5096
<212> TYPE: DNA
<213> ORGANISM: Haemophilus influenzae
<220> FEATURE:
<221> NAME/KEY: misc_feature
<222> LOCATION: (1)..(5096)
<223> OTHER INFORMATION: Encodes IgA1 protease

<400> SEQUENCE: 5
catcattacg ccttaaatta ccaaaagtg cggtaaaaaa tagccaattt tttaaaaaat     60
atcaaaaatc attatcatta cctcgtaaat gtaattcaag ttttgagcga tttatgctat    120
aaaacccact cattataaaa atgaagacaa cttgcaaact atcaatgcaa cacagccaag    180
atttgaatca acttgtagcc gtatatcaaa ttgtgtccta tcaaatctac tttttaaact    240
taattaataa agacagcttc tatgctaaat aaaaaattca aactcaattt tattgcactt    300
actgtcgcct acgcattaac ccctatacaa gaagccgcgt tagtgagaga cgatgtggat    360
```

```
tatcaaatat tccgtgattt tgcagagaat aaagggaagt tttctgttgg tgcaacaaat    420
gtgctggtaa aggataaaaa taataaagat ttgggcactg ccttacctaa cggtattccg    480
atgattgatt ttagcgtggt agatgtagat aaacgcattg ccacattgat aaatccacaa    540
tatgtagtag gtgtaaaaca cgttagtaac ggcgtgagtg aactcacttt tggtaactta    600
aacggcaata tgaataatgg caatgccaag gcacaccgag atgtatcttc agaagaaaat    660 agatatttt  ccgttgagaa aaatgagtat ccaactaaat tgaatggaaa aacagtaact    720
acggaagatc aaactcaaaa acgccgtgaa gactactata tgccacgtct tgataaattt    780
gttacggaag ttgcaccaat agaggcttca accgcaagta gtgatgctgg cacatataat    840
gatcagaata aatatcctgc ttttgtaaga ctaggaagtg gtagtcaatt tatttataaa    900
aaaggagata attacagctt aatttttaaat aatcatgagg ttggaggcaa taatcttaaa    960
ttggtgggcg atgcctatac ctatggtatt gcaggtacac cttataaagt aaaccacgag   1020
aataatggac taattggttt tgcaattca  aaagaggaac acagcgatcc aaaaggaata   1080
ttatctcaag atcctcttac caattatgct gttttaggcg acagtggctc cccattattt   1140
gtatatgata gagaaaaagg aaaatggctt tttcttgggt cttatgattt ttgggcgggt   1200
tataacaaaa atcttggca  agaatggaat atttataaat ctcaatttac taaagatgtt   1260
ctcaataaag atagtgcagg ttctttaatt ggttccaaga cagattatag ttggtcttct   1320
aatggcaaga caagtacgat tacggggaggg gagaaatctt taaatgttga tttagctgac   1380
ggaaaagata aacctaatca cgggaaaagt gttacatttg aagggagtgg aacgcttacc   1440
ttaaataata atatcgatca aggtgcaggc ggattattct tgaaggcga ttatgaagtt    1500 aaaggtactt ctgataatac tacttggaaa ggagcaggtg tctctgttgc cgaaggaaaa   1560
actgtaacgt ggaaagtgca taatcctcaa tatgatcgtt agcaaaaat tggcaaaggg   1620 acattaattg ttgaaggaac aggagataat aaaggttcgc taaaagtggg cgatggcacc   1680
gttattttaa aacaacaaac aaatggttcg ggacaacacg cttttgcttc tgtagggatt   1740
gtaagtggtc gctcaactct tgtgcttaat gatgataaac aagtagatcc aaattcaatt   1800
tactttggct ttagaggcgg tcgattagac ttaaacggta attcactaac ctttgatcac   1860
atcagaaata ttgatgatgg tgcaagacta gttaatcata atatgactaa tgcctcaaat   1920
ataacgatta ctggggaaag tctaattaca gatccaaata caattactcc atataatata   1980
gacgcaccag atgaagataa tccttatgcc tttcgacgga ttaaagatgg aggacagctc   2040
tatttaaatt tggaaaatta cacttattat gcgttaagaa aaggtgcgag cactcgttca   2100
gaattaccta aaaatagtgg cgaaagcaat gaaaattggc tatatatggg taaaacttcc   2160
gatgaagcca aaagaaatgt aatgaaccat atcaacaacg agcgtatgaa tggctttaat   2220 ggttatttg  gcgaggaaga gggtaaaaat aacggtaatc taaatgtgac ttttaaaggc   2280
aaaagtgagc aaaatcgctt tttattaaca ggcggtacaa accttaatgg cgatttaacg   2340
gttgaaaaag gcaccttatt cctttcaggc agaccaacac cgcacgcaag agatattgca   2400
ggtatttctt cgacaaaaaa agatcctcac tttgctgaaa ataatgaagt ggtagtagaa   2460
gatgactgga ttaaccgcaa ttttaaagca accacaatga acgtgactgg caatgcctca   2520
ctttattcag gtcgcaatgt tgcaaacatt acgtcaaata tcacagcttc taataaagca   2580
caagttcata tcggctataa aacaggcgat accgtttgtg tacgttctga ctatacgggc   2640
tatgtgactt gtactactga caagttatcc gataaagccc ttaatagctt taatccaacc   2700
aatctacgcg gcaatgtaaa tttaaccgaa agtgcaaact ttgtcttagg caaagccaac   2760
```

```
ttattcggca caattcaaag cagaggaaat agccaagtac gtttaaccga aaatagccat    2820
tggcatttaa caggaaatag tgatgttcat caattagatc tagcaaatgg gcatattcat    2880
ttaaattcag cagacaattc aaacaatgtg acaaaatata acacgctgac tgtgaatagc    2940
ttatcaggta acggttcttt ctattattta actgatcttt ccaataaaca aggcgacaaa    3000
gttgttgtaa ctaaatccgc cacaggtaac tttacattac aagtggcaga taaaacaggc    3060
gagccaaatc ataatgaact cacacttttt gatgcttcaa aagctcaaag agatcatttg    3120
aatgtgtcat tagttgggaa taccgttgat ttaggtgctt ggaaatataa attacgtaat    3180
gttaatggac gttacgattt gtataaccca gaggtggaaa aaagaaatca aactgtcgat    3240
acgacaaata tcacaacacc taataatatt caagctgatg tgcctagcgt accaagtaac    3300
aatgaagaaa tagcccgtgt tgatgaagca ccagttccac cacctgcgcc tgctacacca    3360
tcagagacaa ctgaaacagt ggctgaaaat agtaagcaag aaagtaaaac agtagagaaa    3420
aacgagcaag acgcaaccga gacaacagct caaaatagag aagttgcaaa agaagctaaa    3480
tcaaatgtaa aagctaatac tcaaacaaat gaagtagctc aaagtggaag tgaaaccaag    3540
gaaactcaaa cgactgaaac aaaagaaaca gctacggtag aaaaagaaga aaaggctaaa    3600
gtagaaacag agaaaactca agaagtccct aaagtgactt ctcaagtgtc tccgaaacag    3660
gaacagtctg aaactgttca accgcaagca gagcctgctc gtgaaaatga tccgactgtt    3720
aatataaaag agcctcaatc tcaaacaaat acaacagcag acactgaaca acctgcgaaa    3780
gagactagct caaatgttga acaaccagtg acagaaagca caacagtaaa cactggaaac    3840
tctgtagtgg aaaatccaga gaatacaaca cctgctacaa ctcaacctac ggttaattca    3900
gaaagcagta ataagccaaa gaatagacat agaagaagtg ttcgctcagt tccgcataat    3960
gttgaaccag ctacaacaag tagcaacgat cgttctacag tagcattgtg cgatctcaca    4020
agtacaaaca caaatgcggt actttctgat gcaagggcaa aagcacaatt tgttgcatta    4080
aatgtgggga aagcagtttc tcaacatatt agccagttag aaatgaataa cgaggggcaa    4140
tataacgttt gggtatctaa tacttcaatg aacaaaaatt attcctcaag tcaatatcgt    4200
cgttttagtt ctaaaagtac gcaaactcaa ctgggttggg atcaaacaat ctcaaacaat    4260
gttcagttag gtggcgtgtt tacttatgtt cgcaatagta acaactttga taaggcaaca    4320
agtaaaaata ctctagcaca agttaatttc tattctaaat attatgcgga taatcattgg    4380
tatttgggca ttgatttagg ctacggcaag ttccaaagca aattacaaac taatcataat    4440
gcgaaatttg ctcgccatac tgcacaattt ggtttaaccg caggcaaagc atttaatctt    4500
ggcaattttg gtattacgcc aatagtaggc gtgcgttata gctatttatc aaacgctgat    4560
tttgcattag atcaagctcg cattaaagta aatccaatat ctgtcaaaac agcctttgct    4620
caagttgatt taagttatac ttatcactta ggcgagtttt ccgttacgcc aattttgtct    4680
gctcgatatg atgcaaacca aggcagcgga aaaattaatg taaatggata tgattttgct    4740
tacaacgtgg aaaaccaaca gcaatataac gcagggctta aattgaaata tcataatgtg    4800
aaattaagtc taataggcgg attaacaaaa gcgaaacaag cggaaaaaca aaaaactgca    4860
gaattaaaaac taagttttag tttttaataa gcctgtttga attaacgtta taaacaacaa    4920
agccctgtgt attacagggc tttatttttg aatgaaattc agtgattaag tgcggtgaaa    4980
aatcagcgca ttttttattt ttaacgtaaa aacgctggaa tattttctc atatgctgag    5040
attttgtctt cgtgctgaag ggttaaaccg atattatcta aaccgtttag caaaca         5096
```

```
<210> SEQ ID NO 6
<211> LENGTH: 1541
<212> TYPE: PRT
<213> ORGANISM: Haemophilus influenzae
<220> FEATURE:
<221> NAME/KEY: misc_feature
<222> LOCATION: (1)..(1541)
<223> OTHER INFORMATION: Full-length precursor IgA1 protease

<400> SEQUENCE: 6

Met Leu Asn Lys Lys Phe Lys Leu Asn Phe Ile Ala Leu Thr Val Ala
1               5                   10                  15

Tyr Ala Leu Thr Pro Tyr Thr Glu Ala Ala Leu Val Arg Asp Asp Val
            20                  25                  30

Asp Tyr Gln Ile Phe Arg Asp Phe Ala Glu Asn Lys Gly Lys Phe Ser
        35                  40                  45

Val Gly Ala Thr Asn Val Leu Val Lys Asp Lys Asn Asn Lys Asp Leu
    50                  55                  60

Gly Thr Ala Leu Pro Asn Gly Ile Pro Met Ile Asp Phe Ser Val Val
65                  70                  75                  80

Asp Val Asp Lys Arg Ile Ala Thr Leu Ile Asn Pro Gln Tyr Val Val
                85                  90                  95

Gly Val Lys His Val Ser Asn Gly Val Ser Glu Leu His Phe Gly Asn
            100                 105                 110

Leu Asn Gly Asn Met Asn Asn Gly Asn Ala Lys Ala His Arg Asp Val
        115                 120                 125

Ser Ser Glu Glu Asn Arg Tyr Phe Ser Val Lys Asn Glu Tyr Pro
    130                 135                 140

Thr Lys Leu Asn Gly Lys Thr Val Thr Thr Glu Asp Gln Thr Gln Lys
145                 150                 155                 160

Arg Arg Glu Asp Tyr Tyr Met Pro Arg Leu Asp Lys Phe Val Thr Glu
                165                 170                 175

Val Ala Pro Ile Glu Ala Ser Thr Ala Ser Ser Asp Ala Gly Thr Tyr
            180                 185                 190

Asn Asp Gln Asn Lys Tyr Pro Ala Phe Val Arg Leu Gly Ser Gly Ser
        195                 200                 205

Gln Phe Ile Tyr Lys Lys Gly Asp Asn Tyr Ser Leu Ile Leu Asn Asn
    210                 215                 220

His Glu Val Gly Gly Asn Asn Leu Lys Leu Val Gly Asp Ala Tyr Thr
225                 230                 235                 240

Tyr Gly Ile Ala Gly Thr Pro Tyr Lys Val Asn His Glu Asn Asn Gly
                245                 250                 255

Leu Ile Gly Phe Gly Asn Ser Lys Glu Glu His Ser Asp Pro Lys Gly
            260                 265                 270

Ile Leu Ser Gln Asp Pro Leu Thr Asn Tyr Ala Val Leu Gly Asp Ser
        275                 280                 285

Gly Ser Pro Leu Phe Val Tyr Asp Arg Glu Lys Gly Lys Trp Leu Phe
    290                 295                 300

Leu Gly Ser Tyr Asp Phe Trp Ala Gly Tyr Asn Lys Lys Ser Trp Gln
305                 310                 315                 320

Glu Trp Asn Ile Tyr Lys Ser Gln Phe Thr Lys Asp Val Leu Asn Lys
                325                 330                 335

Asp Ser Ala Gly Ser Leu Ile Gly Ser Lys Thr Asp Tyr Ser Trp Ser
            340                 345                 350

Ser Asn Gly Lys Thr Ser Thr Ile Thr Gly Gly Glu Lys Ser Leu Asn
```

```
            355                 360                 365
Val Asp Leu Ala Asp Gly Lys Asp Lys Pro Asn His Gly Lys Ser Val
    370                 375                 380
Thr Phe Glu Gly Ser Gly Thr Leu Thr Leu Asn Asn Asn Ile Asp Gln
385                 390                 395                 400
Gly Ala Gly Gly Leu Phe Phe Glu Gly Asp Tyr Glu Val Lys Gly Thr
                405                 410                 415
Ser Asp Asn Thr Thr Trp Lys Gly Ala Gly Val Ser Val Ala Glu Gly
            420                 425                 430
Lys Thr Val Thr Trp Lys Val His Asn Pro Gln Tyr Asp Arg Leu Ala
        435                 440                 445
Lys Ile Gly Lys Gly Thr Leu Ile Val Glu Gly Thr Gly Asp Asn Lys
    450                 455                 460
Gly Ser Leu Lys Val Gly Asp Gly Thr Val Ile Leu Lys Gln Gln Thr
465                 470                 475                 480
Asn Gly Ser Gly Gln His Ala Phe Ala Ser Val Gly Ile Val Ser Gly
                485                 490                 495
Arg Ser Thr Leu Val Leu Asn Asp Asp Lys Gln Val Asp Pro Asn Ser
            500                 505                 510
Ile Tyr Phe Gly Phe Arg Gly Gly Arg Leu Asp Leu Asn Gly Asn Ser
        515                 520                 525
Leu Thr Phe Asp His Ile Arg Asn Ile Asp Asp Gly Ala Arg Leu Val
    530                 535                 540
Asn His Asn Met Thr Asn Ala Ser Asn Ile Thr Ile Thr Gly Glu Ser
545                 550                 555                 560
Leu Ile Thr Asp Pro Asn Thr Ile Thr Pro Tyr Asn Ile Asp Ala Pro
                565                 570                 575
Asp Glu Asp Asn Pro Tyr Ala Phe Arg Arg Ile Lys Asp Gly Gly Gln
            580                 585                 590
Leu Tyr Leu Asn Leu Glu Asn Tyr Thr Tyr Ala Leu Arg Lys Gly
        595                 600                 605
Ala Ser Thr Arg Ser Glu Leu Pro Lys Asn Ser Gly Glu Ser Asn Glu
    610                 615                 620
Asn Trp Leu Tyr Met Gly Lys Thr Ser Asp Glu Ala Lys Arg Asn Val
625                 630                 635                 640
Met Asn His Ile Asn Asn Glu Arg Met Asn Gly Phe Asn Gly Tyr Phe
                645                 650                 655
Gly Glu Glu Glu Gly Lys Asn Asn Gly Asn Leu Asn Val Thr Phe Lys
            660                 665                 670
Gly Lys Ser Glu Gln Asn Arg Phe Leu Leu Thr Gly Thr Asn Leu
        675                 680                 685
Asn Gly Asp Leu Thr Val Glu Lys Gly Thr Leu Phe Leu Ser Gly Arg
    690                 695                 700
Pro Thr Pro His Ala Arg Asp Ile Ala Gly Ile Ser Ser Thr Lys Lys
705                 710                 715                 720
Asp Pro His Phe Ala Glu Asn Asn Glu Val Val Glu Asp Asp Trp
                725                 730                 735
Ile Asn Arg Asn Phe Lys Ala Thr Thr Met Asn Val Thr Gly Asn Ala
            740                 745                 750
Ser Leu Tyr Ser Gly Arg Asn Val Ala Asn Ile Thr Ser Asn Ile Thr
        755                 760                 765
Ala Ser Asn Lys Ala Gln Val His Ile Gly Tyr Lys Thr Gly Asp Thr
    770                 775                 780
```

-continued

Val Cys Val Arg Ser Asp Tyr Thr Gly Tyr Val Thr Cys Thr Thr Asp
785                 790                 795                 800

Lys Leu Ser Asp Lys Ala Leu Asn Ser Phe Asn Pro Thr Asn Leu Arg
            805                 810                 815

Gly Asn Val Asn Leu Thr Glu Ser Ala Asn Phe Val Leu Gly Lys Ala
        820                 825                 830

Asn Leu Phe Gly Thr Ile Gln Ser Arg Gly Asn Ser Gln Val Arg Leu
    835                 840                 845

Thr Glu Asn Ser His Trp His Leu Thr Gly Asn Ser Asp Val His Gln
850                 855                 860

Leu Asp Leu Ala Asn Gly His Ile His Leu Asn Ser Ala Asp Asn Ser
865                 870                 875                 880

Asn Asn Val Thr Lys Tyr Asn Thr Leu Thr Val Asn Ser Leu Ser Gly
            885                 890                 895

Asn Gly Ser Phe Tyr Tyr Leu Thr Asp Leu Ser Asn Lys Gln Gly Asp
        900                 905                 910

Lys Val Val Thr Lys Ser Ala Thr Gly Asn Phe Thr Leu Gln Val
    915                 920                 925

Ala Asp Lys Thr Gly Glu Pro Asn His Asn Glu Leu Thr Leu Phe Asp
930                 935                 940

Ala Ser Lys Ala Gln Arg Asp His Leu Asn Val Ser Leu Val Gly Asn
945                 950                 955                 960

Thr Val Asp Leu Gly Ala Trp Lys Tyr Lys Leu Arg Asn Val Asn Gly
            965                 970                 975

Arg Tyr Asp Leu Tyr Asn Pro Glu Val Glu Lys Arg Asn Gln Thr Val
        980                 985                 990

Asp Thr Thr Asn Ile Thr Thr Pro Asn Asn Ile Gln Ala Asp Val Pro
    995                 1000                1005

Ser Val Pro Ser Asn Asn Glu Glu Ile Ala Arg Val Asp Glu Ala
    1010                1015                1020

Pro Val Pro Pro Ala Pro Ala Thr Pro Ser Glu Thr Thr Glu
    1025                1030                1035

Thr Val Ala Glu Asn Ser Lys Gln Glu Ser Lys Thr Val Glu Lys
    1040                1045                1050

Asn Glu Gln Asp Ala Thr Glu Thr Thr Ala Gln Asn Arg Glu Val
    1055                1060                1065

Ala Lys Glu Ala Lys Ser Asn Val Lys Ala Asn Thr Gln Thr Asn
    1070                1075                1080

Glu Val Ala Gln Ser Gly Ser Glu Thr Lys Glu Thr Gln Thr Thr
    1085                1090                1095

Glu Thr Lys Glu Thr Ala Thr Val Glu Lys Glu Glu Lys Ala Lys
    1100                1105                1110

Val Glu Thr Glu Lys Thr Gln Glu Val Pro Lys Val Thr Ser Gln
    1115                1120                1125

Val Ser Pro Lys Gln Glu Gln Ser Glu Thr Val Gln Pro Gln Ala
    1130                1135                1140

Glu Pro Ala Arg Glu Asn Asp Pro Thr Val Asn Ile Lys Glu Pro
    1145                1150                1155

Gln Ser Gln Thr Asn Thr Thr Ala Asp Thr Glu Gln Pro Ala Lys
    1160                1165                1170

Glu Thr Ser Ser Asn Val Glu Gln Pro Val Thr Glu Ser Thr Thr
    1175                1180                1185

| | | | | | | | | | | |
|---|---|---|---|---|---|---|---|---|---|---|
| Val | Asn | Thr | Gly | Asn | Ser | Val | Val | Glu | Asn | Pro | Glu | Asn | Thr | Thr |
| 1190 | | | | | 1195 | | | | | 1200 | | | | |
| Pro | Ala | Thr | Thr | Gln | Pro | Thr | Val | Asn | Ser | Glu | Ser | Ser | Asn | Lys |
| 1205 | | | | | 1210 | | | | | 1215 | | | | |
| Pro | Lys | Asn | Arg | His | Arg | Arg | Ser | Val | Arg | Ser | Val | Pro | His | Asn |
| 1220 | | | | | 1225 | | | | | 1230 | | | | |
| Val | Glu | Pro | Ala | Thr | Thr | Ser | Ser | Asn | Asp | Arg | Ser | Thr | Val | Ala |
| 1235 | | | | | 1240 | | | | | 1245 | | | | |
| Leu | Cys | Asp | Leu | Thr | Ser | Thr | Asn | Thr | Asn | Ala | Val | Leu | Ser | Asp |
| 1250 | | | | | 1255 | | | | | 1260 | | | | |
| Ala | Arg | Ala | Lys | Ala | Gln | Phe | Val | Ala | Leu | Asn | Val | Gly | Lys | Ala |
| 1265 | | | | | 1270 | | | | | 1275 | | | | |
| Val | Ser | Gln | His | Ile | Ser | Gln | Leu | Glu | Met | Asn | Asn | Glu | Gly | Gln |
| 1280 | | | | | 1285 | | | | | 1290 | | | | |
| Tyr | Asn | Val | Trp | Val | Ser | Asn | Thr | Ser | Met | Asn | Lys | Asn | Tyr | Ser |
| 1295 | | | | | 1300 | | | | | 1305 | | | | |
| Ser | Ser | Gln | Tyr | Arg | Arg | Phe | Ser | Ser | Lys | Ser | Thr | Gln | Thr | Gln |
| 1310 | | | | | 1315 | | | | | 1320 | | | | |
| Leu | Gly | Trp | Asp | Gln | Thr | Ile | Ser | Asn | Asn | Val | Gln | Leu | Gly | Gly |
| 1325 | | | | | 1330 | | | | | 1335 | | | | |
| Val | Phe | Thr | Tyr | Val | Arg | Asn | Ser | Asn | Asn | Phe | Asp | Lys | Ala | Thr |
| 1340 | | | | | 1345 | | | | | 1350 | | | | |
| Ser | Lys | Asn | Thr | Leu | Ala | Gln | Val | Asn | Phe | Tyr | Ser | Lys | Tyr | Tyr |
| 1355 | | | | | 1360 | | | | | 1365 | | | | |
| Ala | Asp | Asn | His | Trp | Tyr | Leu | Gly | Ile | Asp | Leu | Gly | Tyr | Gly | Lys |
| 1370 | | | | | 1375 | | | | | 1380 | | | | |
| Phe | Gln | Ser | Lys | Leu | Gln | Thr | Asn | His | Asn | Ala | Lys | Phe | Ala | Arg |
| 1385 | | | | | 1390 | | | | | 1395 | | | | |
| His | Thr | Ala | Gln | Phe | Gly | Leu | Thr | Ala | Gly | Lys | Ala | Phe | Asn | Leu |
| 1400 | | | | | 1405 | | | | | 1410 | | | | |
| Gly | Asn | Phe | Gly | Ile | Thr | Pro | Ile | Val | Gly | Val | Arg | Tyr | Ser | Tyr |
| 1415 | | | | | 1420 | | | | | 1425 | | | | |
| Leu | Ser | Asn | Ala | Asp | Phe | Ala | Leu | Asp | Gln | Ala | Arg | Ile | Lys | Val |
| 1430 | | | | | 1435 | | | | | 1440 | | | | |
| Asn | Pro | Ile | Ser | Val | Lys | Thr | Ala | Phe | Ala | Gln | Val | Asp | Leu | Ser |
| 1445 | | | | | 1450 | | | | | 1455 | | | | |
| Tyr | Thr | Tyr | His | Leu | Gly | Glu | Phe | Ser | Val | Thr | Pro | Ile | Leu | Ser |
| 1460 | | | | | 1465 | | | | | 1470 | | | | |
| Ala | Arg | Tyr | Asp | Ala | Asn | Gln | Gly | Ser | Gly | Lys | Ile | Asn | Val | Asn |
| 1475 | | | | | 1480 | | | | | 1485 | | | | |
| Gly | Tyr | Asp | Phe | Ala | Tyr | Asn | Val | Glu | Asn | Gln | Gln | Gln | Tyr | Asn |
| 1490 | | | | | 1495 | | | | | 1500 | | | | |
| Ala | Gly | Leu | Lys | Leu | Lys | Tyr | His | Asn | Val | Lys | Leu | Ser | Leu | Ile |
| 1505 | | | | | 1510 | | | | | 1515 | | | | |
| Gly | Gly | Leu | Thr | Lys | Ala | Lys | Gln | Ala | Glu | Lys | Gln | Lys | Thr | Ala |
| 1520 | | | | | 1525 | | | | | 1530 | | | | |
| Glu | Leu | Lys | Leu | Ser | Phe | Ser | Phe | | | | | | | |
| 1535 | | | | | 1540 | | | | | | | | | |

<210> SEQ ID NO 7
<211> LENGTH: 6021
<212> TYPE: DNA
<213> ORGANISM: Haemophilus influenzae
<220> FEATURE:
<221> NAME/KEY: misc_feature
<222> LOCATION: (1)..(6021)
<223> OTHER INFORMATION: Encodes IgA1 protease

<400> SEQUENCE: 7

```
ttttgagcga tttatgctat aaagttcgcc cattataaag atgaagacaa cttgcaaact    60
atcaacgcaa cacagccaaa atttgaatca acttgtaacc gtatatcaaa ttgtgtccta   120
tcaaatctac tttttaaact taattaataa ggacagcttc tatgctaaat aaaaaattca   180
aactcaattt tattgcgctt actgtcgcct acgcattaac cccttataca gaagccgcgt   240
tagtgagaga cgatgtggat tatcaaatat ccgtgatttt gcagagaat aaagggaagt    300
tttctgttgg tgcaacaaat gtggaagtga gagataaaaa gaaccaatct ttaggcagtg   360
ccttacctaa cggtattccg atgattgatt ttagcgtggt ggatgtagat aagagaattg   420
ccacgttggt aaatccacaa tatgtagtag gcgtaaaaca cgttagtaac ggcgtgagtg   480
aactacattt tggtaactta aacggcaata tgaataatgg caatgctaaa tcgcaccgag   540
atgtatcctc tgaagaaaac cgatattaca ccgttgaaaa aaataatttc cctacagaga   600
atgtaacatc tttcacaaca aaagaagaac aagatgctca aaacgccgt gaagattatt    660
atatgcctcg ccttgataaa tttgttaccg aagttgcacc aatagaggct tcaactgcaa   720
acaacaataa aggagagtat aacaattctg ataaataccc agcttttgta agacttggta   780
gtggctctca atttatctat aaaaaaggaa gtcgttatca attaatcttg acggaaaagg   840
ataaacaagg aaatctgttg agaaactggg atgttggtgg agataatctc gaactagttg   900
gtaatgctta tacctatggt attgcaggta caccttataa agtaaaccac gagaataatg   960
gactaattgg ttttggcaat tcaaaagagg aacacagcga tccaaaagga atattatctc  1020
aagatcctct taccaattat gctgttttag gcgacagtgg ctcccatta tttgtatatg   1080
atagagaaaa aggaaaatgg cttttttcttg atcctatga tttctgggcg ggttataaca  1140
aaaaatcttg gcaagaatgg aatatctata acatgaatt tgcagaaaaa atttatcaac   1200
aatatagtgc aggttctta actggttcta acacccaata tacttggcaa gccactggca   1260
gtacaagtac gattacgggg ggagggaac ctttaagtgt tgatttaact gacggaaag    1320
ataaacctaa tcacggaaaa agtatcactc ttaaaggaag tggaacactt accttaaata  1380
atcatatcga tcaaggtgca ggcggcttgt tttttgaagg cgattatgaa gttaaaggca  1440
cttctgatag taccacttgg aaaggagcgg gcgtttctgt tgctgatgga aaaacagtaa  1500
cgtggaaagt acataaccg aaatatgatc gattagctaa aattggtaaa gggacattag   1560
ttgtagaagg aaaagggaaa atgaaggat tacttaaagt tggcgatggt actgttatct   1620
taaaacagaa agctgatgcc aataataaag ttcaagcctt ttcacaagta ggtatagtga  1680
gtggtcgctc aacccttgtg cttaatgatg ataaacaagt agatccaaat tcaatttact  1740
ttggctttag aggcggtcga ttagatttaa acggtaattc actaaccttt gaccacatca  1800
gaaatattga tgatggggca agagtggtta atcataatat gaccaatacc tcaaatataa  1860
cgattactgg ggaaagtcta attacaaatc caaatacaat tacttcatat aatatagaag  1920
cacaagatga cgaccaccct ttacgaattc gttcaatacc gtacagacag ctgtattta   1980
atcaggataa cagatcctat tacacattaa aaaaggtgc tagcactcgt tcagaattgc  2040
ctcaaaacag cggagaaagc aacgaaaatt ggttatatat gggtagaact tccgatgaag  2100
ccaaaagaaa tgtaatgaac catatcaaca acgagcgtat gaatggcttt aatggttatt   2160
ttggcgagga agaaactaag gcaactcaaa acggcaaatt aaacgttacc tttaatggca  2220
```

```
aaagtgatca aaatcgcttt ttattaacag gcggaacaaa ccttaatggc gatttaaatg    2280
ttgaaaaagg cacattattc ctttcaggca gacctacacc gcacgcaaga gatattgcgg    2340
gtatttcttc aacgaagaaa gatcctcact tcactgaaaa taatgaagtg gtggtagaag    2400
acgactggat taaccgcaat tttaaagcaa ccacaatgaa cgtgactggc aatgcctcac    2460
tttattcggg acgcaatgtt gcaaatatta cttcaaatat cacagcttct aataatgcac    2520
aagtgcatat tggctataaa acaggcgata ccgtttgtgt acgttctgac tatacgggct    2580
atgtaacttg ccataatagc aatttatcgg aaaaagcact caatagtttt aatccaacca    2640
atctacgcgg caatgtaaat ttaaccgaaa atgcaagctt taccttaggc aaggctaact    2700
tattcggcac aattcaaagc attggaacta gccaagttaa tttaaaagaa aatagccatt    2760
ggcatttaac aggcaatagc aatgttaatc agttaaattt aaccaatggg catattcatt    2820
taaatgcaca aaacgatgct aataaagtaa ctacatataa cacactgaca gtgaatagct    2880
tatcaggtaa cggttctttc tattattggg ttgattttac caataataaa agtaacaaag    2940
ttgttgtaaa taaatccgcc acaggtaact ttacattaca agtagcagat aaaacaggcg    3000
agccaaatca taatgaactc acgctttttg atgcttcaaa tgctacaaga aataatttag    3060
aagtaacact agctaatggc agtgttgatc gaggtgcttg gaaatataaa ttacgtaatg    3120
ttaatggacg ttacgattta tataacccag aggtggaaaa aagaaatcaa actgtcgata    3180
cgacaaatat cacaacacct aatgatattc aagctgatgc acctagcgca caaagtaaca    3240
atgaagaaat agcccgtgtt gaaacaccag ttccaccacc tgcacctgct actgaatcag    3300
caatagcaag cgagcaacca gaaactcgtc ctgcagaaac cgctcaacca gcgatggaag    3360
agacaaatac tgctaactca acggaaactg ctccaaaatc tgataccgca acacaaactg    3420
aaaatccaaa ttcagaaagt gttccatcag agacaactga aaaagtggct gaaaatcctc    3480
cgcaagaaaa tgaaacagtc gcgaaaaacg agcaagaagc aaccgaacca acacctcaaa    3540
atggagaagt tgcaaaagaa gatcaaccaa ctgtagaagc taacactcaa acaaatgaag    3600
ccacccaaag tgagggcaaa accgaggaaa ctcaaacggc tgaaacaaaa tctgaaccta    3660
cagagagtgt aactgtatca gaaaatcaac cagaaaaaac tgtttctcaa tcaacagaag    3720
ataaggttgt tgtagaaaaa gaggaaaagg ctaaagtaga aacagaggaa actcaaaaag    3780
ccccacaagt gacttctaaa gagcctccga acaagcaga gcctgctcct gaagaagttc    3840
cgactgatac aaatgcagaa gaagctcaag ctctacagca aacacaaccg acaactgttg    3900
ctgcggcaga gacgacttcg ccaaacagta aaccagcgga agaaactcaa caaccaagtg    3960
aaaaaactaa cgctgaacct gtaacgcctg tagtatcaga aaatacggct acccaaccaa    4020
cagaaacaga ggaaacggct aaagtagaaa aagagaaaac tcaagaagtc cctcaagtgg    4080
cttctcaaga atctcctaaa caggaacagc ctgcagctaa accacaagct caaactaaac    4140
cgcaagcaga gcctgctcgt gaaaatgttc tgactactaa aaatgtagga gagcctcaac    4200
ctcaagctca accgcagaca caatcgacag cagttcctac gacgggggaa actgcagcga    4260
acagtaaacc tgcagctaaa ccacaagctc aagctaaacc gcaaacagag cctgctcgtg    4320
aaaatgtttc gactgttaat acaaaagagc ctcaatcgca aacaagtgca acagtaagca    4380
ctgaacaacc tgcgaaagag actagctcaa atgttgaaca acctgcacca gagaattcaa    4440
taaatactgg atctgcaacc acaatgacaa aaactgctga aaatccgat aaaccacaaa    4500
tggaaactgt gaccgaaaat gatcgtcagc ctgaagctaa tactgttgcg gataattctg    4560
tagcaaataa ttcagaaagc agtgagtcaa agagtagacg tagaagaagt gttagccagc    4620
```

```
ctaaagagac ttctgctgaa gaaacaacag tagcttctac tcaagaaaca acagtggata    4680
attcagtatc tactccaaaa ccacgaagca gaagaactcg tagatcagtg cagacaaata    4740
gttacgagcc agtggaacta cctactgaaa atgcggagaa tgcggagaat gtgcaatcgg    4800
gaaataatgt ggctaattca caaccagcat acgcaatct cacaagtaaa aacaccaatg     4860
cggtactttc taatgcaatg gcaaaagcac aatttgttgc attaaatgta gggaaagccg    4920
tttctcaaca tattagccag ttagaaatga ataacgaggg gcaatataac gtttggatat    4980
ctaatacttc aatgaacaaa aattattcct cagagcaata tcgtcgtttt agttctaaaa    5040
gtacgcaaac tcaacttggt tgggatcaaa caatctcaaa caatgttcag ttaggtggcg    5100
tgtttactta tgttcgcaat agtaacaact ttgataaggc aagcagtaaa aatactctag    5160
cacaagttaa tttctattct aaatattatg cggataatca ttggtatttg ggcattgatt    5220
taggctacgg caagttccaa agcaacctac aaaccaataa taatgcgaaa tttgctcgcc    5280
atactgcaca aattggttta accgcaggca aagcatttaa tcttggcaat tttgctgtta    5340
aaccaactgt aggggttcgt tatagttact tatcaaacgc tgattttgca ttagctcaag    5400
atcgcattaa agtaaatcca atatctgtca aaacagcctt tgctcaagtt gatttaagtt    5460
atacttatca cttaggcgag ttttccatta cgccaatttt gtctgctcga tatgatgcaa    5520
atcaaggcaa tggcaaaatt aatgtaagtg tatatgattt tgcttacaac gtggaaaacc    5580
aacagcaata taacgcggga cttaaattga aatatcataa tgtgaaatta agtctaattg    5640
gtggattaac aaaagcaaaa caagcggaaa acaaaaaac agcggaagtg aaactaagtt    5700
ttagttttta ataagcctgt ttgaattagc gttatagacg acaaagccct gtgtattaca    5760
gggctttatt tttgaatgaa attcagtgat taagtgcggt gaaaaatcag ctcatttttt    5820
atttttaacg taaaaacgct ggaatatttt tttcgtatgc tgagatttttg tcttcgtgct    5880 gcaaggttaa gccgatattg tccaatccgt ttaacaaaca atgacggcgg aattcatcca    5940
gttcaaagtg ataaactttta tccccaacag tgaccgtcat cgcttctaaa tctacgtgga    6000
tttgcttgct ttcatttgcc c                                             6021
```

<210> SEQ ID NO 8
<211> LENGTH: 1849
<212> TYPE: PRT
<213> ORGANISM: Haemophilus influenzae
<220> FEATURE:
<221> NAME/KEY: misc_feature
<222> LOCATION: (1)..(1849)
<223> OTHER INFORMATION: Full-length precursor IgA1 protease

<400> SEQUENCE: 8

```
Met Leu Asn Lys Lys Phe Lys Leu Asn Phe Ile Ala Leu Thr Val Ala
1               5                   10                  15

Tyr Ala Leu Thr Pro Tyr Thr Glu Ala Ala Leu Val Arg Asp Asp Val
            20                  25                  30

Asp Tyr Gln Ile Phe Arg Asp Phe Ala Glu Asn Lys Gly Lys Phe Ser
        35                  40                  45

Val Gly Ala Thr Asn Val Glu Val Arg Asp Lys Lys Asn Gln Ser Leu
    50                  55                  60

Gly Ser Ala Leu Pro Asn Gly Ile Pro Met Ile Asp Phe Ser Val Val
65                  70                  75                  80

Asp Val Asp Lys Arg Ile Ala Thr Leu Val Asn Pro Gln Tyr Val Val
                85                  90                  95
```

```
Gly Val Lys His Val Ser Asn Gly Val Ser Glu Leu His Phe Gly Asn
            100                 105                 110
Leu Asn Gly Asn Met Asn Asn Gly Asn Ala Lys Ser His Arg Asp Val
        115                 120                 125
Ser Ser Glu Glu Asn Arg Tyr Tyr Thr Val Glu Lys Asn Asn Phe Pro
    130                 135                 140
Thr Glu Asn Val Thr Ser Phe Thr Thr Lys Glu Glu Gln Asp Ala Gln
145                 150                 155                 160
Lys Arg Arg Glu Asp Tyr Tyr Met Pro Arg Leu Asp Lys Phe Val Thr
                165                 170                 175
Glu Val Ala Pro Ile Glu Ala Ser Thr Ala Asn Asn Lys Gly Glu
            180                 185                 190
Tyr Asn Asn Ser Asp Lys Tyr Pro Ala Phe Val Arg Leu Gly Ser Gly
        195                 200                 205
Ser Gln Phe Ile Tyr Lys Lys Gly Ser Arg Tyr Gln Leu Ile Leu Thr
    210                 215                 220
Glu Lys Asp Lys Gln Gly Asn Leu Leu Arg Asn Trp Asp Val Gly Gly
225                 230                 235                 240
Asp Asn Leu Glu Leu Val Gly Asn Ala Tyr Thr Tyr Gly Ile Ala Gly
                245                 250                 255
Thr Pro Tyr Lys Val Asn His Glu Asn Asn Gly Leu Ile Gly Phe Gly
            260                 265                 270
Asn Ser Lys Glu Glu His Ser Asp Pro Lys Gly Ile Leu Ser Gln Asp
        275                 280                 285
Pro Leu Thr Asn Tyr Ala Val Leu Gly Asp Ser Gly Ser Pro Leu Phe
    290                 295                 300
Val Tyr Asp Arg Glu Lys Gly Lys Trp Leu Phe Leu Gly Ser Tyr Asp
305                 310                 315                 320
Phe Trp Ala Gly Tyr Asn Lys Lys Ser Trp Gln Glu Trp Asn Ile Tyr
                325                 330                 335
Lys His Glu Phe Ala Glu Lys Ile Tyr Gln Gln Tyr Ser Ala Gly Ser
            340                 345                 350
Leu Thr Gly Ser Asn Thr Gln Tyr Thr Trp Gln Ala Thr Gly Ser Thr
        355                 360                 365
Ser Thr Ile Thr Gly Gly Gly Glu Pro Leu Ser Val Asp Leu Thr Asp
    370                 375                 380
Gly Lys Asp Lys Pro Asn His Gly Lys Ser Ile Thr Leu Lys Gly Ser
385                 390                 395                 400
Gly Thr Leu Thr Leu Asn Asn His Ile Asp Gln Gly Ala Gly Gly Leu
                405                 410                 415
Phe Phe Glu Gly Asp Tyr Glu Val Lys Gly Thr Ser Asp Ser Thr Thr
            420                 425                 430
Trp Lys Gly Ala Gly Val Ser Val Ala Asp Gly Lys Thr Val Thr Trp
        435                 440                 445
Lys Val His Asn Pro Lys Tyr Asp Arg Leu Ala Lys Ile Gly Lys Gly
    450                 455                 460
Thr Leu Val Val Glu Gly Lys Gly Lys Asn Glu Gly Leu Leu Lys Val
465                 470                 475                 480
Gly Asp Gly Thr Val Ile Leu Lys Gln Lys Ala Asp Ala Asn Asn Lys
                485                 490                 495
Val Gln Ala Phe Ser Gln Val Gly Ile Val Ser Gly Arg Ser Thr Leu
            500                 505                 510
Val Leu Asn Asp Asp Lys Gln Val Asp Pro Asn Ser Ile Tyr Phe Gly
```

```
            515                 520                 525
Phe Arg Gly Arg Leu Asp Leu Asn Gly Asn Ser Leu Thr Phe Asp
        530                 535                 540

His Ile Arg Asn Ile Asp Asp Gly Ala Arg Val Val Asn His Asn Met
545                 550                 555                 560

Thr Asn Thr Ser Asn Ile Thr Ile Thr Gly Glu Ser Leu Ile Thr Asn
                565                 570                 575

Pro Asn Thr Ile Thr Ser Tyr Asn Ile Glu Ala Gln Asp Asp His
            580                 585                 590

Pro Leu Arg Ile Arg Ser Ile Pro Tyr Arg Gln Leu Tyr Phe Asn Gln
            595                 600                 605

Asp Asn Arg Ser Tyr Tyr Thr Leu Lys Lys Gly Ala Ser Thr Arg Ser
        610                 615                 620

Glu Leu Pro Gln Asn Ser Gly Glu Ser Asn Glu Asn Trp Leu Tyr Met
625                 630                 635                 640

Gly Arg Thr Ser Asp Glu Ala Lys Arg Asn Val Met Asn His Ile Asn
                645                 650                 655

Asn Glu Arg Met Asn Gly Phe Asn Gly Tyr Phe Gly Glu Glu Glu Thr
            660                 665                 670

Lys Ala Thr Gln Asn Gly Lys Leu Asn Val Thr Phe Asn Gly Lys Ser
        675                 680                 685

Asp Gln Asn Arg Phe Leu Leu Thr Gly Gly Thr Asn Leu Asn Gly Asp
    690                 695                 700

Leu Asn Val Glu Lys Gly Thr Leu Phe Leu Ser Gly Arg Pro Thr Pro
705                 710                 715                 720

His Ala Arg Asp Ile Ala Gly Ile Ser Ser Thr Lys Lys Asp Pro His
                725                 730                 735

Phe Thr Glu Asn Asn Glu Val Val Glu Asp Asp Trp Ile Asn Arg
            740                 745                 750

Asn Phe Lys Ala Thr Thr Met Asn Val Thr Gly Asn Ala Ser Leu Tyr
        755                 760                 765

Ser Gly Arg Asn Val Ala Asn Ile Thr Ser Asn Ile Thr Ala Ser Asn
    770                 775                 780

Asn Ala Gln Val His Ile Gly Tyr Lys Thr Gly Asp Thr Val Cys Val
785                 790                 795                 800

Arg Ser Asp Tyr Thr Gly Tyr Val Thr Cys His Asn Ser Asn Leu Ser
                805                 810                 815

Glu Lys Ala Leu Asn Ser Phe Asn Pro Thr Asn Leu Arg Gly Asn Val
            820                 825                 830

Asn Leu Thr Glu Asn Ala Ser Phe Thr Leu Gly Lys Ala Asn Leu Phe
        835                 840                 845

Gly Thr Ile Gln Ser Ile Gly Thr Ser Gln Val Asn Leu Lys Glu Asn
    850                 855                 860

Ser His Trp His Leu Thr Gly Asn Ser Asn Val Asn Gln Leu Asn Leu
865                 870                 875                 880

Thr Asn Gly His Ile His Leu Asn Ala Gln Asn Asp Ala Asn Lys Val
                885                 890                 895

Thr Thr Tyr Asn Thr Leu Thr Val Asn Ser Leu Ser Gly Asn Gly Ser
            900                 905                 910

Phe Tyr Tyr Trp Val Asp Phe Thr Asn Asn Lys Ser Asn Lys Val Val
        915                 920                 925

Val Asn Lys Ser Ala Thr Gly Asn Phe Thr Leu Gln Val Ala Asp Lys
    930                 935                 940
```

```
Thr Gly Glu Pro Asn His Asn Glu Leu Thr Leu Phe Asp Ala Ser Asn
945                 950                 955                 960

Ala Thr Arg Asn Asn Leu Glu Val Thr Leu Ala Asn Gly Ser Val Asp
                965                 970                 975

Arg Gly Ala Trp Lys Tyr Lys Leu Arg Asn Val Asn Gly Arg Tyr Asp
            980                 985                 990

Leu Tyr Asn Pro Glu Val Glu Lys Arg Asn Gln Thr Val Asp Thr Thr
        995                 1000                1005

Asn Ile Thr Thr Pro Asn Asp Ile Gln Ala Asp Ala Pro Ser Ala
    1010                1015                1020

Gln Ser Asn Asn Glu Glu Ile Ala Arg Val Glu Thr Pro Val Pro
    1025                1030                1035

Pro Pro Ala Pro Ala Thr Glu Ser Ala Ile Ala Ser Glu Gln Pro
    1040                1045                1050

Glu Thr Arg Pro Ala Glu Thr Ala Gln Pro Ala Met Glu Glu Thr
    1055                1060                1065

Asn Thr Ala Asn Ser Thr Glu Thr Ala Pro Lys Ser Asp Thr Ala
    1070                1075                1080

Thr Gln Thr Glu Asn Pro Asn Ser Glu Ser Val Pro Ser Glu Thr
    1085                1090                1095

Thr Glu Lys Val Ala Glu Asn Pro Pro Gln Glu Asn Glu Thr Val
    1100                1105                1110

Ala Lys Asn Glu Gln Glu Ala Thr Glu Pro Thr Pro Gln Asn Gly
    1115                1120                1125

Glu Val Ala Lys Glu Asp Gln Pro Thr Val Glu Ala Asn Thr Gln
    1130                1135                1140

Thr Asn Glu Ala Thr Gln Ser Glu Gly Lys Thr Glu Glu Thr Gln
    1145                1150                1155

Thr Ala Glu Thr Lys Ser Glu Pro Thr Glu Ser Val Thr Val Ser
    1160                1165                1170

Glu Asn Gln Pro Glu Lys Thr Val Ser Gln Ser Thr Glu Asp Lys
    1175                1180                1185

Val Val Val Glu Lys Glu Glu Lys Ala Lys Val Glu Thr Glu Glu
    1190                1195                1200

Thr Gln Lys Ala Pro Gln Val Thr Ser Lys Glu Pro Pro Lys Gln
    1205                1210                1215

Ala Glu Pro Ala Pro Glu Glu Val Pro Thr Asp Thr Asn Ala Glu
    1220                1225                1230

Glu Ala Gln Ala Leu Gln Gln Thr Gln Pro Thr Thr Val Ala Ala
    1235                1240                1245

Ala Glu Thr Thr Ser Pro Asn Ser Lys Pro Ala Glu Glu Thr Gln
    1250                1255                1260

Gln Pro Ser Glu Lys Thr Asn Ala Glu Pro Val Thr Pro Val Val
    1265                1270                1275

Ser Glu Asn Thr Ala Thr Gln Pro Thr Glu Thr Glu Glu Thr Ala
    1280                1285                1290

Lys Val Glu Lys Glu Lys Thr Gln Glu Val Pro Gln Val Ala Ser
    1295                1300                1305

Gln Glu Ser Pro Lys Gln Glu Gln Pro Ala Ala Lys Pro Gln Ala
    1310                1315                1320

Gln Thr Lys Pro Gln Ala Glu Pro Ala Arg Glu Asn Val Leu Thr
    1325                1330                1335
```

```
Thr Lys Asn Val Gly Glu Pro Gln Pro Gln Ala Gln Pro Gln Thr
1340                1345                1350

Gln Ser Thr Ala Val Pro Thr Gly Glu Thr Ala Ala Asn Ser
1355                1360                1365

Lys Pro Ala Ala Lys Pro Gln Ala Gln Ala Lys Pro Gln Thr Glu
1370                1375                1380

Pro Ala Arg Glu Asn Val Ser Thr Val Asn Thr Lys Glu Pro Gln
1385                1390                1395

Ser Gln Thr Ser Ala Thr Val Ser Thr Glu Gln Pro Ala Lys Glu
1400                1405                1410

Thr Ser Ser Asn Val Glu Gln Pro Ala Pro Glu Asn Ser Ile Asn
1415                1420                1425

Thr Gly Ser Ala Thr Thr Met Thr Glu Thr Ala Glu Lys Ser Asp
1430                1435                1440

Lys Pro Gln Met Glu Thr Val Thr Glu Asn Asp Arg Gln Pro Glu
1445                1450                1455

Ala Asn Thr Val Ala Asp Asn Ser Val Ala Asn Asn Ser Glu Ser
1460                1465                1470

Ser Glu Ser Lys Ser Arg Arg Arg Arg Ser Val Ser Gln Pro Lys
1475                1480                1485

Glu Thr Ser Ala Glu Glu Thr Thr Val Ala Ser Thr Gln Glu Thr
1490                1495                1500

Thr Val Asp Asn Ser Val Ser Thr Pro Lys Pro Arg Ser Arg Arg
1505                1510                1515

Thr Arg Arg Ser Val Gln Thr Asn Ser Tyr Glu Pro Val Glu Leu
1520                1525                1530

Pro Thr Glu Asn Ala Glu Asn Ala Glu Asn Val Gln Ser Gly Asn
1535                1540                1545

Asn Val Ala Asn Ser Gln Pro Ala Leu Arg Asn Leu Thr Ser Lys
1550                1555                1560

Asn Thr Asn Ala Val Leu Ser Asn Ala Met Ala Lys Ala Gln Phe
1565                1570                1575

Val Ala Leu Asn Val Gly Lys Ala Val Ser Gln His Ile Ser Gln
1580                1585                1590

Leu Glu Met Asn Asn Glu Gly Gln Tyr Asn Val Trp Ile Ser Asn
1595                1600                1605

Thr Ser Met Asn Lys Asn Tyr Ser Ser Glu Gln Tyr Arg Arg Phe
1610                1615                1620

Ser Ser Lys Ser Thr Gln Thr Gln Leu Gly Trp Asp Gln Thr Ile
1625                1630                1635

Ser Asn Asn Val Gln Leu Gly Gly Val Phe Thr Tyr Val Arg Asn
1640                1645                1650

Ser Asn Asn Phe Asp Lys Ala Ser Ser Lys Asn Thr Leu Ala Gln
1655                1660                1665

Val Asn Phe Tyr Ser Lys Tyr Tyr Ala Asp Asn His Trp Tyr Leu
1670                1675                1680

Gly Ile Asp Leu Gly Tyr Gly Lys Phe Gln Ser Asn Leu Gln Thr
1685                1690                1695

Asn Asn Asn Ala Lys Phe Ala Arg His Thr Ala Gln Ile Gly Leu
1700                1705                1710

Thr Ala Gly Lys Ala Phe Asn Leu Gly Asn Phe Ala Val Lys Pro
1715                1720                1725

Thr Val Gly Val Arg Tyr Ser Tyr Leu Ser Asn Ala Asp Phe Ala
```

|     |     |     |     |     |     |     |     |     |     |     |
| --- | --- | --- | --- | --- | --- | --- | --- | --- | --- | --- |
|     |     |     |     | 1730 |     |     |     | 1735 |     |     |     | 1740 |

Leu Ala Gln Asp Arg Ile Lys Val Asn Pro Ile Ser Val Lys Thr
    1745                             1750                          1755

Ala Phe Ala Gln Val Asp Leu Ser Tyr Thr Tyr His Leu Gly Glu
    1760                             1765                          1770

Phe Ser Ile Thr Pro Ile Leu Ser Ala Arg Tyr Asp Ala Asn Gln
    1775                             1780                          1785

Gly Asn Gly Lys Ile Asn Val Ser Val Tyr Asp Phe Ala Tyr Asn
    1790                             1795                          1800

Val Glu Asn Gln Gln Gln Tyr Asn Ala Gly Leu Lys Leu Lys Tyr
    1805                             1810                          1815

His Asn Val Lys Leu Ser Leu Ile Gly Gly Leu Thr Lys Ala Lys
    1820                             1825                          1830

Gln Ala Glu Lys Gln Lys Thr Ala Glu Val Lys Leu Ser Phe Ser
    1835                             1840                          1845

Phe

<210> SEQ ID NO 9
<211> LENGTH: 5088
<212> TYPE: DNA
<213> ORGANISM: Haemophilus influenzae
<220> FEATURE:
<221> NAME/KEY: misc_feature
<222> LOCATION: (1)..(5088)
<223> OTHER INFORMATION: Encodes IgA1 protease

<400> SEQUENCE: 9

```
aaacccactc attataaaaa tgaagacaac ttgcaaacta tcaatgcaac acagccaaga      60
tttgaatcaa cttgtagccg tatatcaaat tgtgtcctat caaatctact tttaaactt     120
aattaataaa gacagcttct atgctaaata aaaaattcaa actcaattt attgcactta     180
ctgtcgccta cgcattaacc ccttatacag aagccgcgtt agtgagagac gatgtggatt    240
atcaaatatt tcgtgatttt gcagagaata aagggaagtt ttctgttggt gcaacaaatg    300
tggaagtgag agataaaaat aaccgaccct taggcaatgt tttacctaat ggtattccga    360
tgattgattt tagtgttgtg gatgtagata gagaattgc cacgttggta aatccacaat    420
atgtagtagg cgtaaaacac gttagtaacg gcgtgagtga actacatttt gggaacttaa    480
atggcaatat gaataatggc aatgctaaag cacaccgaga tgtatcctct gaagaaaacc    540
gatattacac cgttgaaaaa aacgagtatc aactaaatt aaatggaaaa gcagtaacta    600
ctgaagatca agctcaaaaa cgccgtgaag attattatat gccacgtctt gataaatttg    660
ttaccgaagt tgcaccaata gaggcttcaa ctgatagtag tacagcgggg acatataata    720
ataaagataa atatccttac tttgtaagac ttggtagtgg tactcaattt atttatgaaa    780
atggaacacg ctatgaatta tggttaggta agaagggca gaaaagcgat gcgggcggct    840
ataatcttaa attagttggt aatgcttata cctatgtat gcaggtacg ccttatgaag    900
taaatcacga gaacgatggg cttatcggct tcggcaactc aaataatgaa tacattaatc    960
caaaagaaat attatccaaa aaccacctta ctaattacgc tgttttaggg acagcggat   1020
ccccattatt tgtatatgat agagaaaaag gaaatggctt ttccttggt tcttatgatt   1080
actgggctgg ttataacaaa aaatcttggc aggaatggaa tatctataaa cctgaatttg   1140
cagaaaaaat ttatgaacaa tatagtgcag gttctttaat tggttccaag acagattata   1200
gttggtcttc taatggcaag acaagtacga ttacgggagg ggagaaatct ttaaatgttg   1260
```

```
atttagctga cggaaaagat aaacctaatc acgggaaaag tgttacattt gaagggagtg    1320
gaacgcttac cttaaataat aatatcgatc aaggtgcagg cggattattc tttgaaggcg    1380
attatgaagt taaaggtact tctgataata ctacttggaa aggagcaggt gtctctgttg    1440
ccgaaggaaa aactgtaacg tggaaagtgc ataatcctca atatgatcgt ttagcaaaaa    1500
ttggcaaagg gacattaatt gttgaaggaa caggagataa taaaggttcg ctaaaagtgg    1560
gcgatggcac cgttatttta aaacaacaaa caaatggttc gggacaacac gcttttgctt    1620
ctgtagggat tgtaagtggt cgctcaactc ttgtgcttaa tgatgataaa caagtagatc    1680
caaattcaat ttactttgga tttagaggcg gtcgattaga tttaaacggt aattcactaa    1740
cctttgacca catcagaaat attgatgaag gtgcgagact ggttaatcac agtaccagta    1800
aacactctac agtgacaatt actggggata atttgattac agatccaaat aatgtctcta    1860
tatattatgt aaaaccacta gaggacgata atccttatgc cattcggcaa ataaaatatg    1920
gataccaact ctattttaat gaagaaaaca gaacttatta tgcattaaaa aaagatgcta    1980
gtattcgctc agaatttcct caaaacagag gagaaagcaa taatagttgg ctatatatgg    2040
gaacagagaa agctgacgct caaaaaaatg caatgaacca tatcaacaac gagcgtatga    2100
atggctttaa cggttatttt ggtgaggaag aaggtaaaaa taacggtaat ctaaatgtga    2160
cttttaaagg caaaagtgag caaaatcgct ttttattaac aggcggaaca aaccttaatg    2220
gcgatttaaa tgttcaacaa ggtacattat tcctttctgg cagacctaca ccacacgcaa    2280
gagatattgc gggtatttct tcaacgaaga aagattcaca cttttctgaa ataatgaag     2340 tggtggtaga agacgactgg attaaccgca attttaaagc aacaaatatt aatgtaacca    2400
ataacgcaac cctttattca ggtcgcaatg ttgaaagtat tacttcaaat atcacagctt    2460
ctaataatgc aaaagtgcat atcggctata agcaggcga taccgtttgt gtacgttctg     2520
actatacggg ctatgtgact tgtactactg acaagttatc cgataaagcc cttaatagct    2580
ttaatccaac caatctacgc ggcaatgtaa atttaaccga aagtgcaaac tttgtcttag    2640
gcaaagccaa cttattcggc acaattcaaa gcagaggaaa tagccaagta cgtttaaccg    2700
aaaatagcca ttggcattta acaggaaata gtgatgttca tcaattagat ctagcaaatg    2760
ggcatattca tttaaattca gcagacaatt caaacaatgt gacaaaatat aacacgctga    2820
ctgtgaatag cttatcaggt aacggttctt tctattattt aactgatctt tccaataaac    2880
aaggcgacaa agttgttgta actaaatccg ccacaggtaa ctttacatta caagtggcag    2940
ataaaacagg cgagccaaat cataatgaac tcacactttt tgatgcttca aaagctcaaa    3000
gagatcattt gaatgtgtca ttagttggga ataccgttga tttaggtgct tggaaatata    3060
aattacgtaa tgttaatgga cgttacgatt tgtataaccc agaggtggaa aaagaaatc     3120 aaactgtcga tacgacaaat atcacaacac ctaataatat tcaagctgat gtgcctagcg    3180
taccaagtaa caatgaagaa atagcccgtg ttgatgaagc accagttcca ccacctgcgc    3240
ctgctacacc atcagagaca actgaaacag tggctgaaaa tagtaagcaa gaaagtaaaa    3300
cagtagagaa aaacgagcaa gacgcaaccg agacaacagc tcaaaataga gaagttgcaa    3360
aagaagctaa atcaaatgta aaagctaata ctcaaacaaa tgaagtagct caaagtggaa    3420
gtgaaaccaa ggaaactcaa acgactgaaa caaagaaac agctacggta gaaaaagaag    3480
aaaaggctaa agtagaaaca gagaaaactc aagaagtccc taaagtgact tctcaagtgt    3540
ctccgaaaca ggaacagtct gaaactgttc aaccgcaagc agagcctgct cgtgaaaatg    3600
atccgactgt taatataaaa gagcctcaat ctcaaacaaa tacaacagca gacactgaac    3660
```

-continued

```
aacctgcgaa agagactagc tcaaatgttg aacaaccagt gacagaaagc acaacagtaa    3720
acactggaaa ctctgtagtg gaaaatccag agaatacaac acctgctaca actcaaccta    3780
cggttaattc agaaagcagt aataagccaa agaatagaca tagaagaagt gttcgctcag    3840
ttccgcataa tgttgaacca gctacaacaa gtagcaacga tcgttctaca gtagcattgt    3900
gcgatctcac aagtacaaac acaaatgcgg tactttctga tgcaagggca aaagcacaat    3960
ttgttgcatt aaatgtgggg aaagcagttt ctcaacatat tagccagtta gaaatgaata    4020
acgaggggca atataacgtt tgggtatcta atacttcaat gaacaaaaat tattcctcaa    4080
gtcaatatcg tcgttttagt tctaaaagta cgcaaactca actgggttgg gatcaaacaa    4140
tctcaaacaa tgttcagtta ggtggcgtgt ttacttatgt tcgcaatagt aacaactttg    4200
ataaggcaac aagtaaaaat actctagcac aagttaattt ctattctaaa tattatgcgg    4260
ataatcattg gtatttgggc attgatttag gctacggcaa gttccaaagc aaattacaaa    4320
ctaatcataa tgcgaaattt gctcgccata ctgcacaatt tggtttaacc gcaggcaaag    4380
catttaatct tggcaatttt ggtattacgc caatagtagg cgtgcgttat agctatttat    4440
caaacgctga ttttgcatta gatcaagctc gcattaaagt aaatccaata tctgtcaaaa    4500
cagcctttgc tcaagttgat ttaagttata cttatcactt aggcgagttt tccgttacgc    4560
caattttgtc tgctcgatat gatgcaaacc aaggcagcgg aaaaattaat gtaaatggat    4620
atgattttgc ttacaacgtg gaaaaccaac agcaatataa cgcagggctt aaattgaaat    4680
atcataatgt gaaattaagt ctaataggcg gattaacaaa agcgaaacaa gcggaaaaac    4740
aaaaaactgc agaattaaaa ctaagtttta gttttaata agcctgtttg aattaacgtt     4800
ataaacaaca aagccctgtg tattacaggg ctttatttttt gaatgaaatt cagtgattaa    4860
gtgcggtgaa aaatcagcgc atttttttatt tttaacgtaa aaacgctgga atattttttct   4920
catatgctga gattttgtct tcgtgctgaa gggttaaacc gatattatct aaaccgttta    4980
gcaaacaatg gcggcgaaat tcatcaagct caaaagtata aactttatcc ccatacgtga    5040
ccgtcatcgc ttctaaatct atgtggattt gcttgctttc atttgccc                 5088
```

<210> SEQ ID NO 10
<211> LENGTH: 1545
<212> TYPE: PRT
<213> ORGANISM: Haemophilus influenzae
<220> FEATURE:
<221> NAME/KEY: misc_feature
<222> LOCATION: (1)..(1545)
<223> OTHER INFORMATION: Full-length precursor IgA1 protease

<400> SEQUENCE: 10

```
Met Leu Asn Lys Lys Phe Lys Leu Asn Phe Ile Ala Leu Thr Val Ala
1               5                   10                  15

Tyr Ala Leu Thr Pro Tyr Thr Glu Ala Ala Leu Val Arg Asp Asp Val
                20                  25                  30

Asp Tyr Gln Ile Phe Arg Asp Phe Ala Glu Asn Lys Gly Lys Phe Ser
            35                  40                  45

Val Gly Ala Thr Asn Val Glu Val Arg Asp Lys Asn Asn Arg Pro Leu
        50                  55                  60

Gly Asn Val Leu Pro Asn Gly Ile Pro Met Ile Asp Phe Ser Val Val
65                  70                  75                  80

Asp Val Asp Lys Arg Ile Ala Thr Leu Val Asn Pro Gln Tyr Val Val
                85                  90                  95
```

-continued

```
Gly Val Lys His Val Ser Asn Gly Val Ser Glu Leu His Phe Gly Asn
            100                 105                 110
Leu Asn Gly Asn Met Asn Asn Gly Asn Ala Lys Ala His Arg Asp Val
            115                 120                 125
Ser Ser Glu Glu Asn Arg Tyr Tyr Thr Val Glu Lys Asn Glu Tyr Pro
        130                 135                 140
Thr Lys Leu Asn Gly Lys Ala Val Thr Thr Glu Asp Gln Ala Gln Lys
145                 150                 155                 160
Arg Arg Glu Asp Tyr Tyr Met Pro Arg Leu Asp Lys Phe Val Thr Glu
                165                 170                 175
Val Ala Pro Ile Glu Ala Ser Thr Asp Ser Ser Thr Ala Gly Thr Tyr
            180                 185                 190
Asn Asn Lys Asp Lys Tyr Pro Tyr Phe Val Arg Leu Gly Ser Gly Thr
        195                 200                 205
Gln Phe Ile Tyr Glu Asn Gly Thr Arg Tyr Glu Leu Trp Leu Gly Lys
    210                 215                 220
Glu Gly Gln Lys Ser Asp Ala Gly Gly Tyr Asn Leu Lys Leu Val Gly
225                 230                 235                 240
Asn Ala Tyr Thr Tyr Gly Ile Ala Gly Thr Pro Tyr Glu Val Asn His
                245                 250                 255
Glu Asn Asp Gly Leu Ile Gly Phe Gly Asn Ser Asn Asn Glu Tyr Ile
            260                 265                 270
Asn Pro Lys Glu Ile Leu Ser Lys Pro Leu Thr Asn Tyr Ala Val
        275                 280                 285
Leu Gly Asp Ser Gly Ser Pro Leu Phe Val Tyr Asp Arg Glu Lys Gly
    290                 295                 300
Lys Trp Leu Phe Leu Gly Ser Tyr Asp Tyr Trp Ala Gly Tyr Asn Lys
305                 310                 315                 320
Lys Ser Trp Gln Glu Trp Asn Ile Tyr Lys Pro Glu Phe Ala Glu Lys
                325                 330                 335
Ile Tyr Glu Gln Tyr Ser Ala Gly Ser Leu Ile Gly Ser Lys Thr Asp
            340                 345                 350
Tyr Ser Trp Ser Ser Asn Gly Lys Thr Ser Thr Ile Thr Gly Gly Glu
        355                 360                 365
Lys Ser Leu Asn Val Asp Leu Ala Asp Gly Lys Asp Lys Pro Asn His
    370                 375                 380
Gly Lys Ser Val Thr Phe Glu Gly Ser Gly Thr Leu Thr Leu Asn Asn
385                 390                 395                 400
Asn Ile Asp Gln Gly Ala Gly Gly Leu Phe Phe Glu Gly Asp Tyr Glu
                405                 410                 415
Val Lys Gly Thr Ser Asp Asn Thr Thr Trp Lys Gly Ala Gly Val Ser
            420                 425                 430
Val Ala Glu Gly Lys Thr Val Thr Trp Lys Val His Asn Pro Gln Tyr
        435                 440                 445
Asp Arg Leu Ala Lys Ile Gly Lys Gly Thr Leu Ile Val Glu Gly Thr
    450                 455                 460
Gly Asp Asn Lys Gly Ser Leu Lys Val Gly Asp Gly Thr Val Ile Leu
465                 470                 475                 480
Lys Gln Gln Thr Asn Gly Ser Gly Gln His Ala Phe Ala Ser Val Gly
                485                 490                 495
Ile Val Ser Gly Arg Ser Thr Leu Val Leu Asn Asp Asp Lys Gln Val
            500                 505                 510
Asp Pro Asn Ser Ile Tyr Phe Gly Phe Arg Gly Gly Arg Leu Asp Leu
```

-continued

```
            515                 520                 525
Asn Gly Asn Ser Leu Thr Phe Asp His Ile Arg Asn Ile Asp Glu Gly
        530                 535                 540

Ala Arg Leu Val Asn His Ser Thr Ser Lys His Ser Thr Val Thr Ile
545                 550                 555                 560

Thr Gly Asp Asn Leu Ile Thr Asp Pro Asn Val Ser Ile Tyr Tyr
                565                 570                 575

Val Lys Pro Leu Glu Asp Asp Asn Pro Tyr Ala Ile Arg Gln Ile Lys
                580                 585                 590

Tyr Gly Tyr Gln Leu Tyr Phe Asn Glu Glu Asn Arg Thr Tyr Tyr Ala
            595                 600                 605

Leu Lys Lys Asp Ala Ser Ile Arg Ser Glu Phe Pro Gln Asn Arg Gly
        610                 615                 620

Glu Ser Asn Asn Ser Trp Leu Tyr Met Gly Thr Glu Lys Ala Asp Ala
625                 630                 635                 640

Gln Lys Asn Ala Met Asn His Ile Asn Asn Glu Arg Met Asn Gly Phe
                645                 650                 655

Asn Gly Tyr Phe Gly Glu Glu Gly Lys Asn Asn Gly Asn Leu Asn
            660                 665                 670

Val Thr Phe Lys Gly Lys Ser Glu Gln Asn Arg Phe Leu Leu Thr Gly
            675                 680                 685

Gly Thr Asn Leu Asn Gly Asp Leu Asn Val Gln Gln Gly Thr Leu Phe
690                 695                 700

Leu Ser Gly Arg Pro Thr Pro His Ala Arg Asp Ile Ala Gly Ile Ser
705                 710                 715                 720

Ser Thr Lys Lys Asp Ser His Phe Ser Glu Asn Asn Glu Val Val Val
                725                 730                 735

Glu Asp Asp Trp Ile Asn Arg Asn Phe Lys Ala Thr Asn Ile Asn Val
                740                 745                 750

Thr Asn Asn Ala Thr Leu Tyr Ser Gly Arg Asn Val Glu Ser Ile Thr
            755                 760                 765

Ser Asn Ile Thr Ala Ser Asn Asn Ala Lys Val His Ile Gly Tyr Lys
        770                 775                 780

Ala Gly Asp Thr Val Cys Val Arg Ser Asp Tyr Thr Gly Tyr Val Thr
785                 790                 795                 800

Cys Thr Thr Asp Lys Leu Ser Asp Lys Ala Leu Asn Ser Phe Asn Pro
                805                 810                 815

Thr Asn Leu Arg Gly Asn Val Asn Leu Thr Glu Ser Ala Asn Phe Val
                820                 825                 830

Leu Gly Lys Ala Asn Leu Phe Gly Thr Ile Gln Ser Arg Gly Asn Ser
            835                 840                 845

Gln Val Arg Leu Thr Glu Asn Ser His Trp His Leu Thr Gly Asn Ser
        850                 855                 860

Asp Val His Gln Leu Asp Leu Ala Asn Gly His Ile His Leu Asn Ser
865                 870                 875                 880

Ala Asp Asn Ser Asn Asn Val Thr Lys Tyr Asn Thr Leu Thr Val Asn
                885                 890                 895

Ser Leu Ser Gly Asn Gly Ser Phe Tyr Tyr Leu Thr Asp Leu Ser Asn
                900                 905                 910

Lys Gln Gly Asp Lys Val Val Val Thr Lys Ser Ala Thr Gly Asn Phe
            915                 920                 925

Thr Leu Gln Val Ala Asp Lys Thr Gly Glu Pro Asn His Asn Glu Leu
        930                 935                 940
```

```
Thr Leu Phe Asp Ala Ser Lys Ala Gln Arg Asp His Leu Asn Val Ser
945                 950                 955                 960

Leu Val Gly Asn Thr Val Asp Leu Gly Ala Trp Lys Tyr Lys Leu Arg
                965                 970                 975

Asn Val Asn Gly Arg Tyr Asp Leu Tyr Asn Pro Glu Val Glu Lys Arg
            980                 985                 990

Asn Gln Thr Val Asp Thr Thr Asn Ile Thr Thr Pro Asn Asn Ile Gln
        995                 1000                1005

Ala Asp Val Pro Ser Val Pro Ser Asn Asn Glu Glu Ile Ala Arg
    1010            1015            1020

Val Asp Glu Ala Pro Val Pro Pro Pro Ala Pro Ala Thr Pro Ser
    1025            1030            1035

Glu Thr Thr Glu Thr Val Ala Glu Asn Ser Lys Gln Glu Ser Lys
    1040            1045            1050

Thr Val Glu Lys Asn Glu Gln Asp Ala Thr Glu Thr Thr Ala Gln
    1055            1060            1065

Asn Arg Glu Val Ala Lys Glu Ala Lys Ser Asn Val Lys Ala Asn
    1070            1075            1080

Thr Gln Thr Asn Glu Val Ala Gln Ser Gly Ser Glu Thr Lys Glu
    1085            1090            1095

Thr Gln Thr Thr Glu Thr Lys Glu Thr Ala Thr Val Glu Lys Glu
    1100            1105            1110

Glu Lys Ala Lys Val Glu Thr Glu Lys Thr Gln Glu Val Pro Lys
    1115            1120            1125

Val Thr Ser Gln Val Ser Pro Lys Gln Glu Gln Ser Glu Thr Val
    1130            1135            1140

Gln Pro Gln Ala Glu Pro Ala Arg Glu Asn Asp Pro Thr Val Asn
    1145            1150            1155

Ile Lys Glu Pro Gln Ser Gln Thr Asn Thr Thr Ala Asp Thr Glu
    1160            1165            1170

Gln Pro Ala Lys Glu Thr Ser Ser Asn Val Glu Gln Pro Val Thr
    1175            1180            1185

Glu Ser Thr Thr Val Asn Thr Gly Asn Ser Val Val Glu Asn Pro
    1190            1195            1200

Glu Asn Thr Thr Pro Ala Thr Thr Gln Pro Thr Val Asn Ser Glu
    1205            1210            1215

Ser Ser Asn Lys Pro Lys Asn Arg His Arg Arg Ser Val Arg Ser
    1220            1225            1230

Val Pro His Asn Val Glu Pro Ala Thr Thr Ser Ser Asn Asp Arg
    1235            1240            1245

Ser Thr Val Ala Leu Cys Asp Leu Thr Ser Thr Asn Thr Asn Ala
    1250            1255            1260

Val Leu Ser Asp Ala Arg Ala Lys Ala Gln Phe Val Ala Leu Asn
    1265            1270            1275

Val Gly Lys Ala Val Ser Gln His Ile Ser Gln Leu Glu Met Asn
    1280            1285            1290

Asn Glu Gly Gln Tyr Asn Val Trp Val Ser Asn Thr Ser Met Asn
    1295            1300            1305

Lys Asn Tyr Ser Ser Ser Gln Tyr Arg Arg Phe Ser Ser Lys Ser
    1310            1315            1320

Thr Gln Thr Gln Leu Gly Trp Asp Gln Thr Ile Ser Asn Asn Val
    1325            1330            1335
```

| | | | | | | | | | | |
|---|---|---|---|---|---|---|---|---|---|---|
| Gln | Leu | Gly | Gly | Val | Phe | Thr | Tyr | Val | Arg | Asn | Ser | Asn | Asn | Phe |
| | 1340 | | | | | 1345 | | | | | 1350 | | | |
| Asp | Lys | Ala | Thr | Ser | Lys | Asn | Thr | Leu | Ala | Gln | Val | Asn | Phe | Tyr |
| | 1355 | | | | | 1360 | | | | | 1365 | | | |
| Ser | Lys | Tyr | Tyr | Ala | Asp | Asn | His | Trp | Tyr | Leu | Gly | Ile | Asp | Leu |
| | 1370 | | | | | 1375 | | | | | 1380 | | | |
| Gly | Tyr | Gly | Lys | Phe | Gln | Ser | Lys | Leu | Gln | Thr | Asn | His | Asn | Ala |
| | 1385 | | | | | 1390 | | | | | 1395 | | | |
| Lys | Phe | Ala | Arg | His | Thr | Ala | Gln | Phe | Gly | Leu | Thr | Ala | Gly | Lys |
| | 1400 | | | | | 1405 | | | | | 1410 | | | |
| Ala | Phe | Asn | Leu | Gly | Asn | Phe | Gly | Ile | Thr | Pro | Ile | Val | Gly | Val |
| | 1415 | | | | | 1420 | | | | | 1425 | | | |
| Arg | Tyr | Ser | Tyr | Leu | Ser | Asn | Ala | Asp | Phe | Ala | Leu | Asp | Gln | Ala |
| | 1430 | | | | | 1435 | | | | | 1440 | | | |
| Arg | Ile | Lys | Val | Asn | Pro | Ile | Ser | Val | Lys | Thr | Ala | Phe | Ala | Gln |
| | 1445 | | | | | 1450 | | | | | 1455 | | | |
| Val | Asp | Leu | Ser | Tyr | Thr | Tyr | His | Leu | Gly | Glu | Phe | Ser | Val | Thr |
| | 1460 | | | | | 1465 | | | | | 1470 | | | |
| Pro | Ile | Leu | Ser | Ala | Arg | Tyr | Asp | Ala | Asn | Gln | Gly | Ser | Gly | Lys |
| | 1475 | | | | | 1480 | | | | | 1485 | | | |
| Ile | Asn | Val | Asn | Gly | Tyr | Asp | Phe | Ala | Tyr | Asn | Val | Glu | Asn | Gln |
| | 1490 | | | | | 1495 | | | | | 1500 | | | |
| Gln | Gln | Tyr | Asn | Ala | Gly | Leu | Lys | Leu | Lys | Tyr | His | Asn | Val | Lys |
| | 1505 | | | | | 1510 | | | | | 1515 | | | |
| Leu | Ser | Leu | Ile | Gly | Gly | Leu | Thr | Lys | Ala | Lys | Gln | Ala | Glu | Lys |
| | 1520 | | | | | 1525 | | | | | 1530 | | | |
| Gln | Lys | Thr | Ala | Glu | Leu | Lys | Leu | Ser | Phe | Ser | Phe | | | |
| | 1535 | | | | | 1540 | | | | | 1545 | | | |

<210> SEQ ID NO 11
<211> LENGTH: 5536
<212> TYPE: DNA
<213> ORGANISM: Haemophilus influenzae
<220> FEATURE:
<221> NAME/KEY: misc_feature
<222> LOCATION: (1)..(5536)
<223> OTHER INFORMATION: Encodes IgA1 protease

<400> SEQUENCE: 11

```
aaagatgaag acaacttgca aattatcaac gcaacacagc caaaatttga atcaacttgt      60
aaccgtatat caaattgtgt cctatcaaat ctactttta aacttaatta ataaggacag     120
cttctatgct aaataaaaaa ttcaaactca attttattgc gcttactgtc gcctacgcat     180
taaccccta tacagaagct gcgttagtga gagacgatgt ggattatcaa atatttcgtg     240
atttgcaga aataaaggg agattttctg ttggtgcaac aaatgtggaa gtgagagata     300
aaataacca ctctttaggc aatgttttac ctaatggcat tccgatgatt gattttagtg     360
ttgtggatgt agataaacgc atcgccacat tgataaatcc acaatatgta gtaggtgtaa     420
aacacgttag taacggcgtg agtgaactac attttgggaa cttaaatggc aatatgaata     480
atggcaatga taaatcgcac cgagatgtat cttcagaaga aaatagatat ttttccgttg     540
agaaaaatga gtatccaact aaattgaatg aaaagcagt aactactgaa gatcaaactc     600
aaaaacgccg tgaagactac tatatgccac gtcttgataa atttgttacc gaagttgcac     660
caatagaggc ttcaactgca agtagtgatg ctggcacata taatgatcag ataaatatc     720
ctgcttttgt aagactagga agtggtagtc aatttattta taaaaaagga gataattaca     780
```

```
gcttaatttt aaataatcat gaggttggag gcaataatct taaattggtg ggcgatgcct      840
atacctatgg tattgcaggc acaccttata aagtaaacca cgaaaataat ggactaattg      900
gttttggcaa ttcaaaagag gaacacagcg atccaaaagg aatattatct caagatccgc      960
ttaccaatta tgctgtttta ggcgacagtg gctccccatt atttgtatat gatagagaaa     1020
aaggaaaatg gcttttttct gggtcttatg attttttggc aggttataac aaaaaatctt     1080
ggcaagaatg gaatatttat aaacctgaat ttgcaaaaac tgttctagat aaagatactg     1140
caggttcttt aactggttct aacacccaat acaattggaa tcctactggc aaaacaagcg     1200
ttatttctaa tggttctgaa tctctaaatg ttgatttatt cgatagtagt caggatactg     1260
actctaagaa gaacaatcac ggaaaaagtg tgactcttag aggaagtgga acgcttacct     1320
taaataataa tatcgatcaa ggcgcaggcg gcttgttctt tgaaggagat tatgaagtta     1380
aaggcacttc tgatagtacc acttggaaag gagctggcgt ttctgttgct gatggaaaaa     1440
cagtaacgtg gaaagtacat aaccccgaaat ctgatcgttt agctaaaatc ggcaaaggaa     1500
cattaattgt agaaggaaag ggagaaaata aaggttcgct aaaagtgggc gatggtactg     1560
ttatcttaaa acaacaagct gatgccaata taaagttaa agccttttca caagtaggta     1620
tagtaagtgg tcgctcaact gttgtactta atgatgataa gcaagtagat ccaaattcca     1680
tttactttgg ctttagaggt ggtcgattag atgccaatgg caataatctc acttttgaac     1740
atatccgtaa tattgatgat ggcgcaagac tagtaaatca caataccagc aaaacctcta     1800
ctgtaacaat tactggggaa agtctaatta cagatccaaa tacaattact ccatataata     1860
tagacgcacc agatgaagat aatccttatg cctttcgacg gattaaagat ggaggacagc     1920
tctatttaaa tttggaaaat tacacttatt atgcgttaag aaaaggtgcg agcactcgtt     1980
cagaattacc taaaaatagt ggcgaaagca atgaaaattg gctatatatg ggtaaaactt     2040
ccgatgaagc caaagaaat gtaatgaacc atatcaacaa cgagcgtatg aatggcttta     2100
acggttattt tggcgaggaa gagggtaaaa ataacggtaa tctaaatgtg acttttaaag     2160
gcaaaagtga gcaaaatcgc ttttattaa caggcggaac aaaccttaat ggcgatttaa     2220
aggttgaaaa aggcacatta ttcctttctg gcagaccaac accgcacgca agagatattg     2280
caggtatttc ttcgacaaaa aaagatcaac actttgctga aaataatgaa gtggtagtag     2340
aagatgactg gattaaccgc aattttaag caacaaatat taatgtaacc aataacgcaa     2400
cccttattc aggtcgcaat gttgcaaaca ttacttcaaa tatcacagct tctgataatg     2460
caaaagtaca tattggctat aaagcaggcg ataccgtttg tgtacgttct gactatacgg     2520
gctatgtgac ttgcactact gacaagttat ccgataaagc ccttaatagc tttaacgcca     2580
ccaatgtatc tggcaatgta aatttatcag gtaatgcaaa cttttgtctta ggcaaagcta     2640
acttattcgg cacaattagc ggcacgggaa atagccaagt acgtttaacc gaaaatagcc     2700
attggcattt aacaggcgat agcaatgtta atcagttaaa tttagacaag ggcatattc     2760
atttaaatgc acaaaacgat gcaaataaag taactacata taacacgctg actgtgaata     2820
gcttatcagg taacggttct ttctattatt taactgatct ttccaataaa caaggcgaca     2880
aagttgttgt aactaaatcc gccacaggta acttttacatt acaagtggca gataaaacag     2940
gcgagcctac aaaaaatgaa ctcacgcttt ttgatgcgtc aaatgctaca agaaataatt     3000
tgaatgtgtc attagttggg aataccgttg atttaggtgc ttggaaatat aaattacgta     3060
atgttaatgg acgttacgat ttgtataacc cagaggtgga aaaagaaat caaactgtcg     3120
```

```
atacgacaaa tatcacaaca cctaataata ttcaagctga tgtgcctagc gtaccaagta    3180
acaatgaaga aatagcccgt gttgaaacac cagttccacc acctgcgcct gctacaccat    3240
cagagacaac tgaaacagtg gctgaaaata gtaagcaaga aagtaaaaca gtagagaaaa    3300
acgagcaaga cgcaaccgag acaacagctc aaaatggaga agttgcagaa gaagctaaac    3360
caagtgtaaa agctaatact caaacaaatg aagtggctca aagtggaagt gaaaccgagg    3420
aaactcaaac gactgaaata aaagaaacag ctaaagtaga aaagaggaa aaggctaaag     3480 tagaaaaaga ggaaaaggct aaagtagaaa aagatgaaat tcaagaagca cctcaaatgg    3540
cttctgaaac gtctccgaaa caagcaaagc ctgctcctaa agaagtttca actgatacga    3600
aagtagaaga aactcaagtt caagctcaac cgcaaacaca atcgacaact gttgctgcgg    3660
cagaggcaac ttcgccaaac agtaaaccag cggaagaaac tcaaccaagt gaaaaaacta    3720
acgcagaacc tgtaacgcct gtagtatcaa aaaatcaaac agaaaatacg accgaccaac    3780
caacagaaag agagaaaacg gctaaagtag aaacagagaa aactcaagag cccctcaag     3840 tggcttctca agcgtctccg aaacaggaac agtctgaaac tgttcaaccg caagcagtgc    3900
ttgaaagtga aaatgttccg actgttaata atgcagaaga agttcaagct caactgcaaa    3960
cacaaacaag tgcaacagta agcactaaac aacctgcacc agagaattca ataaatactg    4020
gatctgcaac cgcaataaca gaaactgctg aaaaatccga taaccacaa acggaaactg     4080 cggcttcgac tgaagatgct agtcagcata aagcgaatac tgttgcggat aattctgtag    4140
caaataattc agaaagcagt gagccaaaga gtagacgtag aagaagtatt agccagcctc    4200
aagagacttc tgctgaagaa acaacagcag cttctactga cgaaacaaca atagctgata    4260
attcaaaacg cagtaagcca aatcgtagaa gtagaagaag tgttcgctcg gaaccaactg    4320
ttacaaatgg cagcgatcgt tctacagtag cattgcgcga tctcacaagt acaaacacaa    4380
atgcggtaat ttctgatgca atggcaaaag cacaatttgt tgcattaaat gtggggaaag    4440
cagtttctca acatattagc cagttagaaa tgaataacga ggggcaatat aacgtttggg    4500
tatctaatac ttcaatgaac gaaaattatt cctcaagtca atatcgtcgt tttagttcta    4560
aaagtacgca aactcaactt ggttgggatc aaacaatctc aaacaatgtt cagttaggtg    4620
gcgtgtttac ttatgttcgc aatagtaaca actttgataa ggcaagcagt aaaaatactc    4680
tagcacaagt taatttctat tctaaatatt atgcggataa tcattggtat ttgggcattg    4740
atttaggcta cggcaagttc caaagcaacc taaaaaccaa tcataatgcg aaatttgctc    4800
gccatactgc acaatttggt ttaaccgcag gcaaagcatt taatcttggc aattttggta    4860
ttacgccaat agtaggcgtg cgttatagct atttatcaaa cgctaatttt gcattagcta    4920
aagatcgcat taaagtaaat ccaatatctg tcaaaacagc ctttgctcaa gttgatttaa    4980
gttatactta tcacttaggc gagttttccg ttacgccaat tttgtctgct cgatatgata    5040
caaatcaagg cagcggaaaa attaatgtaa atcaatatga ttttgcttac aacgtggaaa    5100
accaacagca atataacgca gggcttaaat tgaaatatca taatgtgaaa ttaagtctaa    5160
taggcggatt aacaaaagcg aaacaagcgg aaaaacaaaa aactgcagaa ttaaaactaa    5220
gttttagttt ttaataagcc tgtttgaatt aacgttataa acaacaaagc cctgtgtctt    5280
acagggcttt attttgaat gaaattcagt gattaagtgc ggtgaaaaat cagcgcattt      5340 tttatttta acgtaaaaac gctggaatat ttttctcgta tgctgagatt ttgtcttcgt     5400
gctgaagagt taagccgata ttatctaaac cgtttagcaa acaatggcgg cggaattcga    5460
gctcggtacc cggggatcct ctagagtcga cctgcaggca tgcaagcttg gcgtaatcat    5520
```

```
ggtcatagct gtttcc                                                    5536
```

<210> SEQ ID NO 12
<211> LENGTH: 1702
<212> TYPE: PRT
<213> ORGANISM: Haemophilus influenzae
<220> FEATURE:
<221> NAME/KEY: misc_feature
<222> LOCATION: (1)..(1702)
<223> OTHER INFORMATION: Full-length precursor IgA1 protease

<400> SEQUENCE: 12

```
Met Leu Asn Lys Lys Phe Lys Leu Asn Phe Ile Ala Leu Thr Val Ala
1               5                   10                  15

Tyr Ala Leu Thr Pro Tyr Thr Glu Ala Ala Leu Val Arg Asp Asp Val
            20                  25                  30

Asp Tyr Gln Ile Phe Arg Asp Phe Ala Glu Asn Lys Gly Arg Phe Ser
        35                  40                  45

Val Gly Ala Thr Asn Val Glu Val Arg Asp Lys Asn Asn His Ser Leu
    50                  55                  60

Gly Asn Val Leu Pro Asn Gly Ile Pro Met Ile Asp Phe Ser Val Val
65                  70                  75                  80

Asp Val Asp Lys Arg Ile Ala Thr Leu Ile Asn Pro Gln Tyr Val Val
                85                  90                  95

Gly Val Lys His Val Ser Asn Gly Val Ser Glu Leu His Phe Gly Asn
            100                 105                 110

Leu Asn Gly Asn Met Asn Asn Gly Asn Asp Lys Ser His Arg Asp Val
        115                 120                 125

Ser Ser Glu Glu Asn Arg Tyr Phe Ser Val Glu Lys Asn Glu Tyr Pro
    130                 135                 140

Thr Lys Leu Asn Gly Lys Ala Val Thr Thr Glu Asp Gln Thr Gln Lys
145                 150                 155                 160

Arg Arg Glu Asp Tyr Tyr Met Pro Arg Leu Asp Lys Phe Val Thr Glu
                165                 170                 175

Val Ala Pro Ile Glu Ala Ser Thr Ala Ser Ser Asp Ala Gly Thr Tyr
            180                 185                 190

Asn Asp Gln Asn Lys Tyr Pro Ala Phe Val Arg Leu Gly Ser Gly Ser
        195                 200                 205

Gln Phe Ile Tyr Lys Lys Gly Asp Asn Tyr Ser Leu Ile Leu Asn Asn
    210                 215                 220

His Glu Val Gly Gly Asn Asn Leu Lys Leu Val Gly Asp Ala Tyr Thr
225                 230                 235                 240

Tyr Gly Ile Ala Gly Thr Pro Tyr Lys Val Asn His Glu Asn Asn Gly
                245                 250                 255

Leu Ile Gly Phe Gly Asn Ser Lys Glu Glu His Ser Asp Pro Lys Gly
            260                 265                 270

Ile Leu Ser Gln Asp Pro Leu Thr Asn Tyr Ala Val Leu Gly Asp Ser
        275                 280                 285

Gly Ser Pro Leu Phe Val Tyr Asp Arg Glu Lys Gly Lys Trp Leu Phe
    290                 295                 300

Leu Gly Ser Tyr Asp Phe Trp Ala Gly Tyr Asn Lys Lys Ser Trp Gln
305                 310                 315                 320

Glu Trp Asn Ile Tyr Lys Pro Glu Phe Ala Lys Thr Val Leu Asp Lys
                325                 330                 335

Asp Thr Ala Gly Ser Leu Thr Gly Ser Asn Thr Gln Tyr Asn Trp Asn
```

-continued

```
                340                 345                 350
Pro Thr Gly Lys Thr Ser Val Ile Ser Asn Gly Ser Glu Ser Leu Asn
            355                 360                 365
Val Asp Leu Phe Asp Ser Ser Gln Asp Thr Asp Ser Lys Lys Asn Asn
        370                 375                 380
His Gly Lys Ser Val Thr Leu Arg Gly Ser Gly Thr Leu Thr Leu Asn
385                 390                 395                 400
Asn Asn Ile Asp Gln Gly Ala Gly Gly Leu Phe Phe Glu Gly Asp Tyr
                405                 410                 415
Glu Val Lys Gly Thr Ser Asp Ser Thr Thr Trp Lys Gly Ala Gly Val
            420                 425                 430
Ser Val Ala Asp Gly Lys Thr Val Thr Trp Lys Val His Asn Pro Lys
        435                 440                 445
Ser Asp Arg Leu Ala Lys Ile Gly Lys Gly Thr Leu Ile Val Glu Gly
    450                 455                 460
Lys Gly Glu Asn Lys Gly Ser Leu Lys Val Gly Asp Gly Thr Val Ile
465                 470                 475                 480
Leu Lys Gln Gln Ala Asp Ala Asn Asn Lys Val Lys Ala Phe Ser Gln
                485                 490                 495
Val Gly Ile Val Ser Gly Arg Ser Thr Val Val Leu Asn Asp Asp Lys
            500                 505                 510
Gln Val Asp Pro Asn Ser Ile Tyr Phe Gly Phe Arg Gly Gly Arg Leu
        515                 520                 525
Asp Ala Asn Gly Asn Asn Leu Thr Phe Glu His Ile Arg Asn Ile Asp
    530                 535                 540
Asp Gly Ala Arg Leu Val Asn His Asn Thr Ser Lys Thr Ser Thr Val
545                 550                 555                 560
Thr Ile Thr Gly Glu Ser Leu Ile Thr Asp Pro Asn Thr Ile Thr Pro
                565                 570                 575
Tyr Asn Ile Asp Ala Pro Asp Glu Asp Asn Pro Tyr Ala Phe Arg Arg
            580                 585                 590
Ile Lys Asp Gly Gly Gln Leu Tyr Leu Asn Leu Glu Asn Tyr Thr Tyr
        595                 600                 605
Tyr Ala Leu Arg Lys Gly Ala Ser Thr Arg Ser Glu Leu Pro Lys Asn
    610                 615                 620
Ser Gly Glu Ser Asn Glu Asn Trp Leu Tyr Met Gly Lys Thr Ser Asp
625                 630                 635                 640
Glu Ala Lys Arg Asn Val Met Asn His Ile Asn Asn Glu Arg Met Asn
                645                 650                 655
Gly Phe Asn Gly Tyr Phe Gly Glu Glu Glu Gly Lys Asn Asn Gly Asn
            660                 665                 670
Leu Asn Val Thr Phe Lys Gly Lys Ser Glu Gln Asn Arg Phe Leu Leu
        675                 680                 685
Thr Gly Gly Thr Asn Leu Asn Gly Asp Leu Lys Val Glu Lys Gly Thr
    690                 695                 700
Leu Phe Leu Ser Gly Arg Pro Thr Pro His Ala Arg Asp Ile Ala Gly
705                 710                 715                 720
Ile Ser Ser Thr Lys Lys Asp Gln His Phe Ala Glu Asn Asn Glu Val
                725                 730                 735
Val Val Glu Asp Asp Trp Ile Asn Arg Asn Phe Lys Ala Thr Asn Ile
            740                 745                 750
Asn Val Thr Asn Asn Ala Thr Leu Tyr Ser Gly Arg Asn Val Ala Asn
        755                 760                 765
```

-continued

Ile Thr Ser Asn Ile Thr Ala Ser Asp Asn Ala Lys Val His Ile Gly
        770                 775                 780

Tyr Lys Ala Gly Asp Thr Val Cys Val Arg Ser Asp Tyr Thr Gly Tyr
785                 790                 795                 800

Val Thr Cys Thr Thr Asp Lys Leu Ser Asp Lys Ala Leu Asn Ser Phe
                805                 810                 815

Asn Ala Thr Asn Val Ser Gly Asn Val Asn Leu Ser Gly Asn Ala Asn
            820                 825                 830

Phe Val Leu Gly Lys Ala Asn Leu Phe Gly Thr Ile Ser Gly Thr Gly
        835                 840                 845

Asn Ser Gln Val Arg Leu Thr Glu Asn Ser His Trp His Leu Thr Gly
    850                 855                 860

Asp Ser Asn Val Asn Gln Leu Asn Leu Asp Lys Gly His Ile His Leu
865                 870                 875                 880

Asn Ala Gln Asn Asp Ala Asn Lys Val Thr Thr Tyr Asn Thr Leu Thr
                885                 890                 895

Val Asn Ser Leu Ser Gly Asn Gly Ser Phe Tyr Tyr Leu Thr Asp Leu
            900                 905                 910

Ser Asn Lys Gln Gly Asp Lys Val Val Thr Lys Ser Ala Thr Gly
    915                 920                 925

Asn Phe Thr Leu Gln Val Ala Asp Lys Thr Gly Glu Pro Thr Lys Asn
    930                 935                 940

Glu Leu Thr Leu Phe Asp Ala Ser Asn Ala Thr Arg Asn Asn Leu Asn
945                 950                 955                 960

Val Ser Leu Val Gly Asn Thr Val Asp Leu Gly Ala Trp Lys Tyr Lys
            965                 970                 975

Leu Arg Asn Val Asn Gly Arg Tyr Asp Leu Tyr Asn Pro Glu Val Glu
            980                 985                 990

Lys Arg Asn Gln Thr Val Asp Thr Thr Asn Ile Thr Thr Pro Asn Asn
        995                 1000                1005

Ile Gln Ala Asp Val Pro Ser Val Pro Ser Asn Asn Glu Glu Ile
    1010                1015                1020

Ala Arg Val Glu Thr Pro Val Pro Pro Ala Pro Ala Thr Pro
    1025                1030                1035

Ser Glu Thr Thr Glu Thr Val Ala Glu Asn Ser Lys Gln Glu Ser
    1040                1045                1050

Lys Thr Val Glu Lys Asn Glu Gln Asp Ala Thr Glu Thr Thr Ala
    1055                1060                1065

Gln Asn Gly Glu Val Ala Glu Glu Ala Lys Pro Ser Val Lys Ala
    1070                1075                1080

Asn Thr Gln Thr Asn Glu Val Ala Gln Ser Gly Ser Glu Thr Glu
    1085                1090                1095

Glu Thr Gln Thr Thr Glu Ile Lys Glu Thr Ala Lys Val Glu Lys
    1100                1105                1110

Glu Glu Lys Ala Lys Val Glu Lys Glu Lys Ala Lys Val Glu
    1115                1120                1125

Lys Asp Glu Ile Gln Glu Ala Pro Gln Met Ala Ser Glu Thr Ser
    1130                1135                1140

Pro Lys Gln Ala Lys Pro Ala Pro Lys Glu Val Ser Thr Asp Thr
    1145                1150                1155

Lys Val Glu Glu Thr Gln Val Gln Ala Gln Pro Gln Thr Gln Ser
    1160                1165                1170

-continued

```
Thr Thr Val Ala Ala Ala Glu Ala Thr Ser Pro Asn Ser Lys Pro
1175                1180                1185

Ala Glu Glu Thr Gln Pro Ser Glu Lys Thr Asn Ala Glu Pro Val
1190                1195                1200

Thr Pro Val Val Ser Lys Asn Gln Thr Glu Asn Thr Thr Asp Gln
1205                1210                1215

Pro Thr Glu Arg Glu Lys Thr Ala Lys Val Glu Thr Glu Lys Thr
1220                1225                1230

Gln Glu Pro Pro Gln Val Ala Ser Gln Ala Ser Pro Lys Gln Glu
1235                1240                1245

Gln Ser Glu Thr Val Gln Pro Gln Ala Val Leu Glu Ser Glu Asn
1250                1255                1260

Val Pro Thr Val Asn Asn Ala Glu Glu Val Gln Ala Gln Leu Gln
1265                1270                1275

Thr Gln Thr Ser Ala Thr Val Ser Thr Lys Gln Pro Ala Pro Glu
1280                1285                1290

Asn Ser Ile Asn Thr Gly Ser Ala Thr Ala Ile Thr Glu Thr Ala
1295                1300                1305

Glu Lys Ser Asp Lys Pro Gln Thr Glu Thr Ala Ala Ser Thr Glu
1310                1315                1320

Asp Ala Ser Gln His Lys Ala Asn Thr Val Ala Asp Asn Ser Val
1325                1330                1335

Ala Asn Asn Ser Glu Ser Ser Glu Pro Lys Ser Arg Arg Arg Arg
1340                1345                1350

Ser Ile Ser Gln Pro Gln Glu Thr Ser Ala Glu Glu Thr Thr Ala
1355                1360                1365

Ala Ser Thr Asp Glu Thr Thr Ile Ala Asp Asn Ser Lys Arg Ser
1370                1375                1380

Lys Pro Asn Arg Arg Ser Arg Arg Ser Val Arg Ser Glu Pro Thr
1385                1390                1395

Val Thr Asn Gly Ser Asp Arg Ser Thr Val Ala Leu Arg Asp Leu
1400                1405                1410

Thr Ser Thr Asn Thr Asn Ala Val Ile Ser Asp Ala Met Ala Lys
1415                1420                1425

Ala Gln Phe Val Ala Leu Asn Val Gly Lys Ala Val Ser Gln His
1430                1435                1440

Ile Ser Gln Leu Glu Met Asn Asn Glu Gly Gln Tyr Asn Val Trp
1445                1450                1455

Val Ser Asn Thr Ser Met Asn Glu Asn Tyr Ser Ser Ser Gln Tyr
1460                1465                1470

Arg Arg Phe Ser Ser Lys Ser Thr Gln Thr Gln Leu Gly Trp Asp
1475                1480                1485

Gln Thr Ile Ser Asn Asn Val Gln Leu Gly Gly Val Phe Thr Tyr
1490                1495                1500

Val Arg Asn Ser Asn Asn Phe Asp Lys Ala Ser Ser Lys Asn Thr
1505                1510                1515

Leu Ala Gln Val Asn Phe Tyr Ser Lys Tyr Tyr Ala Asp Asn His
1520                1525                1530

Trp Tyr Leu Gly Ile Asp Leu Gly Tyr Gly Lys Phe Gln Ser Asn
1535                1540                1545

Leu Lys Thr Asn His Asn Ala Lys Phe Ala Arg His Thr Ala Gln
1550                1555                1560

Phe Gly Leu Thr Ala Gly Lys Ala Phe Asn Leu Gly Asn Phe Gly
```

```
                 1565                1570                1575
Ile Thr Pro Ile Val Gly Val Arg Tyr Ser Tyr Leu Ser Asn Ala
    1580                1585                1590

Asn Phe Ala Leu Ala Lys Asp Arg Ile Lys Val Asn Pro Ile Ser
    1595                1600                1605

Val Lys Thr Ala Phe Ala Gln Val Asp Leu Ser Tyr Thr Tyr His
    1610                1615                1620

Leu Gly Glu Phe Ser Val Thr Pro Ile Leu Ser Ala Arg Tyr Asp
    1625                1630                1635

Thr Asn Gln Gly Ser Gly Lys Ile Asn Val Asn Gln Tyr Asp Phe
    1640                1645                1650

Ala Tyr Asn Val Glu Asn Gln Gln Tyr Asn Ala Gly Leu Lys
    1655                1660                1665

Leu Lys Tyr His Asn Val Lys Leu Ser Leu Ile Gly Gly Leu Thr
    1670                1675                1680

Lys Ala Lys Gln Ala Glu Lys Gln Lys Thr Ala Glu Leu Lys Leu
    1685                1690                1695

Ser Phe Ser Phe
    1700

<210> SEQ ID NO 13
<211> LENGTH: 5085
<212> TYPE: DNA
<213> ORGANISM: Haemophilus influenzae
<220> FEATURE:
<221> NAME/KEY: misc_feature
<222> LOCATION: (1)..(5085)
<223> OTHER INFORMATION: Encodes IgA1 protease from Rd strain

<400> SEQUENCE: 13
atgctaaata aaaaattcaa actcaattt  attgcgctta ctgtcgccta cgcattaacc      60
ccttatacag aagctgcgtt agtgagagac gatgtggatt atcaaatatt tcgtgatttt     120
gcagaaaata aagggagatt ttctgttggt gcaacaaatg tggaagtgag agataaaaat     180
aaccactctt taggcaatgt tttacctaat ggcattccga tgattgattt tagtgttgtg     240
gatgtagata acgcatcgc cacattgata aatccacaat atgtagtagg tgtaaaacac     300
gttagtaacg gcgtgagtga actacatttt gggaacttaa atggcaatat gaataatggc     360
aatgctaaat cgcaccgaga tgtatcttca gaagaaaata gatatttttc cgttgagaaa     420
aatgagtatc caactaaatt gaatggaaaa gcagtaacta ctgaagatca aactcaaaaa     480
cgccgtgaag actactatat gccacgtctt gataaatttg ttaccgaagt tgcaccaata     540
gaggcttcaa ctgcaagtag tgatgctggc acatataatg atcagaataa atatcctgct     600
tttgtaagac taggaagtgg tagtcaattt atttataaaa aaggagataa ttacagctta     660
attttaaata tcatgaggt tggaggcaat aatcttaaat tggtgggcga tgcctatacc     720
tatggtattg caggcacacc ttataaagta aaccacgaaa ataatggact aattggtttt     780
ggcaattcaa agaggaaca cagcgatcca aaaggaatat tatctcaaga tccgcttacc     840
aattatgctg ttttaggcga cagtggctcc ccattatttg tatatgatag agaaaaagga     900
aaatggcttt ttcttgggtc ttatgatttt tgggcaggtt ataacaaaaa atcttggcaa     960
gaatggaata tttataaacc tgaatttgca aaaactgttc tagataaaga tactgcaggt    1020
tctttaactg gttctaacac ccaatacaat tggaatccta ctggcaaaac aagcgttat     1080 tctaatggtt ctgaatctct aaatgttgat ttattcgata gtagtcagga tactgactct    1140
```

-continued

```
aagaagaaca atcacggaaa aagtgtgact cttagaggaa gtggaacgct taccttaaat    1200
aataatatcg atcaaggcgc aggcggcttg ttctttgaag gagattatga agttaaaggc    1260
acttctgata gtaccacttg gaaaggagct ggcgtttctg ttgctgatgg aaaaacagta    1320
acgtggaaag tacataaccc gaaatctgat cgtttagcta aaatcggcaa aggaacatta    1380
attgtagaag gaaagggaga aaataaaggt tcgctaaaag tgggcgatgg tactgttatc    1440
ttaaaacaac aagctgatgc caataataaa gttaaagcct tttcacaagt aggtatagta    1500
agtggtcgct caactgttgt acttaatgat gataagcaag tagatccaaa ttccatttac    1560
tttggcttta gaggtggtcg attagatgcc aatggcaata atctcacttt tgaacatatc    1620
cgtaatattg atgatggcgc aagactagta aatcacaata ccagcaaaac ctctactgta    1680
acaattactg gggaaagtct aattacagat ccaaatacaa ttactccata ataatatagac   1740 gcaccagatg aagataatcc ttatgccttt cgacggatta agatggagg acagctctat     1800 ttaaatttgg aaaattacac ttattatgcg ttaagaaaag gtgcgagcac tcgttcagaa    1860
ttacctaaaa atagtggcga aagcaatgaa aattggctat atatgggtaa aacttccgat    1920
gaagccaaaa gaaatgtaat gaaccatatc aacaacgagc gtatgaatgg ctttaacggt    1980
tattttggcg aggaagaggg taaaaataac ggtaatctaa atgtgacttt taaaggcaaa    2040
agtgagcaaa atcgcttttt attaacaggc ggaacaaacc ttaatggcga tttaaaggtt    2100
gaaaaaggca cattattcct ttctggcaga ccaaacaccgc acgcaagaga tattgcaggt   2160
atttcttcga caaaaaaaga tcaacacttt gctgaaaata atgaagtggt agtagaagat    2220
gactggatta accgcaattt taaagcaaca aatattaatg taaccaataa cgcaacccttt    2280 tattcaggtc gcaatgttgc aaacattact tcaaatatca cagcttctga taatgcaaaa     2340
gtacatattg gctataaagc aggcgatacc gtttgtgtac gttctgacta tacgggctat    2400
gtgacttgca ctactgacaa gttatccgat aaagcccttaa atagctttaa cgccaccaat    2460
gtatctggca atgtaaattt atcaggtaat gcaaactttg tcttaggcaa agctaactta    2520
ttcggcacaa ttagcggcac gggaaatagc caagtacgtt taaccgaaaa tagccattgg    2580
catttaacag gcgatagcaa tgttaatcag ttaaattag acaaggggca tattcattta     2640
aatgcacaaa acgatgcaaa taaagtaact acatataaca cgctgactgt gaatagctta    2700
tcaggtaacg gttctttcta ttatttaact gatctttcca ataaacaagg cgacaaagtt    2760
gttgtaacta atccgccac aggtaacttt acattacaag tggcagataa aacaggcgag     2820
cctacaaaaa atgaactcac gcttttttgat gcgtcaaatg ctacaagaaa taatttgaat    2880
gtgtcattag ttgggaatac cgttgattta ggtgcttgga atataaaatt acgtaatgtt    2940
aatggacgtt acgatttgta taacccagag gtggaaaaaa gaaatcaaac tgtcgatacg    3000
acaaatatca caacacctaa taatattcaa gctgatgtgc ctagcgtacc aagtaacaat    3060
gaagaaatag cccgtgttga acaccagtt ccaccacctg cgcctgctac accatcagag     3120
acaactgaaa cagtggctga aaatagtaag caagaaagta aacagtaga gaaaacgag     3180 caagacgcaa ccgagacaac agctcaaaat ggagaagttg cagaagaagc taaaccaagt    3240
gtaaaagcta atactcaaac aaatgaagtg gctcaaagtg gaagtgaaac cgaggaaact    3300
caaacgactg aaataaaaga aacagctaaa gtagaaaaag aggaaaaggc taaagtagaa    3360
aaagatgaaa ttcaagaagc acctcaaatg gcttctgaaa cgtctccgaa acaagcaaag    3420
cctgctccta aagaagtttc aactgatacg aaagtagaag aaactcaagt tcaagctcaa    3480
ccgcaaacac aatcgacaac tgttgctgcg gcagaggcaa cttcgccaaa cagtaaacca    3540
```

```
gcggaagaaa ctcaaccaag tgaaaaaact aacgctgaac ctgtaacgcc tgtagtatca   3600
aaaaatcaaa cagaaaatac gaccgaccaa ccaacagaaa gagagaaaac ggctaaagta   3660
gaaacagaga aaactcaaga accccctcaa gtggcttctc aagcgtctcc gaaacaggaa   3720
cagtctgaaa ctgttcaacc gcaagcagtg cttgaaagtg aaaatgttcc gactgttaat   3780
aatgcagaag aagttcaagc tcaactgcaa acacaaacaa gtgcaacagt aagcactaaa   3840
caacctgcac cagagaattc aataaatact ggatctgcaa ccgcaataac agaaactgct   3900
gaaaaatccg ataaccaca aacggaaact gcggcttcga ctgaagatgc tagtcagcat   3960
aaagcgaata ctgttgcgga taattctgta gcaaataatt cagaaagcag tgatccaaag   4020
agtagacgta gaagaagtat tagccagcct caagagactt ctgctgaaga acaacagca   4080 gcttctactg acgaaacaac aatagctgat aattcaaaac gcagtaagcc aaatcgtaga   4140
agtagaagaa gtgttcgctc ggaaccaact gttacaaatg gcagcgatcg ttctacagta   4200
gcattgcgcg atctcacaag tacaaacaca atgcggtaa tttctgatgc aatggcaaaa   4260
gcacaatttg ttgcattaaa tgtggggaaa gcagtttctc aacatattag ccagttagaa   4320
atgaataacg aggggcaata taacgttttgg gtatctaata cttcaatgaa cgaaaaattat   4380 tcctcaagtc aatatcgtcg ttttagttct aaaagtacgc aaactcaact tggttgggat   4440
caaacaatct caaacaatgt tcagttaggt ggcgtgttta cttatgttcg caatagtaac   4500
aactttgata aggcaagcag taaaaatact ctagcacaag ttaatttcta ttctaaatat   4560
tatgcggata tcattggta tttgggcatt gatttaggct acggcaagtt ccaaagcaac   4620
ctaaaaacca atcataatgc gaaatttgct cgccatactg cacaatttgg tttaaccgca   4680
ggcaaagcat ttaatcttgg caattttggt attacgccaa tagtaggcgt gcgttatagc   4740
tatttatcaa acgctaattt tgcattagct aaagatcgca ttaaagtaaa tccaatatct   4800
gtcaaaacag cctttgctca gttgattta agttatactt atcacttagg cgagttttcc   4860
gttacgccaa ttttgtctgc tcgatatgat acaaatcaag gcagcggaaa aattaatgta   4920
aatcaatatg attttgctta caacgtggaa aaccaacagc aatataacgc agggcttaaa   4980
ttgaaatatc ataatgtgaa attaagtcta ataggcggat taacaaaagc gaaacaagcg   5040
gaaaaacaaa aaactgcaga attaaaacta agtttttagtt tttaa   5085
```

<210> SEQ ID NO 14
<211> LENGTH: 1694
<212> TYPE: PRT
<213> ORGANISM: Haemophilus influenzae
<220> FEATURE:
<221> NAME/KEY: misc_feature
<222> LOCATION: (1)..(1694)
<223> OTHER INFORMATION: Full-length precursor IgA1 protease from Rd
      strain

<400> SEQUENCE: 14

Met Leu Asn Lys Lys Phe Lys Leu Asn Phe Ile Ala Leu Thr Val Ala
1               5                   10                  15

Tyr Ala Leu Thr Pro Tyr Thr Glu Ala Ala Leu Val Arg Asp Asp Val
                20                  25                  30

Asp Tyr Gln Ile Phe Arg Asp Phe Ala Glu Asn Lys Gly Arg Phe Ser
            35                  40                  45

Val Gly Ala Thr Asn Val Glu Val Arg Asp Lys Asn Asn His Ser Leu
        50                  55                  60

Gly Asn Val Leu Pro Asn Gly Ile Pro Met Ile Asp Phe Ser Val Val

```
                65                  70                  75                  80
Asp Val Asp Lys Arg Ile Ala Thr Leu Ile Asn Pro Gln Tyr Val Val
                    85                  90                  95

Gly Val Lys His Val Ser Asn Gly Val Ser Glu Leu His Phe Gly Asn
                    100                 105                 110

Leu Asn Gly Asn Met Asn Asn Gly Asn Ala Lys Ser His Arg Asp Val
                    115                 120                 125

Ser Ser Glu Glu Asn Arg Tyr Phe Ser Val Lys Asn Glu Tyr Pro
                130                 135                 140

Thr Lys Leu Asn Gly Lys Ala Val Thr Thr Glu Asp Gln Thr Gln Lys
145                 150                 155                 160

Arg Arg Glu Asp Tyr Tyr Met Pro Arg Leu Asp Lys Phe Val Thr Glu
                    165                 170                 175

Val Ala Pro Ile Glu Ala Ser Thr Ala Ser Ser Asp Ala Gly Thr Tyr
                    180                 185                 190

Asn Asp Gln Asn Lys Tyr Pro Ala Phe Val Arg Leu Gly Ser Gly Ser
                    195                 200                 205

Gln Phe Ile Tyr Lys Lys Gly Asp Asn Tyr Ser Leu Ile Leu Asn Asn
                    210                 215                 220

His Glu Val Gly Gly Asn Asn Leu Lys Leu Val Gly Asp Ala Tyr Thr
225                 230                 235                 240

Tyr Gly Ile Ala Gly Thr Pro Tyr Lys Val Asn His Glu Asn Asn Gly
                    245                 250                 255

Leu Ile Gly Phe Gly Asn Ser Lys Glu Glu His Ser Asp Pro Lys Gly
                    260                 265                 270

Ile Leu Ser Gln Asp Pro Leu Thr Asn Tyr Ala Val Leu Gly Asp Ser
                    275                 280                 285

Gly Ser Pro Leu Phe Val Tyr Asp Arg Glu Lys Gly Lys Trp Leu Phe
                290                 295                 300

Leu Gly Ser Tyr Asp Phe Trp Ala Gly Tyr Asn Lys Lys Ser Trp Gln
305                 310                 315                 320

Glu Trp Asn Ile Tyr Lys Pro Glu Phe Ala Lys Thr Val Leu Asp Lys
                    325                 330                 335

Asp Thr Ala Gly Ser Leu Thr Gly Ser Asn Thr Gln Tyr Asn Trp Asn
                    340                 345                 350

Pro Thr Gly Lys Thr Ser Val Ile Ser Asn Gly Ser Glu Ser Leu Asn
                    355                 360                 365

Val Asp Leu Phe Asp Ser Ser Gln Asp Thr Asp Ser Lys Lys Asn Asn
                    370                 375                 380

His Gly Lys Ser Val Thr Leu Arg Gly Ser Gly Thr Leu Thr Leu Asn
385                 390                 395                 400

Asn Asn Ile Asp Gln Gly Ala Gly Gly Leu Phe Phe Glu Gly Asp Tyr
                    405                 410                 415

Glu Val Lys Gly Thr Ser Asp Ser Thr Thr Trp Lys Gly Ala Gly Val
                    420                 425                 430

Ser Val Ala Asp Gly Lys Thr Val Thr Trp Lys Val His Asn Pro Lys
                    435                 440                 445

Ser Asp Arg Leu Ala Lys Ile Gly Lys Gly Thr Leu Ile Val Glu Gly
                    450                 455                 460

Lys Gly Glu Asn Lys Gly Ser Leu Lys Val Gly Asp Gly Thr Val Ile
465                 470                 475                 480

Leu Lys Gln Gln Ala Asp Ala Asn Asn Lys Val Lys Ala Phe Ser Gln
                    485                 490                 495
```

-continued

Val Gly Ile Val Ser Gly Arg Ser Thr Val Leu Asn Asp Asp Lys
            500                 505                 510

Gln Val Asp Pro Asn Ser Ile Tyr Phe Gly Phe Arg Gly Arg Leu
            515                 520                 525

Asp Ala Asn Gly Asn Asn Leu Thr Phe Glu His Ile Arg Asn Ile Asp
530                 535                 540

Asp Gly Ala Arg Leu Val Asn His Asn Thr Ser Lys Thr Ser Thr Val
545                 550                 555                 560

Thr Ile Thr Gly Glu Ser Leu Ile Thr Asp Pro Asn Thr Ile Thr Pro
            565                 570                 575

Tyr Asn Ile Asp Ala Pro Asp Glu Asp Asn Pro Tyr Ala Phe Arg Arg
            580                 585                 590

Ile Lys Asp Gly Gly Gln Leu Tyr Leu Asn Leu Glu Asn Tyr Thr Tyr
            595                 600                 605

Tyr Ala Leu Arg Lys Gly Ala Ser Thr Arg Ser Glu Leu Pro Lys Asn
            610                 615                 620

Ser Gly Glu Ser Asn Glu Asn Trp Leu Tyr Met Gly Lys Thr Ser Asp
625                 630                 635                 640

Glu Ala Lys Arg Asn Val Met Asn His Ile Asn Asn Glu Arg Met Asn
            645                 650                 655

Gly Phe Asn Gly Tyr Phe Gly Glu Glu Glu Gly Lys Asn Asn Gly Asn
            660                 665                 670

Leu Asn Val Thr Phe Lys Gly Lys Ser Glu Gln Asn Arg Phe Leu Leu
            675                 680                 685

Thr Gly Gly Thr Asn Leu Asn Gly Asp Leu Lys Val Glu Lys Gly Thr
            690                 695                 700

Leu Phe Leu Ser Gly Arg Pro Thr Pro His Ala Arg Asp Ile Ala Gly
705                 710                 715                 720

Ile Ser Ser Thr Lys Lys Asp Gln His Phe Ala Glu Asn Asn Glu Val
            725                 730                 735

Val Val Glu Asp Asp Trp Ile Asn Arg Asn Phe Lys Ala Thr Asn Ile
            740                 745                 750

Asn Val Thr Asn Asn Ala Thr Leu Tyr Ser Gly Arg Asn Val Ala Asn
            755                 760                 765

Ile Thr Ser Asn Ile Thr Ala Ser Asp Asn Ala Lys Val His Ile Gly
            770                 775                 780

Tyr Lys Ala Gly Asp Thr Val Cys Val Arg Ser Asp Tyr Thr Gly Tyr
785                 790                 795                 800

Val Thr Cys Thr Thr Asp Lys Leu Ser Asp Lys Ala Leu Asn Ser Phe
            805                 810                 815

Asn Ala Thr Asn Val Ser Gly Asn Val Asn Leu Ser Gly Asn Ala Asn
            820                 825                 830

Phe Val Leu Gly Lys Ala Asn Leu Phe Gly Thr Ile Ser Gly Thr Gly
            835                 840                 845

Asn Ser Gln Val Arg Leu Thr Glu Asn Ser His Trp His Leu Thr Gly
            850                 855                 860

Asp Ser Asn Val Asn Gln Leu Asn Leu Asp Lys Gly His Ile His Leu
865                 870                 875                 880

Asn Ala Gln Asn Asp Ala Asn Lys Val Thr Thr Tyr Asn Thr Leu Thr
            885                 890                 895

Val Asn Ser Leu Ser Gly Asn Gly Ser Phe Tyr Tyr Leu Thr Asp Leu
            900                 905                 910

```
Ser Asn Lys Gln Gly Asp Lys Val Val Thr Lys Ser Ala Thr Gly
            915                 920                 925

Asn Phe Thr Leu Gln Val Ala Asp Lys Thr Gly Glu Pro Thr Lys Asn
        930                 935                 940

Glu Leu Thr Leu Phe Asp Ala Ser Asn Ala Thr Arg Asn Asn Leu Asn
945                 950                 955                 960

Val Ser Leu Val Gly Asn Thr Val Asp Leu Gly Ala Trp Lys Tyr Lys
                965                 970                 975

Leu Arg Asn Val Asn Gly Arg Tyr Asp Leu Tyr Asn Pro Glu Val Glu
            980                 985                 990

Lys Arg Asn Gln Thr Val Asp Thr Thr Asn Ile Thr Thr Pro Asn Asn
        995                 1000                1005

Ile Gln Ala Asp Val Pro Ser Val Pro Ser Asn Glu Glu Ile
    1010                1015                1020

Ala Arg Val Glu Thr Pro Val Pro Pro Ala Pro Ala Thr Pro
    1025                1030                1035

Ser Glu Thr Thr Glu Thr Val Ala Glu Asn Ser Lys Gln Glu Ser
    1040                1045                1050

Lys Thr Val Glu Lys Asn Glu Gln Asp Ala Thr Glu Thr Thr Ala
    1055                1060                1065

Gln Asn Gly Glu Val Ala Glu Glu Ala Lys Pro Ser Val Lys Ala
    1070                1075                1080

Asn Thr Gln Thr Asn Glu Val Ala Gln Ser Gly Ser Glu Thr Glu
    1085                1090                1095

Glu Thr Gln Thr Thr Glu Ile Lys Glu Thr Ala Lys Val Glu Lys
    1100                1105                1110

Glu Glu Lys Ala Lys Val Glu Lys Asp Glu Ile Gln Glu Ala Pro
    1115                1120                1125

Gln Met Ala Ser Glu Thr Ser Pro Lys Gln Ala Lys Pro Ala Pro
    1130                1135                1140

Lys Glu Val Ser Thr Asp Thr Lys Val Glu Glu Thr Gln Val Gln
    1145                1150                1155

Ala Gln Pro Gln Thr Gln Ser Thr Thr Val Ala Ala Ala Glu Ala
    1160                1165                1170

Thr Ser Pro Asn Ser Lys Pro Ala Glu Glu Thr Gln Pro Ser Glu
    1175                1180                1185

Lys Thr Asn Ala Glu Pro Val Thr Pro Val Val Ser Lys Asn Gln
    1190                1195                1200

Thr Glu Asn Thr Thr Asp Gln Pro Thr Glu Arg Glu Lys Thr Ala
    1205                1210                1215

Lys Val Glu Thr Glu Lys Thr Gln Glu Pro Pro Gln Val Ala Ser
    1220                1225                1230

Gln Ala Ser Pro Lys Gln Glu Gln Ser Glu Thr Val Gln Pro Gln
    1235                1240                1245

Ala Val Leu Glu Ser Glu Asn Val Pro Thr Val Asn Asn Ala Glu
    1250                1255                1260

Glu Val Gln Ala Gln Leu Gln Thr Gln Thr Ser Ala Thr Val Ser
    1265                1270                1275

Thr Lys Gln Pro Ala Pro Glu Asn Ser Ile Asn Thr Gly Ser Ala
    1280                1285                1290

Thr Ala Ile Thr Glu Thr Ala Glu Lys Ser Asp Lys Pro Gln Thr
    1295                1300                1305

Glu Thr Ala Ala Ser Thr Glu Asp Ala Ser Gln His Lys Ala Asn
```

```
                    1310                1315                 1320
Thr Val Ala Asp Asn Ser Val Ala Asn Ser Glu Ser Ser Asp
            1325                1330                1335
Pro Lys Ser Arg Arg Arg Ser Ile Ser Gln Pro Gln Glu Thr
            1340                1345                1350
Ser Ala Glu Glu Thr Thr Ala Ala Ser Thr Asp Glu Thr Thr Ile
            1355                1360                1365
Ala Asp Asn Ser Lys Arg Ser Lys Pro Asn Arg Arg Ser Arg Arg
            1370                1375                1380
Ser Val Arg Ser Glu Pro Thr Val Thr Asn Gly Ser Asp Arg Ser
            1385                1390                1395
Thr Val Ala Leu Arg Asp Leu Thr Ser Thr Asn Thr Asn Ala Val
            1400                1405                1410
Ile Ser Asp Ala Met Ala Lys Ala Gln Phe Val Ala Leu Asn Val
            1415                1420                1425
Gly Lys Ala Val Ser Gln His Ile Ser Gln Leu Glu Met Asn Asn
            1430                1435                1440
Glu Gly Gln Tyr Asn Val Trp Val Ser Asn Thr Ser Met Asn Glu
            1445                1450                1455
Asn Tyr Ser Ser Ser Gln Tyr Arg Arg Phe Ser Ser Lys Ser Thr
            1460                1465                1470
Gln Thr Gln Leu Gly Trp Asp Gln Thr Ile Ser Asn Asn Val Gln
            1475                1480                1485
Leu Gly Gly Val Phe Thr Tyr Val Arg Asn Ser Asn Asn Phe Asp
            1490                1495                1500
Lys Ala Ser Ser Lys Asn Thr Leu Ala Gln Val Asn Phe Tyr Ser
            1505                1510                1515
Lys Tyr Tyr Ala Asp Asn His Trp Tyr Leu Gly Ile Asp Leu Gly
            1520                1525                1530
Tyr Gly Lys Phe Gln Ser Asn Leu Lys Thr Asn His Asn Ala Lys
            1535                1540                1545
Phe Ala Arg His Thr Ala Gln Phe Gly Leu Thr Ala Gly Lys Ala
            1550                1555                1560
Phe Asn Leu Gly Asn Phe Gly Ile Thr Pro Ile Val Gly Val Arg
            1565                1570                1575
Tyr Ser Tyr Leu Ser Asn Ala Asn Phe Ala Leu Ala Lys Asp Arg
            1580                1585                1590
Ile Lys Val Asn Pro Ile Ser Val Lys Thr Ala Phe Ala Gln Val
            1595                1600                1605
Asp Leu Ser Tyr Thr Tyr His Leu Gly Glu Phe Ser Val Thr Pro
            1610                1615                1620
Ile Leu Ser Ala Arg Tyr Asp Thr Asn Gln Gly Ser Gly Lys Ile
            1625                1630                1635
Asn Val Asn Gln Tyr Asp Phe Ala Tyr Asn Val Glu Asn Gln Gln
            1640                1645                1650
Gln Tyr Asn Ala Gly Leu Lys Leu Lys Tyr His Asn Val Lys Leu
            1655                1660                1665
Ser Leu Ile Gly Gly Leu Thr Lys Ala Lys Gln Ala Glu Lys Gln
            1670                1675                1680
Lys Thr Ala Glu Leu Lys Leu Ser Phe Ser Phe
            1685                1690

<210> SEQ ID NO 15
```

<211> LENGTH: 231
<212> TYPE: DNA
<213> ORGANISM: Haemophilus influenzae
<220> FEATURE:
<221> NAME/KEY: misc_feature
<222> LOCATION: (1)..(231)
<223> OTHER INFORMATION: Partial nucleotide sequence for IgA1 protease from 7768 strain

<400> SEQUENCE: 15

```
tgcgcctgct acaccatcag agacaactct aaaacagtgg ctgaaaataa tccgcaagaa    60
agtgaaacag tagagaaaaa cgagcaagac gcaaccgaga caacagctca aatggagaa    120
attacaaaag aagctaaacc aagtgtaaaa gctaacactc aaacaaatga agtggctcaa    180
agtggaagtg aaaccgagga aactcaaacg actgaaacaa agaaacagc t              231
```

<210> SEQ ID NO 16
<211> LENGTH: 235
<212> TYPE: DNA
<213> ORGANISM: Haemophilus influenzae
<220> FEATURE:
<221> NAME/KEY: modified_base
<222> LOCATION: (137)..(137)
<223> OTHER INFORMATION: a, c, t, g, unknown or other
<220> FEATURE:
<221> NAME/KEY: misc_feature
<222> LOCATION: (1)..(235)
<223> OTHER INFORMATION: Partial nucleotide sequence for IgA1 protease from 6338 strain

<400> SEQUENCE: 16

```
atcagagaca actaaaacag tggctgaaaa tagtaagcaa gaaagtaaaa caatagcgaa    60
aaacgagcaa gacgcaaccg agacaagatc tcaaaatgat gaagttgcaa agaagctaa    120
accaagtgta gaagctnatc ctcaaacaaa tgaagtggct caaagtggaa gcaaaaccga    180
ggaaactcaa acgactgaaa caaagaaac agctaaagta gaaaagaga aaacg           235
```

<210> SEQ ID NO 17
<211> LENGTH: 749
<212> TYPE: DNA
<213> ORGANISM: Haemophilus influenzae
<220> FEATURE:
<221> NAME/KEY: misc_feature
<222> LOCATION: (1)..(749)
<223> OTHER INFORMATION: Partial nucleotide sequence for IgA1 protease from 2509 strain

<400> SEQUENCE: 17

```
aaatcaaaat ggtttaata gaacaggaac agggtattcg attgtagctg atacgaaaga    60
aacggttatg attacgcata atacgataa tggagaaatt ttcaaggaga agtggtatt    120
caaatcagaa tttactgagg atattgataa atacaaagaa aacagacctg atctgacagc    180
cactggaatg aaatctactg gaacaaattc ctatgctatt acttataaga cagtaacagc    240
tgaagaagct ccaaaagaac cactaaaaat ggataaccg catacattat ctattgaaaa    300
taaaaaacca gttgctgttg ttaaaccaga agaaactcca aatggtgtta cgtctcacaa    360
gcattctgaa actgatccaa aatctgatac cgcaacacaa gctgataatc caaattcaga    420
aagtgttcca tcagagacaa ttgaaaaagt ggctgaaaat agtccgcaag aaagtgaaac    480
agtagcgaaa aacgagcaag aagccgccga acaacacct caaaatgatg aagttgcaaa    540
agctcaatca gtgcagaaa ctaaggctaa acaaatgaa gtggctcaaa gtggaagtga    600
agccgaggaa actcaagagg ctgaaactac tcgcgagcct gaaataaatt ctactgaagt    660
```

| actgaagaaa cagcagtgga aaattatcca acaagcagtg aaccaaagag tagacgtaga | 720 |
| agaaatgtta gctcgtcttc aaataatat | 749 |

<210> SEQ ID NO 18
<211> LENGTH: 5719
<212> TYPE: DNA
<213> ORGANISM: Haemophilus influenzae
<220> FEATURE:
<221> NAME/KEY: misc_feature
<222> LOCATION: (1)..(5719)
<223> OTHER INFORMATION: Encodes IgA1 protease from aegyptius strain

<400> SEQUENCE: 18

| accgccatta cgcaaagaca actaaaagaa atgcaagttg aaaataaaaa aatgttttct | 60 |
| gttcataatg gcatcattaa cgccttaaat tagccaaaag tgcggtggaa aatacgccaa | 120 |
| tttttaaaa aatatcaaaa attattatca ttacctcgta aatgtaattc aagttttgag | 180 |
| cgatttatgc tataaagctc gctcattata aaatgaaga caacttgcaa actatcgacg | 240 |
| caacacagcc aagatttgaa tcaacttgta accgtatatc aaattgtgtc ctatcaaatc | 300 |
| tacttttttaa acttaattaa taaggacagc ttctatgcta aataaaaat tcaaactcaa | 360 |
| ttttattgcg cttactgtcg cctacgcatt aaccccttat acagaagctg cgttagtgag | 420 |
| agacgatgtg gattatcaaa tatttcgtga ttttgcagaa ataaaggga gattttctgt | 480 |
| tggtgcaaca aatgtggaag tgagagataa aaataaccac tctttaggca atgctttacc | 540 |
| taatggcatt ccgatgattg atttagtgt tgtggatgtg aataaacgta ttggtacatt | 600 |
| agtcgatccg caatatattg tgagcgtaaa acacgcacat caatatatga atgactttta | 660 |
| ttttggacat tataacggac accgtgatgt ttctaatgat gaaaataaat atagtgtagt | 720 |
| cacacaaaat aatgttaatt caagtgaaaa gtgggatgtt aataagcgat tagacgacta | 780 |
| taatatgcct cgtttaaata aatttgttac cgaggttgca ccaactaccc ctacattagc | 840 |
| aggagacgat ttagaaacct ataaagataa agaaaaatat ccgtcctttg tacgagtagg | 900 |
| tgctggtcgc caattagtat atgaaaaagg aagccgccat gtagaaggta atgaacatgg | 960 |
| agaggattta aaagatcttt cagttgcata taattatgct atcggtggta caccttatga | 1020 |
| agggattaat attgatcctt cccaaagtaa aaaaggactt atcggttttg gagatagtcg | 1080 |
| caaagatcac gttattgata ctaaaatttt actctcccaa gctcccctaa ccaactacgg | 1140 |
| cgtattaggc gatagtggtt cccctttatt tgcttttgat aaacaacaaa acaaatggat | 1200 |
| ttttatcggg ccttatactt attgggcagg ctatgagaaa aaatcttggc aagaatggaa | 1260 |
| tatttataaa actactttg ctgatggtat aaaaaaccga gataacgcta aacctgtgcc | 1320 |
| tttctctaac aaagaatatc gttggacaaa cactacaaat catcaaagtg aaataaaaaa | 1380 |
| cactgatcat actattactg taacactccc ctcagatcca gatcgacttg ttaattatca | 1440 |
| gaaagaagaa acaagaata ctgggcaaaa tgtaattttt gaaggaaatg gtaattctaa | 1500 |
| aaatacactt gttttagaaa ataatatcaa tcaaggtgct ggcggtttat tctttaaagg | 1560 |
| caactatgaa gttaaaggaa caactgacaa tattacttgg gtaggcggcg gaattgatgt | 1620 |
| tgctgaagga aaaacagtca cgtggaaagt acataatcct gaaaaagacc atttagctaa | 1680 |
| aattggtaaa gggaagctaa ttgttgaagg caaaggagat aataaaggtt cgctaaaagt | 1740 |
| gggcgatggc acagtagttt taaaacaaca acaactaca ggacaacacg ctttttgcttc | 1800 |
| tgtagggatt gtaagtggtc gctcaactgt tgtgcttaat gatgataaac aagtagatcc | 1860 |
| aaattcaatt tactttggtt ttagaggcgg tcgattagac ttaaacggta attcacttac | 1920 |

```
atttgaccac atcagaaata ttgatgatgg ggcaagacta gttaatcata atatgactaa      1980
tgcctcaaat ataacgatta ctggggaaag tctaattaca gatccaaaga aaattaatcc      2040
atattatata aaagcacgag aggaagataa tccttatgcc tttcgatgga tcaaagatgg      2100
agaacagctc tattttaatc tagaaaatta cacttattat gcgttaagaa aaggtggtaa      2160
agctaactcg caacttcctt ataatgacaa agaaagcaac gaaaactggc tatatatggg      2220
taaaaatgcc gatgaagcca aaagaaatgt aatgaagcat atcaacaacg agcgtatgaa      2280
tggctttaac ggttattttg gtgaggaaga aggtaaagat aacggtaatc taaacgttac      2340
ctttaaaggt aaaaccgagc aaaatcgctt tttattaaca ggcggaacaa accttaatgg      2400
caatttaaag gttgaacaag gtacattatt cctttctggc agaccaacac cgcacgcaag      2460
agatattgcg ggtatttctt caacaaagaa agactcacac tttgctgaaa ataatgaagt      2520
ggtggtagaa gacgactgga ttaaccgcaa ttttaaagca actacaatga acgtgactgg      2580
caatgcctca ctttattcag gacgcaatgt tgaaagcatt acttcaaata tcacagcttc      2640
tagcaaagca caagtgcata tcggctataa aaaggcgac accgtttgtg tgcgttctga      2700 ctatcgggc tatgtgactt gccataatgg cgatttatcg gaaaaagccc ttaatagctt      2760
taacgccact aatgtatttg gtaatgtaaa tttatcaggt aatgcaaact ttaccttagg      2820
caaagctaat ttgcatggat caattcaggc aggtggaaac agccaagtgc atttaaccga      2880
aaatagccat tggtatttaa caggcgatag taatgttcat cagttagatt taaaaaatgg      2940
acatattcat ttaaattcag ctgataataa aaataatgtg acaaaatata atacgctcaa      3000
tattagcaat ttatcaggta acggttcttt ctattattta actgatcttt ctaaaaatca      3060
gggcgataaa gttgttgtaa ccaaatccgc caaaggtaac tttacattac aagtagcaga      3120
taaaacaggc gaacctacaa aaaatgaact cacgcttttt gatgcttcaa atgctacaag      3180
aagtaattta gtagtgacat tagcaaatgg cagtgttgat cgaggtgctt ggaaatacaa      3240
attacgtgaa aacaatggac gttacgattt gtataaccca gaagtagaaa aagacatca      3300 aactgtcgat acgccaagtg ttgaaatgcc taatgatatg caagctgatg cacctagcgc      3360
accaagcaac aatgaagaaa tagcccgtgt tgatgcaccc gttccaccac cagcaccacc      3420
tgcacctgct actggatcag caatggcaaa agagcaacca aaaactcgtc ctgcagaaac      3480
cgctcaacca acaatggaag agacaaaggc tgctaactca acggaaactg ctccaaaatc      3540
tgatacaaca acacaagctg atacttcaaa ttcagaaagt gttccatcag agacaactga      3600
aacagtggct gaaaatagtc cgcaagaaag tgcatcagta gagaaaaatg cagaagaagc      3660
aaccgagaca acacctcaaa atgatgaagt tgcaaaagaa gctaaaccaa ctgtagagac      3720
taaggatcaa acaaatgaaa tgactcaaag tggaagtgaa ataccacag aaactcaagc      3780 agaaaataaa gtttctcaac caacagaaac agataaaata gctacggtag aaacagagga      3840
gacggctaga gtagaaaaag aggaaactca agtagcttct caaacgtttc caaaacaaga      3900
agaaccagaa atgactaaac agcaagctga gcctgaaaca aggaatgttc cgattgttaa      3960
taatctagaa gaagctcaac cgcaaacaaa accgataact gttgctacgg cagagacacc      4020
tacatcaaac agtaaatcag cagaaaaaac tcaaccaagt ggagaaacta acgctgaacc      4080
tgtaacgcct gtagtcgtat cagaaaatca accagaaaat acgatttctc aaccaacaga      4140
agatacggtt gttaaagtag aaacagaaga aacgcctaaa gtagaaacgg ggggaactaa      4200
agaagcccct caagtagctt ctcaaacgtc tccgaaacaa gaagagcctg aaactgttca      4260
```

| accgcaagcg gagcctgctc aagagaattc tccgactgtt aataatgtag aagaagctca | 4320 |
| accgcaaaca caaccgacaa tagttgcagc gaaagagata actgcaccaa acagtgcgca | 4380 |
| gaaagaaact gcccaatctg tagctaatcc aaaaacagct gaacaacctg tgacagtaag | 4440 |
| cactgaaaac cctgtagtgg aaaatccaga gaataccact caacctgcgg ttaattcaga | 4500 |
| agcagttcaa ccagaaacag cgacaacagg aactgttagt cagcctaaag aggcttctac | 4560 |
| tgatgaaaca acagtggctt ctactgatga acaacaggg acttctgctg aagaaacaac | 4620 |
| tgtagctgat aattcagaag ccagtaaacc gaagcgcaga tctagaagag atgttagctc | 4680 |
| aactccgcat aatgttgagc cagctgttac aggtggtggt agagatcgtt ctgcagtagt | 4740 |
| agtaccatta cgtgatctca caagtacaaa caccaatgcg gtactttctg acgcaatggc | 4800 |
| aaaagcacaa tttgttgcat taaatgtagg gaaagcagtt tctcaacata ttagccagtt | 4860 |
| agaaatgaat aacgagggac aatataacgt ttgggtgtcg aatacctcta tgaacgaaaa | 4920 |
| ttattcctca gatcaatatc gtcgttttag ttctaaaagt gcgcaaactc aacttggttg | 4980 |
| ggatcaaaca atctcgaaca atgttcagtt aggtggcata ttgacttatg ttcgcaatag | 5040 |
| taacagcttt gataaggcaa gcagtaaaaa caccttagca caagcaaatt tctattctaa | 5100 |
| atattatgca gataatcatt ggtatttagc ggtggattta ggctatggta atttccaaag | 5160 |
| caacttacaa actaatcata atgcgaaatt tgatcgccat actgcacaaa ttggtttaac | 5220 |
| cgcaggcaaa gcatttaatc ttggcaatgt tgctgttaaa ccaactgtgg gggttcgtta | 5280 |
| tagttactta tcaaacgctg attttgcatt agatcaagat cgcattaaag taaatcctat | 5340 |
| atctgtcaaa acagcctttg ctcaagttga tttaagttat acttataact taggcgagtt | 5400 |
| tgccattacg ccaattttgt ctgctcgata tgatgccaat caaggcaatg caaaattaa | 5460 |
| tgtaagtgga tatgctttg cttacaatgt ggaaaaccaa cagcaatata acgcaggact | 5520 |
| taaattgaaa tatcataatg tgaaattaag tctaatgggt ggattaacaa agcaaaaca | 5580 |
| agcggaaaaa caaaaaactg ctgaagtaaa actaagtttt agtttttaat aagcctgttt | 5640 |
| gaattaatgt tataaacaac aaagccctgt gtattacagg gctttatttt tgaatgaaat | 5700 |
| tcagtgatta agtgcggtg | 5719 |

<210> SEQ ID NO 19
<211> LENGTH: 1764
<212> TYPE: PRT
<213> ORGANISM: Haemophilus influenzae
<220> FEATURE:
<221> NAME/KEY: misc_feature
<222> LOCATION: (1)..(1764)
<223> OTHER INFORMATION: Full-length precursor IgA1 protease from
      aegyptius strain

<400> SEQUENCE: 19

Met Leu Asn Lys Lys Phe Lys Leu Asn Phe Ile Ala Leu Thr Val Ala
1               5                   10                  15

Tyr Ala Leu Thr Pro Tyr Thr Glu Ala Ala Leu Val Arg Asp Asp Val
            20                  25                  30

Asp Tyr Gln Ile Phe Arg Asp Phe Ala Glu Asn Lys Gly Arg Phe Ser
        35                  40                  45

Val Gly Ala Thr Asn Val Glu Val Arg Asp Lys Asn Asn His Ser Leu
    50                  55                  60

Gly Asn Ala Leu Pro Asn Gly Ile Pro Met Ile Asp Phe Ser Val Val
65                  70                  75                  80

Asp Val Asn Lys Arg Ile Gly Thr Leu Val Asp Pro Gln Tyr Ile Val

```
            85                  90                  95
Ser Val Lys His Ala His Gln Tyr Met Asn Asp Phe Tyr Phe Gly His
            100                 105                 110
Tyr Asn Gly His Arg Asp Val Ser Asn Asp Glu Asn Lys Tyr Ser Val
            115                 120                 125
Val Thr Gln Asn Asn Val Asn Ser Ser Glu Lys Trp Asp Val Asn Lys
            130                 135                 140
Arg Leu Asp Asp Tyr Asn Met Pro Arg Leu Asn Lys Phe Val Thr Glu
145                 150                 155                 160
Val Ala Pro Thr Thr Pro Thr Leu Ala Gly Asp Asp Leu Glu Thr Tyr
                165                 170                 175
Lys Asp Lys Glu Lys Tyr Pro Ser Phe Val Arg Val Gly Ala Gly Arg
                180                 185                 190
Gln Leu Val Tyr Glu Lys Gly Ser Arg His Val Glu Gly Asn Glu His
                195                 200                 205
Gly Glu Asp Leu Lys Asp Leu Ser Val Ala Tyr Asn Tyr Ala Ile Gly
            210                 215                 220
Gly Thr Pro Tyr Glu Gly Ile Asn Ile Asp Pro Ser Gln Ser Lys Lys
225                 230                 235                 240
Gly Leu Ile Gly Phe Gly Asp Ser Arg Lys Asp His Val Ile Asp Thr
                245                 250                 255
Lys Ile Leu Leu Ser Gln Ala Pro Leu Thr Asn Tyr Gly Val Leu Gly
            260                 265                 270
Asp Ser Gly Ser Pro Leu Phe Ala Phe Asp Lys Gln Gln Asn Lys Trp
            275                 280                 285
Ile Phe Ile Gly Pro Tyr Thr Tyr Trp Ala Gly Tyr Glu Lys Lys Ser
290                 295                 300
Trp Gln Glu Trp Asn Ile Tyr Lys Thr Thr Phe Ala Asp Gly Ile Lys
305                 310                 315                 320
Asn Arg Asp Asn Ala Lys Pro Val Pro Phe Ser Asn Lys Glu Tyr Arg
                325                 330                 335
Trp Thr Asn Thr Thr Asn His Gln Ser Glu Ile Lys Asn Thr Asp His
                340                 345                 350
Thr Ile Thr Val Thr Leu Pro Ser Asp Pro Asp Arg Leu Val Asn Tyr
            355                 360                 365
Gln Lys Glu Glu Asn Lys Asn Thr Gly Gln Asn Val Ile Phe Glu Gly
            370                 375                 380
Asn Gly Asn Ser Lys Asn Thr Leu Val Leu Glu Asn Asn Ile Asn Gln
385                 390                 395                 400
Gly Ala Gly Gly Leu Phe Phe Lys Gly Asn Tyr Glu Val Lys Gly Thr
                405                 410                 415
Thr Asp Asn Ile Thr Trp Val Gly Gly Ile Asp Val Ala Glu Gly
            420                 425                 430
Lys Thr Val Thr Trp Lys Val His Asn Pro Glu Lys Asp His Leu Ala
            435                 440                 445
Lys Ile Gly Lys Gly Lys Leu Ile Val Glu Gly Lys Gly Asp Asn Lys
            450                 455                 460
Gly Ser Leu Lys Val Gly Asp Gly Thr Val Val Leu Lys Gln Gln Thr
465                 470                 475                 480
Thr Thr Gly Gln His Ala Phe Ala Ser Val Gly Ile Val Ser Gly Arg
                485                 490                 495
Ser Thr Val Val Leu Asn Asp Asp Lys Gln Val Asp Pro Asn Ser Ile
                500                 505                 510
```

```
Tyr Phe Gly Phe Arg Gly Gly Arg Leu Asp Leu Asn Gly Asn Ser Leu
            515                 520                 525

Thr Phe Asp His Ile Arg Asn Ile Asp Asp Gly Ala Arg Leu Val Asn
        530                 535                 540

His Asn Met Thr Asn Ala Ser Asn Ile Thr Ile Thr Gly Glu Ser Leu
545                 550                 555                 560

Ile Thr Asp Pro Lys Lys Ile Asn Pro Tyr Tyr Ile Lys Ala Arg Glu
                565                 570                 575

Glu Asp Asn Pro Tyr Ala Phe Arg Trp Ile Lys Asp Gly Glu Gln Leu
                580                 585                 590

Tyr Phe Asn Leu Glu Asn Tyr Thr Tyr Tyr Ala Leu Arg Lys Gly Gly
            595                 600                 605

Lys Ala Asn Ser Gln Leu Pro Tyr Asn Asp Lys Glu Ser Asn Glu Asn
            610                 615                 620

Trp Leu Tyr Met Gly Lys Asn Ala Asp Glu Ala Lys Arg Asn Val Met
625                 630                 635                 640

Lys His Ile Asn Asn Glu Arg Met Asn Gly Phe Asn Gly Tyr Phe Gly
                645                 650                 655

Glu Glu Glu Gly Lys Asp Asn Gly Asn Leu Asn Val Thr Phe Lys Gly
            660                 665                 670

Lys Thr Glu Gln Asn Arg Phe Leu Leu Thr Gly Gly Thr Asn Leu Asn
            675                 680                 685

Gly Asn Leu Lys Val Glu Gln Gly Thr Leu Phe Leu Ser Gly Arg Pro
            690                 695                 700

Thr Pro His Ala Arg Asp Ile Ala Gly Ile Ser Ser Thr Lys Lys Asp
705                 710                 715                 720

Ser His Phe Ala Glu Asn Asn Glu Val Val Val Glu Asp Asp Trp Ile
                725                 730                 735

Asn Arg Asn Phe Lys Ala Thr Thr Met Asn Val Thr Gly Asn Ala Ser
            740                 745                 750

Leu Tyr Ser Gly Arg Asn Val Glu Ser Ile Thr Ser Asn Ile Thr Ala
            755                 760                 765

Ser Ser Lys Ala Gln Val His Ile Gly Tyr Lys Lys Gly Asp Thr Val
770                 775                 780

Cys Val Arg Ser Asp Tyr Thr Gly Tyr Val Thr Cys His Asn Gly Asp
785                 790                 795                 800

Leu Ser Glu Lys Ala Leu Asn Ser Phe Asn Ala Thr Asn Val Phe Gly
                805                 810                 815

Asn Val Asn Leu Ser Gly Asn Ala Asn Phe Thr Leu Gly Lys Ala Asn
            820                 825                 830

Leu His Gly Ser Ile Gln Ala Gly Gly Asn Ser Gln Val His Leu Thr
            835                 840                 845

Glu Asn Ser His Trp Tyr Leu Thr Gly Asp Ser Asn Val His Gln Leu
            850                 855                 860

Asp Leu Lys Asn Gly His Ile His Leu Asn Ser Ala Asp Asn Lys Asn
865                 870                 875                 880

Asn Val Thr Lys Tyr Asn Thr Leu Asn Ile Ser Asn Leu Ser Gly Asn
                885                 890                 895

Gly Ser Phe Tyr Tyr Leu Thr Asp Leu Ser Lys Asn Gln Gly Asp Lys
            900                 905                 910

Val Val Val Thr Lys Ser Ala Lys Gly Asn Phe Thr Leu Gln Val Ala
            915                 920                 925
```

```
Asp Lys Thr Gly Glu Pro Thr Lys Asn Glu Leu Thr Leu Phe Asp Ala
    930                 935                 940

Ser Asn Ala Thr Arg Ser Asn Leu Val Val Thr Leu Ala Asn Gly Ser
945                 950                 955                 960

Val Asp Arg Gly Ala Trp Lys Tyr Lys Leu Arg Glu Asn Asn Gly Arg
                965                 970                 975

Tyr Asp Leu Tyr Asn Pro Glu Val Glu Arg Arg His Gln Thr Val Asp
            980                 985                 990

Thr Pro Ser Val Glu Met Pro Asn Asp Met Gln Ala Asp Ala Pro Ser
        995                 1000                1005

Ala Pro Ser Asn Asn Glu Glu Ile Ala Arg Val Asp Ala Pro Val
    1010                1015                1020

Pro Pro Pro Ala Pro Ala Pro Ala Thr Gly Ser Ala Met Ala
    1025                1030                1035

Lys Glu Gln Pro Lys Thr Arg Pro Ala Glu Thr Ala Gln Pro Thr
    1040                1045                1050

Met Glu Glu Thr Lys Ala Ala Asn Ser Thr Glu Thr Ala Pro Lys
    1055                1060                1065

Ser Asp Thr Thr Thr Gln Ala Asp Thr Ser Asn Ser Glu Ser Val
    1070                1075                1080

Pro Ser Glu Thr Thr Glu Thr Val Ala Glu Asn Ser Pro Gln Glu
    1085                1090                1095

Ser Ala Ser Val Glu Lys Asn Ala Glu Ala Thr Glu Thr Thr
    1100                1105                1110

Pro Gln Asn Asp Glu Val Ala Lys Glu Ala Lys Pro Thr Val Glu
    1115                1120                1125

Thr Lys Asp Gln Thr Asn Glu Met Thr Gln Ser Gly Ser Glu Asn
    1130                1135                1140

Thr Thr Glu Thr Gln Ala Glu Asn Lys Val Ser Gln Pro Thr Glu
    1145                1150                1155

Thr Asp Lys Ile Ala Thr Val Glu Thr Glu Glu Thr Ala Arg Val
    1160                1165                1170

Glu Lys Glu Glu Thr Gln Val Ala Ser Gln Thr Phe Pro Lys Gln
    1175                1180                1185

Glu Glu Pro Glu Met Thr Lys Gln Gln Ala Glu Pro Glu Thr Arg
    1190                1195                1200

Asn Val Pro Ile Val Asn Asn Leu Glu Glu Ala Gln Pro Gln Thr
    1205                1210                1215

Lys Pro Ile Thr Val Ala Thr Ala Glu Thr Pro Thr Ser Asn Ser
    1220                1225                1230

Lys Ser Ala Glu Lys Thr Gln Pro Ser Gly Glu Thr Asn Ala Glu
    1235                1240                1245

Pro Val Thr Pro Val Val Ser Glu Asn Gln Pro Glu Asn Thr
    1250                1255                1260

Ile Ser Gln Pro Thr Glu Asp Thr Val Lys Val Glu Thr Glu
    1265                1270                1275

Glu Thr Pro Lys Val Glu Thr Gly Gly Thr Lys Glu Ala Pro Gln
    1280                1285                1290

Val Ala Ser Gln Thr Ser Pro Lys Gln Glu Glu Pro Glu Thr Val
    1295                1300                1305

Gln Pro Gln Ala Glu Pro Ala Gln Glu Asn Ser Pro Thr Val Asn
    1310                1315                1320

Asn Val Glu Glu Ala Gln Pro Gln Thr Gln Pro Thr Ile Val Ala
```

-continued

```
             1325                1330                1335

Ala Lys Glu Ile Thr Ala Pro Asn Ser Ala Gln Lys Glu Thr Ala
     1340                1345                1350

Gln Ser Val Ala Asn Pro Lys Thr Ala Glu Gln Pro Val Thr Val
     1355                1360                1365

Ser Thr Glu Asn Pro Val Val Glu Asn Pro Glu Asn Thr Thr Gln
     1370                1375                1380

Pro Ala Val Asn Ser Glu Ala Val Gln Pro Glu Thr Ala Thr Thr
     1385                1390                1395

Gly Thr Val Ser Gln Pro Lys Glu Ala Ser Thr Asp Glu Thr Thr
     1400                1405                1410

Val Ala Ser Thr Asp Glu Thr Thr Gly Thr Ser Ala Glu Glu Thr
     1415                1420                1425

Thr Val Ala Asp Asn Ser Glu Ala Ser Lys Pro Lys Arg Arg Ser
     1430                1435                1440

Arg Arg Asp Val Ser Ser Thr Pro His Asn Val Glu Pro Ala Val
     1445                1450                1455

Thr Gly Gly Gly Arg Asp Arg Ser Ala Val Val Pro Leu Arg
     1460                1465                1470

Asp Leu Thr Ser Thr Asn Thr Asn Ala Val Leu Ser Asp Ala Met
     1475                1480                1485

Ala Lys Ala Gln Phe Val Ala Leu Asn Val Gly Lys Ala Val Ser
     1490                1495                1500

Gln His Ile Ser Gln Leu Glu Met Asn Asn Glu Gly Gln Tyr Asn
     1505                1510                1515

Val Trp Val Ser Asn Thr Ser Met Asn Glu Asn Tyr Ser Ser Asp
     1520                1525                1530

Gln Tyr Arg Arg Phe Ser Ser Lys Ser Ala Gln Thr Gln Leu Gly
     1535                1540                1545

Trp Asp Gln Thr Ile Ser Asn Asn Val Gln Leu Gly Gly Ile Leu
     1550                1555                1560

Thr Tyr Val Arg Asn Ser Asn Ser Phe Asp Lys Ala Ser Ser Lys
     1565                1570                1575

Asn Thr Leu Ala Gln Ala Asn Phe Tyr Ser Lys Tyr Tyr Ala Asp
     1580                1585                1590

Asn His Trp Tyr Leu Ala Val Asp Leu Gly Tyr Gly Asn Phe Gln
     1595                1600                1605

Ser Asn Leu Gln Thr Asn His Asn Ala Lys Phe Asp Arg His Thr
     1610                1615                1620

Ala Gln Ile Gly Leu Thr Ala Gly Lys Ala Phe Asn Leu Gly Asn
     1625                1630                1635

Val Ala Val Lys Pro Thr Val Gly Val Arg Tyr Ser Tyr Leu Ser
     1640                1645                1650

Asn Ala Asp Phe Ala Leu Asp Gln Asp Arg Ile Lys Val Asn Pro
     1655                1660                1665

Ile Ser Val Lys Thr Ala Phe Ala Gln Val Asp Leu Ser Tyr Thr
     1670                1675                1680

Tyr Asn Leu Gly Glu Phe Ala Ile Thr Pro Ile Leu Ser Ala Arg
     1685                1690                1695

Tyr Asp Ala Asn Gln Gly Asn Gly Lys Ile Asn Val Ser Gly Tyr
     1700                1705                1710

Ala Phe Ala Tyr Asn Val Glu Asn Gln Gln Gln Tyr Asn Ala Gly
     1715                1720                1725
```

```
Leu Lys Leu Lys Tyr His Asn Val Lys Leu Ser Leu Met Gly Gly
    1730                1735                1740

Leu Thr Lys Ala Lys Gln Ala Glu Lys Gln Lys Thr Ala Glu Val
    1745                1750                1755

Lys Leu Ser Phe Ser Phe
    1760

<210> SEQ ID NO 20
<211> LENGTH: 613
<212> TYPE: DNA
<213> ORGANISM: Haemophilus influenzae
<220> FEATURE:
<221> NAME/KEY: misc_feature
<222> LOCATION: (1)..(613)
<223> OTHER INFORMATION: Partial nucleotide sequence for IgA1 protease
      from 8625 strain

<400> SEQUENCE: 20
ggaagaacag gtataagcaa ttcaataatt attgatggac catctccgta tgtgacaatt      60
atacataaag acccaaatgg aactgttcta gatgatacac tagcattaag agaaaaattc     120
gaagaatcag tcgataaata caaacttcat tttactggat taatcgctga caaaattgca     180
aaagaaaaac tgaatactta cgtcctcact tataaaaaag cagacgaagc tatgcctgca     240
gacgaagcta tgccaactga tgtacctagt acttctgtta ctggatcaac aatggcaaac     300
gagcaaccag aaactcgtcc tgcaaaaatc gctcaacccg cgatggaaga gacagatact     360
gctcacatat cgggatctga accacaggct gatacaacac aagctgatac ttcaaattca     420
gaaagtgttc catcagagac aactaaaaca gtggctgaaa ataatccgca agaaagtgca     480
acagcagaga aaaacgagca agaagtcgcc gagacaacac tcaaaatgga gaagttgca      540 aaagaagctc aaccaactgt agaagctagc actcaaacaa atgaagtcgc ccaaaatgga     600
agcgaaaaag agg                                                        613

<210> SEQ ID NO 21
<211> LENGTH: 1413
<212> TYPE: DNA
<213> ORGANISM: Haemophilus influenzae
<220> FEATURE:
<221> NAME/KEY: misc_feature
<222> LOCATION: (1)..(1413)
<223> OTHER INFORMATION: Partial nucleotide sequence for IgA1 protease
      from HK284 strain

<400> SEQUENCE: 21
gcaacaaatg tggaagtgag agataaaaat aaccaatctt taggcagtgc cttacctaac      60
ggtattccga tgattgattt tagtgtggtg gatgtaaata acgtattgg tacattagtg      120 gatccgcaat atattgtaag cgtaaaacac gcacacaaac atataaatga ctttattt       180 gggcattata acggacaccg tgatgttct gatgatgaaa ataaatatag tgtggtcaca      240
caaaataatg ttaaaccaaa tgaagactgg cacgtagata gcgattaga tgactataac      300 atgcctcgtt taaataaatt tgtgaccgag gttgcaccaa ctacgcctac attagcagga      360
gacgatttag aaacctataa agataaagaa aaatatccgt cctttgtacg agtaggtgct     420
ggtactcagt ttgtttatga aaaaggttct tactatgttg aaaaaactac ccgtaataat     480
gatattaaat tcttagatga ggcatatcgc tatgctatcg gtggtacacc ttatgaaggg     540
attaatattg atccttccca agtaaaaaaa ggacttatag gttttggaga tagccgtgaa     600
aatcacgtta ttgatgctaa aactttgctt tctcaagacc cacttaccaa ctacggcgta     660
```

```
ttaggcgata gtggctcgcc tttatttgct tttgataaac aacaaaacaa atgggttttt      720
atcgggcctt atacttattg ggctggctat ggtaaaaaat cttggcaaga atggaatatt      780
tataaaaaag attttgctga taatataaaa aaacgagata acgctgaagc tgtgcctttc      840
tctacttcag aatatcattg gacaaacact acaaatcatc aaagtgaaat aaaaaacact      900
gatcatacaa ttactgtaac actcccctca gatccaaata gacttgttaa tttccaacaa      960
aaagaacatt tacaaacagg acaaaatgta acatttgacg atagcactaa taatgggaaa     1020
ggcacactta ttttagatga tcatatcaat caaggtgctg gcggtttatt ctttaaagga     1080
aactatgaag ttaaaggaaa aacggacgat attacttggg taggcggcgg aattgatgtt     1140
gcagaaggaa agaagttgt ttggaaagta cataatcctg aaaaagatca tttagccaag     1200
attggtaaag gaacattaat tgttgagggc aaagggaata ataaaggttc gctaaaagtg     1260
ggcgatggta ctgtcgtttt aaaacaacaa acgaatggtt cgggagaaca cgcttttgct     1320
tctgtaggga ttgtaagtgg tcgctcaacc gttgtgctta atgatgataa acaagtagat     1380
ccaaattcaa tttactttgg ctttagaggc ggt                                  1413

<210> SEQ ID NO 22
<211> LENGTH: 1477
<212> TYPE: DNA
<213> ORGANISM: Haemophilus influenzae
<220> FEATURE:
<221> NAME/KEY: misc_feature
<222> LOCATION: (1)..(1477)
<223> OTHER INFORMATION: Partial nucleotide sequence for IgA1 protease
      from Da66 strain

<400> SEQUENCE: 22
gcaacaaatg tggaagtgag agataaaaaa aataataatt tgggcagcgt gctacctaaa       60
gatattccta tgattgactt tagtgttgtg gatgtagata aacgcattgc cacattgata      120
aatccacaat atgttgtggg ggtaaaaacg gttggtaacg gtgtgggtga actacatttt      180
gggaatttaa atgggaattg gaaccctaaa tttggaaatt ctattcagca tcgagatgta      240
tcttgggagg aaaacagata ttacactgtt gaaaaaaata atttttcttc tgaattaaac      300
ggaaaaacac aaaataacga aaaagataaa cagtatacat ctaataaaaa agatgttcct      360
tccgaattat atggacaagc cttagttaaa gaacagcaaa accaaaaacg ccgtgaagat      420
tattatatgc cacgccttga taaatttgtt accgaagttg caccgataga ggcttcaact      480
acaagtagtg atgctggaac atataatgat cagaataaat atcctgcttt tgtgagatta      540
ggaagtggct ctcaatttat ctataaaaaa ggaagccatt atgaattaat tttagaagag      600
aaaaacgaga aaaaggaaat aatacacaga tgggatgtag gtggagataa tcttaaatta      660
gttggtaacg cttataccta tggtattgca ggcacgcctt ataaagtgaa tcatacagac      720
gatggactca ttgggtttgg tgattcaacc gaagatcata acgatccaaa agagatatta      780
tctcgtaaac cgcttactaa ttatgctgtc ttgggagata gtggctcacc gttatttgtt      840
tatgataaat ctaaagagaa atggcttttc cttggtgctt atgattttg gggagggtat      900 aagaaaaaat cttggcaaga atggaatatt tataaaccac aatttgctga aaatattctc      960
aaaaaagaca gtgctggttt actgaaaggt aatacgcaat ataactggac aagcaaaggt     1020
aatacaagct tgatatctgg aacatctgaa tcattaagtg ttgatttagt ggataataaa     1080
aatctcaatc atgggaaaaa tgttacgttt gaaggaagtg gaaaccttac cttaaataat     1140
aatatcgatc aaggtgcagg cggattgttc tttgaaggtg attatgaagt taaaggcact     1200
```

-continued

```
tcagaaaata cgacttggaa aggggctggt atatctgttg ctgaaggaaa aacagtaaag    1260
tggaaagtgc ataaccctca atttgatcgt ttagctaaaa ttggtaaagg aaagctaatt    1320
gttgaaggaa gaggagataa taaaggttcg ctaaaagtgg gcgatggcac agttgtttta    1380
aaacaacaaa caactacagg acaacacgct tttgcttctg taggaattgt aagtggtcgc    1440
tcaactgttg tacttaatga tgataaccaa gtagatc                             1477
```

<210> SEQ ID NO 23
<211> LENGTH: 1739
<212> TYPE: PRT
<213> ORGANISM: Artificial Sequence
<220> FEATURE:
<223> OTHER INFORMATION: Description of Artificial Sequence: Synthetic consensus sequence for H. influenzae IgA1 proteases

<400> SEQUENCE: 23

```
Met Leu Asn Lys Lys Phe Lys Leu Asn Phe Ile Ala Leu Thr Val Ala
1               5                   10                  15

Tyr Ala Leu Thr Pro Tyr Thr Glu Ala Ala Leu Val Arg Asp Asp Val
            20                  25                  30

Asp Tyr Gln Ile Phe Arg Asp Phe Ala Glu Asn Gly Lys Phe Ser
        35                  40                  45

Val Gly Ala Thr Asn Val Glu Val Arg Asp Lys Asn Asn His Ser Leu
    50                  55                  60

Gly Asn Ala Leu Pro Asn Gly Ile Pro Met Ile Asp Phe Ser Val Val
65                  70                  75                  80

Asp Val Asp Lys Arg Ile Ala Thr Leu Ile Asn Pro Gln Tyr Val Val
                85                  90                  95

Gly Val Lys His Val Ser Asn Gly Val Ser Glu Leu His Phe Gly Asn
            100                 105                 110

Leu Asn Gly Asn Met Asn Asn Gly Asn Ala Lys Ser His Arg Asp Val
        115                 120                 125

Ser Ser Glu Glu Asn Arg Tyr Phe Ser Val Glu Lys Asn Glu Tyr Pro
    130                 135                 140

Thr Lys Leu Asn Gly Lys Ala Val Thr Thr Glu Asp Gln Asp Thr Gln
145                 150                 155                 160

Lys Arg Arg Glu Asp Tyr Tyr Met Pro Arg Leu Asp Lys Phe Val Thr
                165                 170                 175

Glu Val Ala Pro Ile Glu Ala Ser Thr Ala Ser Ser Asp Ala Gly Thr
            180                 185                 190

Tyr Asn Asp Gln Asn Lys Tyr Pro Ala Phe Val Arg Leu Gly Ser Gly
        195                 200                 205

Ser Gln Phe Ile Tyr Lys Lys Gly Asp Asn Tyr Ser Leu Ile Leu Asn
    210                 215                 220

Asn His Glu Val Gly Gly Asn Asn Leu Lys Leu Val Gly Asp Ala Tyr
225                 230                 235                 240

Thr Tyr Gly Ile Ala Gly Thr Pro Tyr Lys Val Asn His Glu Asn Asn
                245                 250                 255

Gly Leu Ile Gly Phe Gly Asn Ser Lys Glu Glu His Ser Asp Pro Lys
            260                 265                 270

Gly Ile Leu Ser Gln Asp Pro Leu Thr Asn Tyr Ala Val Leu Gly Asp
        275                 280                 285

Ser Gly Ser Pro Leu Phe Val Tyr Asp Arg Glu Lys Gly Lys Trp Leu
    290                 295                 300
```

```
Phe Leu Gly Ser Tyr Asp Phe Trp Ala Gly Tyr Asn Lys Lys Ser Trp
305                 310                 315                 320

Gln Glu Trp Asn Ile Tyr Lys Pro Glu Phe Ala Lys Thr Val Leu Asp
                325                 330                 335

Lys Asp Ser Ala Gly Ser Leu Thr Gly Ser Asn Thr Gln Tyr Asn Trp
            340                 345                 350

Asn Pro Thr Gly Lys Thr Ser Thr Ile Thr Gly Gly Glu Glu Ser Leu
        355                 360                 365

Asn Val Asp Leu Ala Asp Gly Lys Asp Thr Asp Ser Lys Lys Pro
370                 375                 380

Asn His Gly Lys Ser Val Thr Phe Glu Gly Ser Gly Thr Leu Thr Leu
385                 390                 395                 400

Asn Asn Asn Ile Asp Gln Gly Ala Gly Gly Leu Phe Phe Glu Gly Asp
                405                 410                 415

Tyr Glu Val Lys Gly Thr Ser Asp Asn Thr Thr Trp Lys Gly Ala Gly
            420                 425                 430

Val Ser Val Ala Asp Gly Lys Thr Val Thr Trp Lys Val His Asn Pro
        435                 440                 445

Lys Tyr Asp Arg Leu Ala Lys Ile Gly Lys Gly Thr Leu Ile Val Glu
450                 455                 460

Gly Lys Gly Asp Asn Lys Gly Ser Leu Lys Val Gly Asp Gly Thr Val
465                 470                 475                 480

Ile Leu Lys Gln Gln Ala Asp Ala Asn Asn Lys Gln His Ala Phe Ala
                485                 490                 495

Gln Val Gly Ile Val Ser Gly Arg Ser Thr Leu Val Leu Asn Asp Asp
            500                 505                 510

Lys Gln Val Asp Pro Asn Ser Ile Tyr Phe Gly Phe Arg Gly Gly Arg
        515                 520                 525

Leu Asp Leu Asn Gly Asn Ser Leu Thr Phe Asp His Ile Arg Asn Ile
530                 535                 540

Asp Asp Gly Ala Arg Leu Val Asn His Asn Met Ser Lys Thr Ser Asn
545                 550                 555                 560

Ile Thr Ile Thr Gly Glu Ser Leu Ile Thr Asp Pro Asn Thr Ile Thr
                565                 570                 575

Pro Tyr Asn Ile Asp Ala Pro Asp Glu Asp Asn Pro Tyr Ala Phe Arg
            580                 585                 590

Arg Ile Lys Asp Gly Gly Gln Leu Tyr Leu Asn Leu Glu Asn Tyr Thr
        595                 600                 605

Tyr Tyr Ala Leu Arg Lys Gly Ala Ser Thr Arg Ser Glu Leu Pro Lys
610                 615                 620

Asn Ser Gly Glu Ser Asn Glu Asn Trp Leu Tyr Met Gly Lys Thr Ser
625                 630                 635                 640

Asp Glu Ala Lys Arg Asn Val Met Asn His Ile Asn Asn Glu Arg Met
                645                 650                 655

Asn Gly Phe Asn Gly Tyr Phe Gly Glu Glu Gly Lys Asn Asn Gly
            660                 665                 670

Asn Leu Asn Val Thr Phe Lys Gly Lys Ser Glu Gln Asn Arg Phe Leu
        675                 680                 685

Leu Thr Gly Gly Thr Asn Leu Asn Gly Asp Leu Lys Val Glu Lys Gly
690                 695                 700

Thr Leu Phe Leu Ser Gly Arg Pro Thr Pro His Ala Arg Asp Ile Ala
705                 710                 715                 720

Gly Ile Ser Ser Thr Lys Lys Asp Pro His Phe Ala Glu Asn Asn Glu
```

```
                     725                 730                 735
Val Val Val Glu Asp Asp Trp Ile Asn Arg Asn Phe Lys Ala Thr Asn
                 740                 745                 750

Ile Asn Val Thr Gly Asn Ala Ser Leu Tyr Ser Gly Arg Asn Val Ala
             755                 760                 765

Asn Ile Thr Ser Asn Ile Thr Ala Ser Asn Asn Ala Lys Val His Ile
         770                 775                 780

Gly Tyr Lys Ala Gly Asp Thr Val Cys Val Arg Ser Asp Tyr Thr Gly
785                 790                 795                 800

Tyr Val Thr Cys Thr Thr Asp Lys Leu Ser Asp Lys Ala Leu Asn Ser
                 805                 810                 815

Phe Asn Ala Thr Asn Leu Arg Gly Asn Val Asn Leu Ser Glu Asn Ala
             820                 825                 830

Asn Phe Val Leu Gly Lys Ala Asn Leu Phe Gly Thr Ile Gln Ser Arg
         835                 840                 845

Gly Asn Ser Gln Val Arg Leu Thr Glu Asn Ser His Trp His Leu Thr
     850                 855                 860

Gly Asp Ser Asn Val His Gln Leu Asp Leu Ala Asn Gly His Ile His
865                 870                 875                 880

Leu Asn Ala Ala Asp Asp Ala Asn Lys Val Thr Lys Tyr Asn Thr Leu
                 885                 890                 895

Thr Val Asn Ser Leu Ser Gly Asn Gly Ser Phe Tyr Tyr Leu Thr Asp
             900                 905                 910

Leu Ser Asn Lys Gln Gly Asp Lys Val Val Thr Lys Ser Ala Thr
         915                 920                 925

Gly Asn Phe Thr Leu Gln Val Ala Asp Lys Thr Gly Glu Pro Asn His
     930                 935                 940

Asn Glu Leu Thr Leu Phe Asp Ala Ser Asn Ala Thr Arg Asn Asn Leu
945                 950                 955                 960

Asn Val Ser Leu Val Gly Asn Thr Val Asp Leu Gly Ala Trp Lys Tyr
                 965                 970                 975

Lys Leu Arg Asn Val Asn Gly Arg Tyr Asp Leu Tyr Asn Pro Glu Val
             980                 985                 990

Glu Lys Arg Asn Gln Thr Val Asp Thr Thr Asn Ile Thr Thr Pro Asn
         995                 1000                1005

Asn Ile Gln Ala Asp Val Pro Ser Val Pro Ser Asn Asn Glu Glu
         1010                1015                1020

Ile Ala Arg Val Asp Glu Ala Pro Val Pro Pro Ala Pro Ala
         1025                1030                1035

Thr Ser Ala Ala Glu Gln Pro Thr Arg Pro Ala Glu Thr Ala Gln
         1040                1045                1050

Pro Met Glu Glu Thr Ala Asn Ser Thr Glu Thr Ala Pro Lys Ser
         1055                1060                1065

Asp Thr Thr Gln Asn Ser Glu Ser Val Pro Ser Glu Thr Thr Glu
         1070                1075                1080

Thr Val Ala Glu Asn Ser Lys Gln Glu Ser Lys Thr Val Glu Lys
         1085                1090                1095

Asn Glu Gln Asp Ala Thr Glu Thr Thr Ala Gln Asn Gly Glu Val
         1100                1105                1110

Ala Lys Glu Ala Lys Pro Asn Val Lys Ala Asn Thr Gln Thr Asn
         1115                1120                1125

Glu Val Ala Gln Ser Gly Ser Glu Thr Glu Glu Thr Gln Thr Thr
         1130                1135                1140
```

```
Glu Thr Lys Thr Glu Thr Ala Thr Val Glu Lys Glu Lys Ala
    1145                1150                1155

Lys Val Glu Lys Glu Asp Glu Ile Gln Glu Ala Pro Gln Met Ala
    1160                1165                1170

Ser Glu Thr Ser Pro Lys Gln Ala Lys Pro Ala Pro Lys Glu Val
    1175                1180                1185

Ser Thr Asp Thr Lys Val Glu Glu Thr Gln Val Gln Ala Gln Pro
    1190                1195                1200

Gln Thr Gln Ser Thr Thr Val Ala Ala Glu Ala Thr Ser Pro
    1205                1210                1215

Asn Ser Lys Pro Ala Glu Glu Thr Gln Pro Ser Glu Lys Thr Asn
    1220                1225                1230

Ala Glu Pro Val Thr Pro Val Val Ser Lys Asn Gln Thr Glu Asn
    1235                1240                1245

Thr Thr Asp Gln Pro Thr Glu Arg Glu Lys Thr Ala Lys Val Glu
    1250                1255                1260

Thr Glu Lys Thr Gln Glu Val Pro Gln Val Ala Ser Gln Ala Ser
    1265                1270                1275

Pro Lys Gln Glu Gln Ser Glu Thr Val Gln Pro Gln Ala Glu Pro
    1280                1285                1290

Ala Arg Glu Asn Val Pro Thr Val Asn Asn Ala Glu Glu Val Ile
    1295                1300                1305

Ala Glu Pro Gln Ser Gln Thr Ser Ala Thr Ala Ser Thr Glu Gln
    1310                1315                1320

Pro Ala Lys Glu Thr Ser Ile Asn Thr Gly Ser Ala Thr Ala Ile
    1325                1330                1335

Thr Glu Thr Ala Glu Lys Ser Asp Lys Pro Gln Thr Glu Thr Ala
    1340                1345                1350

Ala Val Thr Glu Asp Ala Ser Gln His Lys Ala Asn Thr Val Ala
    1355                1360                1365

Asp Asn Ser Val Ala Asn Asn Ser Glu Ser Ser Asp Pro Lys Ser
    1370                1375                1380

Arg Arg Arg Arg Ser Ile Ser Gln Pro Gln Glu Thr Ser Ala Glu
    1385                1390                1395

Glu Thr Thr Ala Ala Ser Thr Gln Glu Thr Thr Ile Ala Asp Asn
    1400                1405                1410

Ser Lys Lys Pro Lys Asn Arg His Arg Arg Ser Arg Arg Ser Val
    1415                1420                1425

Pro His Asn Val Glu Pro Ala Thr Thr Asn Gly Asn Asp Arg Ser
    1430                1435                1440

Thr Val Ala Leu Arg Asp Leu Thr Ser Thr Asn Thr Asn Ala Val
    1445                1450                1455

Leu Ser Asp Ala Met Ala Lys Ala Gln Phe Val Ala Leu Asn Val
    1460                1465                1470

Gly Lys Ala Val Ser Gln His Ile Ser Gln Leu Glu Met Asn Asn
    1475                1480                1485

Glu Gly Gln Tyr Asn Val Trp Val Ser Asn Thr Ser Met Asn Glu
    1490                1495                1500

Asn Tyr Ser Ser Ser Gln Tyr Arg Arg Phe Ser Ser Lys Ser Thr
    1505                1510                1515

Gln Thr Gln Leu Gly Trp Asp Gln Thr Ile Ser Asn Asn Val Gln
    1520                1525                1530
```

```
Leu Gly Gly Val Phe Thr Tyr Val Arg Asn Ser Asn Asn Phe Asp
    1535                1540                1545

Lys Ala Ser Ser Lys Asn Thr Leu Ala Gln Val Asn Phe Tyr Ser
    1550                1555                1560

Lys Tyr Tyr Ala Asp Asn His Trp Tyr Leu Gly Ile Asp Leu Gly
    1565                1570                1575

Tyr Gly Lys Phe Gln Ser Asn Leu Gln Thr Asn His Asn Ala Lys
    1580                1585                1590

Phe Ala Arg His Thr Ala Gln Phe Gly Leu Thr Ala Gly Lys Ala
    1595                1600                1605

Phe Asn Leu Gly Asn Phe Gly Ile Thr Pro Ile Val Gly Val Arg
    1610                1615                1620

Tyr Ser Tyr Leu Ser Asn Ala Asp Phe Ala Leu Ala Gln Asp Arg
    1625                1630                1635

Ile Lys Val Asn Pro Ile Ser Val Lys Thr Ala Phe Ala Gln Val
    1640                1645                1650

Asp Leu Ser Tyr Thr Tyr His Leu Gly Glu Phe Ser Val Thr Pro
    1655                1660                1665

Ile Leu Ser Ala Arg Tyr Asp Ala Asn Gln Gly Ser Gly Lys Ile
    1670                1675                1680

Asn Val Asn Gly Tyr Asp Phe Ala Tyr Asn Val Glu Asn Gln Gln
    1685                1690                1695

Gln Tyr Asn Ala Gly Leu Lys Leu Lys Tyr His Asn Val Lys Leu
    1700                1705                1710

Ser Leu Ile Gly Gly Leu Thr Lys Ala Lys Gln Ala Glu Lys Gln
    1715                1720                1725

Lys Thr Ala Glu Leu Lys Leu Ser Phe Ser Phe
    1730                1735

<210> SEQ ID NO 24
<211> LENGTH: 1014
<212> TYPE: PRT
<213> ORGANISM: Haemophilus influenzae
<220> FEATURE:
<221> NAME/KEY: misc_feature
<222> LOCATION: (26)..(1014)
<223> OTHER INFORMATION: Mature, soluble form of IgA1 protease from Rd
      strain

<400> SEQUENCE: 24

Met Leu Asn Lys Lys Phe Lys Leu Asn Phe Ile Ala Leu Thr Val Ala
1               5                   10                  15

Tyr Ala Leu Thr Pro Tyr Thr Glu Ala Ala Leu Val Arg Asp Asp Val
                20                  25                  30

Asp Tyr Gln Ile Phe Arg Asp Phe Ala Glu Asn Lys Gly Arg Phe Ser
            35                  40                  45

Val Gly Ala Thr Asn Val Glu Val Arg Asp Lys Asn Asn His Ser Leu
        50                  55                  60

Gly Asn Val Leu Pro Asn Gly Ile Pro Met Ile Asp Phe Ser Val Val
65                  70                  75                  80

Asp Val Asp Lys Arg Ile Ala Thr Leu Ile Asn Pro Gln Tyr Val Val
                85                  90                  95

Gly Val Lys His Val Ser Asn Gly Val Ser Glu Leu His Phe Gly Asn
            100                 105                 110

Leu Asn Gly Asn Met Asn Asn Gly Asn Ala Lys Ser His Arg Asp Val
        115                 120                 125
```

-continued

```
Ser Ser Glu Glu Asn Arg Tyr Phe Ser Val Glu Lys Asn Glu Tyr Pro
    130                 135                 140

Thr Lys Leu Asn Gly Lys Ala Val Thr Thr Glu Asp Gln Thr Gln Lys
145                 150                 155                 160

Arg Arg Glu Asp Tyr Tyr Met Pro Arg Leu Asp Lys Phe Val Thr Glu
                165                 170                 175

Val Ala Pro Ile Glu Ala Ser Thr Ala Ser Ser Asp Ala Gly Thr Tyr
            180                 185                 190

Asn Asp Gln Asn Lys Tyr Pro Ala Phe Val Arg Leu Gly Ser Gly Ser
                195                 200                 205

Gln Phe Ile Tyr Lys Lys Gly Asp Asn Tyr Ser Leu Ile Leu Asn Asn
210                 215                 220

His Glu Val Gly Gly Asn Asn Leu Lys Leu Val Gly Asp Ala Tyr Thr
225                 230                 235                 240

Tyr Gly Ile Ala Gly Thr Pro Tyr Lys Val Asn His Glu Asn Asn Gly
                245                 250                 255

Leu Ile Gly Phe Gly Asn Ser Lys Glu Glu His Ser Asp Pro Lys Gly
            260                 265                 270

Ile Leu Ser Gln Asp Pro Leu Thr Asn Tyr Ala Val Leu Gly Asp Ser
            275                 280                 285

Gly Ser Pro Leu Phe Val Tyr Asp Arg Glu Lys Gly Lys Trp Leu Phe
        290                 295                 300

Leu Gly Ser Tyr Asp Phe Trp Ala Gly Tyr Asn Lys Lys Ser Trp Gln
305                 310                 315                 320

Glu Trp Asn Ile Tyr Lys Pro Glu Phe Ala Lys Thr Val Leu Asp Lys
                325                 330                 335

Asp Thr Ala Gly Ser Leu Thr Gly Ser Asn Thr Gln Tyr Asn Trp Asn
            340                 345                 350

Pro Thr Gly Lys Thr Ser Val Ile Ser Asn Gly Ser Glu Ser Leu Asn
        355                 360                 365

Val Asp Leu Phe Asp Ser Ser Gln Asp Thr Asp Ser Lys Lys Asn Asn
370                 375                 380

His Gly Lys Ser Val Thr Leu Arg Gly Ser Gly Thr Leu Thr Leu Asn
385                 390                 395                 400

Asn Asn Ile Asp Gln Gly Ala Gly Gly Leu Phe Phe Glu Gly Asp Tyr
                405                 410                 415

Glu Val Lys Gly Thr Ser Asp Ser Thr Thr Trp Lys Gly Ala Gly Val
            420                 425                 430

Ser Val Ala Asp Gly Lys Thr Val Thr Trp Lys Val His Asn Pro Lys
        435                 440                 445

Ser Asp Arg Leu Ala Lys Ile Gly Lys Gly Thr Leu Ile Val Glu Gly
    450                 455                 460

Lys Gly Glu Asn Lys Gly Ser Leu Lys Val Gly Asp Gly Thr Val Ile
465                 470                 475                 480

Leu Lys Gln Gln Ala Asp Ala Asn Asn Lys Val Lys Ala Phe Ser Gln
                485                 490                 495

Val Gly Ile Val Ser Gly Arg Ser Thr Val Leu Asn Asp Asp Lys
            500                 505                 510

Gln Val Asp Pro Asn Ser Ile Tyr Phe Gly Phe Arg Gly Gly Arg Leu
        515                 520                 525

Asp Ala Asn Gly Asn Asn Leu Thr Phe Glu His Ile Arg Asn Ile Asp
    530                 535                 540

Asp Gly Ala Arg Leu Val Asn His Asn Thr Ser Lys Thr Ser Thr Val
```

-continued

```
545                 550                 555                 560
Thr Ile Thr Gly Glu Ser Leu Ile Thr Asp Pro Asn Thr Ile Thr Pro
                565                 570                 575
Tyr Asn Ile Asp Ala Pro Asp Glu Asp Asn Pro Tyr Ala Phe Arg Arg
                580                 585                 590
Ile Lys Asp Gly Gly Gln Leu Tyr Leu Asn Leu Glu Asn Tyr Thr Tyr
                595                 600                 605
Tyr Ala Leu Arg Lys Gly Ala Ser Thr Arg Ser Glu Leu Pro Lys Asn
                610                 615                 620
Ser Gly Glu Ser Asn Glu Asn Trp Leu Tyr Met Gly Lys Thr Ser Asp
625                 630                 635                 640
Glu Ala Lys Arg Asn Val Met Asn His Ile Asn Asn Glu Arg Met Asn
                645                 650                 655
Gly Phe Asn Gly Tyr Phe Gly Glu Glu Gly Lys Asn Asn Gly Asn
                660                 665                 670
Leu Asn Val Thr Phe Lys Gly Lys Ser Glu Gln Asn Arg Phe Leu Leu
                675                 680                 685
Thr Gly Gly Thr Asn Leu Asn Gly Asp Leu Lys Val Glu Lys Gly Thr
                690                 695                 700
Leu Phe Leu Ser Gly Arg Pro Thr Pro His Ala Arg Asp Ile Ala Gly
705                 710                 715                 720
Ile Ser Ser Thr Lys Lys Asp Gln His Phe Ala Glu Asn Asn Glu Val
                725                 730                 735
Val Val Glu Asp Asp Trp Ile Asn Arg Asn Phe Lys Ala Thr Asn Ile
                740                 745                 750
Asn Val Thr Asn Asn Ala Thr Leu Tyr Ser Gly Arg Asn Val Ala Asn
                755                 760                 765
Ile Thr Ser Asn Ile Thr Ala Ser Asp Asn Ala Lys Val His Ile Gly
                770                 775                 780
Tyr Lys Ala Gly Asp Thr Val Cys Val Arg Ser Asp Tyr Thr Gly Tyr
785                 790                 795                 800
Val Thr Cys Thr Thr Asp Lys Leu Ser Asp Lys Ala Leu Asn Ser Phe
                805                 810                 815
Asn Ala Thr Asn Val Ser Gly Asn Val Asn Leu Ser Gly Asn Ala Asn
                820                 825                 830
Phe Val Leu Gly Lys Ala Asn Leu Phe Gly Thr Ile Ser Gly Thr Gly
                835                 840                 845
Asn Ser Gln Val Arg Leu Thr Glu Asn Ser His Trp His Leu Thr Gly
                850                 855                 860
Asp Ser Asn Val Asn Gln Leu Asn Leu Asp Lys Gly His Ile His Leu
865                 870                 875                 880
Asn Ala Gln Asn Asp Ala Asn Lys Val Thr Thr Tyr Asn Thr Leu Thr
                885                 890                 895
Val Asn Ser Leu Ser Gly Asn Gly Ser Phe Tyr Tyr Leu Thr Asp Leu
                900                 905                 910
Ser Asn Lys Gln Gly Asp Lys Val Val Thr Lys Ser Ala Thr Gly
                915                 920                 925
Asn Phe Thr Leu Gln Val Ala Asp Lys Thr Gly Glu Pro Thr Lys Asn
                930                 935                 940
Glu Leu Thr Leu Phe Asp Ala Ser Asn Ala Thr Arg Asn Asn Leu Asn
945                 950                 955                 960
Val Ser Leu Val Gly Asn Thr Val Asp Leu Gly Ala Trp Lys Tyr Lys
                965                 970                 975
```

Leu Arg Asn Val Asn Gly Arg Tyr Asp Leu Tyr Asn Pro Glu Val Glu
            980                 985                 990

Lys Arg Asn Gln Thr Val Asp Thr  Thr Asn Ile Thr Thr  Pro Asn Asn
        995                 1000                1005

Ile Gln  Ala Asp Val Pro
    1010

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 25

His His His His His His
1               5

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: Encodes 6xHis tag

<400> SEQUENCE: 26
caccatcacc atcaccat                                                 18

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      c-myc epitope tag

<400> SEQUENCE: 27

Glu Gln Lys Leu Ile Ser Glu Glu Asp Leu
1               5                   10

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(30)
<223> OTHER INFORMATION: Encodes c-myc epitope tag

<400> SEQUENCE: 28
gagcaaaagc tcatttctga agaggacttg                                    30

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic

```
                hemagglutinin epitope tag

<400> SEQUENCE: 29

Tyr Pro Tyr Asp Val Pro Asp Tyr Ala
1               5

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(27)
<223> OTHER INFORMATION: Encodes hemagglutinin epitope tag

<400> SEQUENCE: 30 taccottatg atgtgccaga ttatgcc                                        27

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      VSV-G (vesicular stomatitis virus G) epitope tag

<400> SEQUENCE: 31

Tyr Thr Asp Ile Glu Met Asn Arg Leu Gly Lys
1               5                   10

<210> SEQ ID NO 32
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(33)
<223> OTHER INFORMATION: Encodes VSV-G (vesicular stomatitus virus G)
      epitope tag

<400> SEQUENCE: 32
tatacagaca tagagatgaa ccgacttgga aag                                 33

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      herpes simplex virus (HSV) epitope tag

<400> SEQUENCE: 33

Gln Pro Glu Leu Ala Pro Glu Asp Pro Glu Asp
1               5                   10

<210> SEQ ID NO 34
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: misc_feature
<222> LOCATION: (1)..(33)
<223> OTHER INFORMATION: Encodes herpes simplex virus (HSV) epitope tag

<400> SEQUENCE: 34
cagccagaac tcgccccgga agaccccgag gat                                    33

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic
      V5 epitope tag from simian virus

<400> SEQUENCE: 35

Gly Lys Pro Ile Pro Asn Pro Leu Leu Gly Leu Asp Ser Thr
1               5                   10

<210> SEQ ID NO 36
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(42)
<223> OTHER INFORMATION: Encodes V5 epitope tag from simian virus

<400> SEQUENCE: 36
ggcaaaccaa tcccaaaccc actgctgggc ctggatagta ct                          42

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      FLAG epitope tag

<400> SEQUENCE: 37

Asp Tyr Lys Asp Asp Asp Asp Lys Gly
1               5

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(27)
<223> OTHER INFORMATION: Encodes FLAG epitope tag

<400> SEQUENCE: 38
gattacaaag acgatgacga taaagga                                           27

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: misc_feature
<222> LOCATION: (1)..(5)
<223> OTHER INFORMATION: Portion of inhibitor that binds elastase

<400> SEQUENCE: 39

Cys Thr Leu Glu Tyr
1               5

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(4)
<223> OTHER INFORMATION: Residues 229-232 of hinge region of IgA1
      molecule

<400> SEQUENCE: 40

Pro Ser Pro Ser
1

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(5)
<223> OTHER INFORMATION: Residues 229-233 of hinge region of IgA1
      molecule

<400> SEQUENCE: 41

Pro Ser Pro Ser Thr
1               5

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence: Synthetic
      consensus furin cleavage site
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Arg or Lys

<400> SEQUENCE: 42

Arg Xaa Xaa Arg
1

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: Synthetic
      Factor Xa cleavage site
<220> FEATURE:
<221> NAME/KEY: MOD_RES
```

```
<222> LOCATION: (2)..(2)
<223> OTHER INFORMATION: Glu or Asp

<400> SEQUENCE: 43

Ile Xaa Gly Arg
1

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      enterokinase cleavage site

<400> SEQUENCE: 44

Asp Asp Asp Asp Lys
1               5

<210> SEQ ID NO 45
<211> LENGTH: 12
<212> TYPE: PRT
<213> ORGANISM: Haemophilus influenzae
<220> FEATURE:
<221> NAME/KEY: misc_feature
<222> LOCATION: (1)..(12)
<223> OTHER INFORMATION: Residues 792-803 of H. influenzae Rd IgA1
      protease

<400> SEQUENCE: 45

Cys Val Arg Ser Asp Tyr Thr Gly Tyr Val Thr Cys
1               5                   10

<210> SEQ ID NO 46
<211> LENGTH: 22
<212> TYPE: PRT
<213> ORGANISM: Homo sapiens

<400> SEQUENCE: 46

Pro Val Pro Ser Thr Pro Pro Thr Pro Ser Pro Ser Thr Pro Pro Thr
1               5                   10                  15

Pro Ser Pro Ser Cys Cys
            20

<210> SEQ ID NO 47
<211> LENGTH: 9
<212> TYPE: PRT
<213> ORGANISM: Homo sapiens

<400> SEQUENCE: 47

Pro Val Pro Pro Pro Pro Pro Cys Cys
1               5

<210> SEQ ID NO 48
<211> LENGTH: 21
<212> TYPE: PRT
<213> ORGANISM: Homo sapiens

<400> SEQUENCE: 48

Pro Val Pro Ser Thr Pro Pro Thr Pro Ser Pro Ser Thr Pro Pro Thr
1               5                   10                  15

Pro Ser Pro Ser Cys
            20

<210> SEQ ID NO 49
```

```
<211> LENGTH: 4
<212> TYPE: PRT
<213> ORGANISM: Homo sapiens

<400> SEQUENCE: 49

Val Ser Pro Val
1
```

IGA1 PROTEASE POLYPEPTIDE AGENTS AND USES THEREOF

RELATED APPLICATION INFORMATION

The present application is the National Stage application under 35 U.S.C. 371 of International Application No. PCT/US2010/031733, filed Apr. 20, 2010, which claims priority to and benefit of U.S. provisional patent application 61/170,935, filed Apr. 20, 2009, the entire contents of each of which are incorporated by reference herein.

GOVERNMENT SUPPORT

This invention was made with U.S. government support under the National Institutes of Health COBRE program of the National Center for Research Resources grant number P20 RR016443 to Todd Holyoak and grant number P20 RR17708 to Todd Holyoak; the National Institutes of Health National Center for Research Resources grant number UL1 RR025752 to Andrew G. Plaut; and the National Institutes of Health grant number R21 DK071675 to Andrew G. Plaut. The government of the United States of America has certain rights in the invention.

SEQUENCE LISTING

The present specification makes reference to a Sequence Listing (submitted electronically as a .txt file named "sequence_listing.txt" concurrently with other documents associated with this application on Apr. 20, 2010, as amended on Mar. 25, 2014). The .txt file was generated on Mar. 11, 2014 and is 209 kb in size. The entire contents of the Sequence Listing are herein incorporated by reference.

BACKGROUND OF THE INVENTION

Deposition of immunoglobulin A1 (IgA1) in human tissues and organs is a characteristic of many human diseases including IgA nephropathy, dermatitis herpetiformis, and Henoch-Schoenlein purpura. IgA nephropathy (IgAN) is the most common form of glomerulonephritis throughout the world (Emancipator et al. 1998 and Emancipator et al. 2005). IgAN is characterized by presence of mesangial deposits containing complexes of IgA1. Clinical symptoms of IgAN include proteinuria, hematuria, and hypertension that may evolve into end-stage renal disease.

IgA1 proteases are bacterial enzymes that specifically cleave IgA1 molecules at their hinge regions (See FIG. 1). Recently, systemically administered IgA1 protease has been shown to remove glomerular IgA immune complexes in a mouse model of IgAN (Lamm et al. 2008). Thus, IgA1 protease is a promising therapeutic agent for treatment of IgA1 deposition diseases such as IgAN.

SUMMARY OF THE INVENTION

The present invention encompasses the recognition that IgA1 protease therapy can be improved through development of new IgA1 protease polypeptide agents. The present invention provides systems for generating, identifying, and/or characterizing IgA1 protease polypeptide agents, as well as compositions containing IgA1 protease polypeptide agents and methods of using them.

In some aspects of the invention, provided are polypeptide agents useful in the treatment and/or amelioration of IgA1 deposition diseases. In some embodiments, polypeptide agents comprise a polypeptide backbone whose amino acid sequence shares at least 45% overall identity with a consensus sequence for *Haemophilus influenzae* IgA1 protease polypeptides (SEQ ID NO: 23) but differs from that of IgA1 protease polypeptide from the Rd strain of *H. influenzae* (SEQ ID NO: 24). In such embodiments, the amino acid sequence of the polypeptide backbone differs from SEQ ID NO: 24 in that the polypeptide backbone lacks sequences found C-terminal to residue 975 of SEQ ID NO: 24 and/or the polypeptide backbone has an amino acid sequence that differs from that of SEQ ID NO: 24 in at least one region corresponding to a surface epitope. In some embodiments, polypeptide agents comprise a polypeptide backbone whose amino acid sequence shares at least 45% overall sequence identity with SEQ ID NO: 23 and at least one pendant group covalently attached to the polypeptide backbone.

In one aspect of the invention, provided are methods comprising a step of administering to an individual having deposits of IgA1 a polypeptide agent of the invention.

In one aspect of the invention, provided are methods useful for identifying inhibitors of IgA1 proteases. In some embodiments, such methods comprise steps of (a) consulting a three-dimensional model of an IgA1 protease; (b) determining physical characteristics of candidate inhibitors of the IgA1 protease based on the three-dimensional structure model; (c) testing candidate inhibitors for ability to inhibit IgA1 protease activity; and (d) identifying an inhibitor from among candidate inhibitors based on performance on the test and corresponding physical characteristics.

In one aspect of the invention, provided are agents that inhibit IgA1 protease activity. In some embodiments, such agents have a three-dimensional structure dimensioned to fit within the enzyme active cleft of IgA1 protease, e.g., a cleft defined by residues H100, D164, Y239, L285, S288, F310, W311 of *H. influenzae* Rd IgA1 protease. In some embodiments, such agents bind to certain other domains that are important for IgA1 protease activity and/or specificity.

DEFINITIONS

Adverse event: The term "adverse event" as used herein has its art understood meaning and refers to any untoward medical occurrence in a patient or clinical investigation subject administered a pharmaceutical product. An adverse event does not necessarily have to have a causal relationship with the treatment administered.

Adverse reaction: The term "adverse reaction" as used herein had its art understood meaning and refers to any noxious and unintended responses to a medicinal product related to any dose.

Combination Therapy: The term "combination therapy", as used herein, refers to those situations in which two or more different pharmaceutical agents are administered in overlapping regimens so that the subject is simultaneously exposed to both agents. In some embodiments, combination therapies involve administration of multiple individual doses of an IgA1 protease polypeptide agent and/or of another pharmaceutical agent, spaced out over time. Doses of a IgA1 protease polypeptide agent and another pharmaceutical agent may be administered in the same amounts and/or according to the same schedule or alternatively may be administered in different amounts and/or according to different schedules.

Corresponding to: As used herein, the phrase "corresponding to," when used to describe positions or sites within nucleotide sequences, is used herein as it is understood in the art. As is well known in the art, two or more nucleotide sequences can be aligned using standard bioinformatic tools, including programs such as BLAST, ClustalX, Sequencher, and etc. Even though the two or more sequences may not match exactly and/or do not have the same length, an alignment of the sequences can still be performed and, if desirable, a "consensus" sequence generated. Indeed, programs and algorithms used for alignments typically tolerate definable levels of differences, including insertions, deletions, inversions, polymorphisms, point mutations, etc. Such alignments can aid in the determination of which positions in one nucleotide sequence correspond to which positions in other nucleotide sequences.

Dosing Regimen: A "dosing regimen", as that term is used herein, refers to a set of unit doses (typically more than one) that are administered individually separated by periods of time. The recommended set of doses (i.e., amounts, timing, route of administration, etc.) for a particular pharmaceutical agent constitutes its dosing regimen.

Initiation: As used herein, the term "initiation" when applied to a dosing regimen can be used to refer to a first administration of a pharmaceutical agent to a subject who has not previously received the pharmaceutical agent. Alternatively or additionally, the term "initiation" can be used to refer to administration of a particular unit dose of a pharmaceutical agent during therapy of a patient.

IgA1 protease: As used herein, the term "IgA1 protease" refers to an enzyme polypeptide that cleaves IgA1 molecules preferentially over IgA2 molecules. In some embodiments, an IgA1 protease cleaves human IgA1. In some embodiments, an IgA1 protease preferentially cleaves IgA1 over IgA2 by at least two-fold, at least three-fold, at least four-fold, at least five-fold, at least six-fold, at least seven-fold, at least eight-fold, at least nine-fold, at least ten-fold, at least twenty-fold, or more than at least twenty-fold. In some embodiments, an IgA1 protease does not show detectable cleavage of IgA2.

IgA1 protease activity: As used herein, the phrase "IgA1 protease activity" is used interchangeably with "IgA1 protease polypeptide activity" and refers to ability to cleave IgA1 molecules. In some embodiments, IgA1 protease activity refers to ability to cleave human IgA1 molecules.

IgA1 protease polypeptide: A polypeptide showing at least 45% overall sequence identity with one or more IgA1 proteases, and having an ability to cleave human IgA1 is an "IgA1 protease polypeptide", as that term is used herein. In some embodiments, an IgA1 protease polypeptide has at least 45% overall sequence identity with one or more IgA1 proteases listed in Table 1. In some embodiments, an IgA1 protease polypeptide shows at least 50%, at least 55%, at least 60%, at least 65%, at least 70%, at least 75%, at least 80%, at least 85%, at least 90%, at least 95%, at least 96%, at least 97%, at least 98% or at least 99% overall sequence identity with a listed IgA1 protease polypeptide. In some embodiments, an IgA1 protease polypeptide further shares at least one characteristic sequence element with the listed IgA1 protease polypeptide.

IgA1 protease polypeptide agent: An "IgA1 protease polypeptide agent", as that term is used herein, is an agent having a polypeptide backbone whose amino acid sequence is identical to that of an IgA1 protease polypeptide. In some embodiments, an IgA1 protease polypeptide agent has a polypeptide backbone with an amino acid sequence that is identical to that of an IgA1 protease; in some embodiments, an IgA1 protease polypeptide agent has a polypeptide backbone with an amino acid sequence that is shorter than that of an IgA1 protease polypeptide. In some embodiments, an IgA1 protease polypeptide agent has an polypeptide backbone that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, or more than at 20% shorter as compared to the length (in number of amino acid residues) of a polypeptide backbone of the mature soluble form of a corresponding IgA1 protease polypeptide. In some embodiments, an IgA1 protease polypeptide agent has a polypeptide backbone comprising a domain with an amino acid sequence that has at least 45%, at least 50%, at least 55%, at least 60%, at least 65%, at least 70%, at least 75%, at least 80%, at least 85%, at least 90%, at least 95%, at least 97%, at least 98%, or at least 99% overall sequence identity to the corresponding domain of an IgA1 protease. In some embodiments, an IgA1 protease polypeptide agent has one or more pendant groups covalently attached to its polypeptide backbone that differ from those present on an IgA1 protease polypeptide.

Pharmaceutical agent: As used herein, the phrase "pharmaceutical agent" refers to any agent that, when administered to a subject, has a therapeutic effect and/or elicits a desired biological and/or pharmacological effect.

Pharmaceutically acceptable carrier or excipient: As used herein, the term "pharmaceutically acceptable carrier or excipient" means a non-toxic, inert solid, semi-solid or liquid filler, diluent, encapsulating material or formulation auxiliary of any type.

Reference IgA1 protease polypeptide: As used herein, the term "reference IgA1 protease polypeptide" refers to a full-length, wild-type version of an IgA1 protease. In some embodiments, modified versions of reference IgA1 protease polypeptides are generated as potential therapeutics for an IgA1 deposition disease. In some embodiments, a reference IgA1 protease polypeptide is a known IgA1 protease. In some embodiments, a reference IgA1 protease polypeptide has the same amino acid sequence as that of an IgA1 protease polypeptide listed in Table 1.

Serious adverse event: The term "serious adverse event", as used herein, has its art-understood meaning and refers to any untoward medical occurrence that at any dose, for example, results in death, is life threatening, requires inpatient hospitalization (or prolongation of existing hospitalization), results in persistent or significant disability or incapacity (defined as a substantial disruption of a patient's ability to carry out normal life functions), etc. In some embodiments, a serious adverse event is a "serious adverse drug experience", as that term is used by the United States Food and Drug Administration, for example as defined in 21 CFR §310.305(b), which says that a serious adverse event is any adverse drug experience occurring at any dose that results in any of the following outcomes: death, a life-threatening adverse drug experience, inpatient hospitalization or prolongation of existing hospitalization, a persistent or significant disability/incapacity, or a congenital anomaly/birth defect. Important medical events that may not result in death, be life-threatening, or require hospitalization may be considered a serious adverse drug experience when, based upon appropriate medical judgment, they may jeopardize the patient or subject and may require medical or surgical intervention to prevent one of the outcomes listed in this definition. Examples of such medical events include allergic bronchospasm requiring intensive treatment in an emergency room or at home, blood dyscrasias or convulsions that do not result in inpatient hospitalization, or the development of drug dependency or drug abuse.

Susceptible to: The term "susceptible to" is used herein to refer to an individual having higher risk (typically based on genetic predisposition, environmental factors, personal history, or combinations thereof) of developing a particular disease or disorder, or symptoms thereof, than is observed in the general population.

Therapeutically effective amount: The term "therapeutically effective amount" of an pharmaceutical agent or combination of agents is intended to refer to an amount of agent(s) which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). A therapeutically effective amount is commonly administered in a dosing regimen that may comprise multiple unit doses. For any particular pharmaceutical agent, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific pharmaceutical agent employed; the duration of the treatment; and like factors as is well known in the medical arts.

Treatment: As used herein, the term "treatment" (also "treat" or "treating") refers to any administration of a pharmaceutical agent that partially or completely alleviates, ameliorates, relieves, inhibits, delays onset of, reduces severity of and/or reduces incidence of one or more symptoms or features of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

Unit dose: The term "unit dose", as used herein, refers to a discrete administration of a pharmaceutical agent, typically in the context of a dosing regiment.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 3A-H show an amino acid sequence alignment of sequences from IgA1 proteases from *Haemophilus influenzae*. *H. influenzae* IgA1 proteases are listed in Table 1. Of these, amino acid sequences from proteases whose full nucleotide sequences were available (e.g., proteases from Rd strain (SEQ ID NO: 14), aegyptius strain (SEQ ID NO: 19), GenBank Accession No. M87489 (SEQ ID NO: 12), GenBank Accession No. X59800 (SEQ ID NO: 2), GenBank Accession No. 64357 (SEQ ID NO: 4), GenBank Accession No. 87492 (SEQ ID NO: 61, GenBank Accession No. M87490 (SEQ ID NO: 10), and GenBank Accession No. M87491 (SEQ ID NO: 8)) were used in the alignment. Depicted is a sequence alignment generated using Clustal W software (see the website whose address is "www" followed immediately by ".clustal.org"), with a consensus sequence shown at the bottom (SEQ ID NO: 23).

FIGS. 3A-H show an amino acid sequence alignment of sequences from IgA1 proteases from *Haemophilus influenzae*. *H. influenzae* IgA1 proteases are listed in Table 1. Of these, amino acid sequences from proteases whose full nucleotide sequences were available (e.g., proteases from Rd strain, aegyptius strain, GenBank Accession No. M8749, GenBank Accession No. X59800, GenBank Accession No. 64357, GenBank Accession No. 87492, GenBank Accession No. M87490, and GenBank Accession No. M87491) were used in the alignment. Depicted is a sequence alignment generated using Clustal W software (see the website whose address is "www" followed immediately by ".clustal.org"), with a consensus sequence shown at the bottom.

DETAILED DESCRIPTION OF CERTAIN EMBODIMENTS OF THE INVENTION

Figure 1:
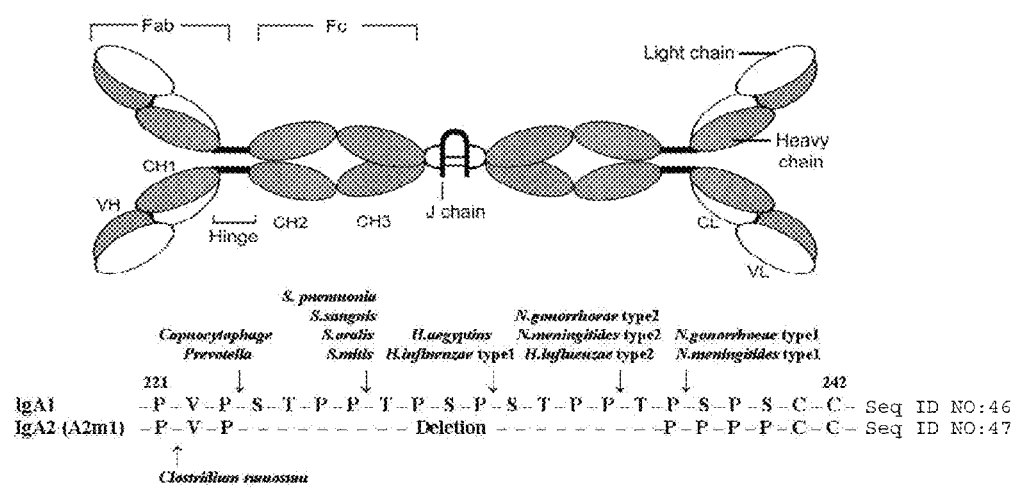
FIG. 1 depicts cleavage sites on dimeric human IgA1 for a variety of IgA1 proteases (SEQ ID NOS 46-47, respectively, in order of appearance). The diagram shows where the hinge is located in each IgA1 heavy chain (indicated by a bracket). The hinge sequence (residues 221-242) is shown below the diagram. Each IgA1 protease cleaves after a proline (arrows), leading to a marked reduction in the size of dimeric IgA1. Absence of the hinge region in IgA2 molecules shortens the heavy chain, and makes it resistant to all IgA1 proteases characterized thus far except for that of *Clostridium ramosum*.

The present invention provides, among other things, IgA1 protease polypeptide agents for use in reducing IgA1 deposits in a subject. Methods of using such IgA1 protease polypeptide agents are also disclosed.

I. IgA1 Protease Polypeptide Agents

Among other things, the present invention has identified regions of *Haemophilus influenzae* IgA1 proteases that can be modified (e.g., by covalent attachment of a pendant group), altered at an amino acid sequence level (e.g. by amino acid substitutions, insertions, deletions, etc.), and/or removed to create beneficial IgA1 protease polypeptide agents as described herein. The present invention incorporates the identification of such regions in the design of novel IgA1 protease polypeptide agents that have therapeutic value. In some embodiments, IgA1 protease polypeptide agents comprise a polypeptide backbone having an amino acid sequence that is related to *H. influenzae* protease polypeptides but different than that of an *H. influenzae* IgA1 protease, in that the polypeptide backbone lacks certain C-terminal sequences and/or in that the polypeptide backbone has an amino acid sequence that differs from that of an *H. influenzae* IgA1 protease in at least one region corresponding to a surface epitope. In some embodiments, the IgA1 protease polypeptide agent comprises a polypeptide backbone whose amino acid sequence is related to *H. influenzae* protease polypeptides and at least one pendant group covalently attached to the polypeptide backbone.

A. Polypeptide Backbones

In some embodiments, an IgA1 protease polypeptide agent has a polypeptide backbone with an amino acid sequence that is identical to that of an *H. influenzae* IgA1 protease.

Nucleotide sequences encoding *H. influenzae* IgA1 protease polypeptides and amino acid sequences of corresponding full length precursor polypeptides are listed in the sequence listing under SEQ ID NO:s listed in Table 1. An amino acid sequence of the mature form of IgA1 protease polypeptide from the Rd strain of *H. influenzae* is provided as amino acid residues 26 to 1014 of SEQ ID NO: 24. (Residues 1 to 25 comprise an N-terminal signal peptide that is cleaved during processing.)

TABLE 1

*H. influenzae* IgA1 proteases

| | | SEQ ID NO: s | |
|---|---|---|---|
| Strain | GenBank accession number | Nucleotide Sequence | Amino acid Sequence (full length precursor) |
| — | X59800 | 1 | 2 |
| | X64357 | 3 | 4 |
| | M87492 | 5 | 6 |
| | M87491 | 7 | 8 |
| | M87490 | 9 | 10 |
| | M87489 | 11 | 12 |
| Rd | NC-000907 (complete genome) | 13 | 14* |
| 7768 | AF274862 | 15 (partial sequence) | — |
| 6338 | AF274860 | 16 (partial sequence) | — |
| 2509 | AF274859 | 17 (partial sequence) | — |
| aegyptius | AF369907 | 18 | 19 |
| 8625 | AJ001741 | 20 (partial sequence) | — |
| HK284 | X82487 | 21 (partial sequence) | — |
| Da66 | X82467 | 22 (partial sequence) | — |
| Consensus | — | — | 23 |

*The mature form of the polypeptide for *H. influenzae* Rd IgA1 protease is provided as amino acid residues 26-1014 of SEQ ID NO: 24.

In some embodiments, an IgA1 protease polypeptide agent has a polypeptide backbone with an amino acid sequence that is shorter than that of an *H. influenzae* IgA1 protease polypeptide. In some embodiments, IgA1 protease polypeptide agents comprise a polypeptide whose amino acid sequence shares at least 45% overall sequence identity with SEQ ID NO: 23 (a consensus sequence for *H. influenzae* IgA1 protease). In some embodiments, IgA1 protease polypeptide agents comprise a polypeptide whose amino acid sequence shares at least 50%, at least 55%, at least 60%, at least 65%, at least 70%, at least 75%, at least 80%, at least 85%, at least 90%, at least 95%, at least 97%, at least 98%, or at least 99% overall sequence identity with SEQ ID NO: 23.

B. Modifications

As discussed above, IgA1 protease polypeptide agents of the present invention generally differ from an *H. influenzae* IgA1 protease polypeptide by at least one modification. Such modifications can involve, for example, alterations in the sequence of the polypeptide backbone (such as, e.g., truncations, substitutions, deletions, insertions, and combinations thereof), attachment of pendant groups to the polypeptide backbone, or both. In many embodiments, such modifications improve the desirability of the IgA1 protease polypeptide agent as a therapeutic (e.g., by reducing immunogenicity, increasing enzymatic activity, increasing ability to reduce deposits of IgA1, increasing bioavailability, increasing half-life of the IgA1 protease polypeptide in a subject, etc).

Truncated IgA1 Protease Polypeptides

Among other things, the present invention has identified regions of *H. influenzae* IgA1 protease polypeptides that tolerate significant structural alteration. That is, alterations to or ablations of such regions have little or no deleterious effects on IgA1 protease polypeptide activity. In some embodiments of the invention, IgA1 protease polypeptide agents are provided that are truncated at such regions. Truncated IgA1 protease polypeptides may be desirable because their reduced sizes may allow them to be less immunogenic than full length IgA1 protease polypeptides.

Truncations

The present invention discloses, among other things, results from crystallographic studies of an *H. influenzae* IgA1 protease polypeptide that suggest that the carboxy terminal portion of the polypeptide exists in unstructured loops and may be dispensible. Such crystallographic studies suggest that up to 20% of the amino acid residues can be removed at the C-terminal end of *H. influenzae* IgA1 protease polypeptide without deleterious effects on IgA1 protease activity. (Percentage calculation is based on the length of the mature, secreted form of the polypeptide, which lacks the N-terminal signal sequence).

As mentioned previously, in gram-negative bacteria, IgA1 protease polypeptides are expressed as a single-chain precursor that undergoes auto-catalytic cleavage to release a mature soluble IgA1 protease polypeptide (see FIG. 2A). The mature soluble form of IgA1 protease polypeptide from the Rd strain of *H. influenzae* is 965 amino acids in length, comprising residues 26 through 1014 of SEQ ID NO: 24. Amino acid residues 1-24 form an N-terminal signal peptide. (Numbering of amino acid positions for *H. influenzae* Rd IgA1 protease throughout this specification is consistent with that of the full length precursor polypeptide (see SEQ ID NO: 14).

The present disclosure reveals structural analyses from crystallographic studies that suggest that the region spanning amino acids 828 through 1014 may tolerate alterations and/or deletions without substantial deleterious effects on IgA1 protease activity.

In many embodiments, IgA1 protease polypeptide agents comprise a polypeptide backbone that lacks sequences found C-terminal to residue 975 of SEQ ID NO: 32. In some embodiments, the polypeptide backbone lacks sequences found C-terminal to residue 975 of SEQ ID NO: 24. In some embodiments, the polypeptide backbone lacks sequences found C-terminal to residue 966 of SEQ ID NO: 24. In some embodiments, the polypeptide backbone lacks sequences found C-terminal to residue 945 of SEQ ID NO: 24. In some embodiments, the polypeptide backbone lacks sequences found C-terminal to residue 936 of SEQ ID NO: 24. In some embodiments, the polypeptide backbone lacks sequences found C-terminal to residue 828 of SEQ ID NO: 24.

Generation of Truncated IgA1 Protease Polypeptides

Truncated IgA1 protease polypeptides can be generated by any of a variety of methods known in the art. For example, nucleic acids encoding truncated IgA1 protease polypeptides can be generated using polymerase chain reaction (PCR) of a template nucleic acid that encodes all or part of a reference IgA1 protease polypeptide. PCR primers can be designed such that only a selected region of the template is amplified, thus generating a truncation mutation.

Alternatively or additionally, nucleic acids (such as those encoding IgA1 proteases) can be selectively cleaved to generate truncated nucleic acids, which can be cloned into a suitable vector and/or amplified by PCR. For example, restriction endonucleases, which specifically cleave at their recognition sites within nucleic acids, can be employed. Alternatively or additionally, truncated IgA1 protease polypeptides can be generated by expression a modified IgA1 protease polypeptide that has been engineered to include one or more cleavage sites for site-specific proteases. Such modified polypeptides can be expressed from nucleic acids that have been manipulated (e.g., by methods such as insertional mutagenesis, site-specific recombination, etc.) to encode cleavage sites in the corresponding polypeptide. Cleavage sites can be strategically placed such that after cleavage, a resulting truncated polypeptide of the desired length is generated.

A variety of site-specific proteases are known in the art and suitable for use in the present invention. To give but a few examples, furin cleaves just downstream of its target cleavage site, canonically (RX(RK)R); SEQ ID NO:42); Factor Xa cleaves after the arginine residue of its preferred cleavage site (I(ED)GR); SEQ ID NO:43); and enterokinase cleaves after the lysine residue in its target cleavage site (DDDDK; SEQ ID NO:44). Site-specific proteases are available from commercial suppliers such as, for example, New England Biolabs (Ipswich, Mass.), QIAGEN (Valencia, Calif.), ProZyme (San Leandro, Calif.), and Bachem Biosciences (King of Prussia, Pa.).

Mapping Antigenic Hotspots

Among other things, the present invention defines regions of IgA1 proteases that act as antigenic hot spots, i.e., epitopes and/or regions that are particularly immunogenic. Present invention provides, among other things, IgA1 protease polypeptide agents that contain sequence alterations as compared with a reference IgA1 protease polypeptide within some antigenic hot spots.

In some embodiments, antigen hot spots of IgA1 protease are determined by epitope mapping experiments. (See, for example, Example 9). In some such embodiments, overlapping peptides from a reference IgA1 protease polypeptide are tested for antigenicity. Antigenicity may be determined, for example, by using a panel of antibodies that recognize IgA1 protease polypeptides. Recognition of a peptide by several antibodies, for example, by more than 10%, 20%, 30%, 40%, 50%, 60%, 70%, 80%, or 90% of the antibodies in the panel tested may indicate that the peptide serves as an antigenic hotspot within an IgA1 protease polypeptide.

Provided in the present disclosure are at least two monoclonal antibodies (mAB IGAN3.3 and mAB IGAN 8.3) and four additional antibodies under development. (See Examples 5 and 9). These antibodies may be used, among other things, for epitope mapping studies as described herein and in Example 9. In some embodiments, epitopes recognized by mAB IGAN3.3, mAB IGAN 8.3 are antigenic hot spots.

In some embodiments, epitopes and regions serving as antigenic hot spots of IgA1 protease are determined by examining models of three-dimensional structures of IgA1 protease polypeptides (such as structures generated from X-ray crystallographic data). In some embodiments, epitopes and regions serving as antigenic hot spots comprise residues that are exposed on the surface of an IgA1 protease polypeptide.

In some embodiments, IgA1 protease polypeptide agents comprise mutations in epitopes and/or regions that are identified as being antigenic hot spots. Examples of such mutations include, but are not limited to, deletion of one or more residues, insertion of one or more residues, substitution of one or more residues, and combinations thereof. In some embodiments, an entire epitope and/or region that is identified as being an antigenic hot spot is deleted from the IgA1 protease polypeptide agent.

Methods for generating such mutations are known in the art and are further described herein in the section titled "Production and characterization of IgA1 protease polypeptide agents." For example, site-directed mutagenesis employs molecular biology techniques known in the art and can be used to generate nucleic acids encoding polypeptides having the desired mutation. As discussed herein, such nucleic acids can be introduced into host cells and their encoded polypeptides expressed and isolated and/or purified for use in the present invention.

Pendant Groups

In some embodiments, provided are IgA1 protease polypeptide agents whose amino acid sequence is similar or identical to that of a reference IgA1 protease polypeptide, but that differs in number, kind, and/or location of pendant groups covalently linked to the polypeptide backbone. In some embodiments, provided are IgA1 protease polypeptide agents comprising a polypeptide backbone whose amino acid sequence shares at least 45% overall sequence identity with SEQ ID NO: 23 and at least one pendant group covalently attached to the polypeptide backbone.

In some embodiments, one pendant group is covalently linked to a given molecule of an IgA1 protease polypeptide agent. In some embodiments, two, three, four, five, six, seven, eight, nine, ten, or more than ten pendant groups are covalently linked to a given molecule of IgA1 protease polypeptide agent.

In some embodiments, pendant groups comprise polyethylene glycol (PEG). "PEGylation" refers to conjugation of polyethylene glycol (PEG) chains on a molecule, such as a peptide or protein. PEG chains are nontoxic, non-antigenic, and highly soluble in water. PEG chains often reduce antigenicity of a biomolecule. Without wishing to be bound by any particular theory, PEG may also prolong the circulating half-life of the biomolecule (that is, the bioavailability of the biomolecule) by preventing its contact with immune cells and/or by retarding degradation in vivo (Roberts et al. (2002), the entire contents of which are herein incorporated by reference). Increasing the molecular mass of a biomolecule after addition of PEG chains can also reduce renal clearance of the biomolecule.

In some embodiments, PEG chains are linear. In some embodiments, PEG chains are branched. In some embodiments, PEG chains have a relative molecular mass ($M_r$) of between approximately 10 and approximately 40 kDa (inclusive of endpoints).

In some embodiments, pendant groups comprise polysialic acid. Polysialylation is attractive because polysialic acids are biodegradable. In some embodiments, colominic acid (CA) is used to polysialylate. Colominic acid is biodegradeable, hydrophilic, linear sialic acid homopolymer whose units are linked via $\alpha$-2,8 glycosidic bonds. Methods of polysialylation are known in the art (see, for example, Gregoriadis et al. (2005), the contents of which are herein incorporated by reference in their entirety), and companies such as Lipoxen Technologies Ltd. of the United Kingdom offer polysialylation services.

In some embodiments, one or more pendant groups is/are attached at one or more particular sites of IgA1 protease polypeptide backbones; in some such embodiments, one or more pendant groups is/are attached to regions of IgA1 proteases that act as antigenic hot spots. In some embodiments, one or more pendant groups is/are attached to regions of IgA1 proteases that are dispensable for IgA1 protease activity. In some embodiments, one or more pendant groups is/are attached within unstructured regions (e.g., regions that appear as unstructured loops in a 3D structure model of an IgA1 protease). In some embodiments, one or more pendant groups is/are attached to polypeptide backbones of IgA1 protease polypeptide agents within a region defined by positions corresponding to residues 820 to 1014 (inclusive) of SEQ ID NO: 23. In some embodiments, one or more pendant groups is/are attached within one or more regions defined by positions corresponding to residues 881-893 of SEQ ID NO: 23, residues 936-945 of SEQ ID NO: 23, and/or residues 966-975 of SEQ ID NO: 23.

Pendant groups may be attached to particular sites of IgA1 protease polypeptides using methods known in the art. For example, PEG can be targeted specifically to thiols of cysteine residues (Brocchini et al. (2006), the entire contents of which are herein incorporated by reference). Reagents to selectively conjugate PEG chains onto cysteine residues are available and include, but are not limited to, PEG-maleimide, PEG-vinylsulfone, PEG-iodoacetamide and PEG-orthopyridyl disulfide.

Additionally or alternatively, transglutaminase can be used to PEGylate selected glutamine residues (Fontana et al. (2008), the entire contents of which are herein by reference. As a further example, glycosyltransferases can be used to transfer PEG to O-glycosylation sites (DeFrees et al. (2006), the entire contents of which are herein incorporated by reference.)

In some embodiments, target sites for specific PEGylation that are not present in a reference IgA1 protease polypeptide are created. For example, for IgA1 proteases that lack or have few cysteine residues, cysteine residues may be introduced by methods known in the art (such as, for example, site-specific recombination and insertional mutagenesis).

In some embodiments, pendant groups are irreversibly attached to the polypeptide backbone of IgA1 protease polypeptide agents. In some embodiments, pendant groups are reversibly attached to the polypeptide backbone of IgA1 protease polypeptide agents. For example, PEG can be reversibly conjugated using bifunctional reagents to bridge amino groups of proteins to an alkylated—SH-containing PEG derivative.

Multiple Modifications

A particular IgA1 protease polypeptide agent may comprise any combination of modifications including, but not limited to, those discussed above. For example, a truncated IgA1 protease polypeptide can also be modified by one or more mutations to alter an antigenic hot spot and/or by the addition of one or more pendant groups.

C. Reference IgA1 Protease Polypeptides

It will be understood by one of ordinary skill in the art that structural information of a given polypeptide can provide structural information about related polypeptides. Accordingly, structural information of IgA1 protease polypeptides of the Rd strain of *H. influenzae* provided by the present disclosure can be used to design modifications of related IgA1 protease polypeptides. For example, IgA1 protease polypeptides of other strains of *H. influenzae* (presented in Table 1) are highly homologous (e.g., have a high percentage of overall sequence identity) to *H. influenzae* Rd IgA1 protease polypeptides (see FIG. 3A-H). Given the homology between such polypeptides, one of ordinary skill of the art would expect that the structural insights provided by the present disclosure can be used to design IgA1 protease polypeptide agents using other *H. influenzae* IgA1 protease polypeptides as a reference IgA1 protease polypeptide.

Moreover, structural insights provided by the present disclosure may well be relevant to IgA1 protease polypeptides from other bacterial species. For example, IgA1 protease polypeptides from other bacterial species that have a high percentage of amino acid sequence identity over the entire sequence, or within a subregion of the sequence, may have structural similarities to *H. influenzae* Rd IgA1 protease polypeptides.

Therefore, one of ordinary skill in the art combining the teachings of the present disclosure with methods known in the art will be able to design, produce, and test IgA1 protease polypeptide agents that are modified versions of IgA1 proteases polypeptides other than *H. influenzae* IgA1 protease polypeptides.

A variety of bacteria produce IgA1 proteases and/or homologues of IgA1 proteases that may be useful (e.g., as reference IgA1 protease polypeptides) in the present invention. These bacteria include, but are not limited to *Clostridium ramosum, Haemophilus influenzae* type 1 and 2, *Neisseria meningitidis* type 1 and 2, *Neissseria gonorrhoeae, Neisseria lactamica, Prevotella melaminogenica, Streptococcus mitis* biovar I, *Streptococcus oxalis, Streptococcus pneumoniae, Streptococus pyogenes, Streptococcus sanguis*, and *Ureaplasma realyticum*.

Table 2 presents a list of bacterial species and strains that produce IgA1 protease polypeptides and/or homologues. Table 2 is not intended to be limiting; i.e., IgA1 protease polypeptides from bacterial species and strains not listed in Table 2 can also be modified to generate IgA1 protease polypeptide agents.

TABLE 2

Bacterial strains that produce IgA1 proteases

| Bacterial species | Strain | GenBank accession number[1] |
|---|---|---|
| *Clostridium ramosum* | — | AY028440 |
| *Haemophilus* | — | X59800 |

TABLE 2-continued

Bacterial strains that produce IgA1 proteases

| Bacterial species | Strain | GenBank accession number[1] |
|---|---|---|
| influenzae | | X64357 |
| | | X64357 |
| | | M87492 |
| | | M87491 |
| | | M87490 |
| | | M87489 |
| | Rd | NC-000907 (complete genome) |
| | 7768 | AF274862 |
| | 6338 | AF274860 |
| | 2509 | AF274859 |
| | aegyptius | AF369907 |
| | 8625 | AJ001741 |
| | HK284 | X82487 |
| | Da66 | X82467 |
| | HK635 | X82488 |
| Neissseria gonorrhoeae | — | A12416 |
| | MS11 | S75490 |
| Neisseria lactamica | NL3327 | AJ001740 |
| | NL3354 | AJ001739 |
| | NL823 | AJ001737 |
| | NL3293 | AJ001738 |
| Neisseria meningitidis | — | AF235032 |
| | Z2491 | AF012203 |
| | B40 | AF012211 |
| | Z4099 | AF012210 |
| | Z4081 | AF012209 |
| | Z4400 | AF012208 |
| | Z3524 | AF012207 |
| | Z40204 | AF012206 |
| | Z3910 | AF012205 |
| | Z3906 | AF012204 |
| | Z2491 | AF012203 |
| | IHN5341 | X82478 |
| | HK284 | X82487 |
| | ETH2 | X82469 |
| | NG093 | X82482 |
| | NCG80 | X82479 |
| | NG117 | X82483 |
| | HF96 | X82475 |
| | HF54 | X82473 |
| | HF48 | X82480 |
| | HF13 | X82474 |
| | NGC65 | X82484 |
| | NCG16 | X82485 |
| | SM1894 | X82476 |
| | EN3771 | X82468 |
| | NG44/76 | X82481 |
| | SM1166 | X82486 |
| | HF159 | X82471 |
| | 81139 | X82477 |
| | HF117 | X82470 |
| | SM1027 | X82472 |
| Streptococcus pneumoniae | — | X94909 |
| | R6 | NC-003098 (complete genome) |
| Streptococus pyogenes | MGAS315 | NC-004070 (complete genome) |
| Streptococcus sanguis | SK85 | Y13461 |
| | SK49 | Y13460 |
| | SK4 | Y13459 |
| | SK162 | Y13458 |
| | SK161 | Y13457 |
| | SK115 | Y13456 |
| | SK112 | Y13455 |
| Ureaplasma urealyticum | — | NC_002162 (complete genome) |

[1]The provided accession numbers relate to GenBank database entries for nucleotide sequences of IgA1 proteases from the specified bacterial species or strain, unless otherwise indicated. (For some bacterial strains, the entire genomic sequence is available in the GenBank database, and the gene encoding the IgA1 protease can be found within that genomic sequence.) The GenBank database is accessible at the website for the National Center for Biotechnology Information. See the website whose address is "http:" followed immediately by "//www.ncbi.nlm.nih.gov".

For example, the present disclosure reveals, among other things, that the C-terminal region (in particular, amino acid residues 828 to 1014 of SEQ ID NO: 24) of an *H. influenzae* IgA1 protease polypeptide can tolerate alteration and/or deletion. Corresponding regions in other, related IgA1 protease polypeptides may also tolerate alteration and/or deletion.

Methods of identifying regions of sequence and/or structural similarity between two polypeptides are known in the art and can be used to identify related IgA1 protease polypeptides and corresponding regions within such IgA1 protease polypeptides. For example, sequence alignment programs such as BLAST (available, for example, on the website of the National Center for Biotechnology Information) or Clustal W (available for example, at the website whose address is "www" followed immediately by ".clustal.org" and at the website whose address is "www" followed immediately by ".ebi.ac.uk/Tools/clustalw2/index.html" (a website hosted by the European Bioinformatics Institute at the European Molecular Biology Laboratory) can be used to identify regions of sequence similarity between two or more polypeptides. BLAST can also be used to compare two or more nucleotide sequences, as can Sequencher, a software program available from GeneCodes (Ann Arbor, Mich.).

For example, sequence alignments can be performed between *H. influenzae* IgA1 protease polypeptides (using, for example, any of the sequences summarized in Table 1) and IgA1 protease polypeptides produced by other bacterial species and/or strains. For example, regions in other IgA1 proteases that bear sequence similarity to the region defined by amino acid residues 828 to 1014 (or subregions thereof) are likely regions that tolerate alteration and/or deletion in such other IgA1 proteases.

C. Production and Characterization of IgA1 Protease Polypeptide Agents

Production of IgA1 Protease Polypeptide Agents

In many embodiments, IgA1 protease polypeptide agents are obtained by producing IgA1 protease polypeptides (i.e., a polypeptide backbone having sequence similarity to an IgA1 protease) and optionally modifying such polypeptides.

Genes encoding IgA1 proteases are known (see Tables 1 and 2) and their sequences have typically been deposited in the GenBank database at the National Center for Biotechnology Information. Genetic material containing genes encoding such IgA1 protease polypeptides, or fragments thereof, are often publicly available through genetic repositories and/or through laboratories who have published gene sequence information for such IgA1 proteases. Such genetic material can be manipulated using, for example, molecular biology techniques, to generate nucleic acids encoding IgA1 protease polypeptides that have been modified as discussed above.

IgA1 protease polypeptides can be produced by any of a variety of methods known in the art. IgA1 protease polypeptides can be recombinantly expressed from such nucleic acids in protein expression systems (such as, for example, expression systems in bacteria, insect cells, and mammalian cells). Methods of constructing gene expression vectors, transforming host cells with such vectors, inducing expression of proteins encoded by such expression vectors, and isolation and purification of such proteins are known in the art. See, for example, U.S. Pat. No. 7,407,653 and Sambrook et al. (2001), the contents of both of which are incorporated by reference in their entirety.

In some embodiments, IgA1 protease polypeptides are modified after expression in an expressions system. In some embodiments, IgA1 protease polypeptides are modified after isolation and/or purification. For example, pendant groups may be covalently attached to IgA1 protease polypeptides. Alternatively or additionally, IgA1 protease polypeptides may be cleaved, for example, to generate a truncated product.

Tags

In some embodiments, IgA1 protease polypeptides are fused to tags. Such tags may be useful, for example, in isolation, purification, and/or detection of polypeptides. Alternatively or additionally, tags may be used as sites to which ligands can bind, to allow complexation of polypeptides to such ligands. Alternatively or additionally, tags can serve as cleavage sites for site-specific proteases.

Tags may be inserted in various positions within an IgA1 protease polypeptide. In many embodiments, at least one tag is inserted on the N-terminal side of an autocatalytic cleavage site, such that after autocatalytic cleavage, the tag is contained within the mature IgA1 protease polypeptide. In some such embodiments, at least one tag is inserted within five, within four, within three, within two, or immediately adjacent to an autocatalytic cleavage site.

To generate an IgA protease polypeptide comprising a tag, a sequence encoding a tag can be ligated in frame to a sequence encoding an IgA1 protease polypeptide using conventional molecular biology techniques. In many embodiments, a tag sequence is ligated upstream of DNA sequence encoding an IgA1 protease auto-catalytic cleavage site such that, upon cleavage of the IgA1 protease precursor polypeptide, a soluble IgA1 protease polypeptide comprising a tag is secreted into bacterial growth media.

Alternatively or additionally, an IgA1 protease polypeptide comprising a tag can be generated by PCR-based site-directed mutagenesis. A number of site-directed mutagenesis methods are known in the art and allow one mutation of specific regions within a polypeptide. Such methods are embodied in a number of commercially available kits that are used to perform site-directed mutagenesis by both conventional and PCR-based methods. Examples of such kits include the Stratagene's EXSITE™ mutagenesis kit (Catalog No. 200502; PCR based)), QUIKCHANGE™ mutagenesis kit (Catalog No. 200518; PCR based)), and CHAMELEON™ double-stranded site-directed mutagenesis kit (Catalog No. 200509).

A tag sequence can be introduced into a PCR fragment by inclusion of a sequence encoding the tag near the 5' or 3' end of one of the PCR primers. PCR fragments are generated in a manner to provide appropriate restriction sites such that fragments can be digested then ligated into a parental vector for replacement of specific amino acid codons.

In some embodiments, the tag has a specific binding affinity for an antibody, so that the resulting polypeptide forms an immuno-complex upon binding antibody. For example, the tag may comprise a unique epitope for which antibodies are readily available. Alternatively or additionally, the tag can comprise metal-chelating amino acids (e.g. His) so that tagged IgA1 protease polypeptides can complex with a metal-chelating resin or bead, for example nickle-NTA beads.

In some embodiments, the tag comprises a detectable marker, such as an enzyme, and/or an amino acid that can be labeled with a detectable marker. Non-limiting examples of detectable markers include, radioisotopes, fluorescent molecules, chromogenic molecules, luminescent molecules, and enzymes. Useful detectable markers in the present invention include biotin for staining with labeled streptavidin conjugate, fluorescent dyes (e.g., fluorescein, Texas Red, rhodamine, green fluorescent protein, and the like), radiolabels (e.g., $^{3}$H, $^{125}$I, $^{35}$S, $^{14}$C, or $^{32}$P), enzymes (e.g., horse radish peroxidase, alkaline phosphatase, glucose oxidase, and others commonly used in an ELISA), and calorimetric labels such as colloidal gold. Patents teaching the use of such detectable markers include U.S. Pat. Nos. 3,817,837; 3,850,752; 3,939,350; 3,996,345; 4,277,437; 4,275,149; and 4,366,241, the entireties of which are incorporated herein by reference.

Non-limiting examples of suitable tags suitable for use in the present invention include epitope tags such as c-Myc, HA, and VSV-G, HSV, FLAG, V5, and 6×HIS (SEQ ID NO: 25). Amino acid and nucleic acid sequence for each tag is shown below.

TABLE 3

Examples of epitope tags

| Tag | Amino acid sequence | Nucleic acid sequence |
|---|---|---|
| 6×His | HHHHHH (SEQ ID NO: 25) | CAC CAT CAC CAT CAC CAT (SEQ ID NO: 26) |
| c-myc | EQKLISEEDL (SEQ ID NO: 27) | GAG CAA AAG CTC ATT TCT GAA GAG GAC TTG (SEQ ID NO: 28) |
| HA | YPYDVPDYA (SEQ ID NO: 29) | TAC CCT TAT GAT GTG CCA GAT TAT GCC (SEQ ID NO: 30) |
| VSV-G | YTDIEMNRLGK (SEQ ID NO: 31) | TAT ACA GAC ATA GAG ATG AAC CGA CTT GGA AAG (SEQ ID NO: 32) |
| HSV | QPELAPEDPED (SEQ ID NO: 33) | CAG CCA GAA CTC GCC CCG GAA GAC CCC GAG GAT (SEQ ID NO: 34) |
| V5 | GKPIPNPLLGLDST (SEQ ID NO: 35) | GGC AAA CCA ATC CCA AAC CCA CTG CTG GGC CTG GAT AGT ACT (SEQ ID NO: 36) |
| FLAG | DYKDDDDKG (SEQ ID NO: 37) | GAT TAC AAA GAC GAT GAC GAT AAA GGA (SEQ ID NO: 38) |

Tagged IgA1 protease polypeptides may be detected in vivo and/or in vitro using the tag. Tags comprising an epitope for an antibody can be detected using anti-tag antibodies and/or antibodies that are conjugated to a detectable marker. The detectable marker can be a naturally occurring or non-naturally occurring amino acid that bears, for example, radio-isotopes (e.g., $^{125}$I, $^{35}$S), fluorescent or luminescent groups, biotin, haptens, antigens and enzymes. Many antibodies to such tags are commercially available, such as, for example, anti-c-myc, anti-HA, anti-VSV-G, anti-HSV, anti-V5, anti-His, and anti-FLAG. Antibodies to tags can also be produced using standard methods, for example, by monoclonal antibody production. (See, for example, Campbell, A. M. (1984), the entire contents of which are herein incorporated by reference). The anti-tag antibodies can then be detectably labeled through the use of radioisotopes, affinity labels (such as biotin, avidin, etc.), enzymatic labels (such as, for example, horseradish peroxidase, alkaline phosphatase, etc.) using methods well known in the art, such as described in international application WO 00/70023 and Harlour and Lane (1989), the entire contents of which are herein incorporated by reference.

Assays for detecting tags include, but are not limited to, Western blot analysis, immunohistochemistry, ELISA, FACS analysis, enzymatic assays, and autoradiography. Means for performing these assays are well known to those of skill in the art. For example, radiolabels may be detected using photographic film or scintillation counters and fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing a colored label.

A tag can be used to isolate IgA1 protease polypeptides from other cellular material. For example, a tag that can be recognized by an antibody can facilitate isolation by immunoprecipitation, using anti-tag antibody affinity columns, and/or using anti-tag antibody conjugated beads. When a 6×His tag (SEQ ID NO: 25) is used, isolation can be performed using a metal-chelate column. (See, for example, Hochuli in *Genetic Engineering: Principles and Methods*, the entire contents of which are herein incorporate by reference). Means for performing these types of purification are well known in the art.

Characterization of IgA1 Protease Polypeptide Agents

In some embodiments, IgA1 protease polypeptide agents are characterized by one or more methods to evaluate their safety, activity, antigenicity efficacy, pharmacokinetic parameters, and/or other characteristics as therapeutic agents for IgA1 deposition diseases. In some embodiments, provided are IgA1 protease polypeptide agents that elicit fewer and/or less severe side effects than does a reference IgA1 protease polypeptide. In some embodiments, provided are IgA1 protease polypeptide agents that are less toxic than a reference IgA1 protease polypeptide.

Activity

In many embodiments, IgA1 protease polypeptide agents are tested for ability to cleave IgA1 molecules. Assays for measuring IgA1-cleaving activity are known in the art and can be used in the practice of the present invention. See, for example, Plaut et al. (1994), the entire contents of which are herein incorporated by reference. In many embodiments, human IgA1 molecules are used as substrates in assays for IgA1-cleaving activity. In some embodiments, purified IgA1 protease polypeptide agents are assayed. In some embodiments, IgA1 protease polypeptide agents present in bacterial media (e.g., media from cultures of bacteria that have been engineered and/or induced to express IgA1 protease polypeptide agents) are assayed. In some embodiments, and IgA1 protease polypeptide agent is considered to have sufficient activity to be used as therapeutic agent if it has at least one unit activity, with one unit activity being equal to one microgram of human IgA1 cleaved per minute at 37° C.

Example 2 describes development of an IgA1 protease polypeptide activity assay that has been developed by the present inventors. As described in Example 2, IgA1 hydrolysis can be determined by measuring amount of Fab (antibody fragment, antibody binding portion) produced per unit time at 37° C.

In some embodiments, provided are IgA1 protease polypeptide agents that cleave IgA1 molecules. In some such embodiments, IgA1 protease polypeptide agents cleave human IgA1 molecules. In some embodiments, provided are IgA1 protease polypeptide agents that have enhanced and/or increased enzymatic activity as compared to a reference IgA1 protease polypeptide.

Antigenicity

In some embodiments, antigenicity of IgA1 protease polypeptide agents is determined. Antigenicity can be determined using methods known in the art, such as, for example, immunization of an animal model and subsequent measurement of titers of antibodies against such polypeptide agents. (See, for example, Example 11 of the present specification.) In some embodiments, antigenicity of one or more IgA1 protease polypeptide agents is compared against antigenicity of a reference IgA1 protease polypeptide (e.g., an unmodified IgA1 protease).

In some embodiments, provided are IgA1 protease polypeptide agents that are less immunogenic than a corresponding unmodified IgA1 protease (herein called a "reference IgA1 protease polypeptide"). In some embodiments, provided are IgA1 protease polypeptide agents that elicit fewer antibodies than does a reference IgA1 protease polypeptide.

Efficacy

In some embodiments, IgA1 protease polypeptide agents are tested for their efficacy in reducing and/or clearing deposits of IgA1. In some embodiments, IgA1 protease polypeptide agents are tested for their efficacy in ameliorating clinical manifestations of IgA1 deposition. In some embodiments, IgA1 protease polypeptide agents are tested for their efficacy in ameliorating symptoms of an IgA1 deposition disease.

Such testing may be accomplished, for example, using an animal model of an IgA1 deposition disease. A number of rat and mouse models for IgAN are available and described. Emancipator et al. 1987 and Gesualdo et al. (1990) (the entire contents of which are herein incorporated by reference) also describe rat and/or mouse models that may be used to assess characteristics of IgA1 protease polypeptide agents of the present invention. In the model described by Gesualdo et al., an IgA antibody/dextran sulfate complex is injected into mice, and immuno-complexes of IgA1 lodges in the kidney. Mice then present with glomerulonephritis, which is typical of cases of human IgAN. Another mouse model of IgAN is described by Lamm et al. 2008 (the entire contents of which are herein incorporated by reference). In such a mouse model, dimers of human IgA1 are complexed to $F(ab')_2$ fragments of goat anti-human antibody and the resulting complexes injected intravenously into normal mice.

Behavior of agents in such animal models is understood to reasonably correlate with activity in a clinical setting. In particular, the model described by Lamm et al. model is expected to closely mimic human IgAN because IgA complexes are closer in molecular composition to IgA1 complexes in human IgAN patients than the IgA complexes used in other models. In the mouse model described by Lamm et al., human IgA1 (as opposed to non-human IgA1) is used to form complexes.

Reduction and/or clearance of IgA1 deposits can be determined, for example, by analysis of tissue biopsies and/or tissue sections. Kidney sections from mouse models of IgAN can be analyzed, for example, by light, immunofluorescence, and/or electron microscopy. For example, kidney sections can be stained using standard immunhistochemical methods and IgA1 deposits can be visualized using labeled antibodies that recognize one or more components of injected complexes (e.g., fluorescently labeled antibodies). Label intensity (e.g., fluorescent intensity) can be scored using a scoring system, and average scores between cohorts can be compared. (For example, scores for a cohort to which a particular IgA1 protease polypeptide agent can be compared to scores for a cohort that received saline or a reference IgA1 protease polypeptide.) Additionally or alternatively, kidney sections from mouse models of IgAN can be visualized by electron micrography of mesangial regions. In electron micrographs, deposits of IgA1 are often visualizable as electron-dense areas.

In some embodiments, an IgA1 protease polypeptide agent is regarded as an effective therapeutic agent when the number of IgA1 deposits scored, and/or the intensity of labels for IgA1 deposits scored, is reduced toward the number of IgA1 deposits observed in a normal kidney. (See also Examples 3 and 12 the present specification.)

Alternatively or additionally, morphological changes such as expansion of mesangial matrix and mesangial hypercellularity can be scored by staining sections of renal cortex (for example, with staining reagents such as PAS (periodic acid-schiff), H&E (hematoxylin & eosin), trichrome, and/or Jones silver). See, for example, Gesualdo et al. 1990. For example, sections of renal cortex can be fixed in 10% formalin, embedded in paraffin, and stained. Expansion of mesangial matrix and mesangial hypercellularity can be scored semiquantitatvely, for example, according to methods described in Nakazawa et al. (1986) (1) and Nakazawa et at (1986) (2), the entire contents of both of which are herein incorporated by reference.

In some scoring systems, normal mesangial matrix is scored as 0. Expansion of mesangial matrix is scored as +1 when widened mesangial stalks are observed, +2 when matrix encroachment on capillary lumens is observed, and +3 when conspicuous widening of mesangial stalk is observed along with a decrease in capillary lumen.

In some embodiments, an IgA1 protease polypeptide agent is regarded as an effective therapeutic agent when it leads to reduction of expansion of mesangial matrix towards a typical morphology of a normal kidney, for example to a score of +2, or +1, or 0.

In some scoring systems, normal mesangial cellularity is scored as 0 and is defined as 3 or fewer cell nuclei per mesangial area. Hypercellularity is scored as +1 when 4 to 6 cell nuclei per mesangial area are observed, as +2 when 4 to 6 cell nuclei per mesangial area are observed in most areas but some areas have 7 or more nuclei, and as +3 when 7 or more cell nuclei per mesangial area are observed in most areas.

In some embodiments, an IgA1 protease polypeptide agent is regarded as an effective therapeutic agent when it leads to reduction of mesangial hypercellularity towards that observed in a normal kidney, for example to a score of +2, or +1, or 0.

In some embodiments, total glomerular area, matrix area, and/or glomerular cellularity are quantified in randomly selected glomeruli from each mouse by computer morphometry (Cue image analysis system, Olympus Corp., Columbia, Md.) (See Gesualdo et al., 1990). For example, cubes of cortex can be fixed in 2.5% gluteraldehyde in 0.1 M sodium cacodylate, post fixed in 1% $OsO_4$, and embedded in Spurr's epoxy (Polysciences, Inc. Warrington, Pa.). 50-70 nm sections can be stained with uranyl acetate and lead hydroxide. Coded grids can be examined in a JEOL JEM 100 EX microscope and matrix, cellularity, and immune deposits can be semiquantified as described in Nakazawa et al. 1986 (2).

In some embodiments, provided are IgA1 protease polypeptide agents that have enhanced and/or increased ability to reduce and/or clear deposits of IgA1 (e.g., human IgA1).

Clinical indications of reduction and/or clearance of IgA1 deposits can also be used to assess efficacy of IgA1 protease polypeptide agents. For example, hematuria (presence of red blood cells in urine) and proteinuria (presence of protein in urine) are clinical manifestations of IgAN. To assess hematuria and/or proteinuria test animals such as mice can be placed in metabolic cages and urine collected for a certain period of time (e.g., 24 hours). Urine is then centrifuged and can be assayed for protein. As described in Nakazawa et al. 1986 (2), presence of protein can be assayed by turbidimetry in 3% sulfalicylic acid and hematuria can be assayed by microscopy. Typically, a normal mouse without IgAN will have less then three red blood cells per high power field (such as at 40× magnification), while mice with IgAN will have greater than 10 red blood cells per high power field.

Subjects can be tested for hematuria and/or proteinuria before administering IgA1 protease polypeptide agent(s) to determine reference values indicative of IgA1 deposition and/or disease. In some embodiments, an IgA1 protease polypeptide agent is considered effective as a therapeutic agent when it leads to a reduction in the concentration of protein in urine. In some embodiments, an IgA1 protease polypeptide agent is considered effective as a therapeutic agent when it leads to a reduction in the number of red blood cells per high power field in urine. In some embodiments, an IgA1 protease polypeptide agent is considered effective as a therapeutic agent if it leads to a reduction of the reference value for hematuria and/or proteinuria of at least 5%, at least 10%, at least 15%, at least 20%, at least 25%, at least 30%, at least 35%, at least 40%, at least 45%, at least 50%, or greater than 50%.

Pharmacokinetics

In some embodiments, pharmacokinetics of IgA1 protease polypeptide agents are characterized. For example, pharmacokinetic parameters such as mean residence time (MRT), total body clearance (CL), volume of distribution at steady state ($V_{ss}$), and area-under-the-curve (AUC) can be estimated by methods known in the art.

Mean residence time refers to the average time that molecules of a drug reside in the body after a dose. Total body clearance describes how quickly drugs are eliminated, metabolized, and/or distributed throughout the body. Total body clearance can be viewed as the proportionality constant relating the rate of these processes and drug concentration. Volume of distribution at steady state ($V_{ss}$), is a parameter that describes steady-state volume of distribution of a drug. $V_{ss}$ is an estimate of drug distribution independent of elimination processes. $V_{ss}$ is most useful for predicting the plasma concentrations following multiple dosing to a steady-state or pseudo-equilibrium. $V_{ss}$ is proportional to the amount of drug in the body versus the plasma concentration of the drug at steady state. Serum concentration of IgA1 protease polypeptide agents can be plotted against time on log-linear graphs and α and area under the curve (AUC) calculations can be estimated using methods known in the art. (See, for example, Rowland et al. (1996) and Shargel et al. (1985), the entire contents of both of which are herein incorporated by reference.)

In some embodiments, provided are IgA1 protease polypeptide agents that exhibit increased bioavailability (e.g., increased half life in a subject) as compared to a reference IgA1 protease polypeptide. In some such embodiments, IgA1 protease polypeptide agents exhibit half lives of at least 20% greater as compared to a reference IgA1 protease polypeptide. In some embodiments, provided are IgA1 protease polypeptide agents that have greater AUC values than that of a reference IgA1 protease polypeptide. In some such embodiments, IgA1 protease polypeptide agents exhibit AUC values of at least 20% greater as compared to a reference IgA1 protease polypeptide.

II. Methods of Using IgA1 Protease Polypeptide Agents

In one aspect of the invention, provided are methods comprising a step of administering to an individual having deposits of IgA1 a polypeptide agent (e.g., an IgA1 protease polypeptide agent) as described herein. In some embodiments, the polypeptide agent is administered in an amount effective to reduce IgA1 deposits. In some embodiments, the individual has deposits of human IgA1.

A. Indications

The present disclosure provides, among other things, examples in which polypeptide agents (e.g., IgA1 protease polypeptide agents) are administered to individuals having deposits of IgA1. In particular, Examples 11 and 12 disclose administering IgA1 protease polypeptide agents to an animal model of IgAN. As explained above, several animal models in which IgA1 deposits are induced are known in the art; behavior of agents in these models are understood to reasonably correlate with activity in a clinical setting.

Abnormal deposition of IgA1 molecules is known to cause renal failure, skin blistering, rash, arthritis, gastrointestinal bleeding and abdominal pain. Several diseases characterized by IgA deposition have been classified and are discussed below. Polypeptide agents of the present invention can be administered to a subject having one or any combination of the diseases below, and/or to subjects having other conditions characterized by deposits of IgA1.

In some embodiments, IgA1 protease polypeptide agents are administered to individuals having an IgA1 deposition disease. In some embodiments, the individual is a human. In some embodiments, the IgA1 is human IgA1.

IgAN

In some embodiments, the individual to which IgA1 protease polypeptide agent is administered has IgAN, a disease of the kidney. IgAN is considered to be an immune-complex-mediated glomerulonephritis, which is characterized by granular deposition of IgA1 in the glomerular mesangial areas. Nephropathy results in proliferative changes in glomerular mesangial cells.

IgAN is one of the most common types of chronic glomerulonephritis and a frequent cause of end-stage renal disease. Mesangial proliferation and extracellular matrix expansion are a common pathologic feature, and both have been observed to correlate with extent of renal injury. These pathologic changes are stimulated by IL-6 (a pro-inflammatory cytokine) and by fibrosis (e.g., by TGF-β and/or other cytokines). Interaction of deposited IgA1 with FCαR may trigger release of cytokines Other immunoglobulins such as IgG and IgM and complement components in renal deposits may be involved in causing injury. Nevertheless, IgA dominates in defining this disease, and the predominant type of IgA molecule in mesangial deposits is IgA1.

Dermatitis Herpetiformis

In some embodiments, the individual to which IgA1 protease polypeptide agent is administered has dermatitis herpetiformis. Dermatitis herpetiformis is a chronic blistering skin disease associated with deposits of IgA1 at the dermal-epidermal junction (Hall et al. (1985), the entire contents of which are herein incorporated by reference). Dermatitis herpetiformis patients have granular IgA1 deposits and have an associated gluten-sensitive enteropathy (GSE).

Henoch-Schoenlein Purpura

In some embodiments, the individual to which IgA1 protease polypeptide agent is administered has Henoch-Schoenlein purpura (HSP), a skin and kidney disease. HSP is characterized by deposition of IgA1-containing immune complexes in tissue. HSP is diagnosed by observing evidence of IgA1 deposition in the skin tissue or kidney via immunofluorescence microscopy. Clinical manifestations of HSP typically include rash, arthralgia, abdominal pain, and renal disease.

B. Routes of Administration

Administration of the therapeutic agent of the present invention can be carried out in a variety of ways, such as, for example, oral ingestion, inhalation, topical application (e.g., cutaneous), subcutaneous, intraperitoneal, parenteral and/or intravenous injection.

For example, compositions containing IgA1 protease polypeptide agents of the present invention can be administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent, i.e., carrier or vehicle.

IgA1 protease polypeptide agents and compositions thereof can be administered, for example, by intravenous, intramuscular, intraperitoneal, intrasternal, subcutaneous, and intra-arterial injection and infusion. In some embodiments, IgA1 protease polypeptide agents and/or compositions thereof are administered by intravenous injection.

Topical administration, in which a composition is brought in contact with tissue(s), may be suitable for dermatitis herpetiformis. "Contacting" is meant to include not only topical application, but also those modes of delivery that introduce a composition or agent into tissues, or into cells of the tissues.

C. Dosing Regimens

In some embodiments, polypeptide agents and/or compositions thereof are administered in a single dose in the range of 100 μg-10 mg/kg body weight. In some embodiments, a single dose is in the range of 1 μg-100 μg/kg body weight. This dosage may be, for example, repeated daily, weekly, monthly, yearly, or as considered appropriate by the treating physician.

Amounts of IgA1 protease polypeptide agents administered in a single dose may depend on the nature and/or severity of the condition being treated and/or on the nature of prior treatments that the patient has undergone. In some embodiments, the attending physician decides the amount of IgA1 protease polypeptide agent with which to treat each individual patient. In some embodiments, the attending physician initially administers low doses of IgA1 protease polypeptide agent(s) of the present invention and observe the patient's response. In some embodiments, larger doses are administered until an optimal therapeutic effect is obtained for the patient, after which dosage is not increased further.

D. Combination Therapies

According to the present invention, IgA1 protease polypeptide agents may be administered in combination with one or more other pharmaceutical agents. For example, IgA1 protease polypeptide agents may be administered in combination with one or more other therapeutic agents for IgA1 deposition diseases (such as agents that ameliorate symptoms of IgA1 deposition diseases), and/or in combination with one or more other pharmaceutical agents (e.g., immunosuppressants, pain relievers, anti-inflammatories, antibiotics, steroidal agents, etc.).

In some embodiments, combination therapies involve administration of multiple individual doses of an IgA1 protease polypeptide agent and/or of one or more other pharmaceutical agents, spaced out over time. In some embodiments, individual IgA1 protease polypeptide agent and doses of one or more other pharmaceutical agents are administered together, according to the same schedule. In other embodiments, IgA1 protease polypeptide agent doses and doses of one or more other pharmaceutical agents are administered according to different schedules.

As would be appreciated by one of skill in the art, the dosage and timing of administration of any particular IgA1 protease polypeptide agent dose or dose of one or more other pharmaceutical agents, or the dosage amount and schedule generally may vary depending on the patient and condition being treated. For example, adverse side effects may call for lowering the dosage of one or the other agent, or of both agents, being administered.

Those of ordinary skill in the art will readily appreciate that the dosage schedule (i.e., amount and timing of individual doses) by which any particular IgA1 protease polypeptide agent is administered may be different for an inventive combination therapy with one or more other pharmaceutical agents than it is alone. Comparably, the dosage schedule for another pharmaceutical agent may be different according to inventive combination therapy regimens than would be used in monotherapy of that other pharmaceutical agent (even for the same disorder, disease or condition).

It may be desirable, for example, to combine administration of IgA1 protease polypeptide agents with pharmaceutical agents that can relieve symptoms of and/or reduce progression of IgA1 deposition diseases. Dietary fish oil supplements can reduce renal inflammation. In some embodiments, one or more fish oil supplements and/or Omega-3 fatty acids (which are a component of fish oil) is/are administered in combination with polypeptide agents of the present invention.

Angiotensin converting enzyme (ACE) inhibitors can reduce the risk of progressive renal disease and renal failure. In some embodiments, one or more ACE inhibitors is/are administered in combination with polypeptide agents of the present invention. Non-limiting examples of ACE inhibitors include alacepril, ancovenin, benazepril, captopril, cetapril, cilazapril, delapril, enalapril, enalaprilat, fentiapril, fosinopril (also known as 'fosenopril'), indalapril, indolapril, lisinopril, moexipril, mugenic acid, pentopril, perindopril, phenacein, pivopril, quinapril, ramipril, ranipril, rentiapril, spirapril, trandolapril, zofenopril, BRL 36378, CGS 14824 (3-([1-ethoxycarbonyl-3-phenyl-(1S)-propyl]-amino)-2,3,4,5-tetrahydro-2-oxo-1-(3S)-benzazepine-1 acetic acid HCl), CGS 14831, CGS 16,617 (3(S)-[[(1S)-5-amino-1-carboxypentyl]amino]-2,3,4,5-tetrahydro-2-oxo-1H-1-1-benzazepine-1-ethanoic acid), CI 925 (2-[2-[[1-(1-(ethoxycarbonyl)-3-phenylpropyl]amino]-1-oxopropyl-6,7-dimethoxy-1,2,3,4-tetrahydro-3-isoquinolinecarboxylic acid), CI 928, K 26, MC 838, Ru 44570, SQ 28853, SQ 27786, and WY-44221.

Angiotensin II receptor blockades (ARBs) sometimes have beneficial effects against hypertension and proteinuria. In some embodiments, one or more ARBs is/are administered in combination with polypeptide agents of the present invention. Non-limiting examples of ARBs include candesartan, eprosartan, irbesartan, losartan, olmesartan, pratosartan, telmisartan, and valsartan.

Corticosteroids may be beneficial their anti-inflammatory and immunosuppressive effects. In some embodiments, one or more corticosteroids is/are administered in combination with polypeptide agents of the present invention. Non-limiting examples of corticosteroids include alclometasone dipropionate, amcinonide, beclomethasone dipropionate, betamethasone, betamethasone benzoate, betamethasone dipropionate, betamethasone sodium phosphate, betamethasone sodium phosphate and acetate, betamethasone valerate, clobetasol proprionate, clocortolone pivalate, cortisol (hydrocortisone), cortisol (hydrocortisone) acetate, cortisol (hydrocortisone) butyrate, cortisol (hydrocortisone) cypionate, cortisol (hydrocortisone) sodium phosphate, cortisol (hydrocortisone) sodium succinate, cortisol (hydrocortisone) valerate, cortisone acetate, desonide, desoximetasone, dexamethasone, dexamethasone acetate, dexamethasone sodium phosphate, diflorasone diacetate, fludrocortisone acetate, flunisolide, fluocinolone acetonide, fluocinonide, fluorometholone, flurandrenolide, halcinonide, medrysone, methylprednisolone, methylprednisolone acetate, methylprednisolone sodium succinate, mometasone furoate, paramethasone acetate, prednisolone, prednisolone acetate, prednisolone sodium phosphate, prednisolone tebutate, prednisone, triamcinolone, triamcinolone acetonide, triamcinolone diacetate, and triamcinolone hexacetonide.

Lipid-lowering agents may also be used in accordance with the present invention. In some embodiments, one or more lipid-lowering agents is/are administered in combination with polypeptide agents of the present invention. Non-limiting examples of lipid-lowering agents include bile acid sequestrant, fibrate, nicotinic acid (i.e., niacin), and statin (i.e., HMG-CoA reductase inhibitor). Statins include, but are not limited to, atorvastatin, cerivastatin, fluvastatin, lovastatin, mevastatin, pitavastatin, pravastatin, rosuvastatin, and simvastatin. Bile acid sequestrants, include, but are not limited to, cholestyramine, colestipol, and colesevelam. Fibrates include, but are not limited to, benzafibrate, ciprofibrate, clofibrate, gemifibrozil, and fenofibrate.

In certain embodiments, IgA1 protease polypeptide agents of the present invention are administered in combination with immunosuppressants. Non-limiting examples of immunosuppressants include antithymocyte globulin (ATG), azathioprine (or other inosine 5'-monophosphate dehydrogenase inhibitors), azodiacarbonide, bisindolyl maleimide VIII, brequinar, corticosteroids, cyclophosphamide, cyclosporine, deoxyspergualin, dexamethasone, IL-2 antagonists (e.g., daclizumab and basiliximab), leflunomide, mercaptopurine, 6-mercaptopurine (6-MP), methotrexate, methylprednisolone, mizoribine, mizoribine monophosphate, mycophenolate mofetil, OKT3, prednisone, sirolimus, tacrolimus (FK506), vitamin D analogs (e.g., MC1288), etc. In some embodiments, the immunosuppressive agent suppresses or reduces immunogenicity of the IgA1 protease polypeptide agent.

In some embodiments, IgA protease polypeptide agents are administered in combination with an anti-inflammatory agent (such as aspirin, ibuprofen, acetaminophen, etc.) and/or a pain reliever.

III. Identification of IgA1 Protease Inhibitors

Figure 12:
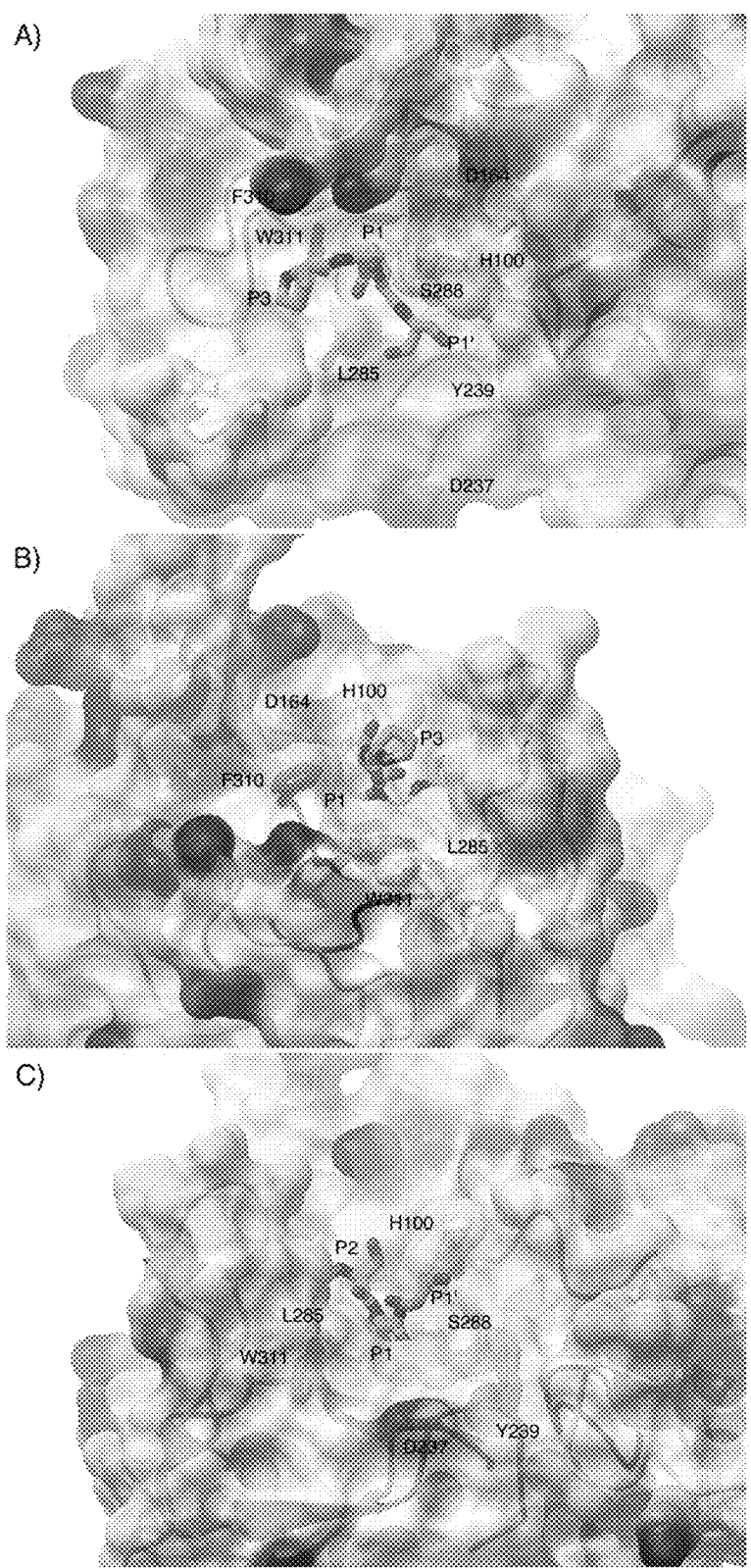
FIG. 12 depicts a surface representation of the active site cleft of IgA1 protease shown in a view A) from above, B) from the N-terminal direction of the hinge peptide and C) from the C-terminal direction of the hinge peptide. The electrostatic surface is rendered semi-transparent with the secondary structure of the protease domain colored in an equivalent fashion to FIG. 11. Those side chains that contribute to the formation of unique surface architecture of the active site are labeled and colored by atom type with the carbon atoms colored according to the loop region of which they are members. The catalytic triad is colored by atom type and rendered in grey. The P3-P1' region (229P-S-P-5232; SEQ ID NO: 40) of the hinge peptide was manually modeled into the active site of *H. influenzae* IgA1 protease based upon the position of the equivalent region in the elastase-turkey ovomucoid inhibitor complex.
Figure 13:
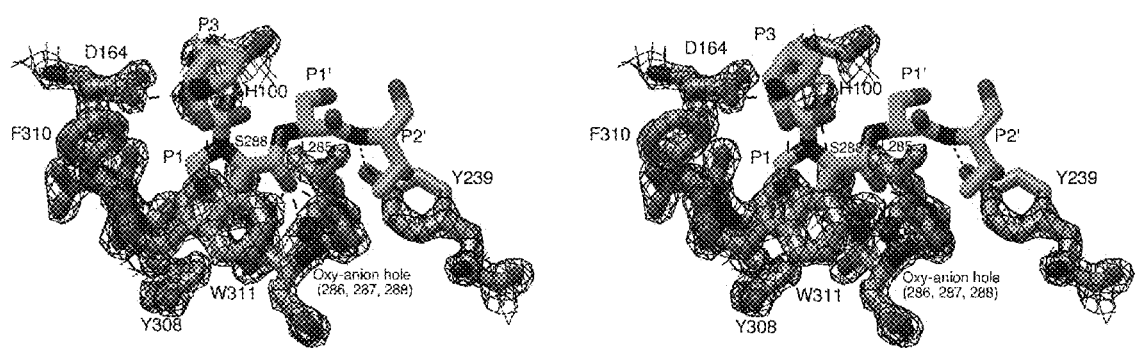
FIG. 13 depicts a stereoview of the active site of IgA1 protease illustrating the recognition of the hinge peptide. The P3-P2' region (229P-S-P-S-T233; SEQ ID NO:41) of the hinge peptide was manually modeled into the active site of IgA1 protease based upon the position of the equivalent region in the elastase-turkey ovomucoid inhibitor complex and is colored by atom type with the carbon atoms being rendered in green. The catalytic triad and residues of IgA1 protease involved in substrate recognition are colored by atom type with the carbon atoms being rendered in grey. Potential hydrogen bonds between the substrate peptide and the enzyme as well as members of the catalytic triad (D164, H100, S288) are illustrated by dashed lines. 2FO-FC density for the protein rendered at 2.5σ is shown as a blue mesh.
Figure 14:
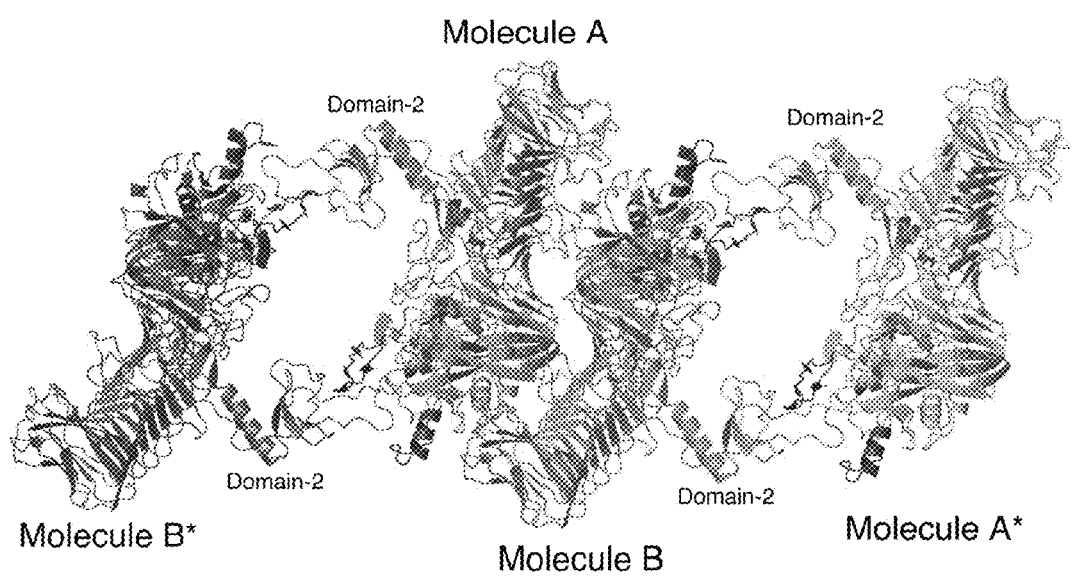
FIG. 14 shows structure diagrams to illustrate crystal packing interactions in the structure of IgA1 protease. The crystallographic dimer (NCS related molecules A and B) present in the ASU are rendered in green and labeled. Molecules A* and B* are related to A and B by crystallographic symmetry and are rendered in cyan and blue, respectively. Loops C in red and D of the protease domains of all molecules are rendered in red and the active site serine residue is shown as a grey ball-and-stick model colored by atom type.

Among other things, the present invention provides information sufficient to define appropriate structural characteristics of agents that interact with (e.g. bind to) IgA1 protease polypeptides (and/or IgA1 protease polypeptide agents as provided herein). For example, among other things, the present invention provides crystal structure information that defines domains that may be important for IgA1 protease polypeptide activity. In particular, the present disclosure provides a crystal structure of a *H. influenzae* Rd IgA1 protease polypeptide that defines the enzyme active site cleft. This enzyme active site cleft is defined by side chains from residues H100, D164, Y239, L285, S288, F310, W311 (See FIG. 12; numbering is based on amino acid positions within the SEQ ID NO: 24, of which amino acid residues 26-1014 are present in a mature form of *H. influenzae* Rd IgA1 protease polypeptide). Without wishing to be bound by any particular theory, agents that fit within and bind such a cleft may be effective inhibitors of IgA1 protease polypeptides.

As described in Example 6, docking studies using crystal structure information suggest that IgA1 substrate molecules bind to a valley formed between domain-2 of *H. influenzae* IgA1 protease (corresponding to residues 564-657 of SEQ ID NO: 14) and the N-terminal protease domain (corresponding to residues 26-337 of SEQ ID NO: 24). Without wishing to be bound by any particular theory, agents that fit within and bind such a valley may be effective inhibitors of IgA1 protease polypeptides.

The present invention also provides structural comparisons that define regions that distinguish IgA1 protease from a structurally related protease haemoglobin protease (HbP). Such regions include such "loop C" (defined by a region corresponding to residues 144-164 of SEQ ID NO: 24) and "loop D: (defined by a region corresponding to residues 205-243 of SEQ ID NO: 24). Without wishing to be bound by any particular theory, agents that bind such domains may be effective inhibitors of IgA1 protease polypeptides. Particularly desirable aspects of such agents may include specificity for IgA1 protease over related proteases such as HbP.

In one aspect of the invention, provided are methods useful in identifying inhibitors of IgA1 proteases. Without wishing to be bound by any particular theory, such inhibitors may have therapeutic value against infections from bacteria that produce such IgA1 protease polypeptides, many of which are pathogenic.

In some embodiments, methods comprise steps of consulting a three-dimensional structure model of an IgA1 protease, determining physical characteristics of candidate inhibitors of the IgA1 protease based on the three-dimensional structure model, testing candidate inhibitors for ability to inhibit IgA1 protease activity, and identifying an inhibitor from among candidate inhibitors based on performance on the test and corresponding physical characteristics. Three-dimensional structure models may be generated, for example, using X-ray crystallographic data. Candidate inhibitors may be identified, for example, from libraries of small molecules and evaluating physical characteristics of such small molecules.

To test ability to inhibit IgA1 protease activity, IgA1 protease activity can be tested in presence and in absence of inhibitors. In some embodiments, candidate inhibitors are tested at more than one concentration. Methods of assaying IgA1 protease activity are known in the art and are described herein (see, for example, the section entitled "Production and characterization of IgA1 protease polypeptide agents and Example 2).

In some embodiments, provided are agents having a three-dimensional structure dimensioned to fit within a cleft defined by residues H100, D164, Y239, L285, S288, F310, W311 of *H. influenzae* Rd IgA1 protease (see SEQ ID NO: 24), which agents inhibit and/or specifically bind IgA1 protease activity.

In some embodiments, provided are agents having a three-dimensional structure dimensioned to fit within a valley defined by residues corresponding to 26-337 of SEQ ID NO: 24 and residues corresponding to 564-657 of SEQ ID NO: 24 in an IgA1 protease, which agents inhibit and/or specifically bind IgA1 protease activity.

In some embodiments, provided are agents that bind to IgA1 proteases in a region corresponding to residues 144-164 of SEQ ID NO: 24 and/or in a region corresponding to residues 205-243 of SEQ ID NO: 24, which agents inhibit and/or specifically bind IgA1 protease activity.

IV. Pharmaceutical Compositions and Formulations

IgA1 protease polypeptide agents and/or IgA1 protease inhibitors provided herein can be used in a composition that is combined with a pharmaceutically acceptable carrier. Such a pharmaceutical composition may also contain diluents, fillers, salts, buffers, stabilizers, solubilizers, encapsulating agents, and/or other materials well known in the art. In some embodiments, IgA1 protease polypeptide agents are complexed with an antibody to form a therapeutic immuno-complex. Such a therapeutic immuno-complex may be particularly useful for treatment of diseases characterized by IgA1 deposition in the kidney since large immuno-complexes are believed to lodge in the renal glomerulus upon administration.

In some embodiments, pharmaceutical compositions include two or more different IgA protease polypeptide agents or IgA1 protease inhibitors that can be administered together and/or sequentially. In some embodiments, a combination of two or more such agents or inhibitors provides a synergistic effect. Without wishing to be bound be any particular theory, such combined and/or sequential administration of different agents or inhibitors may be useful because different polypeptide agents may interact with (e.g., bind to) substrate molecules (e.g. IgA1) in different ways. Thus, combined and/or sequential administration of different IgA1 protease polypeptide agents or IgA1 protease inhibitors may provide an advantage over single polypeptide agent administration.

In some embodiments, pharmaceutical compositions include at least one IgA1 protease polypeptide agent and at least one IgA1 protease (e.g., an IgA1 protease identical in amino acid sequence and pendant groups or lack thereof to a reference IgA1 protease). In some embodiments, a combination of at least one IgA1 protease polypeptide agent and at least one IgA1 protease provides a synergistic effect.

The term "pharmaceutically acceptable" means a non-toxic material that does not interfere with the effectiveness of the biological activity of the active ingredient(s). Pharmaceutically acceptable carriers are generally inert and may, for example, be a solid, semi-solid and/or liquid filler, diluent, encapsulating material, and/or formulation auxiliary of any type. Characteristics of a given carrier may depend on the route of administration used. Suitable carriers include, but are not limited to, saline, buffered saline, dextrose, water, glycerol, ethanol, and combinations thereof. For drugs administered orally, pharmaceutically acceptable carriers may include, without limitation, pharmaceutically acceptable excipients such as inert diluents, disintegrating agents, binding agents, lubricating agents, sweetening agents, flavoring agents, coloring agents, preservatives, and combinations thereof. Suitable inert diluents include, without limitation, sodium and calcium carbonate, sodium and calcium phosphate, and/or lactors. Corn starch and alginic acid are non-limiting examples of suitable disintegrating agents. Binding agents may include, without limitation, starch and gelatin. Lubricating agents include, without limitation, magnesium stearate, stearic acid, and/or talc. If desired, tablets may be coated with a material such as glyceryl monostearate and/or glyceryl distearate, to delay absorption in the gastrointestinal tract.

In general, many pharmaceutically active agents are often provided in salt form. Pharmaceutically acceptable salts can be formed, for example, with inorganic acids such as (without limitation) acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, hydrochloride hydrobromide, hydroiodide, 2-hydroxy-ethanesulfonate, lactate, maleate, methanesulfonate, 2-naphthalenesulfonate, nicotinate, oxalate, thiocyanate, tosylate, undecanoate, and combinations thereof. Non-limiting examples of base salts include ammonium salts, alkali metal salts such as sodium and potassium salts, alkaline earth metal salts such as calcium and magnesium salts, salt with organic bases such as dicyclohexylamine salts, N-methyl-D-glucamine, salts with amino acids such as arginine, lysine, combinations thereof, and so forth. Basic nitrogen-containing groups can be quarternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others. Water or oil-soluble or dispersible products can be obtained thereby.

Characteristics of pharmaceutical compositions for use in accordance with the present invention may depend on the route of administration used. For example, pharmaceutical compositions for parenteral injection may comprise pharmaceutically acceptable sterile aqueous or nonaqueous solutions, dispersions, suspensions or emulsions, and/or sterile powders for reconstitution into sterile injectable solutions or dispersions just prior to use. Non-limiting examples of suitable aqueous and nonaqueous carriers, diluents, solvents and/or vehicles include water, ethanol, polyols (e.g., glycerol, propylene glycol, polyethylene glycol and the like), carboxymethylcellulose and suitable mixtures thereof, vegetable oils (e.g., olive oil) and injectable organic esters such as ethyl oleate. Proper fluidity may be maintained, for example, by using coating materials such as lecithin, by maintaining required particle size in the case of dispersions, and/or by using surfactants. These compositions may also contain adjuvants such as preservatives, wetting agents, emulsifying agents and dispersing agents, and/or compounds to shield immunogenic determinant(s) of the polypeptide agent, if any. Preventing action of microorganisms may be improved by including various antibacterial and antifungal agents (such as, for example, paraben, chlorobutanol, phenol sorbic acid and the like). It may be desirable to include isotonic agents such as sugars, sodium chloride and the like. Prolonged absorption of an injectable pharmaceutical form may be brought about by the inclusion of agents, such as aluminum monostearate and gelatin, which delay absorption.

Injectable depot forms can be made by forming microencapsule matrices of polypeptide agents in biodegradable polymers such as polylactide-polyglycolide, poly(orthoesters) and poly(anhydrides). Depending on the ratio of polypeptide agent to polymer and the nature of the particular polymer employed, the rate of polypeptide agent release can be controlled. Depot injectable formulations are also prepared by entrapping polypeptide agent(s) in liposomes or microemulsions that are compatible with body tissues. Injectable formulations may be sterilized, for example, by filtration through a bacterial-retaining filter and/or by incorporating sterilizing agents in the form of sterile solid compositions that can be dissolved and/or dispersed in sterile water or other sterile injectable media just prior to use.

Pharmaceutical compositions include those suitable for oral, rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural) administration. Formulations may be presented in unit dosage form and may be prepared by conventional pharmaceutical techniques. Such techniques include the step of bringing into association the active ingredient and the pharmaceutical carrier(s) or excipient(s). In general, formulations are prepared by uniformly and intimately bringing into association an active ingredient with liquid carriers or finely divided solid carriers or both, and then, if necessary, shaping the product.

Formulations suitable for parenteral administration may include aqueous and non-aqueous sterile injection solutions that may contain anti-oxidants, buffers, bacteriostats, and/or solutes which render the formulation isotonic with the blood of the intended recipient; and aqueous and non-aqueous sterile suspensions which may include suspending agents and thickening agents. Formulations may be presented in unit-dose dose or multi-dose containers. Extemporaneous injection solutions and suspensions may be prepared from sterile powders, granules and tablets of the kind previously described.

In some embodiments, pharmaceutical compositions (such as, for example, liquid compositions for oral administration) comprise 0.5 to 90% by weight of polypeptide agent. In some embodiments, liquid compositions comprise from about 1 to about 50% by weight of polypeptide agent.

For administration by intravenous, cutaneous or subcutaneous injection, polypeptide agents can be in the form of a pyrogen-free, parenterally acceptable aqueous solution. Preparation of such parenterally acceptable protein solutions, having due regard to pH, isotonicity, stability, and the like, is within the skill in the art. In some embodiments, provided are pharmaceutical composition for intravenous, cutaneous, or subcutaneous injection that comprise, in addition to polypeptide agents of the present invention, an isotonic vehicle such as Sodium Chloride Injection, Ringer's Injection, Dextrose Injection, Dextrose and Sodium Chloride Injection, Lactated Ringer's Injection, and/or other vehicle as known in the art. Pharmaceutical compositions of the present invention may also contain stabilizers, preservatives, buffers, antioxidants, or other additives known to those of skill in the art.

Administration of IgA1 protease inhibitors of the present invention may involve administration via mucosal surfaces, e.g., via inhalation and/or topical administration. For example, drops (e.g., nasal drops), aerosol, or other inhalation methods of administration may be employed to deliver IgA1 protease inhibitors.

Use of timed release or sustained release delivery systems are also included in the invention. A sustained-release matrix, as used herein, is a matrix made of materials, usually polymers, which are degradable by enzymatic or acid/base hydrolysis or by dissolution. Once inserted into the body, the matrix is acted upon by enzymes and body fluids. The sustained-release matrix can be chosen from biocompatible materials such as, for example, liposomes, polylactides (polylactic acid), polyglycolide (polymer of glycolic acid), polylactide co-glycolide (co-polymers of lactic acid and glycolic acid) polyanhydrides, poly(ortho)esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone, silicone, and combinations thereof. In some embodiments, a biodegradable matrix of polylactide, polyglycolide, and/or polylactide co-glycolide (co-polymers of lactic acid and glycolic acid) is used.

The duration of intravenous therapy using the pharmaceutical composition of the present invention will vary, depending on the severity of the disease being treated and the condition and potential idiosyncratic response of each individual patient. It is contemplated that the duration of each application of the therapeutic agent of the present invention will be in the range of 12 to 72 hours of continuous intravenous administration, at a rate of approximately 30 mg/hour. Ultimately the attending physician will decide on the appropriate duration of intravenous therapy using the pharmaceutical composition of the present invention.

Pharmaceutical compositions may comprise other agents that enhance the activity of the composition, compliment its activity or use in treatment, and/or maintain activity of the composition in storage. Such additional factors and/or agents may be included in the composition to produce a synergistic effect and/or to minimize side effects. Additionally or alternatively, administration of the composition of the present invention may be administered concurrently with other therapies, as discussed herein. In some embodiments, pharmaceutical compositions contain one or more additional therapeutic agent(s) (i.e., a therapeutic agent other than an IgA1 protease polypeptide agent of the present invention).

Unless otherwise defined, all technical and scientific terms used herein are accorded the meaning commonly known to one of ordinary skill in the art. All publications, patents, published patent applications, and other references mentioned herein are herein incorporated by reference in their entirety. The embodiments of the invention should not be deemed to be mutually exclusive and can be combined.

EXEMPLIFICATION

The present invention will be better understood in connection with the following Examples, which is intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Production and Purification of Recombinant Haemophilus influenzae IgA1 Protease Polypeptide In the present Example, a recombinant bacterial strain was generated to produce IgA1 protease polypeptide. IgA1 protease polypeptide was then produced and purified in sufficient quantities for use in further studies.
Materials and Methods
Bacterial Culture and Enzyme Recovery Haemophilus culture was done in a microbial culture facility hat meets BL2 large scale requirements. Cultures were grown in a 10 L New Brunswick Bioflo 4500 fermentor using yeast extract medium supplemented for Haemophilus growth. At stationary growth phase, the medium containing the enzyme was separated from the bacterial mass using a Pellicon tangential flow membrane filtration system with varying filter cutoffs. The enzyme concentrate was dialyzed against 25 mM Tris/HCl buffer, pH 7.5, with 0.025% sodium azide.
Anion Exchange Chromatography The bulk of non-IgA1 protease polypeptide proteins were removed by anion exchange chromatography on a 200 ml DE-52 anion-exchange column equilibrated in 25 mM Tris buffer, pH 7.5 and eluted with the same buffer. Under these conditions IgA1 protease polypeptide does not bind; fall-through yield was 70-80%, based on an assay using human IgA1 as a substrate.

Nickel-Affinity Chromatography

Aliquots of the enzyme solution were applied to a Ni-NTA-agarose column and stepwise washed with 25 mM Tris buffer, pH 7.5 containing 20-40 mM imidazole. This washing protocol removes the Haemophilus 5'-nucleotidase, an unwanted nickel-binding protein with Ni affinity slightly less than the IgA1 protease polypeptide. 6HisIgA1 protease polypeptide ("6His" disclosed as SEQ ID NO: 25) was then eluted with 60 mM imidazole and concentrated by positive pressure filtration. At each point enzyme was identified by SDS/PAGE Coomassie stained gels or by Western blots developed with mAb. The final protein concentration was measured by modified Lowry protein assay, and specific activity was determined by assay using IgA1 protein as a substrate.
Results Haemophilus influenzae IgA1 protease polypeptide was selected for drug development. The IgA1 gene of Haemophilus influenzae was modified by the addition of sequence encoding a 6×His tag (comprising six consecutive histidines) (SEQ ID NO: 25) such that the tag was located within a few amino acids of the carboxy-terminus of the secreted protein (shown in FIG. 4). The 6×His tag (SEQ ID NO: 25) was used to help purify the protease polypeptide from bacterial culture media using nickel affinity chromatography. The modified IgA1 gene was re-introduced into an IgA1 protease polypeptide-negative strain, H. influenzae Rd 3-13, by homologous transformation, and isolates were selected by rifampicin resistance screening followed by scoring for restoration of protease polypeptide activity in Rd 3-13 cells using an overlay method as previously described (Gilbert and Plaut (1983), the entire contents of which are herein incorporated by reference). A recombinant strain was identified for production and was designated Haemophilus influenzae Rd 6His ("6His" disclosed as SEQ ID NO: 25).

Figure 5:
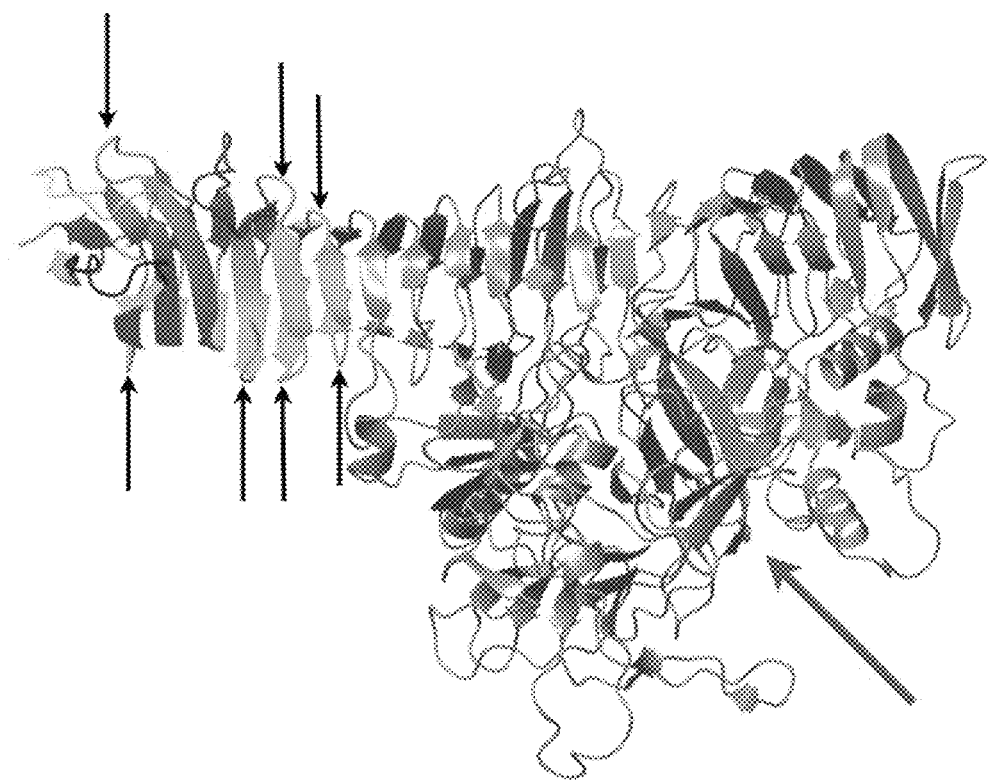
FIG. 5 depicts a representation of the structure of *H. influenzae* IgA1 protease, with arrows indicating regions that are targeted for truncation studies as described in Example 7. The region of the enzyme corresponding to amino acids 25-828 (numbering is based on SEQ ID NO: 24) is colored in grey. The region of the enzyme from 25-828 is colored in grey. In Example 7, this region is not targeted for truncation, as it contains the N-terminal protease domain and domains 2-4, which the structural data indicates are necessary for proteolytic activity and IgA recognition. The region colored in green represents that region of the β-helix that the structural data indicates may be amenable to truncation (828-989 in the crystal structure). (Residues 990-1014 were not present in the crystallized IgA1 protease but would also be amenable to deletion/truncation). Unstructured loops rendered in red (881-893), yellow (936-945) and blue (966-975) indicate those regions in which furin motifs are added in Example 7.

6×His-tagged (SEQ ID NO: 25) enzyme was released into culture medium. Enzyme from concentrated bacteria-free Haemophilus culture medium was purified by anion exchange chromatography (to remove large amounts of irrelevant protein) followed by nickel affinity column purification. Enzyme was eluted from nickel affinity columns using imidazole. IgA1 protease polypeptide enzyme was purified to homogeneity, and its apparent purity is shown on SDS/PAGE gels depicted in FIG. 5.

At least 20 mg of recombinant Rd6×His IgA1 protease polypeptide ("6×His" disclosed as SEQ ID NO: 25) has been purified. IgA1 protease polypeptides were stored at −20° C. in phosphate buffered saline, pH 7.4 until further use. Under such storage conditions, enzyme activity is stable for at least one year.

Example 2

IgA1 Protease Polypeptide Activity Assay

In the present Example, assays to measure activity of IgA1 protease polypeptide were developed in order to carry out biochemical studies of the enzyme, and activity of a mutant H. influenzae IgA1 protease polypeptide was measured.

Human monoclonal IgA1 was purified from plasma of patients with multiple myeloma and radioiodinated for use as a substrate. To measure enzyme activity, products of IgA1 hydrolysis are separated on SDS/PAGE gels and the amount of Fab (antibody fragment, antibody binding portion) produced per unit time at 37° C. is determined.

Figure 2A:
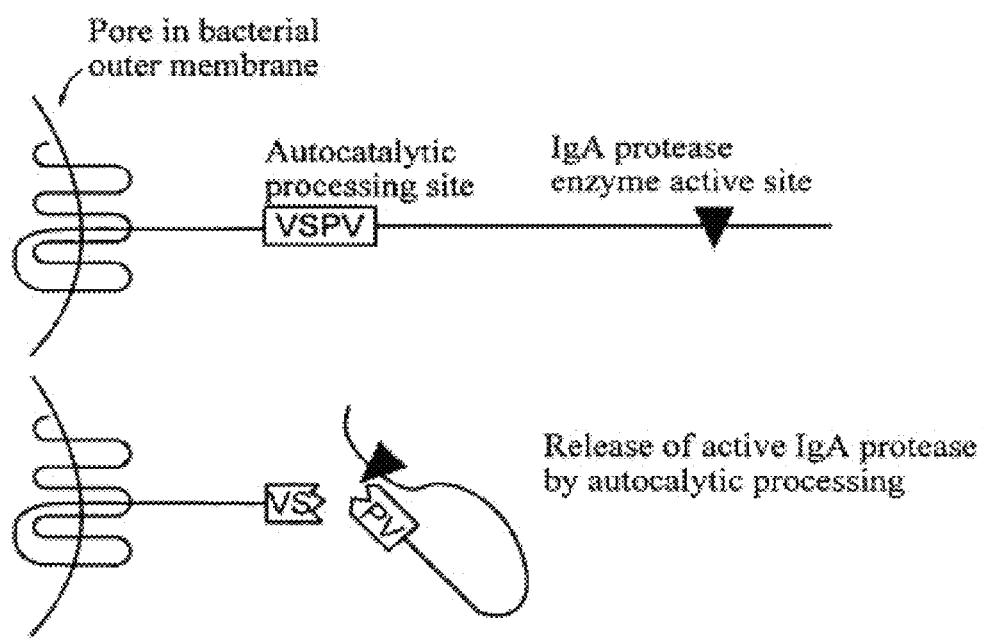
FIG. 2A is a schematic depicting an IgA1 protease precursor undergoing auto-catalytic cleavage and releasing a soluble mature IgA1 protease by auto-catalytic cleavage (site disclosed as SEQ ID NO: 49).
Figure 2B:
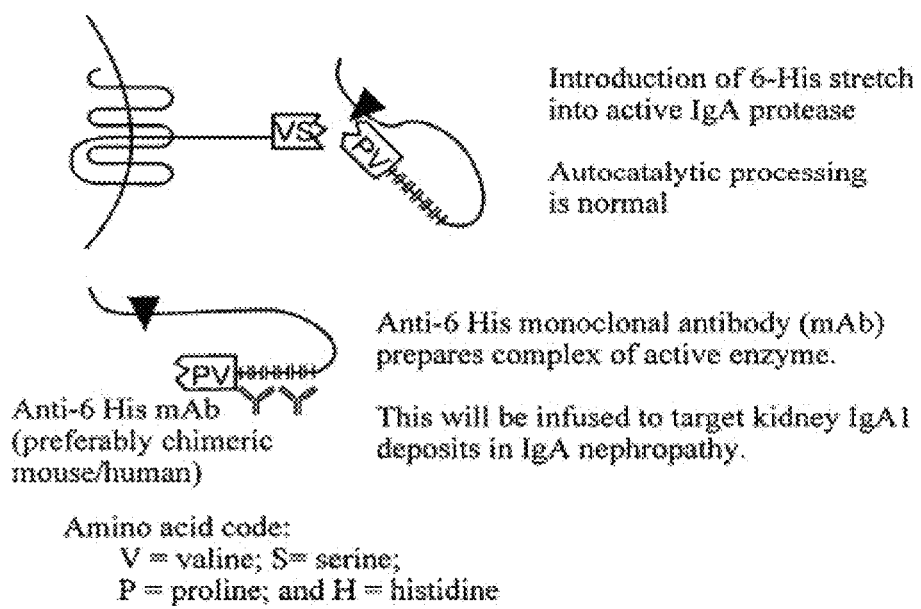
FIG. 2B is a schematic showing an IgA1 protease wherein a 6×His tag (SEQ ID NO: 25) has been fused to the IgA1 protease such that the 6×His tag (SEQ ID NO: 25) is located near the carboxyl terminus of the mature IgA1 protease. A similar scheme can be used to insert a tag into an IgA1 protease polypeptide agent.

H. influenzae IgA1 protease polypeptide is known to be a serine-type protease polypeptide, and this was confirmed by introducing a S288V mutation in the presumed active site to produce strain Rd 3-13. (Numbering for the amino acid position corresponds to the sequence for the H. influenzae IgA1 gene as entered in the database at the National Center for Biotechnology Information (NCBI) under accession number X59800.) The S288V substitution resulted in complete loss of enzymatic activity and interrupted the last (autocatalytic) stage in precursor processing (see FIG. 2), a step that depends on activity.

These results demonstrate successful development of an assay for IgA1 protease activity that can be used in accordance with systems of the invention.

Example 3

Clearance of IgA1 Deposits in an Animal Model of IgA1 Nephropathy

In the present Example, an animal model of IgA1 nephropathy was developed and used to test IgA1 protease polypeptide as a therapy.

A mouse model for IgA1 nephropathy was developed using IgA1 dimers, the main form of IgA1 in glomeruli of IgA1 nephropathy patients. Normal human plasma IgA1 dimers were purified and soluble immune complexes of IgA1 dimers with F(ab')$_2$ fragments of goat anti-human F(ab')2 antibody were made, with IgA1 (the antigen) in two-fold excess. Complexes of IgA1 dimers and F(ab')$_2$ were then injected intravenously into normal mice. (Goat antibody lacking Fc domains were used to maximize deposition of the injected complexes into the glomerular mesangium, rather than allowing the complexes to be cleared by reticuloendothelial tissues.)

Figure 6:
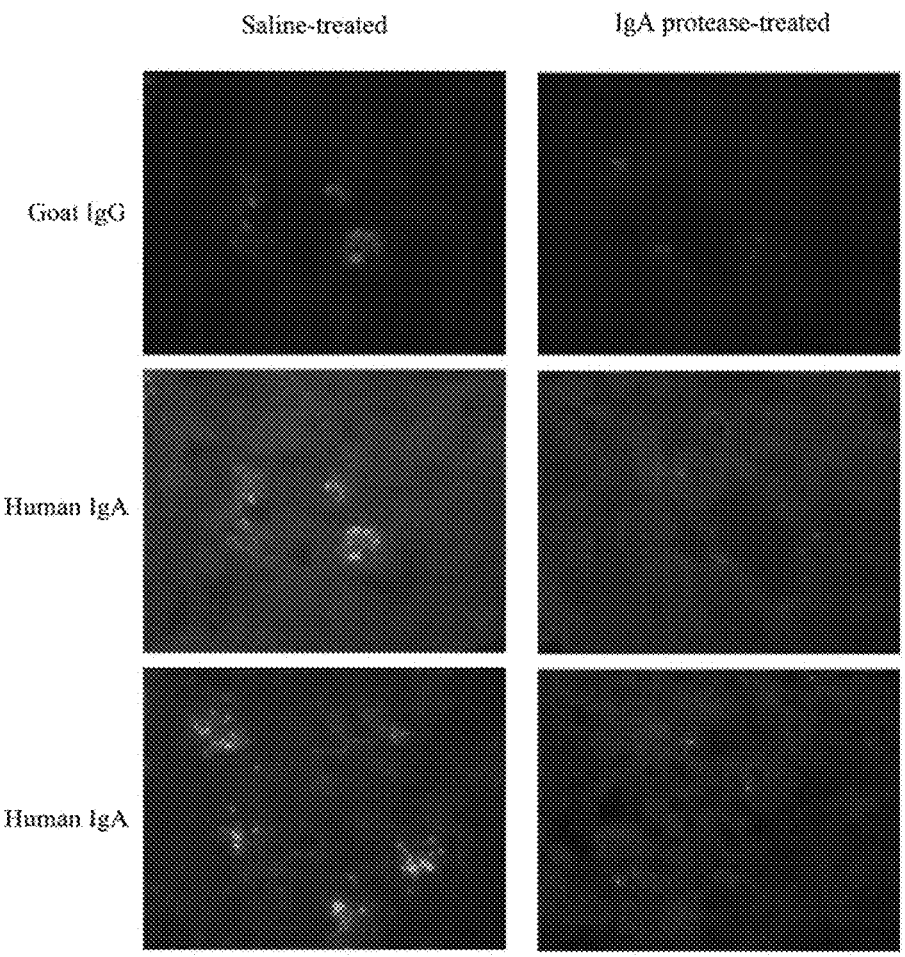
FIG. 6 depicts immunofluorescence photomicrographs of kidneys of mice injected intravenously two hours prior to sacrifice with immune complexes (IC) composed of human IgA1 and goat anti-human F(ab')2 and one hour prior to sacrifice with IgA1 protease or saline. The right column photomicrographs are from IgA1 protease-treated mice and the left column are from saline-treated controls. The top row (rhodamine fluorescence) shows the goat IgG component of the IC. The middle and bottom rows (fluorescein fluorescence) show the human IgA1 component. IgA1 is detected with anti-human F(ab')2 and anti-human Fc alpha in the middle and bottom rows respectively. Note that IgA1 protease has removed most of the deposited IC, both the IgA1 antigen and the IgG.

To test the efficacy of IgA1 protease polypeptide in clearing IgA1 deposits, animals were injected with the active *H. influenzae* IgA1 protease polypeptide, or with saline as a control. IgA1 protease polypeptide, but not saline, injections resulted in rapid and extensive depletion of the mesangial IgA1 protein, a result confirmed in multiple experiments (FIG. 6). Injections of IgA1 protease polypeptide each week for six weeks into normal mice did not result in observable toxicity.

These results demonstrate that administration of IgA1 protease polypeptide can lead to clearance of IgA1 deposits and suggest that IgA1 protease polypeptides could be an effective treatment for human IgA1 nephropathy.

Example 4

Cleavage of IgA1 in Plasma of IgA1 Nephropathy Patients by *H. Influenzae* IgA1 Protease Polypeptide Experiments described in the present Example test whether IgA1 in plasma from IgAN patients can be cleaved by *H. influenzae* IgA1 protease polypeptide (the enzyme used in the animal model in Example 3).

Figure 7:
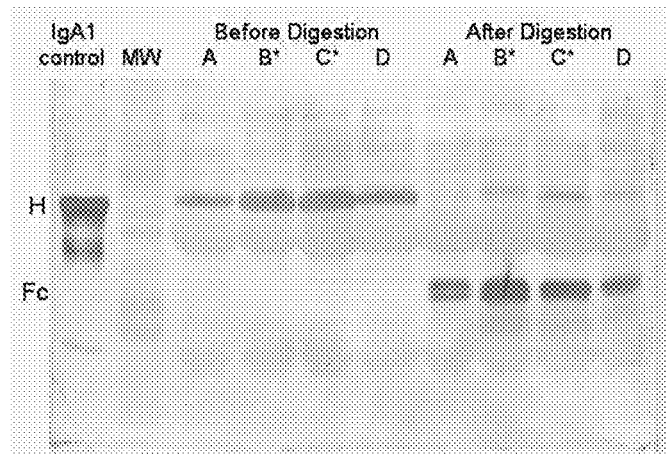
FIG. 7 depicts a Western Blot showing serum IgA1 from IgAN patients (* labeled B & C) and normal subjects (A,D) digested by *H. influenzae* Rd6H is IgA protease ("6H is" disclosed as SEQ ID NO: 25). IgA1 was purified by protein-A Sepharose 4B beads, and the IgA1-bearing beads were incubated with 20 µg/ml protease for one hour at 37° C. The IgA1 heavy chain (H), and its Fc cleavage fragment were detected by goat-anti human alpha chain conjugated with alkaline phosphatase. IgA1 control is a purified human myeloma protein; MW are molecular weight standards. Note that the extent of digestion of patient and normal IgA1 are the same.
Figure 8:
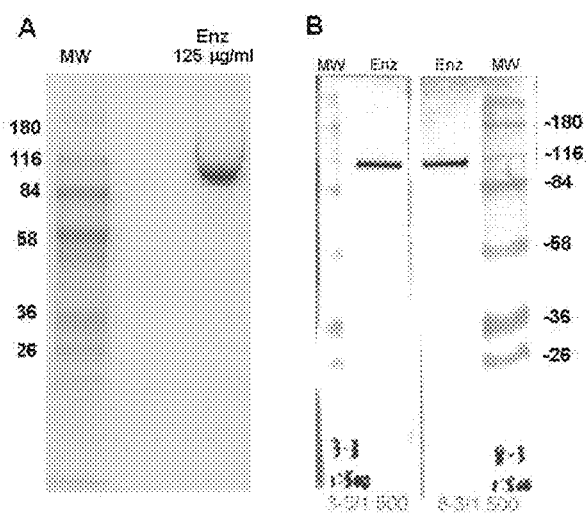
FIG. 8 shows results from experiments characterizing monoclonal antibodies to Rd6H is *H. influenzae* IgA1 protease ("6H is" disclosed as SEQ ID NO: 25). Panel A shows an acrylamide gel through which the purified enzyme was electrophoresed and stained with Coomassie blue. Panel B depicts a Western blot of the same IgA1 protease probed with mAb IGAN 3.3 and IGAN 8.3 diluted 1:500 in buffer. The IgA1 protease appears as a single band in all lanes. 'MW' indicates molecular mass markers.

*H. influenzae* IgA1 protease polypeptide was incubated with plasma of patients with IgAN or with normal plasma. As shown in FIG. 7, Fc fragments (cleavage products of IgA1) were detectable by Western blot analysis in both IgAN and normal samples incubated with IgA1 protease polypeptide, indicating that IgA1 in both normal serum and IgAN serum was cleaved.

These results confirm that IgA1 in patient serum can be cleaved by *H. influenzae* IgA1 protease polypeptide, and that *H. influenzae* IgA1 protease polypeptide is not inhibited by proteinase inhibitors present in normal plasma.

Example 5

Monoclonal Antibodies Against Rd6His IgA1 Protease Polypeptide ("6His" Disclosed as SEQ ID NO: 25)

In the present Example, monoclonal antibodies against recombinant 6xHis-tagged (SEQ ID NO: 25) *H. influenzae* IgA1 protease polypeptide (Rd6His IgA1 protease polypeptide ("6His" disclosed as SEQ ID NO: 25)) are developed. Such antibodies will be useful, among other things, for tracking IgA1 protease polypeptide during therapy and for epitope mapping studies.

Materials and Methods
Immunization of Animals

Rd6His IgA1 protease polypeptide ("6His" disclosed as SEQ ID NO: M has been prepared and purified as described in Example 1, and 2-5 mg of it is being used as antigen to raise additional antibodies. Five Balb/c mice are bled prior to immunization as a control for preexisting antibody. (No antibodies were found in pre-bleeds of mice used to produce mAb IGAN 3.3 and IGAN 8.3.) Mice are immunized by intraperitoneal injection of 25 µg to 100 µg antigen on days 0, 14, and 35. Freund's Complete adjuvant is used for the first injection and Freund's Incomplete adjuvant is used for subsequent injections. On day 45, mice are bled, antibody titer is determined by ELISA, and enzyme detection is confirmed by Western blotting. Dot blots of native protein are used to insure that non-linear epitopes are overlooked. From these evaluations, an animal is chosen for a final immunization on day 56. The final immunization involves both intraperitoneal and intravenous injection of antigen without adjuvant.

Cell-Fusion/Hybridoma Formation and Screening

On day 60, the spleen is removed under sterile conditions and a single cell suspension is made. Splenocytes are fused to mouse myeloma cells using polyethylene glycol to form hybridomas. Cells are plated into eight 96-well plates and maintained in selection conditions (e.g., Hypoxanthine Aminopterin Thymidine (HAT) selection medium) under which only hybridomas (splenocyte/myeloma fusions) proliferate. Once colonies reach ~300 cells, hybridoma clones are assayed by ELISA for antibody expression. Positive clones are isolated and expanded, and two to three vials of hybridoma cells are stored in liquid nitrogen. Conditioned medium from each colony is retested to verify hybridoma stability and utility of produced antibodies.

Monoclonal antibodies produced by candidate hybridomas are then formally characterized by (1) testing for optimal titer in Western blotting of *H. influenzae* IgA1 protease polypeptide in reduced SDS/PAGE gels; (2) identification of antibody isotype; and (3) testing against proteins of the protease polypeptide-negative *H. influenzae* strain Rd225-DK, which has an IgA1 gene deletion, to ensure that the monoclonal antibody is protease polypeptide-specific.

Each monoclonal antibody is then tested for inhibition of enzyme activity using an assay as described previously (Bachovchin et al. (1990), the entire contents of which are herein incorporated by reference). IgA1 protease polypeptide is first mixed with serial dilutions of the antibody at pH 7.4. Human IgA1 myeloma (monoclonal) paraprotein is used as a substrate for IgA1 protease polypeptide, and cleavage products are detected on an SDS/PAGE gel. Active protease polypeptide is used as a positive control and for the four additional antibodies being produced (see below), protease polypeptide that is inhibited by antibody IGAN 8.3 is used as a negative control.

Results

Figure 9:
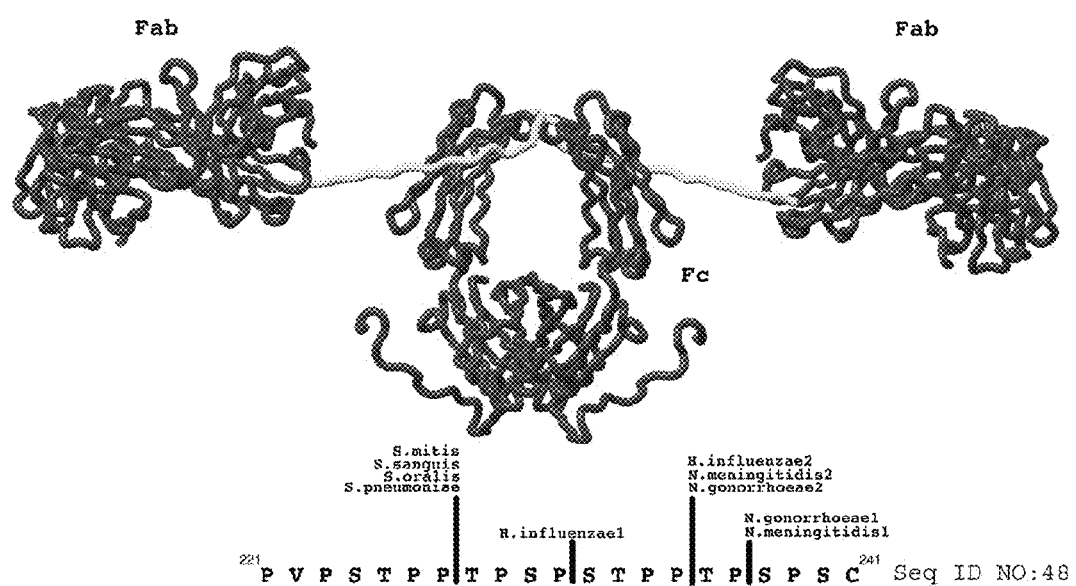
FIG. 9 depicts a model of the structure of dimeric human IgA1 (PDB:1IGA) as determined from x-ray and neutron solution scattering and homology modeling (Comeau et al. (2004)). The Fab and Fc domains are rendered as red tubes and labeled while the hinge domain is rendered in yellow. The sequence of the hinge peptide and the location of the cleavage sites by various members of the IgA protease family are shown in the lower portion of the figure (SEQ ID NO: 48). The numbering utilized for the sequence of IgA1 is that of Torano and Putnam (McGillivary et al. (2005)).

Two murine monoclonal antibodies (designated mAb IGAN 3.3 and IGAN 8.3) to Rd6His IgA1 protease polypeptide ("6His" disclosed as SEQ ID NO: 25) have been developed. These monoclonal antibodies were purified from culture media using affinity chromatography. Both mAb IGAN 3.3 and IGAN 8.3 are IgG antibodies, and because they both detect denatured enzyme on Western blot (see FIG. 9), it is likely that each epitope is linear. These epitopes will be identified in later studies.

IGAN 8.3 antibody was also found to inhibit IgA1 protease polypeptide activity, and identification of its epitope will help elucidate which regions of the protein are needed for activity and/or specificity.

Four additional monoclonal antibodies to *H. influenzae* 6×His-tagged (SEQ ID NO: 25) IgA1 protease polypeptide are being produced and characterized as to isotype, ability to inhibit protease polypeptide function, and epitope identification.

Discussion

Antibodies that are developed and characterized in this Example can be used to determine if there are any uniquely antigenic regions of the protein, identified by epitope mapping, as described in Example 9. During hybridoma screening, many antibody-positive fusions were identified, so preparation of more monoclonal antibodies can be readily accomplished.

Example 6

1.75 Å Crystal Structure of *H. Influenzae* IgA1 Protease Polypeptide

In the present Example, a crystal structure *H. influenzae* IgA1 protease polypeptide was solved and the structural information was analyzed to guide design of modifications to IgA1 protease polypeptide.

Materials and Methods

Chemicals used in this Example were of the highest commercially available purity.

IgA1 Protease Polypeptide Expression and Purification

*H. influenzae* IgA1 protease polypeptide was expressed in strain Rd 6His ("6His" disclosed as SEQ ID NO: 25) as a secreted fusion protein having a C-terminal 6-Histidine tag (SEQ ID NO: 25), as described in Example 1. Bacteria-free fermentor broth (~10 L) was concentrated to ~400 mL using a Pelicon device and precipitated with 60% saturated ammonium sulfate. The pellet was subsequently resuspended in 25 mL of 25 mM HEPES, pH 7.5, 10 mM imidazole, and applied to a 50 mL bed volume of Ni-NTA agarose (Qiagen). The column was washed with several column volumes of 25 mM HEPES pH 7.5, 10 mM imidazole followed by 25 mM HEPES pH 7.5, 50 mM imidazole. Protein was eluted with a gradient of imidazole (50-90 mM, in 25 mM HEPES, pH 7.5) using a BioRad BioLogic Duo Flow FPLC. Fractions containing intact IgA1 protease polypeptide were identified by SDS gel electrophoresis. These fractions were pooled, concentrated to ~10 mL under nitrogen pressure in an Amicon concentrator and passed through a 25 mL bed volume of DE-52 anion exchange resin equilibrated in 25 mM HEPES, pH 7.5 to remove yellow pigment carried over from the fermentation media. Wash through was collected and concentrated in an Amicon concentrator to a volume of approximately 2 mL and applied to a 26/60 Sephacryl S-200 column (GE Biosciences) equilibrated in 25 mM HEPES, pH 7.5. Fractions containing IgA1 protease polypeptide were concentrated to a final protein concentration of 7 mg/mL based upon a predicted extinction coefficient ($\epsilon_{280}$) of 1.04 mL me and a molecular mass of 108,671 Da, both calculated using the ProtParam tool (available at the website address "http:" followed immediately by "//ca.expasy.org/tools/protparam.html") (Gasteiger et al. (2005), the entire contents of which are herein incorporated by reference). Protein was used immediately for crystallization studies.

Crystallization

Initial crystallization conditions for *Haemophilus influenzae* IgA1 protease polypeptide were determined by submission of the protein to the high-throughput crystallization facility at the Hauptman Woodward Institute, Buffalo, N.Y. (See Luft et al. (2003) "A deliberate approach to screening for initial crystallization conditions of biological macromolecules." *Journal of Structural Biology*. 142, 170-179.) Crystals of IgA1 protease polypeptide used for data collection were grown by the hanging-drop method at 4° C. by mixing 4 μL of protein (containing 7 mg/mL IgA1 protease in 25 mM HEPES, pH 7.5) with 2 μL mother liquor (0.1 M sodium acetate, pH 5.0, 0.1 M potassium dihydrogen phosphate and 10% PEG 20,000). Crystals were cryoprotected by transferring them in succession to 20 μL drops containing 40, 50 and 60% saturated sodium malonate prior to cryocooling in liquid nitrogen. (See Holyoak et al. (2003), the entire contents of which are herein incorporated by reference.)

Data Collection

Data on the cryocooled crystals at 100 K were collected at the Stanford Synchrotron Radiation Laboratory, Beamline 11-1, Menlo Park, Calif. All data were integrated and scaled with HKL-2000 (Otwinowski et al. (1997), the entire contents of which are herein incorporated by reference in their entirety.) Data statistics are presented in Table 4.

TABLE 4

Data and Model Statistics for the 1.75 Å structure of *Haemophilus influenzae H. influenzae* IgA1 protease.

| | |
|---|---|
| wavelength (Å) | 0.86 |
| space group | P2$_1$ |
| unit cell dimensions | a = 94.39 Å |
| | b = 131.87 Å |
| | c = 111.81 Å |
| | α = γ = 90.0° |
| | β = 113.11° |
| resolution limit (Å) | 50.0-1.75 |
| no. of unique reflections | 251,843 |
| Completeness[b] (%; all data) | 99.9(99.0) |
| Redundancy[a] | 7.4(5.2) |
| I/σ$_{(I)}$[a] | 16.7(2.0) |
| R$_{merge}$[a,b] | 0.08(0.67) |
| no. of ASU molecules | 2 |
| solvent content (%) | 53 |
| R$_{free}$[a,c] (%) | 18.9(31.2) |
| R$_{work}$[a,d] (%) | 16.0(28.6) |
| estimated coordinate error based on maximum likelihood (Å) | 0.058 |
| bond length rmsd (Å) | 0.016 |
| bond angle rmsd (deg) | 1.614 |
| Ramachandran statistics (most favored, additionally allowed, generously allowed, disallowed) (%) | 87.9, 11.7, 0.4, 0.0 |

[a]Values in parentheses represent statistics for data in the highest-resolution shell. The highest-resolution shell comprises data in the range of 1.81-1.75 Å.
[b]R$_{merge}$ = Σ||I$_{obs}$ − I$_{avg}$|/ΣI$_{obs}$
[c]See Brunger (73) for a description of R$_{free}$.
[d]R$_{work}$ = Σ||F$_{obs}$| − |F$_{calc}$||/Σ|F$_{obs}$|

Structure Determination and Refinement

The structure of IgA1 protease polypeptide was solved by the molecular replacement method. In this procedure, the program Chainsaw (Stein et al. (2008), the entire contents of which are herein incorporated by reference) was used to create a molecular replacement model using the N-terminal domain of hemoglobin protease polypeptide (PDB 1WXR, which shares 36% sequence identity with *H. influenzae* IgA1 protease polypeptide over 536 residues). This model was subsequently used as the search model in Phaser (McCoy et al. (2007), the entire contents of which are herein incorporated by reference). The Phaser solution contained two copies of this domain in the asymmetrical unit. This solution was used as the input for automated model building using ARP/WARP 7.0 (Cohen et al. (2008), Cohen et al. (2004), Joosten et al. (2008), and Morris et al. (2004), the entire contents of each of which are herein incorporated by reference in their entirety). A model that was ~80% complete for both chains was generated using the ARP/wARP software suite. Subsequent correction and further building of the model was carried out utilizing the COOT model-building tool (Emsley et al. (2004), the entire contents of which are herein incorporated by reference). The final model lacks the C-terminal 25 residues, with both models ending at P989. In addition, density in chain A for the region 967-969 was not suitable to build this region and is missing from the final model.

After model building, heteroatom and water addition were carried out using COOT. A final round of TLS refinement was performed in Refmac5 in the CCP4 suite (Murshudov et al. (1997) and Bailey et al. (1994), the entire contents of each of which are herein incorporated by reference). A total of 5 groups per chain were used. Refinements using greater than 5 groups per chain did not significantly improve the $R/R_{free}$ ratio. Optimum TLS groups were determined by submission of the pdb file to the TLSMD server (at the web site "http:" followed immediately by "//skuld.bmsc.washington.edu/~tlsmd/index.html"; (Painter et al. (2005), Painter et al. (2006) (1); and Painter et al. (2006) (2), the entire contents of each of which are herein incorporated by reference). Tight NCS restraints were used during initial rounds of refinement and were removed during final stages of refinement. Both chains in the model have excellent stereochemistry as determined by PROCHECK (Laskowski et al. (1993), the entire contents of which are herein incorporated by reference in their entirety). Final model statistics are presented in Table 1.

IgA1 Fc Domain-IgA1 Protease Polypeptide Docking

Docking of the Fc portion of human IgA1 was accomplished by submission of the structure of the monomer (chain B) of H. influenzae IgA1 protease polypeptide and the structure of the Fc domain of human IgA1 (PDB:1OWO, chains A and B (Herr et al. (2003), the entire contents of which are herein incorporated by reference) to the Cluspro server (available at the website "http:" followed immediately by "//nrc.b-u.edu/cluster/") utilizing DOT software (available at the website "http:" followed immediately by "//www.sdsc.edu/CCMS/DOT/") to carry out docking (Comeau et al. (2004) (1), Comeau et al. (2004) (2), and Mandell et al. (2001), the entire contents of each of which are herein incorporated by reference.)

Three-Dimensional Structure Similarity Comparisons

Structural similarity searches were performed by submission of relevant protein domains of IgA1 protease polypeptide to the DALI server (http://ekhidna.biocenter.helsinki.fi/dali_server) (Holm et al. (2008), the entire contents of which are herein incorporated by reference).

Homology Modeling of IgA1P-2

The sequence of a type 2 IgA1 protease polypeptide (IgA1P-2; Q93T34) from H. influenzae var. aegyptius (71) was aligned with the sequence for the type 1 IgA1 protease polypeptide (IgA1P-1; P44969) corresponding to the enzyme used in the crystallographic studies using ClustalW (Larkin et al. (2007) and Thompson et al. (1994), the entire contents of each of which are herein incorporated by reference). These two proteins share 69% sequence identity over the 964 residues of the secreted IgA1P-1 isozyme visible in the crystal structure. This alignment and the IgA1P-1 structure were used as the input to the automodel script for the program Modeler 9 version 5 (Sali et al. (1993), the entire contents of which are herein incorporated by reference) to produce a 3-dimensional homology model of the entire IgA1P-2 isozyme.

Results

A high resolution structure of H. influenzae IgA1 protease polypeptide was solved to 1.75 Å.

Inspection of the structure (shown in FIG. 4) shows key landmarks, and indicates that H. influenzae IgA1 protease polypeptide has some general features of another SPATE ("serine protease polypeptide autotransporters of the Enterobacteriaceae") family member, Haemoglobin protease polypeptide (HbP), the only other protein in this class with a known structure. Both HbP and H. influenza IgA1 protease polypeptide have an N-terminal trypsin/chymotrypsin-like protease polypeptide domain, a long beta-helix spine, and a small domain previously termed domain-2 that inserts into one of the loops at the end of one of the beta-sheets forming the helix (see FIG. 4).

Based on structural information provided by the crystal structure of H. influenzae, residues 25-828 (from a total 989 in the protein) may be required for activity. Thus, truncation studies may focus upon the removal of the C-terminal ~185 amino acids and the effect of such removal on enzyme function.

Cysteine residues can serve as sites for PEGylation. The crystal structure revealed that the two endogenous cysteine residues are present in a disulfide bond and are inaccessible to modification. Thus, to modify H. influenzae IgA1 protease polypeptide by PEGylation, new cysteine residues that can serve as sites of PEGylation will be introduced into solvent accessible regions that are not involved in substrate recognition and catalysis (as determined at least in part by the crystal structure).

Major domains of *H. inflluenzae* IgA1 protease polypeptide are discussed below.

Protease Polypeptide Domain

*H. influenzae* IgA1 protease polypeptide and HbP share 38% amino acid similarity in the protease polypeptide domain, but the fold pattern is very similar and consistent with other members of the chymotrypsin-like serine protease polypeptide family, with preservation of the oxy-anion hole and catalytic triad. Unlike HbP, however, *H. influenzae* IgA1 protease polypeptide contains a unique 'lid' element that is positioned directly above the catalytic serine. This lid, together with a valley that is formed between IgA1 protease polypeptide domain-2 (corresponding to residues 564-657 of SEQ ID NO: 24) and the N-terminal protease polypeptide domain (corresponding to residues 26-337 of SEQ ID NO: 24), may be integral to the selectivity exhibited by IgA1 protease polypeptide. Certain subdomains on a face of the enzyme can be shown by computational docking experiments to be involved in substrate recognition and binding of the Fc domain of IgA1.

Using our previous experimental data that identified the site at which IgA1 is cleaved by IgA1 protease polypeptide (Chintalacharuvu et al. (2003), Qiu et al. (1996), and Plaut et al. (1974), the entire contents of each of which are herein incorporated by reference), and several structures of various IgA1 molecules available in the protein data bank (available at www.rcsb.org), in silico docking studies that generated a model of the IgA1 protease polypeptide-IgA1 complex were generated (Motiejunas et al. (2008) and Comaeu et al. (2004), the entire contents of both of which are herein incorporated by reference.) The unique, extended loops C and D of the protease polypeptide domain are dynamic elements. It is proposed that through binding the Fc domain of IgA1, the enzyme active site gains access to the hinge peptide. Such a mechanism would allow effective cleavage only in the context of intact IgA1 immunoglobulin. In this model, in the absence of interactions with the Fc domain, one or both of these loops occlude the active site of the protease polypeptide, reducing the ability of the enzyme to interact with small peptide ligands based upon the hinge region sequence.

Beta-Helix Domain

The most dominant feature of the protein is the beta-helical spine that shares only 31% overall sequence identity with HbP in this region, though the two proteins are structurally very similar in the 339-899 segment. (Amino acid numbering is based on the *H. influenzae* IgA1 protease polypeptide sequence). The external face of the beta-helix in *H. influenzae* IgA1 protease polypeptide also contains stacked serine and threonine residues, but unlike HbP the IgA1 protease polypeptide has significant stacking of leucine and isoleucine residues that form the hydrophobic helical core (Tribbick et al. (2002), the entire contents of which are herein incorporated by reference).

Interactions Between Domains and with IgA1 Substrate

Figure 10:
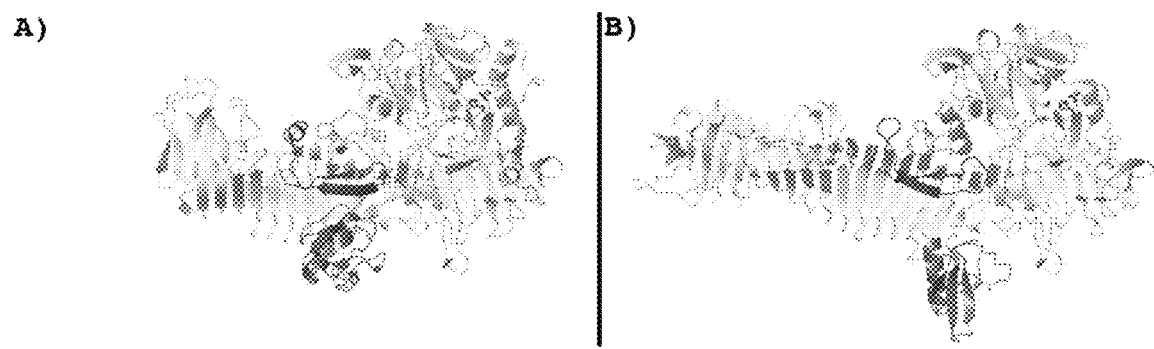
FIG. 10 depicts structures of A) IgA1 protease and B) HbP (1WXR). Both proteins are shown in an identical orientation and scale. The N-terminal protease domain (26-337) is rendered in green and the residues of the catalytic triad are rendered as stick models. Domains-2, -3 and -4 are rendered in blue (564-657), cyan (710-743) and purple (786-819). In addition, a small loop insertion that is variable amongst *H. influenzae* IgA1 protease isozymes (residues 370-387) is rendered in orange. Residue numbering is that of IgA1 protease.
Figure 11:
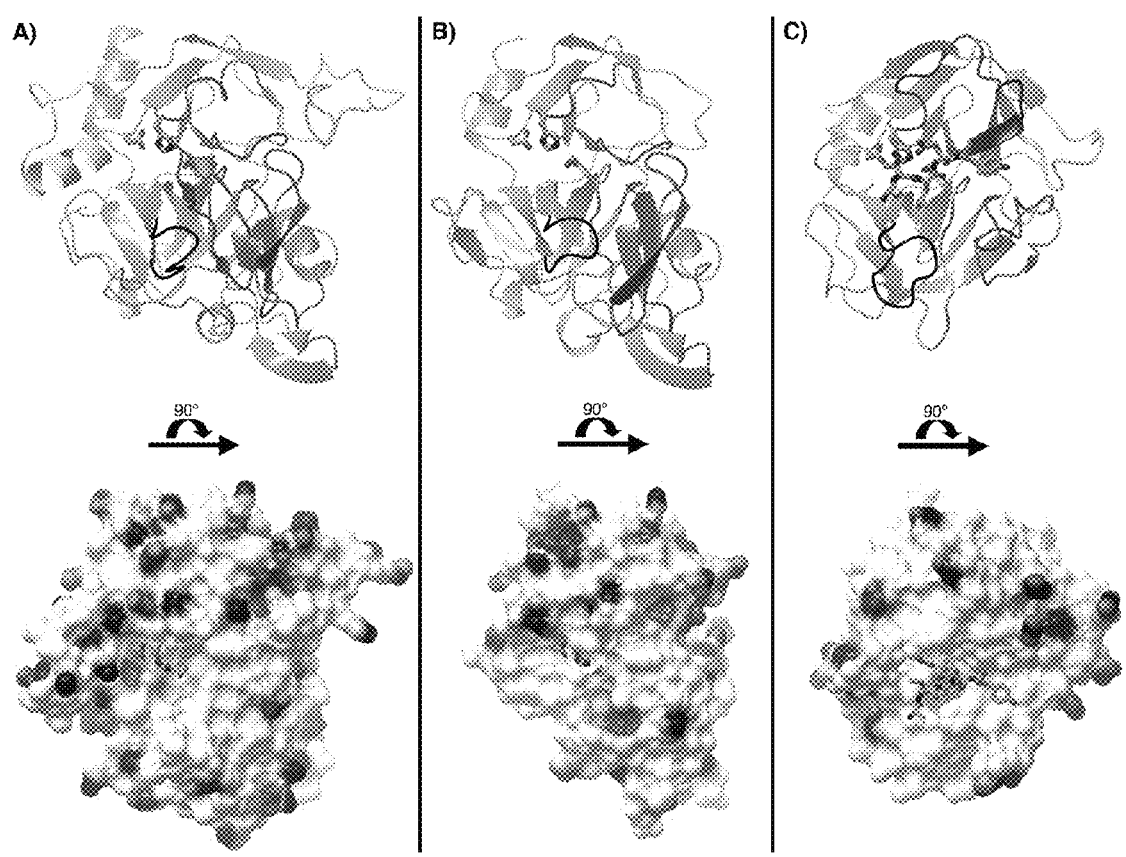
FIG. 11 shows a comparison of the N-terminal chymotrypsin-like domains of A) IgA1 protease, and B) HbP (PDB: 1WXR (Otto et al. (2005))) and C) the structure of elastase (PDB:1PPF (Larkin et al. (2007)). Structural differences in IgA1 protease are highlighted by differential coloring of the molecules according to the loop nomenclature utilized for the chymotrypsin family. The residues of the catalytic triad in each enzyme are rendered as grey stick models. A portion of the bound inhibitor (C-T-L-E-Y (SEQ ID NO: 39); P3-P2') in the elastase-turkey ovomucoid inhibitor complex is rendered as a green stick model colored by atom type to illustrate the subsite locations and active site cleft. Loop A; dark blue 81-91 (34-41), Loop B; red 99-106 (56-64), Loop C; yellow 144-164 (97-103), Loop D; magenta 205-243(143-149), Loop E; cyan 109-134(74-80), Loop 1; orange 261-282 (185-188), Loop 2 black 311-319 (217-225) and Loop 3 green 246-257 (169-174). In addition the N-terminal region residues 26-78 (16-29) that forms a discrete domain in *H. influenzae* IgA1 protease and HbP but is absent in elastase is colored light blue. Residue numbering given is that for IgA1 protease with the corresponding numbering for elastase/chymotrypsin given in parentheses.
Figure 15:
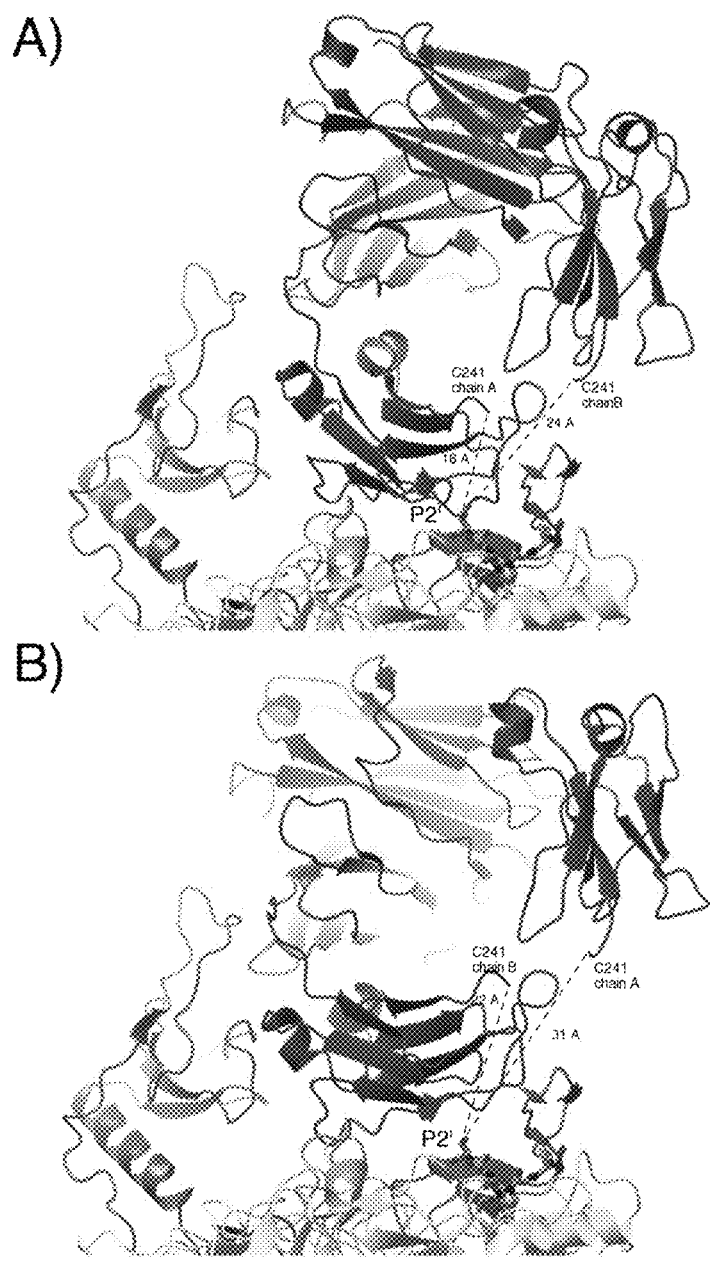
FIG. 15 depicts theoretical models of the interaction between IgA1 protease and the Fc domain of IgA1. The model was calculated using DOT methodology. The IgA1 protease is colored according to the scheme in FIG. 10 while the Fc domain of IgA1 is rendered as a red ribbon diagram. The manually docked hinge peptide (229P-S-P-S-T233; SEQ ID NO:41) is rendered as a green stick model colored by atom type. The N-terminal cysteine (C241) of the Fc domain is labeled as are the approximate distance between the C-terminal P2' residue and the N-terminus of C241.
Figure 16:
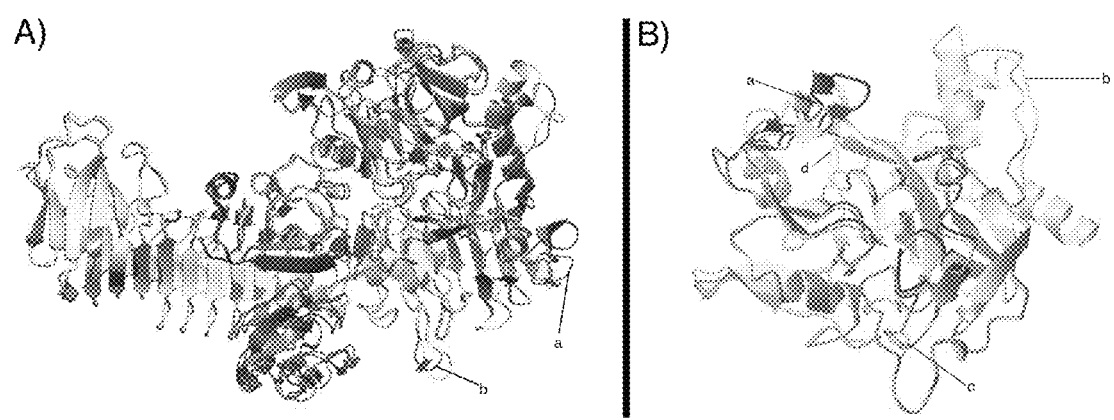
FIG. 16 depicts a comparison of the homology model of *H. influenzae* IgA1 protease type 2 with that of the structure of *H. influenzae* IgA1 protease type 1 determined in this work. In A) the overall structure of the *H. influenzae* IgA1 protease type 2 isozyme (grey ribbon) is compared to that of *H. influenzae* IgA1 protease type 1 (colored according to the scheme in FIG. 4). In A) the labels a and b indicate the loop insertion and truncation present in the α-helix domain of the *H. influenzae* IgA1 protease type 2 structure, respectively. In B) the protease domains of the two isozymes are shown. The coloring of the IgA-1 protease domain is identical to that in FIG. 11. The *H. influenzae* IgA1 protease type 2 molecule is rendered as a light green ribbon and the labels a, b, c and d indicate the truncations and insertions resulting in changes in the structures of loops D, C, E, and 3 respectively.

As mentioned above, and described previously in the context of the structure of HbP (33) domain-2 forms a discrete domain (residues 564-657 of SEQ ID NO: 24) off of the stalk of the β-helix, entering and exiting as an extension of two β-strands forming a sheet in the β-helix (FIGS. 10 and 11). Structural inspection demonstrates that domain-2 in *H. influenzae* IgA1 protease extends from the β-helix at a different angle than the similar domain in HbP likely due to crystal packing interactions with the N-terminal protease domain of an adjacent molecule in the crystalline lattice (FIG. 15). This difference between the orientation of domain-2 relative to the β-helical spine found in the structures of HbP and *H. influenzae* IgA1 protease suggests the potential for independent movement of domain-2 relative to the β-helical spine in the absence of crystal lattice contacts.

Without wishing to be bound by any particular theory, the potential dynamic nature of domain-2 may be important in IgA1 protease function. While similar in its overall fold to the domain in HbP (DALI score of 8.2, 21% sequence identity, 2.3 Å RMSD), in itself similar to chitinase, the domain in *H. influenzae* IgA1 protease differs slightly in structure due predominantly to a loop insertion of ~12 residues in the loop between the two β-strands at the N-terminus of the domain. This domain also possesses structural similarity to the family of integrase proteins, phospholipase (PDB: 1ZLB, Z=3.9), extracellular matrix protein anosmin-1 (PDB:1ZLG, Z=3.6), and N-terminal domain 1-integrase (PDB:1KJK, Z=3.4) with similar RMSD values of 2.0-2.5 Å.

Interaction of domain-2 with the N-terminal protease domain of a symmetry related molecule is of interest, as it suggests the ability of this domain to function in protein-protein interactions and by extrapolation, that domain-2 may contribute to substrate recognition by forming a binding surface for IgA1. In crystals of *H. influenzae* IgA1 protease (Table 4) as in other crystals, crystals are composed of identical repeating microscopic units (unit cells) that are stacked together in a three-dimensional array to form the macroscopic crystal. In monoclinic (P21) crystals of *H. influenzae* IgA1 protease, each one of these unit cells is composed of two smaller asymmetric units (ASU). The ASU is the smallest repeating unit of the crystal lattice. Other molecules in the unit cell can be generated by applying rotation and translation operators on the molecules contained in the ASU as dictated by the crystallographic symmetry. Each ASU of the *H. influenzae* IgA1 protease crystals contains two independent molecules of *H. influenzae* IgA1 protease that are not related to each other by crystallographic symmetry and are termed non-crystallographic symmetry (NCS) related molecules. In the case of *H. influenzae* IgA1 protease these two molecules have essentially identical structures, however by definition they experience different crystallographic environments. Due to the molecular packing of the individual molecules of *H. influenzae* IgA1 protease in the unit cell it is observed that domain-2 of the two independent molecules in one ASU (molecules A and B) interact with the unique loop D of the protease domain in the adjacent ASU (FIG. 15). This interaction between domain-2 and loop D of the protease domain places the extended loop of domain-2 of molecule A directly over the active site of the symmetry related molecule B in the adjacent ASU.

This packing of the protein molecules places domain-2 in the cleft between the extended loops C and D that in the context of chymotrypsin-like proteases, are unique to *H. influenzae* IgA1 protease. It is proposed, without wishing to be bound by any particular theory, that this crystallographic packing interaction between domain-2 and loop D stabilizes the conformations of loops C and D observed in the crystal structure.

In addition to domain-2, *H. influenzae* IgA1 protease and HbP contain two other small domains herein denoted as domain-3 and domain-4 (FIG. 10). These domains are similar to domain-2 in that they are insertions in the β-strands of the β-helix that extend away from the β-helical spine and are located at the base of domain-2 in the cleft the N-terminal protease domain and the β-helical spine (FIG. 10). In comparing the domains in *H. influenzae* IgA1 protease to those found in HbP it is observed that while the domains are projections from the same points in the β-helical spine, there are differences in sequence and structure. Due to the location of these elements on a face of the enzyme that places them in line with the subsite binding cleft of the protease domain, it is proposed that these three subdomains (domains-2, -3, and -4) are involved in forming a unique structure that is involved in recognition and binding of the Fc domain of IgA1.

These results provide valuable information about the structure of *H. influenzae* IgA1 protease polypeptide that can guide design of modifications to the protease polypeptide.

Example 7

Truncation Mutants of IgA1 Protease Polypeptide Expressed in *H. influenzae*

IgA1 protease polypeptides are large in comparison to most other proteolytic enzymes. *H. influenzae* IgA1 protease polypeptide is approximately 109 kDa in size. This large size may present a problem in terms of increased immunogenicity. In the present Example, truncation mutants are generated and used to determine whether any part of the enzyme protein is dispensable without loss of full activity so that antigenic regions can be deleted in a modified IgA1 protease polypeptide suitable for therapy of IgA1 deposition diseases. Creation of truncation mutants is facilitated by insertional mutagenesis of furin cleavage sites at certain positions and by subsequent cleavage by furin.

Materials and Methods

Bacterial culture and enzyme recovery, anion exchange chromatography, and nickel-affinity choromatography are performed as described in Example 1.

Insertional Mutagenesis

Insertional mutagenesis of furin cleavage sites is accomplished using a short sequence substitution in plasmid pJQ/Rd6His ("6His" disclosed as SEQ ID NO: 25), which encodes an active IgA1 protease polypeptide with a 6×His tag (SEQ ID NO: 25) that is retained at the C-terminus of the processed enzyme. To make the construct, a pair of oligonucleotide primers for use in PCR are designed that facilitate the introduction of the RRXR furin substrate tetrapeptide to replace the native sequence. Plasmid DNA with such an IgA1 gene mutation is then introduced into the IgA1 protease polypeptide-negative, rifampicin-sensitive *Haemophilus* strain Rd3-13. Successful transformation results in rifampycin resistance and normal secretion of active IgA1 protease polypeptide. Based on earlier experience with this method (Plaut et al. (2000). "Human lactoferrin proteolytic activity: analysis of the cleaved region in the IgA1 protease polypeptide of *H. influenzae*." Vaccine Suppl. 1:S148-52) which was used to introduce a series of polyHis and influenza virus hemagglutinin epitopes in widely separate regions of the IgA1 gene, IgA1 protease polypeptide activity is expected to be restored in approximately 50% of the transformants.

Cleavage by Furin

Modified *H. influenzae* IgA1 protease polypeptide is cleaved using removable furin in a buffer (such as, for example, Tris HCl buffer, pH 8.0 in 2 mM $CaCl_2$), and stopped by EDTA, a furin inhibitor.

Verification Of Size Reduction

Reduction in size is verified in two ways: change in mobility detected by SDS/PAGE analysis and Western blot analysis of truncated protease polypeptides using an anti-6 His monoclonal antibody (Qiagen) ("6 His" disclosed as SEQ ID NO: 25). Absence of the 6×His motif (SEQ ID NO: 25) is a positive indication for reduction in size. Any ambiguities about changes in enzyme size can be resolved by molecular mass measurement using mass spectroscopy, or by peptide mapping. The ability of six monoclonal antibodies (as described in Example 5) to detect truncated protease polypeptides on Western blots or by immunoprecipitation can also be determined.

Expected Results

Inspection of the three-dimensional structure of *H. influenzae* IgA1 protease polypeptide (see FIG. 4) shows a globular amino-proximal domain comprising the enzyme active site. It is unlikely that mutations modifying this domain would be active, so truncation studies are focused on reducing the length of the long beta-helical region at the carboxy-terminal extent of the protein. No loss of activity had been noted when the 6×His tag (SEQ ID NO: 25) was inserted near the C-terminus, and when native IgA1 protease polypeptide was first cloned from *Haemophilus* strain Rd, it was active even though 10-20 C-terminal residues were missing.

Two distinct recombinant IgA1 protease polypeptides are made by inserting consensus furin cleavage sites near the C-terminus. Furin is the major endopeptidase in the human subtilisin-like proconvertase family (Henrich et al. (2005), the entire contents of which are herein incorporated by reference), and it cleaves the (*) in the sequence RXRR*, the consensus sequence for furin cleavage sites. Site-specific recombination is used to introduce the sequence RXRR at various points along the carboxy-proximal third of the mature protease polypeptide.

Furin cleavage sites are generally placed in unstructured regions of the helix that are not integral to the beta helix so as to be accessible to furin. In this Example, furin cleavage sites are placed in the region spanning amino acid residues 828-1014, for example at positions 966-975 (near the C-terminus at a point where the structure shows a short loop arising from the beta helix (see FIG. 5) or at positions 936-945. After introducing the consensus peptide, IgA1 protease polypeptide activity is tested on IgA1 substrate.

Cleavage is then carried out by purified recombinant furin in solution (Bachem Biosciences).

Truncated enzymes are repurified by sizing and/or affinity chromatography. Size reduction is verified as described in "Materials and Methods," and the shortened protein is then retested for activity.

Example 8

Truncation Mutants of IgA1 Protease Polypeptide Expressed in *B. megaterium*

In *H. influenzae*, the C-terminal autotransporter domain of IgA1 protease polypeptide is required for transport of the N-terminal protease polypeptide domain across the outer membrane, thus placing some restrictions on potential sites for truncation. Experiments in the present Example are directed to creating additional truncation mutants whose creation is not limited by such a requirement. In the present Example, *H. influenzae* IgA1 protease polypeptide is recombinantly expressed in *Bacillus megaterium*, a Gram positive bacterium that lacks an outer membrane.

Materials and Methods

Recombinant Engineering and Protein Expression

*B. megaterium* has become a highly effective expression host for secreted proteins. A gene encoding the protease polypeptide domain of IgA1 protease (amino acids 25-989) is cloned into the multiple-cloning-site of the commercially available vector pHIS1525 (MoBiTec). This plasmid can be manipulated and propagated in *E. coli* and then transformed into *B. megaterium* for protein expression, allowing easy cloning and amplification of the DNA. This system uses a tightly regulated promoter and repressor system for the *B. megaterium* xylose operon, creating a high-level expression system in which protein expression can be induced by adding xylose to the culture medium.

Cloning an IgA1 protease polypeptide gene into the pHIS1525 plasmid places the gene in frame with the LipA signal peptide, directing the protein along the Sec pathway for secretion. Upon export, the signal peptide is cleaved by the endogenous signal peptidase to generate the correct N-terminal A-25 residue, allowing for folding of the IgA1 protease polypeptide. Rapid purification is facilitated by using a 3'-BamHI site that results in the attachment of a C-terminal 6×His tag (SEQ ID NO: 25). Because the IgA1 protease polypeptide gene lacks BamHI sites, novel BamHI sites can be introduced at desired sites and used to create truncation mutants. Some potential sites for BamHI site insertion are illustrated in FIG. 17.

Site directed mutagenesis to introduce novel BamHI sites can be performed using the Stratagene Quik Change protocol. Subsequent digestion of the construct with BamHI and re-IIgA1tion of the linearized plasmid facilitates generation of novel truncated forms. Transformation-competent protoplasts of *B. megaterium* are also commercially available from MoBiTec, further facilitating easy manipulation of bacterial cells to produce truncation IgA1 protease polypeptides.

Purification

Purification of IgA1 protease polypeptide truncation mutants is accomplished as outlined in Example 1 using a combination of Ni-NTA affinity chromatography and anion-exchange chromatography. Such methods are expected to produce a protein preparation of a purity suitable for crystallization studies.

Expected Results

Truncation mutants including those lacking the Type V auto transporter domain are secreted by *B. megaterium* cells, purified, and characterized.

Discussion

By eliminating the Type V autotransporter domain, protein constructs that terminate at any length beyond Domain-4 (amino acid ~820) can be engineered. Experiments with such truncation mutants facilitate establishing an absolute minimum length for catalytically active IgA1 protease polypeptide. This approach also avoids any possible difficulties that may arise with engineered furin cleavage constructs.

Example 9

Epitope Mapping and Site-Specific Modifications of Surface-Exposed Antigenic Regions In the present Example, epitopes recognized by monoclonal antibodies raised against *H. influenzae* IgA1 protease polypeptide (see Example 5) are mapped in order to determine antigenic regions within *H. influenzae* IgA1 protease polypeptide. Knowledge of locations of antigenic regions is used to guide design of site-specific modifications to *H. influenzae* IgA1 protease polypeptide.

Antibodies

As mentioned in Example 5, two monoclonal antibodies to the *H. influenzae* protease polypeptide, mAb IGAN 3.3 and mAb IGAN 8.3, have been produce and purified. mAb IGAN 3.3 and mAb IGAN 8.3 detect IgA1 protease polypeptide on reduced PAGE gels, suggesting that their epitopes are linear. mAb IGAN 8.3 inhibits enzyme activity, whereas mAB IGAN 3.3 does not, suggesting that they recognize different epitopes. Four additional antibodies are being developed.

Epitope Mapping

Peptide display technology (Tribbick et al. (2002) and Aldaz-Carroll et al. (2005), the entire contents of both of which are herein incorporated by reference) is used to identify the epitopes recognized by the panel of six antibodies. Epitope mapping studies are based on the known structure of the enzyme protein, and use custom-made linear solid support-bound peptides prepared with the MULTIPIN™ Peptide Synthesis Technology developed by Mimotopes Pty. Ltd. (Raleigh, N.C.) (Tribbick et al. 2002).

Using a standard epitope mapping protocol, sets of 15-mer oligopeptide homologues of IgA1 protease polypeptide that are offset by three amino acids (hence overlap will be twelve amino acids between adjacent peptides) are synthesized on pins according to the MULTIPIN™ protocol. Each peptide is prepared with an N-terminal acetyl group, except for the first peptide in the set, representing the N-terminal end of the protein. The C-terminal residue of each peptide is covalently linked to the solid support via a spacer segment that moves the peptide well away from the support, preventing masking of epitopes. The strategy of having 15 amino acid residues per peptide and a 12-residue overlap between adjacent peptides should minimize the possibility that a linear epitope would be missed in the mapping process. Peptides are formatted as: Free amine/Acetyl-PEPTIDE-linker/spacer-PIN (solid support).

Approximately 270 peptides attached to their solid phase supports are used for epitope mapping studies with six monoclonal antibodies (developed as described in Example 5). An unrelated IgG monoclonal antibody known to have specificity for other antigens is used as a negative control (to exclude non-specific IgG-peptide binding). Analysis is by standard ELISA methods. An ELISA assay protocol is standardized using a positive control mouse IgG mAb in conjunction with known positive and negative control peptides. These reagents are supplied with the screening peptide library.

An alternative method is to custom synthesize biotinylated peptides that are cleaved from the solid phase and then captured on strepavidin coated plates.

Further Studies

Once locations of epitopes for the six monoclonal antibodies are determined, structure information is used to localize these in the enzyme polypeptide. Antigenic "hot spots" can be identified if an epitope is recognized by more than one monoclonal antibody. Such a region can then become the focus for more refined definition of the epitope structure. As before, a pin-based solid phase peptide set can be used for epitope mapping studies, though shorter peptides with shorter overlap would be used at this stage to identify critical residues. Epitopes that are on the surface of the enzyme polypeptide can be determined (based on our three-dimensional structure). Such epitopes are most likely to be antigenic in subjects to whom IgA1 protease polypeptide is administered. Epitopes that are detected by monoclonal antibodies that inhibit enzyme activity can also be the focus of further studies. Critical amino acids within such epitopes can be replaced by site specific mutagenesis, to determine whether such residues are essential for enzyme specificity or activity. Functional enzyme polypeptides can then be tested for immunogenicity in animals, as described in Example 11.

Example 10

PEGylation of IgA1 Protease Polypeptides

PEGylation of a biomolecule (such as a protein) can reduce immunogenicity and/or increase bioavailability of the biomolecule. In the present Example, PEGylated IgA1 protease polypeptides are generated. Design of PEGylated versions of *H. influenzae* IgA1 protease polypeptide incorporates knowledge of the three-dimensional structure of *H. influenzae* IgA1 protease polypeptide obtained from Example 6 and of antigenic hot spots characterized in Example 9.

Materials and Methods

Thiol Modification

PEGylation at thiol groups of cysteines that are not involved in disulfide bridges is one of the most specific methods available because free cysteines are rarely present in proteins or peptides (Roberts et al. (2002), Brocchini et al. (2006), and Doherty et al. (2005), the entire contents of each of which are herein incorporated by reference). Site-specific PEGylation can nevertheless be accomplished at cysteine residues involved in disulfide bonds if such bonds can be mildly reduced to liberate two cysteine sulfur atoms without disturbing the protein's tertiary structure. Such mild reduction may be accomplished using a bis-thiol alkylating PEG reagent that sequentially undergoes conjugation to form a three-carbon bridge, in which the two sulfur atoms are relinked with PEG, which is then selectively conjugated to the bridge. A useful protocol has been reported in detail (Brocchini et al. 2006).

PEG Molecules

PEG molecules can be linear or branched, and in some embodiments have an $M_r$ of 10-40 kDa. Reagents to selectively conjugate PEG chains onto cysteine residues are available and include PEG-maleimide, -vinylsulfone, -iodoacetamide and -orthopyridyl disulfide.

PEGylation

For free cysteine PEGylation, reactions are carried out under conditions of neutral pH, and reagents are selected to avoid irreversibly denaturing the polypeptide. Activated PEG chains (such as methoxy-PEG-maleimide (PEG-Mal) of 5, 20, and 40 kpa (JenKem Technology USA, Allen, Tex. or Pierce Chemical)) are tested at molar ratios of PEG chains to IgA1 protease polypeptide Rd 6His ("6His" disclosed as SEQ ID NO: 25) of 2, 5, 10, 20, and 50-fold molar excess of PEG. Reactions are carried out in 0.1 M sodium phosphate buffer (pH 7.0, with 2 mM EDTA) with 0.1-0.5 mg/mL purified IgA1 protease polypeptide in the presence of 2 to 15 fold molar excess of TCEP (tris 2-carboxyethyl phosphine hydrochloride, Pierce Chemical). After 6 hours at room temperature, PEGylation mixtures are dialyzed extensively against PBS pH 7.4 to remove unreacted PEG and excess reagents, and products are then examined by size exclusion chromatography and non-reducing SDS-PAGE. (See Doherty et al. (2005), the entire contents of which are herein incorporated by reference.)

Discussion

*H. influenzae* IgA1 protease polypeptide has 989 amino acids (approximately 109 kDa in size) and has few natural residues for site-specific PEGylation.

Figure 4:
FIG. 4 depicts a representation of the structure of *H. influenzae* IgA1 protease solved to 1.75 Å. The N-terminal chymotrypsin-like protease domain and the smaller sub-domains-2, -3, and -4 are colored green, blue, cyan, and purple, respectively. Structural studies indicated that all four of these domains are necessary for IgA protease activity.

The amino-terminus of a protein is often a favored site for making modifications. Nevertheless, structural analysis provided in Example 6 suggests that the amino terminal residue of *H. influenzae* IgA1 protease polypeptide is buried in the enzyme domain, and thus would not be accessible for PEGylation. On the other hand, this protein has only two cysteines, separated by 10-residues (792CVRSDYTGYVTC803 (SEQ ID NO: 45)), and the crystal structure shows that these cysteines form a disulfide bond that helps stabilize the two-stranded beta-sheet found in domain-4 (FIG. 4). Although the inventors had discovered that disulfide reduction of the protease polypeptide using dithiothreitol followed by alkylation did not modify enzyme activity, the crystal structure suggests that even if reduced, the two cysteines may be unavailable for PEGylation because they are buried inside.

As the only two cysteines in this polypeptide are bonded together, site-specific PEGylation may be accomplished by introducing one or more free cysteines as PEGylation sites elsewhere into the enzyme to replace nonessential amino acid(s). Such placements are guided by knowledge of the three-dimensional structure of the polypeptide and/or by knowledge of antigenic hot spots (obtained, for example, by epitope mapping studies).

For example, PEG chains may be attached at one or more particular sites of IgA1 protease polypeptide backbones in regions of IgA1 proteases that act as antigenic hot spots and/or attached to regions of IgA1 proteases that are dispensible for IgA1 protease activity, such as regions that appear as unstructured loops in a 3D structure model of an IgA1 protease. Based on structural knowledge of *H. influenzae* IgA1 protease, PEG chains may be attached within a region defined by positions corresponding to residues 820 to 1014 (inclusive) of SEQ ID NO: 23. Particularly attractive regions for PEGylation are regions defined by positions corresponding to residues 881-893 of SEQ ID NO: 23, residues 936-945 of SEQ ID NO: 23, and/or residues 966-975 of SEQ ID NO: 23.

Discussion

Examples 6-10

It will be understood by one of ordinary skill in the art that structural information of a given polypeptide can provide structural information about related polypeptides. Accordingly, although Examples 6-10 provide and/or incorporate structural information of *H. influenzae* Rd IgA1 protease polypeptides, such structural insights can be used to design modifications of related IgA1 protease polypeptides. For example, IgA1 protease polypeptides of other strains of *H. influenzae* (presented in Table 1) are have a high percentage of overall sequence identity to *H. influenzae* Rd IgA1 protease polypeptides (see FIGS. 3A-H). Given the homology between such polypeptides, one of ordinary skill of the art would expect that the structural insights provided by the present disclosure can be used to design IgA1 protease polypeptide agents using other *H. influenzae* IgA1 protease polypeptides as a reference IgA1 protease polypeptide.

Moreover, structural insights provided by the present disclosure may well be relevant to IgA1 protease polypeptides from other bacterial species. For example, IgA1 protease polypeptides from other bacterial species that have a high percentage of amino acid sequence identity over the entire sequence, or within a subregion of the sequence, may have structural similarities to *H. influenzae* Rd IgA1 protease polypeptides.

Therefore, one of ordinary skill in the art combining the teachings of the present disclosure with methods known in the art will be able to design, produce, and test IgA1 protease polypeptide agents that are modified versions of IgA1 proteases polypeptides other than *H. influenzae* IgA1 protease polypeptides.

Example 11

Immunogenicity of Modified IgA1 Protease Polypeptides in Mice

Reduced immunogenicity is desirable in a therapeutic. In the present Example, immunogenicity of modified IgA1 protease polypeptides, such as those generated in Examples 7-10, is evaluated. PEGylated, truncated, and epitope-modified IgA1 protease polypeptides are examined for their ability to stimulate antibody formation in mice in the presence or absence of immunosuppressive drugs.

Materials and Methods

Administration of Modified IgA1 Protease Polypeptides

Modified IgA1 protease polypeptides are administered in multiple intravenous doses to mice. Antibody (B cell) responses to each modified IgA1 protease polypeptide are measured, and serum antibody is titrated by ELISA. Results are compared with antibody responses and titer elicited by wild type IgA1 protease polypeptide. Enzyme polypeptides (i.e. modified IgA1 protease polypeptides and wild type IgA1 protease polypeptide) for injection are stored at concentrations of 200 μg/mL and adjusted to 1-10 μg IgA1 protease polypeptide per 200 μL in buffer or saline prior to injection. Groups of six Balb/C mice (aged 6-7 weeks) are weighed, pre-bled for detection of pre-existing antibody, and then injected with 200 μL enzyme polypeptide solution intravenously each week for six weeks. Within each week, enzyme polypeptide is administered on day 2, and bleeding is done on day 6.

Measurement and Characterization of Antibody Response

Serum samples are frozen and then all samples are assayed simultaneously using an ELISA assay developed with anti-mouse IgG reagents. Sera are also tested for ability to inhibit activity of Rd6His protease polypeptide ("6His" disclosed as SEQ ID NO: 25), using human IgA1 monoclonal protein as substrate.

Animal Handling

Strictly aseptic methods are used for animal handling. Bleeding is from a small tail incision and blood drops are collected into a sterile container. A maximum of 200 μL of blood is drawn per mouse per blood collection, and digital pressure is used to ensure hemostasis.

Statistical Analyses

Data are analyzed by multiple methods. In a primary analysis, antibody titers elicited by each of the (approximately ten) modified IgA1 protease polypeptides at week six are compared to that elicited by wild type IgA1 protease polypeptide at week six. Analysis of variance (ANOVA) and then Dunnett's t-tests are used to compare each variant with the control, while adjusting for multiple comparisons. In a secondary analysis, antibody titers for each animal are plotted at each week to show the rate of change over time. The mean slope for such a plot for each of the modified variants is compared to the mean slope for the wild type (WT). Depending on the skew of the data, and whether the variance increases with higher titers, these data may be analyzed on the log-transformed scale.

Immunosuppressants

If antibodies develop against wild type or modified IgA1 protease polypeptides in mice, an immunosuppressant such as corticosteroid dexamethasone is used to try to reduce such antibody responses. Experiments with immunosuppressants are done in mice using identical mouse numbers, dosing schedule, blood draw protocol, and ELISA antibody assay as described above in this Example, except that 5 μg dexamethasone per gram body weight in normal saline is given intraperitoneally 24 hours and 1 hour before each enzyme polypeptide injection. (This dexamethasone dosage is midway between the usual intraperitoneal dosage range of 0.5 to 10 5 μg per gram body weight reported by others to be antibody-suppressive).

An increased dosage of 10 μg dexamethasone per gram body weight can be used if antibody levels are reduced but not eliminated to any particular modified IgA1 protease polypeptide.

Mean antibody responses at 6 weeks are then compared between animals who received dexamethasone and those who did not. The mean slope computed from plots of antibody titers versus time in weeks can also be compared between the two groups of animals to see if there is a difference in the rate of change over time. A Bonferroni (or similar) adjustment can be used to control the alpha level at 0.05 once the total number of comparisons that are done is known. For analyzing data from pilot experiments, a less conservative p-value of 0.15 is considered as marginally significant when interpreting results.

Results and Discussion

Power Analysis

From preliminary data on mice that were administered wild type IgA1 protease polypeptide (with and without dexamethasone), an effect size (ES) of between 0.6 and 0.8 was observed for the difference in mean antibody response between mice treated with or without dexamethasone at week 6, where the ES is defined as the difference between the means between the two groups divided by the standard deviation. The observed ES for the difference in slopes (antibody response as a function of time) was 0.9-1.2.

Based on these findings, this study should provide adequate statistical power to detect significant and marginally significant differences. The table below shows raw alpha levels of 0.05 and 0.15 and power for varied effect sizes, which can be used with simple comparisons between any two groups of six animals. For analysis of modified IgA1 protease polypeptides, adjustments are made for multiple comparisons at lower alpha levels. Therefore, for a conservative reference, assuming ten comparisons are made using an extremely rigid alpha value of 0.015 (1/10th of 0.15), this study would have nearly 70% power to find an adjusted marginally significant result if the effect size is 2.0.

TABLE 4

Power (%) for varied effect sizes and alpha levels

| | Power for different effect sizes $\delta = \|\mu_1 - \mu_2\|/\sigma$ | | | | | |
|---|---|---|---|---|---|---|
| 2-sided alpha for test* | 0.750 | 1.000 | 1.250 | 1.500 | 1.750 | 2.000 |
| alpha = .05 | 21% | 34% | 49% | 64% | 77% | 87% |
| alpha = .15 | 42% | 58% | 72% | 84% | 92% | 96% |
| alpha = .015 | 9% | 17% | 28% | 41% | 55% | 69% |

*power calculated for 2-sample t-test with 6 animals per group

Example 12

Efficacy of Modified IgA1 Protease Polypeptides in an Animal Model of IgA1 Nephropathy In the present Example, modified IgA1 protease polypeptides that are drug candidates (e.g., modified versions that are less antigenic than wild type IgA1 protease polypeptide) are tested for efficacy in an established and validated animal model of IgA1 nephropathy.

Materials and Methods

Methods used in this Example are as described previously in Lamm et al. (2008), the entire contents of which are herein incorporated by reference. Protocols are briefly described below.

Mouse Model of IgA1 Nephropathy

Polyclonal human dimeric IgA1 (dIgA1) is purified from human plasma and separated from IgA12 using immobilized jacalin (an IgA1-binding lectin). IgA1 dimers are then complexed with goat $F(ab')_2$ anti-human $F(ab')_2$ antibody (The Jackson Laboratory). $F(ab')_2$ is used rather than complete goat IgG to obviate possible interactions between IgG Fc domains and Fcγ receptors on some murine cells; such a strategy is expected to increase targeting of complexes to the glomerular mesangium. Complexes are then injected into animals as described in Lamm et al. (2008).

Injection of Modified IgA1 Protease Polypeptides

Modified IgA1 protease polypeptides are injected into mice approximately 60 minutes after injections of IgA1 complexes. Group 1 animals (see below) are to be injected intravenously with 20 μg of modified Rd 6-His *H. influenzae* IgA1 protease polypeptide ("6-His" disclosed as SEQ ID NO: 25), and Group 2 animals (controls) are to be injected with equivalent amounts of inhibited protease polypeptide.

Group 1: Ten normal Balb/c mice, injected with immune complexes (IC) that deposit in the glomerular mesangium, to receive active modified IgA1 protease polypeptide.

Group 2: Ten normal Balb/c mice, injected with IC, to receive IgA1 protease polypeptide inactivated by 0.1-1.0 mM phenylmethylsulfonyl fluoride (PMSF, CalBiochem), an irreversible inhibitor that binds to the serine in the enzyme active site.

Histology and Scoring of Kidney Samples

One hour after the last injection of modified or inhibited IgA1 protease polypeptide, kidneys are removed, sectioned on a cryostat, fixed in acetone, and frozen at −20° C. until staining with FITC-labeled $F(ab')_2$ rabbit anti-human IgA1 alpha chain specific), FITC-labeled $F(ab')_2$ rabbit anti-human $F(ab')_2$, and rhodamine-labeled $F(ab')_2$ rabbit anti-goat F(ab')$_2$, all from The Jackson Laboratory. Standard immunofluourescent staining protocols are used.

For analysis, slides are numbered to conceal the identities of samples (experimental or control), after which three pathologists independently score level of fluorescence according to a semi-quantitative system (1+, 2+ etc.). Results are analyzed using a two-sample two-tailed Wilcoxon rank-sum test using an alpha level of 0.05.

Quantitative analysis of clearance of immune complexes from renal tissue can be done using images of renal tissues photographed by a Leica TCS SP2 AOBS confocal microscope outfitted for laser scanning confocal microscopy and by 2-photon microscopy. To avoid bias in glomerulus selection, a section of each kidney can be viewed at 10× magnification using a grid. A randomly selected section can be analyzed for fluorescent pixel intensity. Images are acquired using identical settings for laser intensity and photomultiplier tube gain across experiments. Settings are chosen such that pixel intensities fall below saturation levels. Further, the wavelengths of light collected in each detection channel will be set such that no detectable bleed-through occurs between the different channels. After converting the image to gray scale (where resolution is higher) quantitation will use the options provided in the software. Specifically, using the profile option, a line of one pixel width is drawn across each individual fluorescent element in the field, and fluorescent pixel intensity measured as the mean value along the length of each line. This method does not depend on defining the glomerular boundaries, which offers an advantage since the experimental (modified IgA1 protease polypeptide-treated) sections often have so few fluorescent regions that the boundary of the glomerulus cannot be accurately identified. The mean IC clearance, as measured by this method, is compared between the two groups using a two-sample Student's t-test with a 2-sided alpha level of 0.05.

While a confocal approach is used in many embodiments, in some embodiments, standard fluorescence microscopy using the line option of Scion image software is used. This approach was used in an earlier power analysis. The earlier power analysis indicated that the mean±standard deviation (SD) pixel fluorescence intensity of human IgA1 was 43±8 (n=90, with n being the number of fluorescent elements measured) in the control sample compared to 15±3 (n=90) in the protease polypeptide test sample. These data support the potential for success in this study.

With 10 control and 10 treated animals, over 90% power to detect a mean difference in fluorescence intensity of at least 20 units (for example, 40 in the control group versus 20 in the treated group) can be expected. This power calculation conservatively assumes a standard deviation of 10 within each group (yielding an effect size of 2.0). A study with 10 animals per group would have 80% power to detect an effect size of 1.3 (or a mean difference of 13 units if the standard deviation is truly 10). These estimate of power presume that the mean group difference is compared using a 2-sided t-test with an alpha level of 0.05.

Unless noted otherwise, analyses are performed using the SAS software system for Windows, version 9.1 (SAS Institute, Cary, N.C.) or a comparable commercially available statistical analysis package. Power calculations were done using nQuery Advisor® Version 5.0 software, Statistical Solutions (Saugus, Mass.).

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

REFERENCES

Aldaz-Carroll et al. (2005) "Epitope-mapping studies define two major neutralization sites on the vaccinia virus extracellular enveloped virus glycoprotein B5F," *Journal of Virology*, 79(10):6260-6271

Bachovchin et al. (1990) "Inhibition of IgA1 proteinases from *Neisseria gonorrhoeae* and *Hemophilus influenzae* by peptide prolyl boronic acids," *J. Biol. Chem.* 265: 3738-3743

Bailey et al. (1994) "The Ccp4 Suite—Programs for Protein Crystallography," *Acta Crystallographica Section D: Biological Crystallography*, 50, 760-763

Brocchini et al. (2006) "PEGylation of native disulfide bonds in proteins," *Nature Protocols*. 1(5):2241-2252

Campbell, A. M., (1984) *Monoclonal Antibodies Technology: Laboratory Techniques in Biochemistry and Molecular Biology*, Elsevier Science Publishers, Amsterdam, the Netherlands Chintalacharuvu et al. (2003). "Cleavage of the human immunoglobulin A1 (IgA1) hinge region by IgA1 protease polypeptides requires structures in the Fc region of IgA1." *Infection and Immunity*. 71, 2563-2570

Cohen et al. (2008) "ARP/wARP and molecular replacement: the next generation," *Acta Crystallographica Section D—Biological Crystallography*, 64, 49-60

Cohen et al. (2004) "Towards complete validated models in the next generation of ARP/wARP, *Acta Crystallographica Section D—Biological Crystallography*, 60, 2222-2229

Comeau et al. (2004) "ClusPro: a fully automated algorithm for protein-protein docking," Nucleic Acids Research, 32, W96-W99

Comeau et al. (2004) "ClusPro: An automated docking and discrimination method for the prediction of protein complexes," *Bioinformatics*, 20, 45-50

Doherty et al. (2005) "Site-specific PEGylation of engineered cysteine analogues of recombinant human granulocyte-macrophage colony-stimulating factor," *Bioconjugate Chemistry*, 16, 1291-1298

Emancipator et al. (1987) "Animal models of IgAN" in IgAN, A. Clarkson (ed.), Martinus Nijhoff publishing, Boston, pp. 188-203

Emancipator et al. (1998) "IgAN and Henoch-Schonlein syndrome" in *Heptinstall's Pathology of the Kidney, pp.* 479-539

Emancipator et al. (2005) "IgAN and related diseases" in *Mucosal Immunology,* pp. 1580-1600

Emsley et al. (2004) "Coot: model-building tools for molecular graphics," *Acta Crystallographica Section D: Biological Crystallography,* 60, 2126-2132

Gasteiger et al. (2005) "Protein Identification and Analysis Tools on the ExPaSy Server" in *The Proteomics Protocols Handbook*. pp. 571-607, Humana Press Gesualdo et al. (1990) "Enzymolysis of glomerular immune deposits in vivo with dextranase/protease ameliorates proteinuria, hematuria, and mesangial proliferation in murine experimental IgAN," *Journal of Clinical Investigation,* 86: 715-722

Gilbert and Plaut (1983). "Detection of IgA1 protease polypeptide activity among multiple bacterial colonies." *J. Immunol. Methods*. 57(1-3):247-51

Gregoriadis et al. (2005) "Improving the therapeutic efficacy of peptides and proteins: A role for polysialic acids," *International Journal of Pharmaceutics*, 300(1-2):125-130

Hall et al. (1985), "Characterization of circulating and cutaneous IgA immune complexes in patients with dermatitis herpetiformis," *J. Immunol.* 135(3): 1760-5

Harlour and Lane (1989) *Antibodies*, Cold Spring Harbor Laboratory, pp. 1-726

Henrich et al. (2005) "Proprotein convertase models based on the crystal structures of furin and kexin: explanation of their specificity." *J. Mol. Biol.* 345(2):211-27

Herr et al. (2003) "Insights into IgA-mediated immune responses from the crystal structures of human Fc alpha RI and its complex with IgA-Fc," *Nature*, 423, 614-620

Hochuli in *Genetic Engineering: Principles and Methods* (ed. J K Setlow, Plenum Press, NY, chp 18), pp 87-96

Holm et al. (2008) "Searching protein structure databases with DaliLite v. 3," *Bioinformatics*, 24, 2780-2781

Holyoak et al. (2003) "Malonate: a versatile cryoprotectant and stabilizing solution for salt-grown macromolecular crystals," *Acta Crystallographica Section D: Biological Crystallography.* 59, 2356-2358

Joosten et al. (2008) "A knowledge-driven approach for crystallographic protein model completion," *Acta Crystallographica Secton D—Biological Crystallography*, 64, 416-424

Lamm et al. (2008) "Microbial IgA protease removes IgA immune complexes from mouse glomerul in vivo: potential therapy for IgAN." *American Journal of Pathology*, 172:31-36.

Larkin et al. (2007) "Clustal W and Clustal X version 2.0," *Bioinformatics*, 23, 2947-2948

Laskowski et al. (1993) "Procheck—a program to check the stereochemical quality of protein structures," *Journal of Applied Crystallography*, 26, 283-291

Luft et al. (2003) "A deliberate approach to screening for initial crystallization conditions of biological macromolecules." *Journal of Structural Biology.* 142, 170-179.

McCoy et al. (2007) "Phaser crystallographic software," *Journal of Applied Crystallography.* 40, 658-674

Mandell et al. (2001) "Protein docking using continuum electrostatics and geometric fit," *Protein Engineering*, 14, 105-113

McGillivary et al. (2005) "Characterization of the IgA1 protease from the Brazilian purpuric fever strain F3031 of *Haemophilus influenzae* biogroup aegyptius," *FEMS Micriobiol Lett*, 250 L: 229-236

Morris et al. (2004) "Breaking good resolutions with ARP/wARP," *Journal of Synchrotron Radiation*, 11, 56-59

Motiejunas et al. (2008). "Protein-protein docking by simulating the process of association subject to biochemical constraints." *Proteins.* 71(4):1955-69

Murshudov et al. (1997) "Refinement of macromolecular structures by the maximum-likelihood methods," *Acta Crystallographica Section D: Biological Crystallography*, 53, 240-255

Nakazawa, M. et al. (1986) "Removal of glomerular immune complexes in passive serum sickness nephritis by treatment in vivo with proteolytic enzymes," *Laboratory Investigation*, 55:551-556, Nakazawa, M. et al. (1986) "Proteolytic enzyme treatment reduces glomerular immune deposits and proteinuria in passive Heymann nephritis," *Journal of Experimental Medicine.* 164:1973-1987

Otto et al. (2005) "Crystal structure of hemoglobin protease, a heme binding autotransporter protein from pathogenic *Escherichia coli*," *Journal of Biological Chemistry*, 280: 17339-17345.

Otwinowski et al. (1997) "Processing of X-ray Diffraction Data Collected in Oscillation Mode," *Methods in Enzymology*, 276, 307-326

Painter et al. (2005) "A molecular viewer for the analysis of TLS rigid-body motion in macromolecules," *Acta Crystallographica Section D: Biological Crystallography*, 61, 465-471

Painter et al. (2006) "Optimal description of a protein structure in terms of multiple groups undergoing TLS motion, *Acta Crystallographica Section D: Biological Crystallography*, 62, 439-450

Painter et al. (2006) "TLSMD web server for the generation of multi-group TLS models," *Journal of Applied Crystallography*, 39, 109-11

Plaut et al. (1974). "Specificity of IgA1 Protease polypeptide for Human Immunoglobulins of IgA1 Subclass." *Journal of Clinical Investigation.* 53. A60

Plaut et al. (1994) "IgA-specific prolyl endopeptidases: serine type," *Methods in Enzymology*, 244: 137-151

Qiu et al. (1996). "Analysis of the specificity of bacterial immunoglobulin A (IgA1) protease polypeptides by a comparative study of ape serum IgA1 s as substrates." *Infection and Immunity.* 64, 933-937

Roberts et al. (2002) "Chemistry for peptide and protein PEGylation," *Advanced Drug Delivery Reviews*, 54(4): 459-476

Rowland et al. (1995) *Clinical Pharmacokinetics—Concepts and Applications* (3rd edition), Williams and Wilkins, pp. 70 and 485

Sali et al. (1993) "Comparative protein modelling by satisfaction of spatial restraints," *Journal of Molecular Biology*, 234, 779-815

Sambrook et al. (2001) *Molecular cloning: a laboratory manual* (3$^{rd}$ edition), Cold Spring Harbor Press.

Shargel et al. (1985) "Multicompartment models," in *Applied biopharmaceutics and pharmacokinetics*, Applenton & Lange, Norwalk, Conn., pp. 51-67.

Stein et al. (2008) "CHAINSAW: a program for mutating pdb files used as templates in molecular replacement, *Journal of Applied Crystallography*, 41, 641-643

Thompson et al. (1994) "CLUSTAL W: improving the sensitivity of progressive multiple sequence alignment through sequence weighting, position-specific gap penalties and weight matrix choice," *Nucleic Acids Research*, 22, 4673-4680

Tribbick et al. (2002) "Multipin peptide libraries for antibody and receptor epitope screening and characterization." *J. Immunol. Methods.* 267(1):27-35

EQUIVALENTS

The foregoing has been a description of certain non-limiting preferred embodiments of the invention. Those skilled in the art will recognize, or be able to ascertain using no more than routine experimentation, many equivalents to the specific embodiments of the invention described herein. Those of ordinary skill in the art will appreciate that various changes and modifications to this description may be made without departing from the spirit or scope of the present invention, as defined in the following claims.

To give but a few examples, in the claims articles such as "a", "an", and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim.

Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise. In addition, the invention encompasses compositions made according to any of the methods for preparing compositions disclosed herein.

Where elements are presented as lists, e.g., in Markush group format, it is to be understood that each subgroup of the elements is also disclosed, and any element(s) can be removed from the group. It is further understood that any listing of elements in Markush group format is not intended as a concession that individual elements are not patentably distinct from one another, but rather is intended only to simplify presentation of multiple alternatives.

It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included unless otherwise indicated. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Any embodiment, element, feature, application, or aspect of the compositions and/or methods of the invention can be excluded from any one or more claims. For example, in certain embodiments of the invention the biologically active agent is not an antiproliferative agent. For purposes of brevity, all of the embodiments in which one or more elements, features, purposes, or aspects is excluded are not set forth explicitly herein.

What is claimed is:

1. An IgA1 protease polypeptide comprising a polypeptide backbone whose amino acid sequence shares at least 75% overall sequence identity with SEQ ID NO: 24 and comprises an N-terminal chymotrypsin-like protease domain and subdomains-2 to −4, wherein the IgA1 protease polypeptide has a C-terminal truncation after the subdomain-4, so that it lacks sequences C-terminal to the truncation, which IgA1 protease polypeptide is less immunogenic than full-length polypeptide lacking the C-terminal truncation.

2. An IgA1 protease polypeptide comprising a polypeptide backbone whose amino acid sequence shares at least 75% overall sequence identity with SEQ ID NO: 24 and comprises an N-terminal chymotrypsin-like protease domain and subdomains-2 to -4, wherein the IgA1 protease polypeptide has a C-terminal truncation after the subdomain-4, so that it lacks sequences C-terminal to the truncation, which IgA1 protease polypeptide further comprises at least one polyethylene glycol (PEG) group covalently attached to the polypeptide backbone.

3. The IgA1 protease polypeptide of claim 1, wherein the truncation occurs C-terminal to residue 976 of SEQ ID NO: 24.

4. The IgA1 protease polypeptide of claim 1, wherein the truncation occurs C-terminal to residue 967 of SEQ ID NO: 24.

5. The IgA1 protease polypeptide of claim 1, wherein the truncation occurs C-terminal to residue 946 of SEQ ID NO: 24.

6. The IgA1 protease polypeptide of claim 1, wherein the truncation occurs C-terminal to residue 937 of SEQ ID NO: 24.

7. The IgA1 protease polypeptide of claim 1, wherein the truncation occurs C-terminal to residue 829 of SEQ ID NO: 24.

8. The IgA1 protease polypeptide of claim 1, wherein the polypeptide cleaves IgA1 at a site in its hinge region.

9. The polypeptide of claim 2, wherein the PEG group is covalently attached in a region selected from the group consisting of: residues 881-893 of SEQ ID NO: 24; residues 936-945 of SEQ ID NO: 24, and residues 966-975 of SEQ ID NO: 24.

10. An IgA1 protease polypeptide comprising a polypeptide backbone whose amino acid sequence shares at least 75% overall sequence identity with SEQ ID NO: 24, and wherein the IgA1 protease polypeptide is truncated after residue 936 of SEQ ID NO: 24, so that it lacks sequences C-terminal to the truncation, which IgA1 protease polypeptide is less immunogenic than full-length polypeptide lacking the C-terminal truncation.

11. The IgA1 protease polypeptide of claim 10, wherein the polypeptide is truncated after residue 945 of SEQ ID NO: 24.

12. The IgA1 protease polypeptide of claim 10, wherein the polypeptide is truncated after residue 966 of SEQ ID NO: 24.

13. The IgA1 protease polypeptide of claim 10, wherein the polypeptide is truncated after residue 975 of SEQ ID NO: 24.

14. The IgA1 protease polypeptide of claim 10, further comprising at least one polyethylene glycol (PEG) group covalently attached to the polypeptide.

15. A method comprising a step of administering to an individual having deposits of IgA1 an IgA1 protease polypeptide of claim 1.

16. The method of claim 15, wherein the individual is suffering from a condition selected from the group consisting of IgA1 nephropathy, dermatitis herpetiformis, and Henoch-Schoenlein purpura.

17. The method of claim 15, wherein the individual is suffering from IgA1 nephropathy.

18. The method of claim 15, wherein the IgA1 protease polypeptide is administered in an amount effective such that IgA1 deposits are reduced.

19. The method of claim 15, wherein the IgA1 is human IgA1.

* * * * *